(12) United States Patent
Ruben et al.

(10) Patent No.: US 6,969,519 B2
(45) Date of Patent: Nov. 29, 2005

(54) METHODS OF USING AN AGONISTIC ANTIBODY HUMAN TUMOR NECROSIS FACTOR RECEPTOR (TR17)

(75) Inventors: Steven M. Ruben, Olney, MD (US); Kevin P. Baker, Darnestown, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 199 days.

(21) Appl. No.: 09/961,376

(22) Filed: Sep. 25, 2001

(65) Prior Publication Data

US 2002/0106736 A1 Aug. 8, 2002

Related U.S. Application Data

(63) Continuation-in-part of application No. 09/533,822, filed on Mar. 24, 2000, now abandoned.
(60) Provisional application No. 60/254,874, filed on Dec. 13, 2000, provisional application No. 60/235,991, filed on Sep. 26, 2000, and provisional application No. 60/188,208, filed on Mar. 10, 2000.

(51) Int. Cl.$^7$ ........................ A61K 39/395; G01N 33/53
(52) U.S. Cl. ................. 424/139.1; 424/130.1; 424/133.1; 424/135.1; 424/141.1; 424/143.1; 424/178.1; 424/183.1; 435/7.1; 435/7.2
(58) Field of Search ................. 424/130.1, 143.1, 424/139.1, 133.1, 135.1, 141.1, 178.1, 183.1; 435/7.1, 7.2, 7.21, 7.26; 514/885

(56) References Cited

U.S. PATENT DOCUMENTS 5,969,102 A 10/1999 Bram et al.

FOREIGN PATENT DOCUMENTS

| WO | WO 98/18921 A1 | 5/1998 |
| WO | WO 98/39361 | 9/1998 |
| WO | WO 00/40716 | 7/2000 |
| WO | WO 00/50597 A2 | 8/2000 |
| WO | WO 00/67034 | 9/2000 |
| WO | WO 00/58362 A1 | 10/2000 |

OTHER PUBLICATIONS

Chuntharapai et al. Methods in Enzymology, vol. 288, pp. 15–27.*
Skolnick et al. (2000), Nature Biotechnology, vol. 18, pp. 283–287.*
Canhao et al. (2000) J. Rheumatol., 27(4):1102–1103.*
Fox et al. (1997), Curr Opin Rheumatol, 9(5):393–399.*
Molina et al. (1996), 60(6):699.*
Von Bulow et al., NF–AT Activation Induced by a CAML–Interacting Member of the Tumor Necrosis Factor Receptor Superfamily.(1997) Science 278:138–141.
Groom et al., Association of BAFF/BLyS overexpression and altered B cells differentiation with Sjorgen's Syndrome. *J. Clin. Invest.* (2002) 109:59–68.
Zhang et al., Cutting Edge: A Role for B Lymphocyte Stimulator in Systemic Lupus Erythematosus. *J. Immunol.* (2001) 166:6–10.
Cheema et al., Elevated Serum B Lymphocyte Stimulator Levels in Patients with Systemic Immune–Based Rheumatic Diseases, *Arthritis Rheum.* (2001) 44:1313–1319.
Marriette et al., A Role for B Lymphocyte Stimulator (TALL–1, BAFF, THANK, $_z$TNF4) in Sjögren's Syndrome. 65$^{th}$ Annual American College of Rheumatology Scientific Meeting. Nov. 2001.
Vaux et al., The Buzz about BAFF. *J. Clin. Invest.* (2002) 109:17–18.
Gross et al., TACI and BCMA are Receptors For a TNF Homologue Implicated In B–cell Autoimmune Disease. *Nature* (2000) 404:995–999.
Seshasyaee et al, "Loss of TACI Causes Fatal Lymphoproliferation and Autoimmunity, Establishing TACI as an Inhibitory BLyS Receptor," *Immunity*, 18:279–288 (2003).
Yan et al., "Activation and accumulation of B cells in TACI–deficient mice," *Nature Immunol.*, 2(7):638–643 (Jul. 2001).
Waldmann, TA, "Immunotherapy: Past, Present and Future," *Nature Medicine*, 9:269–277 (2003).
Moore et al., "BLyS: Member of the Tumor Necrosis Factor Family and B Lymphocyte Stimulator," *Science*, 285:260–263 (1999).
Rousset et al., "Cytokine–Induced Proliferation and Immunoglobulin Production of Human B Lymphocytes Triggered through Their CD40 Antigen," *The Journal of Experimental Medicine*, 173:705–710 (1991).

* cited by examiner

*Primary Examiner*—Prema Mertz
(74) *Attorney, Agent, or Firm*—Human Genome Sciences, Inc.

(57) ABSTRACT

The present invention relates to a novel protein, TR17, which is a member of the tumor necrosis factor (TNF) receptor superfamily. In particular, isolated nucleic acid molecules are provided encoding the human TR17. TR17 polypeptides are also provided as anti TR17 antibodies and vectors, host cells and recombinant methods for producing the same. The invention further relates to methods of killing cells using the antibodies of the invention.

12 Claims, 2 Drawing Sheets

```
  1 ATGAGTGGCCTGGGCCGGAGCAGGCGAGGTGGCCGGAGCCGTGTGGACCAGGAGGAGCGC   60
  1  M  S  G  L  G  R  S  R  R  G  G  R  S  R  V  D  Q  E  E  R   20

61 TTTCCACAGGGCCTGTGGACGGGGGTGGCTATGAGATCCTGCCCCGAAGAGCAGTACTGG  120
 21  F  P  Q  G  L  W  T  G  V  A  M  R  S  C  P  E  E  Q  Y  W   40

121 GATCCTCTGCTGGGTACCTGCATGTCCTGCAAAACCATTTGCAACCATCAGAGCCAGCGC  180
 41  D  P  L  L  G  T  C  M  S  C  K  T  I  C  N  H  Q  S  Q  R   60

181 ACCTGTGCAGCCTTCTGCAGGTCACTCAGCTGCCGCAAGGAGCAAGGCAAGTTCTATGAC  240
 61  T  C  A  A  F  C  R  S  L  S  C  R  K  E  Q  G  K  F  Y  D   80

241 CATCTCCTGAGGGACTGCATCAGCTGTGCCTCCATCTGTGGACAGCACCCTAAGCAATGT  300
 81  H  L  L  R  D  C  I  S  C  A  S  I  C  G  Q  H  P  K  Q  C  100

301 GCATACTTCTGTGAGAACAAGCTCAGGAGCCCAGTGAACCTTCCACCAGAGCTCAGGAGA  360
101  A  Y  F  C  E  N  K  L  R  S  P  V  N  L  P  P  E  L  R  R  120

361 CAGCGGAGTGGAGAAGTTGAAAACAATTCAGACAACTCGGGAAGGTACCAAGGATTGGAG  420
121  Q  R  S  G  E  V  E  N  N  S  D  N  S  G  R  Y  Q  G  L  E  140

421 CACAGAGGCTCAGAAGCAAGTCCAGCTCTCCCGGGGCTGAAGCTGAGTGCAGATCAGGTG  480
141  H  R  G  S  E  A  S  P  A  L  P  G  L  K  L  S  A  D  Q  V  160

481 GCCCTGGTCTACAGCACGCTGGGGCTCTGCCTGTGTGCCGTCCTCTGCTGCTTCCTGGTG  540
161  A  L  V  Y  S  T  L  G  L  C  L  C  A  V  L  C  C  F  L  V  180

541 GCGGTGGCCTGCTTCCTCAAGAAGAGGGGGGATCCCTGCTCCTGCCAGCCCCGCTCAAGG  600
181  A  V  A  C  F  L  K  K  R  G  D  P  C  S  C  Q  P  R  S  R  200

601 CCCCGTCAAAGTCCGGCCAAGTCTTCCCAGGATCACGCGATGGAAGCCGGCAGCCCTGTG  660
201  P  R  Q  S  P  A  K  S  S  Q  D  H  A  M  E  A  G  S  P  V  220

661 AGCACATCCCCCGAGCCAGTGGAGACCTGCAGCTTCTGCTTCCCTGAGTGCAGGGCGCCC  720
221  S  T  S  P  E  P  V  E  T  C  S  F  C  F  P  E  C  R  A  P  240

721 ACGCAGGAGAGCGCAGTCACGCCTGGGACCCCCGACCCCACTTGTGCTGGAAGGTGGGGG  780
241  T  Q  E  S  A  V  T  P  G  T  P  D  P  T  C  A  G  R  W  G  260

781 TGCCACACCAGGACCACAGTCCTGCAGCCTTGCCCACACATCCCAGACAGTGGCCTTGGC  840
261  C  H  T  R  T  T  V  L  Q  P  C  P  H  I  P  D  S  G  L  G  280

841 ATTGTGTGTGTGCCTGCCCAGGAGGGGGGCCCAGGTGCATAA 882
281  I  V  C  V  P  A  Q  E  G  G  P  G  *    294
```

FIG. 1

SEQUENCE LISTING

```
<160> NUMBER OF SEQ ID NOS: 7

<210> SEQ ID NO 1
<211> LENGTH: 882
<212> TYPE: DNA
<213> ORGANISM: Homo sapiens
<220> FEATURE:
<221> NAME/KEY: CDS
<222> LOCATION: (1)..(882)

<400> SEQUENCE: 1 atg agt ggc ctg ggc cgg agc agg cga ggt ggc cgg agc cgt gtg gac      48
Met Ser Gly Leu Gly Arg Ser Arg Arg Gly Gly Arg Ser Arg Val Asp
  1               5                  10                  15
```

```
cag gag gag cgc ttt cca cag ggc ctg tgg acg ggg gtg gct atg aga        96
Gln Glu Glu Arg Phe Pro Gln Gly Leu Trp Thr Gly Val Ala Met Arg
         20                  25                  30 tcc tgc ccc gaa gag cag tac tgg gat cct ctg ctg ggt acc tgc atg       144
Ser Cys Pro Glu Glu Gln Tyr Trp Asp Pro Leu Leu Gly Thr Cys Met
 35                  40                  45 tcc tgc aaa acc att tgc aac cat cag agc cag cgc acc tgt gca gcc       192
Ser Cys Lys Thr Ile Cys Asn His Gln Ser Gln Arg Thr Cys Ala Ala
     50                  55                  60 ttc tgc agg tca ctc agc tgc gcc aag gag caa ggc aag ttc tat gac       240
Phe Cys Arg Ser Leu Ser Cys Arg Lys Glu Gln Gly Lys Phe Tyr Asp
 65                  70                  75                  80 cat ctc ctg agg gac tgc atc agc tgt gcc tcc atc tgt gga cag cac       288
His Leu Leu Arg Asp Cys Ile Ser Cys Ala Ser Ile Cys Gly Gln His
                 85                  90                  95 cct aag caa tgt gca tac ttc tgt gag aac aag ctc agg agc cca gtg       336
Pro Lys Gln Cys Ala Tyr Phe Cys Glu Asn Lys Leu Arg Ser Pro Val
            100                 105                 110 aac ctt cca cca gag ctc agg aga cag cgg agt gga gaa gtt gaa aac       384
Asn Leu Pro Pro Glu Leu Arg Arg Gln Arg Ser Gly Glu Val Glu Asn
        115                 120                 125 aat tca gac aac tcg gga agg tac caa gga ttg gag cac aga ggc tca       432
Asn Ser Asp Asn Ser Gly Arg Tyr Gln Gly Leu Glu His Arg Gly Ser
130                 135                 140 gaa gca agt cca gct ctc ccg ggg ctg aag ctg agt gca gat cag gtg       480
Glu Ala Ser Pro Ala Leu Pro Gly Leu Lys Leu Ser Ala Asp Gln Val
145                 150                 155                 160 gcc ctg gtc tac agc acg ctg ggg ctc tgc ctg tgt gcc gtc ctc tgc       528
Ala Leu Val Tyr Ser Thr Leu Gly Leu Cys Leu Cys Ala Val Leu Cys
                165                 170                 175 tgc ttc ctg gtg gcg gtg gcc tgc ttc ctc aag aag agg ggg gat ccc       576
Cys Phe Leu Val Ala Val Ala Cys Phe Leu Lys Lys Arg Gly Asp Pro
            180                 185                 190 tgc tcc tgc cag ccc cgc tca agg ccc cgt caa agt ccg gcc aag tct       624
Cys Ser Cys Gln Pro Arg Ser Arg Pro Arg Gln Ser Pro Ala Lys Ser
        195                 200                 205 tcc cag gat cac gcg atg gaa gcc ggc agc cct gtg agc aca tcc ccc       672
Ser Gln Asp His Ala Met Glu Ala Gly Ser Pro Val Ser Thr Ser Pro
    210                 215                 220 gag cca gtg gag acc tgc agc ttc tgc ttc cct gag tgc agg gcg ccc       720
Glu Pro Val Glu Thr Cys Ser Phe Cys Phe Pro Glu Cys Arg Ala Pro
225                 230                 235                 240 acg cag gag agc gca gtc acg cct ggg acc ccc gac ccc act tgt gct       768
Thr Gln Glu Ser Ala Val Thr Pro Gly Thr Pro Asp Pro Thr Cys Ala
                245                 250                 255 gga agg tgg ggg tgc cac acc agg acc aca gtc ctg cag cct tgc cca       816
Gly Arg Trp Gly Cys His Thr Arg Thr Thr Val Leu Gln Pro Cys Pro
            260                 265                 270 cac atc cca gac agt ggc ctt ggc att gtg tgt gtg cct gcc cag gag       864
His Ile Pro Asp Ser Gly Leu Gly Ile Val Cys Val Pro Ala Gln Glu
        275                 280                 285 ggg ggc cca ggt gca taa                                                882
Gly Gly Pro Gly Ala
    290

<210> SEQ ID NO 2
<211> LENGTH: 293
<212> TYPE: PRT
<213> ORGANISM: Homo sapiens
```

<400> SEQUENCE: 2

```
Met Ser Gly Leu Gly Arg Ser Arg Gly Arg Ser Arg Val Asp
  1               5                  10                  15
Gln Glu Glu Arg Phe Pro Gln Gly Leu Trp Thr Gly Val Ala Met Arg
             20                  25                  30
Ser Cys Pro Glu Glu Gln Tyr Trp Asp Pro Leu Leu Gly Thr Cys Met
         35                  40                  45
Ser Cys Lys Thr Ile Cys Asn His Gln Ser Gln Arg Thr Cys Ala Ala
     50                  55                  60
Phe Cys Arg Ser Leu Ser Cys Arg Lys Glu Gln Gly Lys Phe Tyr Asp
 65                  70                  75                  80
His Leu Leu Arg Asp Cys Ile Ser Cys Ala Ser Ile Cys Gly Gln His
                 85                  90                  95
Pro Lys Gln Cys Ala Tyr Phe Cys Glu Asn Lys Leu Arg Ser Pro Val
                100                 105                 110
Asn Leu Pro Pro Glu Leu Arg Arg Gln Arg Ser Gly Glu Val Glu Asn
            115                 120                 125
Asn Ser Asp Asn Ser Gly Arg Tyr Gln Gly Leu Glu His Arg Gly Ser
130                 135                 140
Glu Ala Ser Pro Ala Leu Pro Gly Leu Lys Leu Ser Ala Asp Gln Val
145                 150                 155                 160
Ala Leu Val Tyr Ser Thr Leu Gly Leu Cys Leu Cys Ala Val Leu Cys
                165                 170                 175
Cys Phe Leu Val Ala Val Ala Cys Phe Leu Lys Lys Arg Gly Asp Pro
            180                 185                 190
Cys Ser Cys Gln Pro Arg Ser Arg Pro Arg Gln Ser Pro Ala Lys Ser
        195                 200                 205
Ser Gln Asp His Ala Met Glu Ala Gly Ser Pro Val Ser Thr Ser Pro
    210                 215                 220
Glu Pro Val Glu Thr Cys Ser Phe Cys Phe Pro Glu Cys Arg Ala Pro
225                 230                 235                 240
Thr Gln Glu Ser Ala Val Thr Pro Gly Thr Pro Asp Pro Thr Cys Ala
                245                 250                 255
Gly Arg Trp Gly Cys His Thr Arg Thr Thr Val Leu Gln Pro Cys Pro
            260                 265                 270
His Ile Pro Asp Ser Gly Leu Gly Ile Val Cys Val Pro Ala Gln Glu
        275                 280                 285
Gly Gly Pro Gly Ala
    290
```

```
<210> SEQ ID NO 3
<211> LENGTH: 733
<212> TYPE: DNA
<213> ORGANISM: Homo sapiens

<400> SEQUENCE: 3
gggatccgga gcccaaatct tctgacaaaa ctcacacatg cccaccgtgc ccagcacctg     60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agccctccca acccccatcg   360
```

-continued

```
agaaaaccat ctccaaagcc aagggcagc cccgagaacc acaggtgtac accctgcccc      420
catcccggga tgagctgacc aagaaccagg tcagcctgac ctgcctggtc aaaggcttct      480
atccaagcga catcgccgtg gagtgggaga gcaatgggca gccggagaac aactacaaga      540
ccacgcctcc cgtgctggac tccgacggct ccttcttcct ctacagcaag ctcaccgtgg      600
acaagagcag gtggcagcag gggaacgtct tctcatgctc cgtgatgcat gaggctctgc      660
acaaccacta cacgcagaag agcctctccc tgtctccggg taaatgagtg cgacggccgc      720
gactctagag gat                                                       733
```

```
<210> SEQ ID NO 4
<211> LENGTH: 9
<212> TYPE: PRT
<213> ORGANISM: Homo sapiens
<220> FEATURE:
<221> NAME/KEY: SITE
<222> LOCATION: (1)..(5)
<223> OTHER INFORMATION: Xaa equal any amino acid
<221> NAME/KEY: SITE
<222> LOCATION: (9)
<223> OTHER INFORMATION: Xaa equal any amino acid

<400> SEQUENCE: 4

Xaa Xaa Xaa Xaa Xaa Glu Gly Ser Xaa
 1               5

<210> SEQ ID NO 5
<211> LENGTH: 9
<212> TYPE: PRT
<213> ORGANISM: Homo sapiens
<220> FEATURE:
<221> NAME/KEY: SITE
<222> LOCATION: (3)
<223> OTHER INFORMATION: Xaa equal is any amino acid

<400> SEQUENCE: 5

Ala Leu Xaa Asn Asp Glu Gly Ser Gly
 1               5

<210> SEQ ID NO 6
<211> LENGTH: 17
<212> TYPE: PRT
<213> ORGANISM: Homo Sapiens

<400> SEQUENCE: 6

Met Leu Gln Asn Ser Ala Val Leu Leu Leu Val Ile Ser Ala Ser
 1               5                  10                  15

Ala

<210> SEQ ID NO 7
<211> LENGTH: 22
<212> TYPE: PRT
<213> ORGANISM: Artificial Sequence
<220> FEATURE:
<221> NAME/KEY: SIGNAL
<222> LOCATION: (1)..(22)
<223> OTHER INFORMATION: consensus signal sequence

<400> SEQUENCE: 7

Met Pro Thr Trp Ala Trp Trp Leu Phe Leu Val Leu Leu Ala Leu
 1               5                  10                  15

Trp Ala Pro Ala Arg Gly
                 20
```

METHODS OF USING AN AGONISTIC ANTIBODY HUMAN TUMOR NECROSIS FACTOR RECEPTOR (TR17)

RELATED APPLICATIONS

This application claims the benefit of priority under 35 U.S.C. § 119(e) based on U.S. Provisional Application Ser. Nos. 60/254,874 filed Dec. 13, 2000 and 60/235,991 filed Sep. 26, 2000; and this application is also a continuation-in-part of U.S. Utility patent application Ser. No. 09/533,822 filed Mar. 24, 2000 now abandoned which claims the benefit of priority under 35 U.S.C. § 119(e) based on U.S. Provisional Application Ser. No. 60/188,208 filed Mar. 10, 2000.

FIELD OF THE INVENTION

The present invention relates to TR17, a novel member of the tumor necrosis factor family of receptors. More specifically, isolated nucleic acid molecules are provided encoding TR17. TR17 polypeptides are also provided, as are vectors, host cells, and recombinant and synthetic methods for producing the same. The invention also relates to diagnostic and therapeutic methods using TR17 nucleic acid molecules and/or polypeptides. The invention further relates to screening methods for identifying agonists and antagonists of TR17 activity.

RELATED ART

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines, which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNF-alpha lymphotoxin-alpha (LT-alpha, also known as TNF-β), LT-β (found in complex heterotrimer LT-2-β), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (A. Meager, *Biologicals* 22:291–295 (1994)).

Many members of the TNF-ligand superfamily are expressed by activated T-cells, implying that they are necessary for T-cell interactions with other cell types which underlie cell ontogeny and functions. (A. Meager, supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (R. Watanabe-Fukunaga et al., *Nature* 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (R. C. Allen et al., *Science* 259:990 (1993)). Targeted mutations of the low affinity nerve growth factor receptor cause a disorder characterized by faulty sensory innovation of peripheral structures (K. F. Lee et al., *Cell* 69:737 (1992)).

TNF alpha and LT-alpha are capable of binding to two TNF receptors (the 55 and 75-kd TNF receptors). A large number of biological effects elicited by TNF and LT-alpha acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF alpha and LT-alpha are involved in the pathogenesis of a wide range of diseases, including endotoxic shock, cerebral malaria, tumors, autoimmune disease, AIDS and graft-host rejection (B. Beutler and C. Von Huffel, *Science* 264:667–668 (1994)). Mutations in the p55 receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., *Cell* 74:845 (1993)).

Apoptosis, or programmed cell death, is a physiologic process essential to the normal development and homeostasis of multicellular organisms (H. Steller, *Science* 267:1445–1449 (1995)). Derangements of apoptosis contribute to the pathogenesis of several human diseases including cancer, neurodegenerative disorders, and acquired immune deficiency syndrome (C. B. Thompson, *Science* 267:1456–1462 (1995)). Recently, much attention has focused on the signal transduction and biological function of two cell surface death receptors, Fas/APO-1 and TNFR-1 (J. L. Cleveland et al., *Cell* 81:479–482 (1995); A. Fraser et al., *Cell* 85:781–784 (1996); S. Nagata et al., *Science* 267:1449–56 (1995)). Both are members of the TNF receptor family, which also include TNFR-2, low affinity NGFR, CD40, and CD30, among others (C. A. Smith et al., *Science* 248: 1019–23 (1990); M. Tewari et al., in *Modular Texts in Molecular and Cell Biology* M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain," which is distantly related to the *Drosophila* suicide gene, reaper (P. Golstein et al., *Cell* 81:185–6 (1995); K. White et al., *Science* 264:677–83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan et al., *Cell* 81:505–512 (1995); M. P. Boldin et al., *J. Biol. Chem.* 270:7795–8 (1995); F. C. Kischkel et al., *EMBO* 14:5579–5588 (1995)), which in turn binds and presumably activates FLICE/MACH1, a member of the ICE/CED-3 family of pro-apoptotic proteases (M. Muzio et al., *Cell* 85: 817–827 (1996); M. P. Boldin et al., *Cell* 85:803–815 (1996)). While the central role of Fas/APO-1 is to trigger cell death, TNFR-1 can signal an array of diverse biological activities-many of which stem from its ability to activate NF-KB (L. A. Tartaglia et al., *Immunol Today* 13:151–153 (1992)). Accordingly, TNFR-1 recruits the multivalent adapter molecule TRADD, which like FADD, also contains a death domain (H. Hsu et al., *Cell* 81:495–504 (1995); H. Hsu et al., Cell 84:299–308 (1996)). Through its associations with a number of signaling molecules including FADD, TRAF2, and RIP, TRADD can signal both apoptosis and NF-kB activation(H. Hsu et al., Cell 84:299–308 (1996); H. Hsu et al., Immunity 4:387–396 (1996)).

Recently, a new apoptosis inducing TNF ligand has been discovered. S. R. Wiley et al., Immunity 3:673–682 (1995), named the new molecule, "TNF-related apoptosis-inducing ligand" or "TRAIL." R. M. Pitti et al., J. Biol. Chem. 271:12687–12690 (1996), named the molecule "Apo-2 ligand" or "Apo-2L." This molecule was also disclosed in co-pending U.S. provisional patent application No. 60/013, 405. For convenience, this molecule will be referred to herein as TRAIL.

Unlike FAS ligand, whose transcripts appear to be largely restricted to stimulated T-cells, significant levels of TRAIL are detected in many human tissues (e.g., spleen, lung, prostate, thymus, ovary, small intestine, colon, peripheral blood lymphocytes, placenta, kidney), and it is constitutively transcribed by some cell lines. It has been shown that TRAIL acts independently from the FAS ligand (S. R. Wiley et al., supra). It has also been shown that TRAIL activates apoptosis rapidly, within a time frame that is similar to death signaling by Fas/Apo-IL, but much faster than TNF-induced apoptosis. S. A. Marsters et al., Current Biology 6:750–752 (1996). The inability of TRAIL to bind TNFR-1, Fas, or the recently identified DR3, suggests that TRAIL may interact with a unique receptor(s). Work to date suggests that there are several unique TNF receptors for TRAIL (see e.g., Pan et a., Science 277:815–821 (1997)).

The effects of TNF family ligands and receptors are varied and influence numerous functions, both normal and abnormal, in the biological processes of the mammalian system. There is a clear need, therefore, for identification and characterization of such receptors and ligands that influence biological activity, both normally and in disease states.

SUMMARY OF THE INVENTION

The present invention provides isolated nucleic acid molecules comprising a polynucleotide encoding at least a portion of TR17. Thus, the present invention provides isolated nucleic acid molecules comprising a polynucleotide encoding the TR17 receptor having the amino acid sequence shown in FIG. 1 (in SEQ ID NO:2).

The present invention also relates to recombinant vectors, which include the isolated nucleic acid molecules of the present invention, and to host cells containing the recombinant vectors, as well as to methods of making such vectors and host cells and for using them for production of TR17 polypeptides or peptides by recombinant techniques.

The invention further provides an isolated TR17 polypeptide having an amino acid sequence encoded by a polynucleotide described herein.

The present invention also provides diagnostic assays such as quantitative and diagnostic assays for detecting levels of TR17 protein. Thus, for instance, a diagnostic assay in accordance with the invention for detecting over-expression of TR17, or soluble form thereof, compared to normal control tissue samples may be used to detect the presence of tumors.

Tumor Necrosis Factor (TNF) family ligands are known to be among the most pleiotropic cytokines, inducing a large number of cellular responses, including cell proliferation, cytotoxicity, anti-viral activity, immunoregulatory activities, hematopoiesis, and the transcriptional regulation of several genes. Cellular response to TNF-family ligands include not only normal physiological responses, but also diseases associated with increased apoptosis or the inhibition of apoptosis. Apoptosis-programmed cell death is a physiological mechanism involved in the deletion of peripheral T lymphocytes of the immune system, and its dysregulation can lead to a number of different pathogenic processes. Diseases associated with increased cell survival, unregulated cell proliferation, or the inhibition of apoptosis, include cancers, autoimmune disorders, viral infections, inflammation, graft vs. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia, and anorexia.

Thus, the invention further provides a method comprising cells which express the TR17 polypeptide with a candidate compound and a TNF-family ligand (e.g. Neutrokine-alpha or APRIL (International Publication Number WO 97/33902; J. Exp. Med. 188(6):1185–1190 (1998)), and assaying for the inhibition of TR17 mediated signalling induced by a TNF-family ligand (e.g., Neutrokine-alpha and APRIL) which involves administering to a cell which expresses the TR17 polypeptide an effective amount of a TR17 agonist capable of decreasing TR17 mediated signalling.

In a further aspect, the present invention is directed to a method for enhancing TR17 mediated signalling induced by a TNF-family ligand (e.g., Neutrokine-alpha and APRIL) which involves administering to a cell which expresses the TR17 polypeptide an effective amount of a TR17 agonist or antagonist capable of increasing TR17 mediated signalling.

Whether any candidate "agonist" or "antagonist" of the present invention can enhance or inhibit TR17 mediated signalling can be determined using art-known TNF-family ligand/receptor cellular response assays, including those described in more detail below (see, e.g., Examples 13 and 14). Thus, in a further aspect, a screening method is provided for determining whether a candidate agonist or antagonist is capable of enhancing or inhibiting a TR17-mediated cellular response to a TNF-family ligand. The method involves contacting cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing the TR17 polypeptide can be contacted with either an endogenous or exogenously administered TNF-family ligand.

BRIEF DESCRIPTION OF THE FIGURES

FIG. 1 shows the nucleotide (SEQ ID NO:1) and deduced amino acid sequence (SEQ ID NO:2) of the TR17 receptor. Predicted amino acids from about 1 to about 165 constitute the extracellular domain (SEQ ID NO:2); amino acids from about 166 to about 186 constitute the transmembrane domain (SEQ ID NO:2); and amino acids from about 187 to about 293 constitute the intracellular domain (SEQ ID NO:2).

Figure 2:
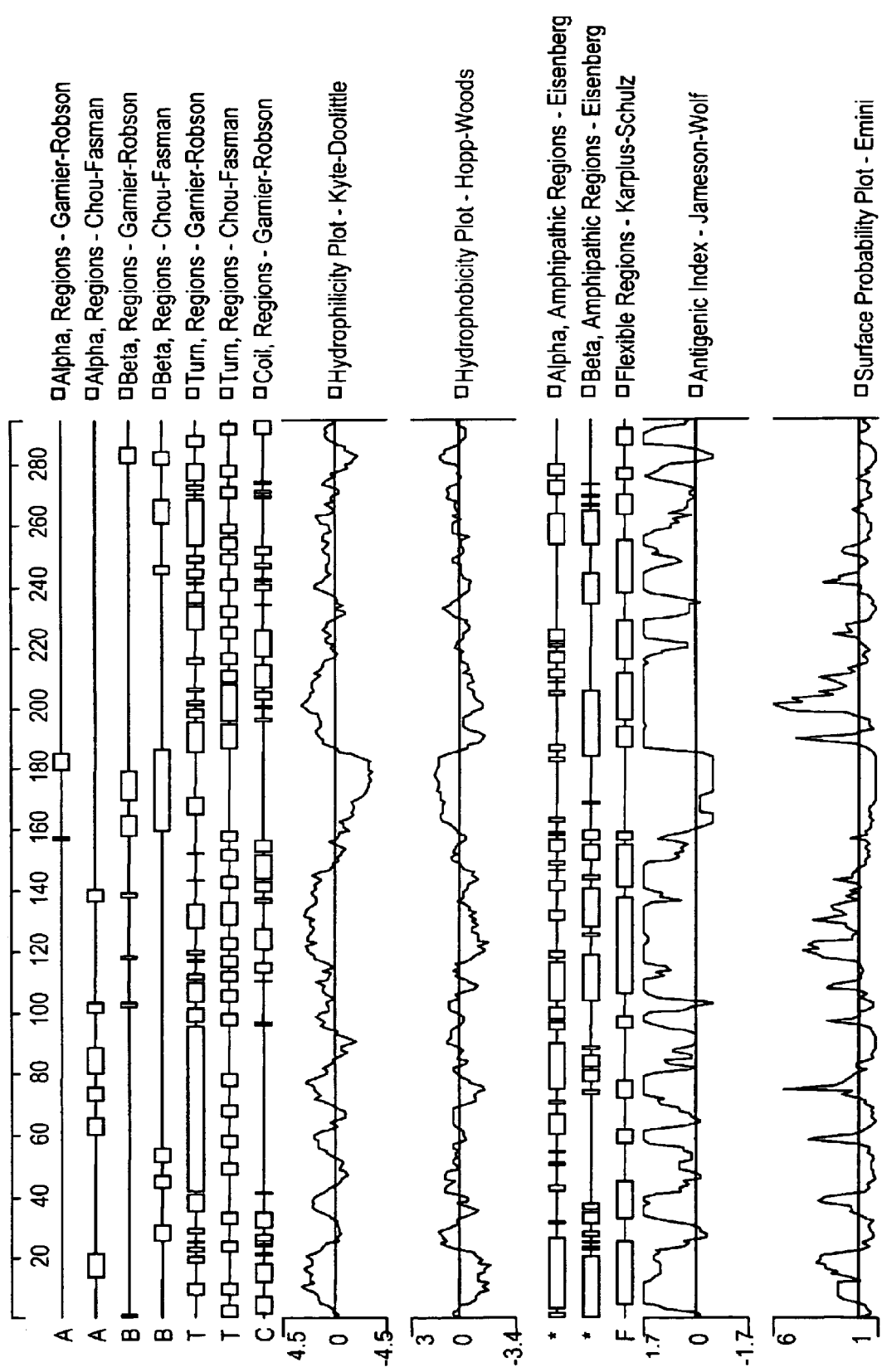
FIG. 2 shows an analysis of the TR17 amino acid sequence. Alpha, beta, turn and coil regions; hydrophilicity; amphipathic regions; flexible regions; antigenic index and surface probability are shown. In the "Antigenic Index—

Jameson-Wolf" graph, amino acid residues 5 to 11, 33 to 36, 57 to 60, 72 to 78, 105 to 110, 115 to 134, 140 to 148, 186 to 216, 222 to 228, 238 to 244, 252 to 255 and 286 to 290 in FIG. 1 (SEQ ID NO:2) correspond to the shown highly antigenic regions of the TR17 protein.

DETAILED DESCRIPTION OF THE PREFERRED EMBODIMENTS

The present invention provides isolated nucleic acid molecules comprising a polynucleotide encoding a TR17 polypeptide having the amino acid sequence shown in FIG. 1 (SEQ ID NO:2).

Nucleic Acid Molecules

The determined nucleotide sequence of the TR17 cDNA of (FIG. 1) SEQ ID NO:1 contains an open reading frame encoding a protein of about 293 amino acid residues, with a deduced molecular weight of about 31.8 kDa. The amino acid sequence of the predicted mature TR17 receptor is shown in SEQ ID NO:2 from amino acid residue about 1 to residue about 293.

As indicated, the present invention also provides the mature form(s) of the TR17 receptors of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide.

The present invention provides a nucleotide sequence encoding the mature TR17 polypeptide having the amino acid sequence shown in FIG. 1. By the mature TR17 protein having the amino acid sequence shown in FIG. 1 is meant the mature form(s) of the TR17 receptor predicted by computer analysis or produced by expression of the coding sequence shown in FIG. 1 in a mammalian cell (e.g., COS cells, as described below). As indicated below, the mature TR17 receptor having the amino acid sequence encoded by the coding sequence shown in FIG. 1, may or may not differ from the predicted mature TR17 protein shown in FIG. 1 (amino acids from about 1 to about 293) depending on the accuracy of the predicted cleavage site based on computer analysis.

Methods for predicting whether a protein has a secretory leader as well as the cleavage point for that leader sequence are available. For instance, the method of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

As one of ordinary skill would appreciate, due to the possibilities of sequencing errors, as well as the variability of cleavage sites for leaders in different known proteins, the predicted TR17 polypeptide, comprises about 293 amino acids, but may be anywhere in the range of 283–303 amino acids. It will further be appreciated that, the domains described herein have been predicted by computer analysis, and accordingly, that depending on the analytical criteria used for identifying various functional domains, the exact "address" of, for example, the extracellular domain, intracellular domain, cysteine-rich motifs, and transmembrane domain of TR17 may differ slightly. For example, the exact location of the TR17 extracellular domain in FIG. 1 (SEQ ID NO:2) may vary slightly (e.g., the address may "shift" by about 1 to about 20 residues, more likely about 1 to about 5 residues) depending on the criteria used to define the domain. In any event, as discussed further below, the invention further provides polypeptides having various residues deleted from the N-terminus and/or C-terminus of the complete TR17, including polypeptides lacking one or more amino acids from the N-tennini of the TR17 extracellular domains described herein, which constitute soluble forms of the extracellular domain of the TR17 polypeptides respectivly.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically. However, a nucleic acid molecule contained in a clone that is a member of a mixed clone library (e.g., a genomic or cDNA library) and that has not been isolated from other clones of the library (e.g., in the form of a homogeneous solution containing the clone without other members of the library) or a chromosome isolated or removed from a cell or a cell lysate (e.g., a "chromosome spread", as in a karyotype), is not "isolated" for the purposes of this invention.

Isolated nucleic acid molecules of the present invention include DNA molecules comprising an open reading frame (ORF) shown in FIG. 1 (SEQ ID NO: 1); DNA molecules comprising the coding sequence for the complete (full-length) and/or mature TR17 protein shown in FIG. 1 (SEQ ID NO:2); and DNA molecules which comprise a sequence substantially different from those described above, but which, due to the degeneracy of the genetic code, still encode the TR17 protein. Of course, the genetic code is well known in the art. Thus, it would be routine for one skilled in the art to generate such degenerate variants.

The invention further provides an isolated nucleic acid molecule having the nucleotide sequence shown in FIG. 1 (SEQ ID NO:1), or a nucleic acid molecule having a sequence complementary thereto. Such isolated molecules, particularly DNA molecules, are useful, for example, as probes for gene mapping by in situ hybridization with chromosomes, and for detecting expression of the TR17 gene in human tissue, for instance, by Northern blot analysis.

The present invention is further directed to fragments of the isolated nucleic acid molecules described herein. By a fragment of an isolated DNA molecule having the nucleotide sequence of the nucleotide sequence shown in FIG. 1 (SEQ ID NO:1) is intended DNA fragments at least about 15 nt, and more preferably at least about 20 nt, at least about 24 nt, still more preferably at least about 30 nt, and even more preferably, at least about 40 nt, at least about 50 nt, at least about 100 nt, at least about 150 nt, at least about 200 nt, at least about 250 nt, at least about 300 nt in length which are useful, for example, as diagnostic probes and primers as discussed herein. Of course, larger fragments 350–1500 nt in length are also useful according to the present invention, as are fragments corresponding to most, if not all, of the nucleotide sequence as shown in FIG. 1 (SEQ ID NO: 1), or the complementary strand thereto. By a fragment at least 20 nt in length, for example, is intended fragments which include 20 or more contiguous bases from the nucleotide sequence of the nucleotide sequence as shown in FIG. 1 (SEQ ID NO: 1). In this context "about" includes the particularly recited size, larger or smaller by several (5, 4, 3, 2, or 1) nucleotides, at either terminus or at both termini. In specific embodiments, the fragments of the invention comprise, or alternatively consist of, nuleotides 13 to 33, 97 to 108, 169 to 180, 214 to 234, 313 to 330, 343 to 402, 418 to 444, 556 to 648, 664 to 684, 712 to 732, 754 to 765, and 856 to 870 of FIG. 1 (SEQ ID NO: 1) or the complementary strand thereto. Polypeptides encoded by these polynucleotide fragments are also encompassed.

Representative examples of TR17 polynucleotide fragments of the invention include, for example, fragments that comprise, or alternatively, consist of, a sequence from about nucleotide 1 to 33, 34 to 66, 67 to 96, 97 to 141, 142 to 174, 175 to 198, 199 to 207, 208 to 264, 265 to 312, 313 to 354, 355 to 390, 391 to 423, 424 to 495, 496 to 558, 559 to 579, 580 to 621, 622 to 660, 661 to 708, 709 to 750, 751 to 810, 811 to 849 and/or 850 to 879, of FIG. 1 (SEQ ID NO:1), or the complementary strand thereto. In this context "about" includes the particularly recited ranges, larger or smaller by several (5, 4, 3, 2, or 1) nucleotides, at either terminus or at both termini.

In specific embodiments, the polynucleotide fragments of the invention comprise, or alternatively, consist of, a sequence from nucleotide 97 to 198, and/or 208 to 312 of FIG. 1 (SEQ ID NO: 1), or the complementary strand thereto.

Preferably, the polynucleotide fragments of the invention encode a polypeptide which demonstrates a TR17 functional activity. By a polypeptide demonstrating a TR17 "functional activity" is meant, a polypeptide capable of displaying one or more known functional activities associated with a full-length (complete) TR17 protein. Such functional activities include, but are not limited to, biological activity (e.g., ability to activate transcription factors NF-AT, AP-1, and/or NFKB), antigenicity (ability to bind (or compete with a TR17 polypeptide for binding) to an anti-TR17 antibody), immunogenicity (ability to generate antibody which binds to a TR17 polypeptide), ability to form multimers with TR17 polypeptides of the invention, and ability to bind to a receptor or ligand for a TR17 polypeptide (e.g., Neutrokine-alpha (International Publication Number WO 98/18921 and APRIL (International Publication Number WO 97/33902; *J Exp. Med.* 188(6):1185–1190 (1998)).

The functional activity of TR17 polypeptides, and fragments, variants derivatives, and analogs thereof, can be assayed by various methods.

For example, in one embodiment where one is assaying for the ability to bind or compete with full-length TR17 polypeptides for binding to anti-TR17 antibody various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a TR17 ligand is identified (e.g., Neutrokine-alpha and APRIL), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., *Microbiol. Rev.* 59:94–123 (1995). In another embodiment, physiological correlates of TR17 binding to its substrates (signal transduction) can be assayed.

In addition, assays described herein (and otherwise known in the art may routinely be applied to measure the ability of TR17 polypeptides and fragments, variants derivatives and analogs thereof to elicit TR17 related biological activity. For example, techniques described herein (see e.g., Examples 12, 13, and 14) and otherwise known in the art may be applied or routinely modified to assay for the ability of the compositions of the invention to inhibit or stimulate B cell proliferation (e.g., Neutrokine-alpha mediated B cell proliferation and APRIL mediated B cell proliferation).

Other methods will be known to the skilled artisan and are within the scope of the invention.

Preferred nucleic acid fragments of the present invention include nucleic acid molecules encoding a member selected from the group: a polypeptide comprising or alternatively, consisting of, the TR17 receptor extracellular domain (amino acid residues from about 1 to about 165 in FIG. 1 (SEQ ID NO:2); a polypeptide comprising, or alternatively consisting of, the TR17 cysteine rich domain (amino acid residues from about 33 to about 104 in FIG. 1 (SEQ ID NO:2) or one or more TR17 cysteine rich motifs amino acid residues from about 33 to 66, and/or 70 to 104 of FIG. 1 (SEQ ID NO:2); a polypeptide comprising, or alternatively consisting of the TR17 transmembrane domain (amino acid residues from about 166 to about 186 in FIG. 1 (SEQ ID NO:2); and/or a polypeptide comprising, or alternatively consisting of, the TR17 intracellular domain (amino acid residues from about 187 to about 293 in FIG. 1 (SEQ ID NO:2)). Since the location of these domains have been predicted by computer analysis, one of ordinary skill would appreciate that the amino acid residues constituting these domains may vary slightly (e.g., by about 1 to 15 amino acid residues) depending on the criteria used to define each domain.

Preferred nucleic acid fragments of the invention encode a full-length TR17 polypeptide lacking the nucleotides encoding the amino terminal methionine in FIG. 1 (SEQ ID NO:1), as it is known that the methionine is cleaved naturally and such sequences may be useful in genetically engineering TR17 expression vectors. Polypeptides encoded by such polynucleotides are also contemplated by the invention.

Preferred nucleic acid fragments of the present invention further include nucleic acid molecules encoding epitope-bearing portions of the TR17 receptor proteins. In particular, such nucleic acid fragments of the present invention include nucleic acid molecules encoding: a polypeptide comprising amino acid residues from about 13 to about 33 in FIG. 1 (SEQ ID NO:2); a polypeptide comprising amino acid residues from about 97 to about 108 in FIG. 1 (SEQ ID NO:2); a polypeptide comprising amino acid residues from about 169 to about 180 in FIG. 1 (SEQ ID NO:2); a polypeptide comprising amino acid residues from about 214 to about 234 in FIG. 1 (SEQ ID NO:2); a polypeptide comprising amino acid residues from about 313 to about 330 in FIG. 1 (SEQ ID NO:2); a polypeptide comprising amino acid residues from about 343 to about 402 in FIG. 1 (SEQ ID NO:2); a polypeptide comprising amino acid residues from about 418 to about 444 in FIG. 1 (SEQ ID NO:2); a polypeptide comprising amino acid residues from about 556 to about 648 in FIG. 1 (SEQ ID NO:2); a polypeptide comprising amino acid residues from about 664 to about 684 in FIG. 1 (SEQ ID NO:2); a polypeptide comprising amino acid residues from about 712 to about 732 in FIG. 1 (SEQ ID NO:2); a polypeptide comprising amino acid residues from about 754 to about 765 in FIG. 1 (SEQ ID NO:2); and a polypeptide comprising amino acid residues from about 856 to about 870 in FIG. 1 (SEQ ID NO:2);. In this context the inventors have determined that the above polypeptide fragments are antigenic regions of the TR17 proteins. Methods for determining other such epitope-bearing portions of the TR17 proteins are described in detail below.

It is believed that the extracellular cysteine rich motifs of TR17 disclosed in FIG. 1 are important for interactions between TR17 and its ligands (e.g., Neutrokine alpha and APRIL). Accordingly, specific embodiments of the invention are directed to polynucleotides encoding polypeptides which comprise, or alternatively consist of, the amino acid sequence of amino acid residues 33 to 66, and/or 70 to 104 of FIG. 1 (SEQ ID NO:2). In a specific embodiment the polynucleotides encoding TR17 polypeptides of the invention comprise, or alternatively consist of one or both of the extracellular cysteine rich motifs disclosed in FIG. 1. Polypeptides encoded by these polynucleotides are also encompassed by the invention.

In additional embodiments, the polynucleotides of the invention encode functional attributes of TR17. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of TR17.

The data representing the structural or functional attributes of TR17 set forth in FIG. 2 and/or Table I, as described above, was generated using the various modules and algorithms of the DNA*STAR set on default parameters. In a preferred embodiment, the data presented in columns VIII, XI, XIII and XIV of Table I can be used to determine regions of TR17 which exhibit a high degree of potential for antigenicity. Regions of high antigenicity are determined from the data presented in columns VIII, XI, XIII and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 2, but may, as shown in Table I, be represented or identified by using tabular representations of the data presented in FIG. 2. The DNA*STAR computer algorithm used to generate FIG. 2 (set on the original default parameters) was used to present the data in FIG. 2 in a tabular format (See Table I). The tabular format of the data in FIG. 2 may be used to easily determine specific boundaries of a preferred region.

The above-mentioned preferred regions set out in FIG. 2 and in Table I, include, but are not limited to, regions of the aforementioned types identified by analysis of the amino acid sequences set out in FIG. 1. As set out in FIG. 2 and in Table I, such preferred regions include Garnier-Robson alpha-regions, beta-regions, turn-regions, and coil-regions, Chou-Fasman alpha-regions, beta-regions, and turn-regions, Kyte-Doolittle hydrophilic regions, Hopp-Woods hydrophobic regions, Eisenberg alpha- and beta-amphipathic regions, Karplus-Schulz flexible regions, Jameson-Wolf regions of high antigenic index and Emini surface-forming regions.

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | T | . | −0.46 | 0.40 | * | * | . | −0.20 | 0.41 |
| Ser | 2 | . | . | . | . | . | T | C | 0.04 | 0.40 | * | * | . | 0.00 | 0.31 |
| Gly | 3 | . | . | . | . | . | T | C | 0.13 | −0.03 | . | * | . | 0.90 | 0.48 |
| Leu | 4 | . | . | . | . | . | T | C | 0.63 | −0.07 | * | * | . | 1.24 | 0.65 |
| Gly | 5 | . | . | . | . | . | . | C | 1.13 | −0.69 | * | * | F | 1.83 | 0.95 |
| Arg | 6 | . | . | . | . | . | . | C | 1.39 | −1.07 | * | * | F | 2.32 | 1.88 |
| Ser | 7 | . | . | . | . | . | . | C | 1.34 | −1.07 | * | * | F | 2.66 | 2.26 |
| Arg | 8 | . | . | . | . | . | T T | . | 1.80 | −1.33 | * | * | F | 3.40 | 2.26 |
| Arg | 9 | . | . | . | . | . | T T | . | 2.31 | −1.76 | * | * | F | 3.06 | 2.26 |
| Gly | 10 | . | . | . | . | . | T T | . | 2.77 | −1.37 | * | * | F | 2.72 | 2.26 |
| Gly | 11 | . | . | . | . | . | T T | . | 1.80 | −1.76 | * | * | F | 2.38 | 2.26 |
| Arg | 12 | . | . | . | . | . | . | C | 2.10 | −1.11 | * | * | F | 1.49 | 0.86 |
| Ser | 13 | . | . | . | . | . | . | C | 1.99 | −1.11 | * | * | F | 1.30 | 1.45 |
| Arg | 14 | . | A | . | . | . | . | C | 1.88 | −1.14 | * | * | F | 1.10 | 2.53 |
| Val | 15 | . | A | . | . | . | . | C | 2.22 | −1.57 | * | * | F | 1.10 | 2.24 |
| Asp | 16 | . | A | . | . | . | . | C | 2.68 | −1.57 | * | * | F | 1.10 | 2.89 |
| Gln | 17 | . | A | . | . | . | . | C | 1.87 | −1.96 | * | * | F | 1.10 | 2.89 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 18 | . | A | . | . | . | . | C | 1.96 | −1.17 | * | * | F | 1.10 | 3.37 |
| Glu | 19 | . | A | . | . | T | . | . | 1.84 | −1.39 | * | * | F | 1.30 | 3.12 |
| Arg | 20 | . | A | . | . | T | . | . | 2.36 | −0.99 | * | * | F | 1.30 | 3.12 |
| Phe | 21 | . | A | . | . | . | . | C | 1.54 | −0.96 | * | . | F | 1.10 | 1.78 |
| Pro | 22 | . | . | . | . | T | T | . | 1.26 | −0.27 | * | . | F | 1.25 | 0.85 |
| Gln | 23 | . | . | . | . | T | T | . | 0.94 | 0.64 | * | * | F | 0.35 | 0.46 |
| Gly | 24 | . | . | . | . | . | T | C | 0.60 | 1.13 | * | . | F | 0.15 | 0.76 |
| Leu | 25 | . | . | . | . | T | T | . | −0.37 | 0.77 | * | * | F | 0.35 | 0.49 |
| Trp | 26 | . | . | . | B | . | . | C | −0.26 | 0.99 | * | . | . | −0.40 | 0.21 |
| Thr | 27 | . | . | . | B | . | . | C | −0.64 | 1.09 | . | * | . | −0.40 | 0.21 |
| Gly | 28 | . | . | . | B | T | . | . | −0.53 | 1.27 | * | * | . | −0.20 | 0.26 |
| Val | 29 | . | . | . | B | T | . | . | −0.49 | 0.59 | . | . | . | −0.20 | 0.48 |
| Ala | 30 | . | . | . | B | . | . | C | −0.34 | 0.06 | . | . | . | 0.20 | 0.44 |
| Met | 31 | . | . | . | . | . | T | C | −0.27 | 0.14 | * | * | . | 0.90 | 0.24 |
| Arg | 32 | . | . | . | . | . | T | C | 0.04 | 0.14 | . | * | . | 1.20 | 0.50 |
| Ser | 33 | . | . | . | . | . | T | C | 0.39 | −0.50 | . | * | F | 2.55 | 0.85 |
| Cys | 34 | . | . | . | . | . | T | C | 1.24 | −1.00 | . | * | F | 3.00 | 1.50 |
| Pro | 35 | . | . | . | . | T | . | . | 1.59 | −1.21 | . | . | F | 2.70 | 1.32 |
| Glu | 36 | . | . | . | . | T | . | . | 1.90 | −0.46 | . | * | F | 2.22 | 1.55 |
| Glu | 37 | . | . | . | . | T | . | . | 1.79 | 0.07 | . | * | F | 1.44 | 3.03 |
| Gln | 38 | . | . | . | . | T | . | . | 1.88 | −0.50 | . | . | F | 2.16 | 3.28 |
| Tyr | 39 | . | . | . | . | T | . | . | 1.73 | −0.50 | . | . | F | 1.98 | 2.93 |
| Trp | 40 | . | . | . | . | T | . | . | 1.13 | 0.19 | . | . | F | 1.20 | 1.39 |
| Asp | 41 | . | . | . | . | . | . | C | 0.79 | 0.87 | . | . | F | 0.43 | 0.66 |
| Pro | 42 | . | . | . | . | T | . | . | 0.48 | 0.90 | * | . | F | 0.51 | 0.42 |
| Leu | 43 | . | . | . | B | T | . | . | −0.19 | 0.63 | * | . | F | 0.19 | 0.57 |
| Leu | 44 | . | . | . | B | T | . | . | −0.54 | 0.29 | . | . | F | 0.37 | 0.18 |
| Gly | 45 | . | . | . | B | T | . | . | −0.56 | 0.90 | . | . | . | −0.20 | 0.12 |
| Thr | 46 | . | . | . | B | T | . | . | −1.22 | 0.86 | . | . | . | −0.20 | 0.19 |
| Cys | 47 | . | . | . | . | T | T | . | −0.97 | 0.74 | . | . | . | 0.20 | 0.12 |
| Met | 48 | . | . | . | . | T | T | . | −0.47 | 0.06 | . | . | . | 0.50 | 0.25 |
| Ser | 49 | . | . | . | . | T | T | . | −0.54 | 0.11 | . | . | . | 0.50 | 0.25 |
| Cys | 50 | . | . | . | . | T | T | . | −0.87 | 0.31 | * | . | . | 0.50 | 0.33 |
| Lys | 51 | . | . | . | B | T | . | . | −0.56 | 0.31 | . | . | . | 0.10 | 0.18 |
| Thr | 52 | . | . | . | B | T | . | . | 0.08 | 0.10 | . | . | . | 0.10 | 0.21 |
| Ile | 53 | . | . | . | B | T | . | . | 0.68 | 0.21 | . | . | . | 0.10 | 0.54 |
| Cys | 54 | . | . | . | B | T | . | . | 0.68 | 0.04 | * | . | . | 0.38 | 0.47 |
| Asn | 55 | . | . | . | B | T | . | . | 1.34 | 0.43 | . | . | . | 0.36 | 0.44 |
| His | 56 | . | . | . | . | T | T | . | 1.41 | 0.34 | . | . | . | 1.49 | 1.08 |
| Gln | 57 | . | . | . | . | T | T | . | 1.41 | −0.34 | . | . | F | 2.52 | 3.95 |
| Ser | 58 | . | . | . | . | T | T | . | 1.63 | −0.43 | . | . | F | 2.80 | 3.54 |
| Gln | 59 | . | . | . | . | T | T | . | 1.71 | −0.26 | . | . | F | 2.52 | 1.40 |
| Arg | 60 | . | A | . | . | T | . | . | 1.12 | −0.26 | * | . | F | 1.69 | 0.81 |
| Thr | 61 | . | A | . | . | T | . | . | 0.46 | −0.16 | * | . | F | 1.41 | 0.61 |
| Cys | 62 | . | A | . | . | T | . | . | −0.21 | 0.24 | * | . | . | 0.38 | 0.31 |
| Ala | 63 | . | A | . | . | T | . | . | 0.20 | 0.41 | * | . | . | −0.20 | 0.08 |
| Ala | 64 | . | A | . | . | T | . | . | −0.10 | 0.41 | * | . | . | −0.20 | 0.11 |
| Phe | 65 | . | A | . | . | T | . | . | −1.02 | 0.31 | * | . | . | 0.10 | 0.29 |
| Cys | 66 | . | . | . | . | T | T | . | −1.01 | 0.43 | * | . | . | 0.20 | 0.23 |
| Arg | 67 | . | . | . | . | T | T | . | −1.01 | 0.31 | . | . | . | 0.50 | 0.31 |
| Ser | 68 | . | . | . | . | T | T | . | −0.31 | 0.39 | . | . | . | 0.50 | 0.19 |
| Leu | 69 | . | . | . | . | T | T | . | 0.32 | −0.40 | . | . | . | 1.10 | 0.70 |
| Ser | 70 | . | . | . | . | T | . | . | 1.02 | −0.97 | * | . | . | 1.20 | 0.71 |
| Cys | 71 | . | A | . | . | T | . | . | 1.69 | −0.97 | . | . | F | 1.00 | 0.92 |
| Arg | 72 | . | A | . | . | T | . | . | 1.23 | −0.96 | . | . | F | 1.64 | 1.93 |
| Lys | 73 | . | A | . | . | T | . | . | 1.58 | −1.21 | . | * | F | 1.98 | 1.43 |
| Glu | 74 | . | A | . | . | T | . | . | 1.69 | −1.60 | . | * | F | 2.32 | 5.33 |
| Gln | 75 | . | A | . | . | T | . | . | 1.74 | −1.39 | * | . | F | 2.66 | 2.36 |
| Gly | 76 | . | . | . | . | T | T | . | 2.41 | 0.63 | * | . | F | 3.40 | 1.85 |
| Lys | 77 | . | . | . | . | T | T | . | 2.27 | −0.63 | * | * | F | 3.06 | 1.78 |
| Phe | 78 | . | . | . | . | T | T | . | 1.41 | −0.13 | * | * | . | 2.27 | 1.40 |
| Tyr | 79 | . | . | . | . | T | T | . | 0.60 | 0.16 | * | * | . | 1.33 | 1.17 |
| Asp | 80 | . | A | . | . | T | . | . | 0.71 | 0.41 | * | * | . | 0.14 | 0.48 |
| His | 81 | . | A | . | . | T | . | . | 1.06 | 0.41 | * | . | . | −0.05 | 1.09 |
| Leu | 82 | . | A | . | . | T | . | . | 0.34 | −0.37 | * | * | . | 0.85 | 1.16 |
| Leu | 83 | . | A | . | . | T | . | . | 0.16 | −0.56 | * | * | . | 1.00 | 0.37 |
| Arg | 84 | . | A | . | . | T | . | . | 0.10 | 0.13 | * | * | . | 0.10 | 0.19 |
| Asp | 85 | . | A | . | . | T | . | . | −0.57 | 0.01 | * | * | . | 0.10 | 0.31 |
| Cys | 86 | . | A | . | . | T | . | . | −1.12 | −0.10 | * | . | . | 0.70 | 0.20 |
| Ile | 87 | . | A | . | . | T | . | . | −0.61 | −0.29 | * | . | . | 0.70 | 0.10 |
| Ser | 88 | . | A | . | . | T | . | . | −0.69 | 0.10 | * | * | . | 0.10 | 0.08 |
| Cys | 89 | . | . | . | . | T | . | . | −1.47 | 0.79 | * | . | . | 0.00 | 0.11 |
| Ala | 90 | . | . | . | . | T | . | . | −1.81 | 0.79 | . | . | . | 0.00 | 0.08 |
| Ser | 91 | . | . | . | . | T | . | . | −1.14 | 0.53 | . | . | . | 0.00 | 0.06 |
| Ile | 92 | . | . | . | . | T | . | . | −0.29 | 0.54 | . | . | . | 0.00 | 0.20 |
| Cys | 93 | . | . | . | . | T | . | . | −0.20 | 0.47 | . | . | . | 0.28 | 0.27 |
| Gly | 94 | . | . | . | . | T | . | . | 0.51 | 0.40 | . | . | . | 0.86 | 0.31 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Gln | 95 | . | . | . | . | T | . | . | 1.10 | 0.01 | * | . | . | F | 1.29 | 0.89 |
| His | 96 | . | . | . | . | . | T | C | 0.73 | −0.27 | * | . | . | F | 2.32 | 2.86 |
| Pro | 97 | . | . | . | . | T | T | . | 1.03 | −0.27 | . | . | . | F | 2.80 | 1.55 |
| Lys | 98 | . | . | . | . | T | T | . | 1.46 | −0.20 | * | . | . | F | 2.37 | 0.90 |
| Gln | 99 | . | . | . | . | T | T | . | 1.10 | 0.16 | * | . | . | . | 1.49 | 1.04 |
| Cys | 100 | . | A | . | . | T | . | . | 0.43 | 0.44 | * | . | . | . | 0.36 | 0.58 |
| Ala | 101 | . | A | . | . | T | . | . | 0.47 | 0.59 | * | . | . | . | 0.08 | 0.16 |
| Tyr | 102 | . | A | B | . | . | . | . | 0.68 | 0.59 | . | . | . | . | −0.60 | 0.16 |
| Phe | 103 | . | A | B | . | . | . | . | 0.68 | 0.59 | . | . | . | . | −0.26 | 0.47 |
| Cys | 104 | . | . | . | . | T | T | . | −0.13 | 0.01 | * | * | . | F | 1.18 | 0.93 |
| Glu | 105 | . | . | . | . | T | T | . | 0.64 | 0.20 | * | * | . | . | 1.52 | 0.49 |
| Asn | 106 | . | . | . | . | T | T | . | 0.93 | −0.56 | * | * | . | F | 3.06 | 1.11 |
| Lys | 107 | . | . | . | . | T | T | . | 0.97 | −0.96 | * | * | . | F | 3.40 | 2.76 |
| Leu | 108 | . | . | . | . | T | . | . | 0.81 | −1.10 | * | * | . | F | 2.86 | 2.47 |
| Arg | 109 | . | . | . | . | T | . | . | 1.48 | −0.46 | * | * | . | F | 2.22 | 1.14 |
| Ser | 110 | . | . | . | . | . | T | C | 0.67 | −0.46 | * | * | . | F | 1.73 | 0.92 |
| Pro | 111 | . | . | . | . | T | T | . | 0.46 | 0.23 | * | * | . | F | 0.99 | 0.92 |
| Val | 112 | . | . | . | . | T | T | . | 0.20 | −0.03 | * | * | . | F | 1.25 | 0.72 |
| Asn | 113 | . | . | . | . | . | T | C | 1.01 | 0.40 | * | * | . | F | 0.79 | 0.83 |
| Leu | 114 | . | . | . | . | . | . | C | 0.09 | 0.01 | * | * | . | F | 0.93 | 0.93 |
| Pro | 115 | . | . | . | . | . | T | C | 0.50 | 0.27 | * | * | . | F | 1.62 | 1.04 |
| Pro | 116 | . | . | . | . | . | T | C | 0.82 | −0.37 | * | * | . | F | 2.56 | 1.26 |
| Glu | 117 | . | . | . | . | T | T | . | 1.68 | −0.77 | . | * | . | F | 3.40 | 3.00 |
| Leu | 118 | . | . | B | . | . | T | . | 1.79 | −1.06 | * | * | . | F | 2.66 | 3.36 |
| Arg | 119 | . | . | . | . | T | . | . | 2.30 | −1.49 | * | . | . | F | 2.52 | 4.26 |
| Arg | 120 | . | . | . | . | T | . | . | 2.17 | −1.53 | . | . | . | F | 2.18 | 3.30 |
| Gln | 121 | . | . | . | . | . | T | C | 2.38 | −1.10 | . | . | . | F | 1.84 | 3.96 |
| Arg | 122 | . | . | . | . | . | T | C | 1.52 | −1.79 | . | . | . | F | 1.50 | 3.50 |
| Ser | 123 | . | . | . | . | . | T | C | 2.33 | −1.14 | . | . | . | F | 1.50 | 1.33 |
| Gly | 124 | . | . | . | . | . | T | C | 2.22 | −1.14 | . | . | . | F | 1.50 | 1.33 |
| Glu | 125 | . | . | . | . | . | . | C | 2.11 | −1.14 | . | * | . | F | 1.64 | 1.09 |
| Val | 126 | . | . | . | . | . | . | C | 1.81 | −0.74 | . | . | . | F | 1.98 | 1.31 |
| Glu | 127 | . | . | . | . | . | . | C | 1.70 | −0.74 | . | . | . | F | 2.32 | 1.77 |
| Asn | 128 | . | . | . | . | T | . | . | 2.00 | −1.17 | . | * | . | F | 2.86 | 1.71 |
| Asn | 129 | . | . | . | . | T | T | . | 2.04 | −0.77 | . | * | . | F | 3.40 | 3.69 |
| Ser | 130 | . | . | . | . | T | T | . | 1.70 | −1.03 | * | * | . | F | 3.06 | 2.86 |
| Asp | 131 | . | . | . | . | T | T | . | 2.67 | −0.60 | * | * | . | F | 2.72 | 1.76 |
| Asn | 132 | . | . | . | . | T | T | . | 2.42 | −1.00 | * | * | . | F | 2.38 | 2.14 |
| Ser | 133 | . | . | . | . | T | T | . | 2.42 | −0.64 | * | * | . | F | 2.04 | 2.51 |
| Gly | 134 | . | . | . | . | T | T | . | 2.08 | −0.63 | . | * | . | F | 1.70 | 2.60 |
| Arg | 135 | . | . | . | . | T | T | . | 1.57 | −0.20 | . | * | . | F | 1.40 | 1.60 |
| Tyr | 136 | . | . | . | . | . | T | C | 1.57 | 0.09 | . | * | . | F | 0.45 | 0.98 |
| Gln | 137 | . | A | . | . | . | . | C | 1.53 | −0.30 | . | * | . | F | 1.10 | 1.72 |
| Gly | 138 | . | A | B | . | . | . | . | 1.94 | −0.23 | . | * | . | . | 1.05 | 1.20 |
| Leu | 139 | . | A | B | . | . | . | . | 1.94 | −0.23 | . | * | . | . | 1.35 | 1.50 |
| Glu | 140 | . | A | . | . | . | . | C | 1.53 | −0.56 | * | * | . | . | 2.00 | 0.85 |
| His | 141 | . | . | . | . | . | T | C | 1.78 | −0.57 | * | . | . | F | 3.00 | 1.16 |
| Arg | 142 | . | . | . | . | . | T | C | 1.19 | −1.00 | . | . | . | F | 2.70 | 2.43 |
| Gly | 143 | . | . | . | . | T | T | . | 1.23 | −1.19 | . | * | . | F | 2.77 | 1.42 |
| Ser | 144 | . | . | . | . | . | T | C | 1.83 | −0.80 | . | * | . | F | 2.44 | 1.40 |
| Glu | 145 | . | . | . | . | . | . | C | 1.24 | −0.87 | . | . | . | F | 2.11 | 1.10 |
| Ala | 146 | . | . | . | . | . | . | C | 0.47 | −0.37 | * | . | . | F | 1.68 | 1.13 |
| Ser | 147 | . | . | . | . | . | . | C | 0.14 | −0.11 | . | . | . | F | 1.70 | 0.69 |
| Pro | 148 | . | . | . | . | . | . | C | 0.14 | −0.07 | * | . | . | F | 1.53 | 0.62 |
| Ala | 149 | . | . | . | . | . | . | C | −0.37 | 0.36 | * | . | . | F | 0.76 | 0.61 |
| Leu | 150 | . | . | . | . | . | T | C | −0.32 | 0.54 | . | * | . | F | 0.49 | 0.37 |
| Pro | 151 | . | . | . | . | . | T | C | −0.54 | 0.16 | . | * | . | F | 0.62 | 0.48 |
| Gly | 152 | . | . | . | . | T | T | . | −0.54 | 0.41 | . | * | . | . | 0.35 | 0.39 |
| Leu | 153 | . | . | . | . | . | T | C | −0.92 | 0.30 | * | * | . | F | 0.45 | 0.64 |
| Lys | 154 | . | . | . | . | . | . | C | −0.33 | 0.11 | * | * | . | F | 0.25 | 0.42 |
| Leu | 155 | . | . | . | . | . | . | C | 0.48 | −0.31 | * | . | . | . | 0.70 | 0.70 |
| Ser | 156 | . | . | . | . | . | T | C | −0.17 | −0.34 | * | * | . | F | 1.20 | 1.48 |
| Ala | 157 | A | . | . | . | . | T | . | −0.41 | −0.39 | . | * | . | F | 0.85 | 0.55 |
| Asp | 158 | . | . | B | . | . | T | . | −0.41 | 0.11 | * | * | . | F | 0.25 | 0.67 |
| Gln | 159 | . | . | B | . | . | T | . | −1.31 | 0.11 | . | * | . | . | 0.10 | 0.41 |
| Val | 160 | . | . | B | B | . | . | . | −0.74 | 0.37 | . | . | . | . | −0.30 | 0.30 |
| Ala | 161 | . | . | B | B | . | . | . | −0.74 | 0.63 | . | . | . | . | −0.60 | 0.29 |
| Leu | 162 | . | . | B | B | . | . | . | −0.47 | 1.01 | * | . | . | . | −0.60 | 0.22 |
| Val | 163 | . | . | B | B | . | . | . | −1.28 | 1.10 | * | . | . | . | −0.60 | 0.43 |
| Tyr | 164 | . | . | B | B | . | . | . | −1.62 | 1.14 | . | . | . | . | −0.60 | 0.35 |
| Ser | 165 | . | . | . | B | T | . | . | −1.58 | 1.07 | . | . | . | . | −0.20 | 0.42 |
| Thr | 166 | . | . | . | B | T | . | . | −1.66 | 1.07 | . | . | . | . | −0.20 | 0.47 |
| Leu | 167 | . | . | . | B | T | . | . | −1.66 | 1.00 | . | . | . | . | −0.20 | 0.16 |
| Gly | 168 | . | . | . | B | T | . | . | −1.47 | 0.93 | . | * | . | . | −0.20 | 0.10 |
| Leu | 169 | . | . | . | B | T | . | . | −1.81 | 1.11 | . | . | . | . | −0.20 | 0.04 |
| Cys | 170 | . | . | B | B | T | . | . | −2.37 | 1.13 | . | . | . | . | −0.20 | 0.04 |
| Leu | 171 | . | . | B | B | . | . | . | −2.87 | 1.09 | . | . | . | . | −0.60 | 0.03 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Cys | 172 | . | . | B | B | . | . | . | -2.72 | 1.34 | . | . | . | -0.60 | 0.03 |
| Ala | 173 | . | . | B | B | . | . | . | -3.04 | 1.23 | . | . | . | -0.60 | 0.03 |
| Val | 174 | . | . | B | B | . | . | . | -2.93 | 1.23 | . | . | . | -0.60 | 0.02 |
| Leu | 175 | . | . | B | B | . | . | . | -3.08 | 1.33 | . | . | . | -0.60 | 0.04 |
| Cys | 176 | . | . | B | B | . | . | . | -3.12 | 1.44 | . | . | . | -0.60 | 0.03 |
| Cys | 177 | . | . | B | B | . | . | . | -3.04 | 1.59 | . | . | . | -0.60 | 0.03 |
| Phe | 178 | . | . | B | B | . | . | . | -3.31 | 1.44 | . | . | . | -0.60 | 0.04 |
| Leu | 179 | . | . | B | B | . | . | . | -3.04 | 1.40 | . | . | . | -0.60 | 0.05 |
| Val | 180 | A | . | . | B | . | . | . | -2.90 | 1.33 | . | . | . | -0.60 | 0.09 |
| Ala | 181 | A | . | . | B | . | . | . | -2.93 | 1.33 | . | . | . | -0.60 | 0.06 |
| Val | 182 | A | . | . | B | . | . | . | -3.08 | 1.33 | * | . | . | -0.60 | 0.06 |
| Ala | 183 | A | . | . | B | . | . | . | -2.33 | 1.33 | * | . | . | -0.60 | 0.07 |
| Cys | 184 | A | . | . | B | . | . | . | -1.48 | 0.69 | . | * | . | -0.26 | 0.13 |
| Phe | 185 | A | . | . | B | . | . | . | -0.51 | 0.19 | . | * | . | 0.38 | 0.35 |
| Leu | 186 | . | . | . | B | T | . | . | -0.27 | -0.46 | * | * | . | 1.72 | 0.69 |
| Lys | 187 | . | . | . | . | T | T | . | 0.59 | -0.53 | * | * | F | 3.06 | 1.27 |
| Lys | 188 | . | . | . | . | T | T | . | 0.97 | -1.10 | . | * | F | 3.40 | 2.45 |
| Arg | 189 | . | . | . | . | T | T | . | 0.97 | -0.46 | . | * | F | 3.06 | 4.59 |
| Gly | 190 | . | . | . | . | T | T | . | 1.37 | -1.57 | . | * | F | 2.72 | 1.23 |
| Asp | 191 | . | . | . | . | T | T | . | 1.51 | -1.19 | . | * | F | 2.23 | 0.82 |
| Pro | 192 | . | . | . | . | T | T | . | 1.47 | -0.61 | . | * | F | 1.89 | 0.23 |
| Cys | 193 | . | . | . | . | T | T | . | 1.21 | -0.21 | . | * | F | 1.59 | 0.39 |
| Ser | 194 | . | . | . | . | T | T | . | 1.21 | -0.21 | . | * | . | 1.78 | 0.37 |
| Cys | 195 | . | . | . | . | T | . | . | 1.26 | -0.21 | . | * | . | 1.92 | 0.46 |
| Gln | 196 | . | . | . | . | . | T | C | 1.37 | -0.26 | . | * | F | 2.56 | 1.16 |
| Pro | 197 | . | . | . | . | T | T | . | 1.37 | -0.83 | . | * | F | 3.40 | 1.69 |
| Arg | 198 | . | . | . | . | T | T | . | 2.14 | -0.79 | . | * | F | 3.06 | 4.88 |
| Ser | 199 | . | . | . | . | T | T | . | 2.44 | -1.36 | . | * | F | 2.72 | 5.52 |
| Arg | 200 | . | . | . | . | . | T | C | 2.81 | -1.36 | . | * | F | 2.18 | 6.18 |
| Pro | 201 | . | . | . | . | T | T | . | 2.60 | -1.40 | . | * | F | 2.04 | 4.23 |
| Arg | 202 | . | . | . | . | T | T | . | 2.22 | -0.97 | . | * | F | 2.04 | 4.88 |
| Gln | 203 | . | . | . | . | . | T | C | 2.16 | -0.86 | . | * | F | 2.18 | 2.52 |
| Ser | 204 | . | . | . | . | . | T | C | 2.16 | -0.86 | * | * | F | 2.52 | 3.26 |
| Pro | 205 | . | . | . | . | . | T | C | 1.74 | -0.90 | * | * | F | 2.86 | 2.23 |
| Ala | 206 | . | . | . | . | T | T | . | 1.96 | -0.51 | . | . | F | 3.40 | 1.72 |
| Lys | 207 | . | . | . | . | . | T | C | 1.84 | -0.51 | . | . | F | 2.86 | 2.23 |
| Ser | 208 | . | . | . | . | . | . | C | 1.81 | -0.90 | * | . | F | 2.59 | 2.41 |
| Ser | 209 | . | . | . | . | . | T | C | 1.52 | -0.83 | . | . | F | 2.72 | 3.24 |
| Gln | 210 | . | . | . | . | . | T | C | 1.13 | -0.83 | . | . | F | 2.65 | 1.64 |
| Asp | 211 | . | . | . | . | . | T | C | 1.72 | -0.21 | * | . | F | 2.28 | 1.21 |
| His | 212 | . | . | . | . | . | T | C | 1.09 | -0.60 | * | . | . | 2.70 | 1.56 |
| Ala | 213 | . | . | . | . | . | . | C | 1.04 | -0.49 | . | . | . | 1.78 | 0.91 |
| Met | 214 | . | . | . | . | . | . | C | 1.04 | -0.46 | . | . | . | 1.51 | 0.54 |
| Glu | 215 | . | . | . | . | T | T | . | 0.83 | -0.07 | * | . | . | 1.64 | 0.53 |
| Ala | 216 | . | . | . | . | T | T | . | -0.02 | -0.14 | * | . | F | 1.52 | 0.81 |
| Gly | 217 | . | . | . | . | . | T | C | -0.29 | -0.00 | * | . | F | 1.05 | 0.61 |
| Ser | 218 | . | . | . | . | . | T | C | -0.01 | -0.23 | * | . | F | 1.05 | 0.47 |
| Pro | 219 | . | . | . | . | . | . | C | 0.29 | 0.26 | . | . | F | 0.25 | 0.67 |
| Val | 220 | . | . | . | . | . | . | C | 0.08 | 0.14 | * | . | F | 0.25 | 0.91 |
| Ser | 221 | . | . | . | . | . | . | C | 0.67 | 0.14 | . | . | F | 0.70 | 1.05 |
| Thr | 222 | . | . | . | . | . | . | C | 0.80 | -0.24 | * | . | F | 1.60 | 1.18 |
| Ser | 223 | . | . | . | . | . | T | C | 0.24 | -0.24 | * | . | F | 2.10 | 2.46 |
| Pro | 224 | . | . | . | . | . | T | C | 0.46 | -0.24 | * | . | F | 2.40 | 1.36 |
| Glu | 225 | . | . | . | . | . | T | C | 1.00 | -0.63 | * | . | F | 3.00 | 1.64 |
| Pro | 226 | . | . | . | . | T | T | . | 0.63 | -0.63 | . | . | F | 2.90 | 1.76 |
| Val | 227 | . | . | . | . | T | . | . | 0.64 | -0.44 | . | . | F | 1.95 | 0.61 |
| Glu | 228 | . | . | . | . | T | . | . | 0.24 | -0.49 | . | . | F | 1.65 | 0.47 |
| Thr | 229 | . | . | . | . | T | . | . | -0.21 | 0.30 | . | . | . | 0.60 | 0.26 |
| Cys | 230 | . | . | . | . | T | T | . | -0.91 | 0.44 | . | . | . | 0.20 | 0.19 |
| Ser | 231 | . | . | . | . | T | T | . | -0.91 | 0.59 | . | . | . | 0.20 | 0.10 |
| Phe | 232 | . | . | . | . | T | T | . | -0.06 | 1.01 | . | . | . | 0.20 | 0.10 |
| Cys | 233 | . | . | . | . | T | T | . | -0.72 | 0.53 | . | . | . | 0.20 | 0.33 |
| Phe | 234 | . | . | . | . | . | . | C | -0.30 | 0.53 | . | * | . | -0.20 | 0.13 |
| Pro | 235 | . | . | . | . | T | . | . | -0.22 | 0.14 | . | * | . | 0.30 | 0.30 |
| Glu | 236 | . | . | . | . | T | . | . | -0.13 | -0.14 | . | * | . | 0.90 | 0.56 |
| Cys | 237 | . | . | . | . | T | . | . | 0.26 | -0.29 | . | * | . | 1.39 | 1.01 |
| Arg | 238 | . | . | . | . | T | . | . | 0.92 | -0.59 | . | * | F | 2.03 | 0.94 |
| Ala | 239 | . | . | . | . | . | T | C | 1.62 | -0.61 | . | * | F | 2.37 | 0.94 |
| Pro | 240 | . | . | . | . | . | T | C | 1.53 | -0.61 | . | * | F | 2.86 | 3.04 |
| Thr | 241 | . | . | . | . | T | T | . | 0.94 | -0.80 | . | * | F | 3.40 | 2.08 |
| Gln | 242 | . | . | . | . | . | T | C | 0.76 | -0.30 | . | * | F | 2.56 | 2.08 |
| Glu | 243 | . | . | . | . | T | . | . | 0.33 | -0.16 | . | * | F | 2.07 | 1.00 |
| Ser | 244 | . | . | . | . | B | T | . | 0.71 | -0.10 | . | . | F | 1.53 | 1.00 |
| Ala | 245 | . | . | . | . | B | T | . | 0.58 | -0.16 | . | . | F | 1.19 | 0.89 |
| Val | 246 | . | . | . | . | B | . | C | 0.58 | -0.13 | . | . | F | 0.65 | 0.51 |
| Thr | 247 | . | . | . | . | . | T | C | 0.37 | 0.36 | . | . | F | 0.45 | 0.55 |
| Pro | 248 | . | . | . | . | T | T | . | 0.37 | 0.40 | . | . | F | 0.65 | 0.84 |

TABLE I-continued

| Res Position | I | II | III | IV | V | VI | VII | VIII | IX | X | XI | XII | XIII | XIV |
|---|---|---|---|---|---|---|---|---|---|---|---|---|---|---|
| Gly 249 | . | . | . | . | T | T | . | 0.46 | -0.10 | . | . | F | 1.40 | 1.89 |
| Thr 250 | . | . | . | . | . | T | C | 0.73 | -0.31 | . | . | F | 1.20 | 2.02 |
| Pro 251 | . | . | . | . | . | . | C | 0.92 | -0.31 | . | . | F | 1.28 | 1.89 |
| Asp 252 | . | . | . | . | . | T | C | 0.64 | -0.17 | . | . | F | 1.76 | 1.02 |
| Pro 253 | . | . | . | . | T | T | . | 0.51 | -0.10 | * | * | F | 2.09 | 0.72 |
| Thr 254 | . | . | . | . | T | T | . | 0.97 | -0.16 | * | * | F | 2.37 | 0.46 |
| Cys 255 | . | . | . | . | T | T | . | 0.99 | -0.59 | * | * | . | 2.80 | 0.54 |
| Ala 256 | . | . | . | . | T | . | . | 0.86 | 0.33 | * | * | . | 1.42 | 0.37 |
| Gly 257 | . | . | . | . | T | T | . | 0.19 | 0.33 | * | * | . | 1.34 | 0.25 |
| Arg 258 | . | . | . | . | T | T | . | 0.37 | 0.41 | * | * | . | 0.76 | 0.25 |
| Trp 259 | . | . | . | . | T | T | . | 0.37 | 0.34 | * | * | . | 0.78 | 0.34 |
| Gly 260 | . | . | . | . | T | T | . | 1.14 | 0.33 | * | * | . | 0.50 | 0.49 |
| Cys 261 | . | . | . | B | T | . | . | 1.42 | -0.10 | * | * | . | 0.70 | 0.49 |
| His 262 | . | . | . | B | T | . | . | 1.46 | 0.39 | * | * | . | 0.10 | 0.68 |
| Thr 263 | . | . | . | B | T | . | . | 0.49 | -0.04 | * | * | F | 0.85 | 0.98 |
| Arg 264 | . | . | . | B | T | . | . | -0.03 | 0.17 | . | * | F | 0.40 | 1.36 |
| Thr 265 | . | . | . | B | T | . | . | 0.31 | 0.29 | . | . | F | 0.25 | 0.83 |
| Thr 266 | . | . | . | B | T | . | . | 0.77 | 0.19 | . | * | F | 0.25 | 0.99 |
| Val 267 | . | . | . | B | T | . | . | 0.13 | 0.13 | . | . | F | 0.25 | 0.78 |
| Leu 268 | . | . | . | B | T | . | . | 0.23 | 0.70 | . | . | F | -0.05 | 0.29 |
| Gln 269 | . | . | . | . | . | T | C | 0.09 | 0.64 | . | * | F | 0.15 | 0.31 |
| Pro 270 | . | . | . | . | T | T | . | -0.49 | 0.66 | * | . | . | 0.20 | 0.57 |
| Cys 271 | . | . | . | . | . | T | C | -0.39 | 0.70 | * | . | . | 0.00 | 0.49 |
| Pro 272 | . | . | . | . | T | T | . | 0.47 | 0.44 | * | . | . | 0.33 | 0.43 |
| His 273 | . | . | . | . | T | . | . | 0.98 | 0.04 | * | * | . | 0.56 | 0.47 |
| Ile 274 | . | . | . | . | . | . | C | 0.63 | -0.00 | * | . | . | 1.24 | 1.17 |
| Pro 275 | . | . | . | . | T | . | . | 0.03 | -0.14 | . | . | F | 1.57 | 0.75 |
| Asp 276 | . | . | . | . | T | T | . | 0.36 | 0.11 | * | . | F | 1.30 | 0.45 |
| Ser 277 | . | . | . | . | T | T | . | -0.32 | 0.04 | * | . | F | 1.17 | 0.64 |
| Gly 278 | . | . | . | . | T | T | . | -1.14 | 0.04 | * | . | F | 1.04 | 0.29 |
| Leu 279 | . | . | . | . | T | T | . | -0.92 | 0.26 | * | . | . | 0.76 | 0.13 |
| Gly 280 | . | . | . | B | T | . | . | -1.57 | 0.83 | . | . | . | -0.07 | 0.05 |
| Ile 281 | . | . | B | B | . | . | . | -1.78 | 1.09 | . | . | . | -0.60 | 0.04 |
| Val 282 | . | . | B | B | . | . | . | -2.07 | 1.09 | . | . | . | -0.60 | 0.07 |
| Cys 283 | . | . | B | B | . | . | . | -1.72 | 0.90 | . | . | . | -0.36 | 0.07 |
| Val 284 | . | . | B | B | . | . | . | -0.91 | 0.87 | . | . | . | -0.12 | 0.18 |
| Pro 285 | . | . | B | . | . | . | . | -0.91 | 0.19 | . | . | . | 0.62 | 0.43 |
| Ala 286 | . | . | . | . | T | . | . | -0.37 | -0.03 | . | . | F | 2.01 | 0.79 |
| Gln 287 | . | . | . | . | T | . | . | 0.28 | -0.17 | . | . | F | 2.40 | 1.05 |
| Glu 288 | . | . | . | . | T | . | . | 0.60 | -0.39 | . | . | F | 2.16 | 1.05 |
| Gly 289 | . | . | . | . | T | . | . | 0.87 | -0.39 | . | . | F | 1.92 | 1.03 |
| Gly 290 | . | . | . | . | . | T | C | 0.69 | -0.39 | . | . | F | 1.53 | 0.60 |
| Pro 291 | . | . | . | . | . | T | C | 0.89 | -0.36 | . | . | F | 1.29 | 0.44 |
| Gly 292 | . | . | . | . | . | T | C | 0.50 | 0.07 | . | . | . | 0.30 | 0.57 |
| Ala 293 | . | . | . | . | . | T | C | 0.11 | 0.07 | . | . | . | 0.30 | 0.74 |

In another aspect, the invention provides an isolated nucleic acid molecule comprising a polynucleotide which hybridizes under stringent hybridization conditions to a portion of the polynucleotide in a nucleic acid molecule of the invention described above, for instance, the complementary strand of nucleotides 13 to 33, 97 to 108, 169 to 180, 214 to 234, 313 to 330, 343 to 402, 418 to 444, 556 to 648, 664 to 684, 712 to 732, 754 to 765, and/or 856 to 870 of SEQ ID NO:1. By "stringent hybridization conditions" is intended overnight incubation at 42° C. in a solution comprising: 50% formamide, 5× SSC (750 mM NaCl, 75 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1× SSC at about 65° C. Polypeptides encoded by these nucleic acids are also encompassed by the invention.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful, for example, as diagnostic probes and primers as discussed above and in more detail below. In this context "about" includes the particularly recited size, larger or smaller by several (5, 4, 3, 2, or 1) nucleotides, at either terminus or at both termini.

By a portion of a polynucleotide of "at least 20 nt in length," for example, is intended 20 or more contiguous nucleotides from the nucleotide sequence of the reference polynucleotide (e.g., the nucleotide sequence as shown in FIG. 1 (SEQ ID NO:1).

Of course, a polynucleotide which hybridizes only to a poly A sequence (such as the 3' terminal poly(A) tract of the TR17 cDNA shown in FIG. 1 (SEQ ID NO:1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

In specific embodiments, the polynucleotides of the invention are less than 110000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise at least 15, at least 30, at least 50, at least 100, or at least 250, at least 500, or at least 1000 contiguous nucleotides of TR17 coding sequence, but consist of less than or equal to 107 kb, 75 kb, 50 kb, 30 kb, 25 kb, 20 kb, 15 kb, 10 kb, or 5 kb of genomic DNA that flanks the 5' or 3' coding nucleotide set forth in FIG. 1 (SEQ ID NO:1). In further embodiments, polynucleotides of the invention comprise at least 15, at least 30, at least 50, at least 100, or at least 250, at least 500, or at least 1000 contiguous nucleotides of TR17 and/or coding sequence, but do not comprise all or a portion of any TR17 intron. In another embodiment, the nucleic acid comprising TR17 coding sequence does not contain coding sequences of a genomic flanking gene (i.e., 5' or 3' to the TR17 gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As indicated, nucleic acid molecules of the present invention which encode a TR17 polypeptide may include, but are not limited to, the coding sequence for the mature polypeptide, by itself; the coding sequence for the mature polypeptide and additional sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of MRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include the TR17 receptor fused to Fc at the N- or C-terminus.

The present invention further relates to variants of the nucleic acid molecules of the present invention, which encode portions, analogs, or derivatives of the TR17 receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding or non-coding regions or both. Alterations in the coding regions may produce conservative or non-conservative amino acid substitutions, deletions, or additions. Especially preferred among these are silent substitutions, additions, and deletions, which do not alter the properties and activities of the TR17 receptor or portions thereof. Also especially preferred in this regard are conservative substitutions.

Further embodiments of the invention include isolated nucleic acid molecules comprising, or alternatively consisting of, a polynucleotide having a nucleotide sequence at least 90% identical, and more preferably at least 95%, 96%, 97%, 98%, or 99% identical to: (a) a nucleotide sequence encoding the polypeptide having the amino acid sequence shown in FIG. 1 (SEQ ID NO:2); (b) a nucleotide sequence encoding the polypeptide having the amino acid sequence in FIG. 1 (SEQ ID NO: 2), but lacking the amino terminal methionine; (c) a nucleotide sequence encoding the polypeptide having the amino acid sequence at positions about 1 to about 293 in FIG. 1 (SEQ ID NO:2); (d) a nucleotide sequence encoding the TR17 extracellular domain; (e) a nucleotide sequence encoding the TR17 cysteine rich domain and/or a nucleotide sequence encoding one, or both TR17 cysteine rich motifs (i.e., amino acid residues 33 to 66 and/or 70 to 104 in FIG. 1 (SEQ ID NO:2)); (f) a nucleotide sequence encoding the TR17 transmembrane domain; (g) a nucleotide sequence encoding the TR17 receptor intracellular domain; (h) a nucleotide sequence encoding the TR17 receptor extracellular and intracellular domains with all or part of the transmembrane domain deleted; and (i) a nucleotide sequence complementary to any of the nucleotide sequences in (a), (b), (c), (d), (e), (f), (g), or (h) above. Polypeptides encoded by these polynucleotides are also encompassed by the invention.

By a polynucleotide having a nucleotide sequence at least, for example, 95% "identical" to a reference nucleotide sequence encoding a TR17 polypeptide is intended that the nucleotide sequence of the polynucleotide is identical to the reference sequence except that the polynucleotide sequence may include up to five mismatches per each 100 nucleotides of the reference nucleotide sequence encoding the TR17 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire TR17 encoding nucleotide sequence shown in FIG. 1 (SEQ ID NO:1), or any TR17 polynucleotide fragment (e.g., a polynucleotide encoding the amino acid sequence of any of the TR17 N- and/or C-terminal deletions described herein), variant, derivative or analog, as described herein.

As a practical matter, whether any particular nucleic acid molecule is at least 90%, 95%, 96%, 97%, 98% or 99% identical to, for instance, the nucleotide sequence shown in FIG. 1 (SEQ ID NO:1) can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty= 1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules comprising, or alternatively consisting of a nucleotide sequence at least 90%, 95%, 96%, 97%, 98%, or 99% identical to the nucleic acid sequence for example, shown in FIG. 1 (SEQ ID NO:1), irrespective of whether they encode a polypeptide having TR17 receptor activity. This is because even where a particular nucleic acid molecule does not encode a polypeptide having TR17 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR17 receptor activity include, inter alia: (1) isolating the TR17 gene or allelic variants thereof in a cDNA library; (2) in situ hybridization (e.g., "FISH") to metaphase chromosomal spreads to provide precise chromosomal location of the TR17 receptor gene, as described in Verma et al., *Human Chromosomes: A Manual of Basic Techniques,* Pergamon Press, New York (1988); and (3) Northern Blot analysis for detecting TR17 receptor MRNA expression in specific tissues.

Preferred, however, are nucleic acid molecules comprising, or alternatively consisting of, a nucleotide sequence at least 90%, 95%, 96%, 97%, 98% or 99% identical to for example, the nucleic acid sequence shown in FIG. 1 (SEQ ID NO:1), which do, in fact, encode a polypeptide having TR17 functional activity. By "a polypeptide having TR17 functional activity" is intended polypeptides exhibiting activity similar, but not necessarily identical, to an activity of the TR17 receptor of the invention (either the full-length protein or, preferably, the mature protein), as measured in a particular biological assay.

Of course, due to the degeneracy of the genetic code, one of ordinary skill in the art will immediately recognize that a large number of the nucleic acid molecules having a sequence at least 90%, 95%, 96%, 97%, 98%, or 99% identical to, for example, the nucleic acid sequence shown in FIG. 1 (SEQ ID NO:1), will encode a polypeptide "having TR17 functional activity." Similarly, a large number of the nucleic acid molecules having a sequence at least 90%, 95%, 96%, 97%, 98%, or 99% identical to, for example, a nucleic acid sequence shown in FIG. 1 will encode a polypeptide "having TR17 functional activity." In fact, since degenerate variants of these nucleotide sequences all encode the same polypeptide, this will be clear to the skilled artisan even without performing a biological assay. It will be further recognized in the art that, for such nucleic acid molecules that are not degenerate variants, a reasonable number will also encode a polypeptide having TR17 functional activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in J. U. Bowie et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Polynucleotide Assays

This invention is also related to the use of TR17 polynucleotides to detect complementary polynucleotides such as, for example, as a diagnostic reagent. Detection of a normal and mutated form of TR17 associated with a dysfunction will provide a diagnostic tool that can add or define a diagnosis of a disease or susceptibility to a disease which results from under-expression over-expression or altered expression of TR17 (or a soluble form thereof), such as, for example, tumors or autoimmune disease.

Individuals carrying mutations in the TR17 gene may be detected at the DNA level by a variety of techniques. Nucleic acids for diagnosis may be obtained from a biological sample from a patient (e.g., a patient's cells, such as from blood, urine, saliva, tissue biopsy and autopsy material). The genomic DNA may be used directly for detection or may be amplified enzymatically by using PCR prior to analysis. (Saiki et al., *Nature* 324:163–166 (1986)). RNA or cDNA may also be used in the same ways. As an example, PCR primers complementary to the nucleic acid encoding TR17 can be used to identify and analyze TR17 expression and mutations. For example, deletions and insertions can be detected by a change in size of the amplified product in comparison to the normal genotype. Point mutations can be identified by hybridizing amplified DNA to radiolabeled TR17 RNA or alternatively, radiolabeled TR17 antisense DNA sequences. Perfectly matched sequences can routinely be distinguished from mismatched duplexes by techniques known in the art, such as, for example, RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis using techniques known in the art. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and S1 protection or the chemical cleavage method (e.g., Cotton et al., *Proc. Natl. Acad. Sci. USA* 85: 4397–4401 (1985)).

Thus, the detection of a specific DNA sequence may be achieved by methods which include, but are not limited to, hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Vectors and Host Cells

The present invention also relates to vectors which include the isolated DNA molecules of the present invention, host cells which are genetically engineered with the recombinant vectors and/or nucleic acids of the invention and the production of TR17 polypeptides or fragments thereof by recombinant techniques.

Host cells can be genetically engineered to incorporate nucleic acid molecules and express polypeptides of the present invention. The polynucleotides may be introduced alone or with other polynucleotides. Such other polynucleotides may be introduced independently, co-introduced or introduced joined to the polynucleotides of the invention.

In accordance with the present invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase, neomycin resistance, or glutamine synthase for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* =1 S2 and *Spodoptera* Sf9 cells; animal cells such as CHO, NSO, COS, 293, and Bowes melanoma cells; and plant cells. Appropriate culture mediums and conditions for the above-described host cells are known in the art.

Vectors which use glutamine synthase (GS) or DHFR as the selectable markers can be amplified in the presence of the drugs methionine sulphoximine or methotrexate, respectively. The availability of drugs which inhibit the function of the enzymes encoded by these selectable markers allows for selection of cell lines in which the vector sequences have been amplified after integration into the host cell's DNA. An advantage of glutamine synthase based vectors are the availabilty of cell lines (e.g., the murine myeloma cell line, NS0) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. Vectors that use glutamine synthase as the selectable marker include the pEE6 expression vector described in Stephens and Cockett, *Nucl. Acids. Res* 17:7110 (1989). A glutamine synthase expression system and components thereof are detailed in PCT publications: WO87/04462; WO86/05807; WO89/01036; WO89/10404; and WO91/06657 which are hereby incorporated in their entireties by reference herein. Additionally, glutamine synthase expression vectors that may be used according to the present invention are commercially available from suppliers including, for example, Lonza Biologics, Inc. (Portsmouth, N. H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are herein incorporated by reference.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

The present invention also relates to host cells containing the above-described vector constructs described herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., TR17 coding sequence), and/or to include genetic material (e.g., heterologous polynucleotide sequences) that is operably associated with TR17 polynucleotides of the invention, and which activates, alters, and/or amplifies endogenous TR17 polynucleotides. For example, techniques known in the art may be used to operably associate heterologous control regions (e.g., promoter and/or enhancer) and endogenous TR17 polynucleotide sequences via homologous recombination (see, e.g., U.S. Pat. No. 5,641,670, issued Jun. 24, 1997; International Publication Number WO 96/29411; International Publication Number WO 94/12650; Koller et al., *Proc. Natl. Acad. Sci. USA* 86:8932–8935 (1989); and Zijlstra et al., *Nature* 342:435–438 (1989), the disclosures of each of which are incorporated by reference in their entireties).

The TR17 polypeptide may be expressed in a modified form, such as a fusion protein (comprising the polypeptide joined via a peptide bond to a heterologous protein sequence (of a different protein)), and may include not only secretion signals but also additional heterologous functional regions. Alternatively, such a fusion protein can be made by protein synthetic techniques, e.g., by use of a peptide synthesizer. Thus, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

In one embodiment, polynucleotides TR17 polypeptides of the invention may be fused to signal sequences which will direct the localization of a protein of the invention to particular compartments of a prokaryotic or eukaryotic cell and/or direct the secretion of a protein of the invention from a prokaryotic or eukaryotic cell. For example, in *E. coli,* one may wish to direct the expression of the protein to the periplasmic space. Examples of signal sequences or proteins (or fragments thereof) to which the polypeptides of the invention may be fused in order to direct the expression of the polypeptide to the periplasmic space of bacteria include, but are not limited to, the pelb signal sequence, the maltose binding protein (MBP) signal sequence, MBP, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, polynucleotides encoding Neutrokine-alpha and/or Neutrokine-alphaSV polypeptides of the invention may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that may be fused to a polypeptide of the invention in order to direct its secretion in mammalian cells include, but are not limited to, the MPIF-1 signal sequence (amino acids 1–21 of GenBank Accession number AAB51134), the stanniocalcin signal sequence (MLQNSAVLLLLVISASA, SEQ ID NO:6), and a consensus signal sequence (MPTWAWWLFLVLLLALWAPARG, SEQ ID NO:7). A suitable signal sequence that may be used in conjunction with baculoviral expression systems is the gp67 signal sequence, (amino acids 1–19 of GenBank Accession Number AAA72759).

A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses, it would be desirable to be able to delete the Fc part after the fusion protein has been expressed, detected and purified in the advantageous manner described. This is the case when the Fc portion proves to be a hindrance to use in therapy and diagnosis, for example, when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., *Journal of Molecular Recognition* 8:52–58 (1995) and K. Johanson et al., *The Journal of Biological Chemistry* 270:16:9459–9471 (1995).

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may also include an initial modified methionine residue, in some cases as a result of host-mediated processes.

In addition, proteins of the invention can be chemically synthesized using techniques known in the art (e.g., see Creighton, Proteins: Structures and Molecular Principles, W.H. Freeman & Co., N.Y. (1983), and Hunkapiller, et al., *Nature* 310:105 111 (1984)). For example, a polypeptide corresponding to a fragment of the TR17 polypeptides of the invention can be synthesized by use of a peptide synthesizer. Furthermore, if desired, nonclassical amino acids or chemical amino acid analogs can be introduced as a substitution or addition into the TR17 polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses TR17 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

In specific embodiments, TR17 polypeptides of the invention are attached to macrocyclic chelators useful for conjugating radiometal ions, including but not limited to, $^{111}$In, $^{177}$Lu, $^{90}$Y, $^{166}$Ho, and $^{53}$Sm, to polypeptides. In a preferred embodiment, the radiometal ion associated with the macrocyclic chelators attached to TR17 polypeptides of the invention is $^{111}$In. In another preferred embodiment, the radiometal ion associated with the macrocyclic chelator attached to TR17 polypeptides of the invention is $^{90}$Y. In specific embodiments, the macrocyclic chelator is 1,4,7,10-tetraazacyclododecane-N,N',N",N'"-tetraacetic acid (DOTA). In other specific embodiments, the DOTA is attached to TR17 polypeptide of the invention via a linker molecule. Examples of linker molecules useful for conjugating DOTA to a polypeptide are commonly known in the art—see, for example, DeNardo et al., Clin Cancer Res. 4(10):2483–90, 1998; Peterson et al., Bioconjug. Chem. 10(4):553–7, 1999; and Zimmerman et al, Nucl. Med. Biol. 26(8):943–50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art could readily adapt the method disclosed therein in order to conjugate chelating agents to other polypeptides.

Also provided by the invention are chemically modified derivatives of TR17 which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10 13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

As mentioned the TR17 proteins of the invention may be modified by either natural processes, such as posttranslational processing, or by chemical modification techniques which are well known in the art. It will be appreciated that the same type of modification may be present in the same or varying degrees at several sites in a given TR17 polypeptide. TR17 polypeptides may be branched, for example, as a result of ubiquitination, and they may be cyclic, with or without branching. Cyclic, branched, and branched cyclic TR17 polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., *Meth Enzymol* 182:626–646 (1990); Rattan et al., *Ann NY Acad Sci* 663:48–62 (1992)).

The TR17 polypeptides of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

TR17 receptor polynucleotides and polypeptides may be used in accordance with the present invention for a variety of applications, particularly those that make use of the chemical and biological properties of TR17. Among these are applications in treatment of tumors, resistance to parasites, bacteria and viruses, to inhibit proliferation of B cells, to induce proliferation of T-cells, endothelial cells and certain hematopoietic cells, to treat restenosis, graft vs. host disease, to regulate anti-viral responses and to prevent certain autoimmune diseases after stimulation of TR17 by an agonist. Additional applications relate to diagnosis and to treatment of disorders of cells, tissues and organisms. These aspects of the invention are discussed further below.

Transgenics and "Knock-outs"

The TR17 proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., *Appl. Microbiol. Biotechnol.* 40:691–698 (1994); Carver et al., *Biotechnology* (NY) 11:1263–1270 (1993); Wright et al., *Biotechnology* (NY) 9:830–834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., *Cell* 56:313–321 (1989)); electroporation of cells or embryos (Lo, *Mol Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, "Transgenic Animals," *Intl. Rev. Cytol.* 115:171–229 (1989), which is incorporated by reference herein in its entirety. Further, the contents of each of the documents recited in this paragraph is herein incorporated by reference in its entirety. Gordon, "Transgenic Animals," Intl. Rev. Cytol. 115:171–229 (1989), which is incorporated by reference herein in its entirety. See also, U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (*Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (*Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of TR17 polypeptides, studying conditions and/or disorders associated with aberrant TR17 expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

TR17 Receptor Polypeptides and Fragments

The TR17 proteins (polypeptides) of the invention may be in monomers or multimers (i.e., dimers, trimers, tetramers, and higher multimers). Accordingly, the present invention relates to monomers and multimers of the TR17 proteins (polypeptides) of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only TR17 proteins of the invention (including TR17 fragments, variants, and fusion proteins, as described herein). These homomers may contain TR17 proteins having identical or different polypeptide sequences. In a specific embodiment, a homomer of the invention is a multimer containing only TR17 proteins having an identical polypeptide sequence. In another specific embodiment, a homomer of the invention is a multimer containing TR17 proteins having different polypeptide sequences (e.g., TR17 mutations containing proteins have polypeptide sequences. In specific embodiments, the multimer of the invention is a homodimer (e.g., containing TR17 proteins having identical or different polypeptide sequences) or a homotrimer (e.g., containing TR17 proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the TR17 gene) in addition to the TR17 proteins of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the TR17 proteins of the invention. Such covalent associations may involve one or more amino acid residues contained in the polypeptide sequence of the protein (e.g., the polypeptide sequence shown in FIG. 1 (SEQ ID NO:2). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TR17 fusion protein. In one example, covalent associations are between the heterologous sequence contained in a fusion protein of the invention (see, e.g., U.S. Pat. No. 5,478,925). In a specific example, the covalent associations are between the heterologous sequence contained in a TR17-Fc fusion protein of the invention (as described herein). In another specific example, covalent associations of fusion proteins of the invention are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more TR17 polypeptides of the invention are joined through synthetic linkers (e.g., peptide, carbohydrate or soluble polymer linkers). Examples include those peptide linkers described in U.S. Pat. No. 5,073,627 (hereby incorporated by reference). Proteins comprising multiple TR17 polypeptides separated by peptide linkers may be produced using conventional recombinant DNA technology.

Another method for preparing multimer TR17 polypeptides of the invention involves use of TR17 polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric TR17 proteins are those described in PCT application WO 94/10308, hereby incorporated by reference. Recombinant fusion proteins comprising a soluble TR17 polypeptide fused to a peptide that dimerizes or trimerizes in solution are expressed in suitable host cells, and the resulting soluble multimeric TR17 is recovered from the culture supernatant using techniques known in the art.

Certain members of the TNF family of proteins are believed to exist in trimeric form (Beutler and Huffel, *Science* 264:667, 1994; Banner et al., *Cell* 73:431, 1993). Thus, trimeric TR17 may offer the advantage of enhanced biological activity. Preferred leucine zipper moieties are those that preferentially form trimers. One example is a leucine zipper derived from lung surfactant protein D (SPD), as described in Hoppe et al. (*FEBS Letters* 344:191, (1994)) and in U.S. patent application Ser. No. 08/446,922, hereby incorporated by reference. Other peptides derived from naturally occurring trimeric proteins may be employed in preparing trimeric TR17.

In another example, proteins of the invention are associated by interactions between Flag® polypeptide sequence contained in Flag®-TR17 fusion proteins of the invention. In a further embodiment, associated proteins of the invention are associated by interactions between heterologous polypeptide sequence contained in Flag®-TR17 fusion proteins of the invention and anti-Flag® antibody.

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the TR17 polypeptide can be substantially purified by the one-step method described in Smith and Johnson, *Gene* 67:31–40 (1988).

Accordingly, in one embodiment, the invention provides an isolated TR17 polypeptide having the amino acid sequence encoded by the amino acid sequence in FIG. 1 (SEQ ID NO:2), or a polypeptide comprising a portion of the above polypeptides, such as for example, a mature TR17 comprising amino acids 1 to 293 of FIG. 1 (SEQ ID NO:2), the TR17 extracellular domain (comprising amino acids 1 to 165 of FIG. 1 (SEQ ID NO:2)), the TR17 cysteine rich domain (comprising amino acids 33 to 104 of FIG. 1 (SEQ ID NO:2)), and/or the TR17 intracellular domain comprising amino acids 187 to 293 of FIG. 1.

Polypeptide fragments of the present invention include polypeptides comprising or alternatively, consisting of: an amino acid sequence contained in FIG. 1 (SEQ ID NO:2); and encoded by a nucleic acid containing a polynucleotide sequence which hybridizes (e.g., under stringent hybridization conditions) to the nucleotide sequence encoded by a nucleic acid containing a polynucleotide sequence which hybridizes to the complementary strand of the nucleotide sequence shown in FIG. 1 (SEQ ID NO:1). Polynucleotides encoding these polypeptides are also encompassed by the invention.

Protein fragments may be "free-standing," or comprised within a larger polypeptide of which the fragment forms a part or region, most preferably as a single continuous region.

Representative examples of polypeptide fragments of the invention, include, for example, fragments that comprise or alternatively, consist of from about amino acid residues: 1 to 32, 33 to 66, 33 to 69, 67 to 104, 70 to 104, 105 to 135, 136 to 165, 166 to 186, 187 to 207, 208 to 238, 239 to 269, and/or 270 to 293 of SEQ ID NO:2 or FIG. 1. Moreover, polypeptide fragments can be at least 10, 20, 30, 40, 50, 60, 70, 80, 90, 100, 110, 120, 130, 140, 150, 175, 200, 250, 300, 350, 400 or 500 amino acids in length. Polynucleotides encoding these polypeptides are also encompassed by the invention. In this context "about" includes the particularly recited ranges, larger or smaller by several (5, 4, 3, 2, or 1) amino acids, at either extreme or at both extremes. Polynucleotides encoding these polypeptides are also encompassed by the invention.

In additional embodiments, the polypeptide fragments of the invention comprise, or alternatively consist of, one or more TR17 domains. Preferred polypeptide fragments of the present invention include a member selected from the group: (a) a polypeptide comprising or alternatively, consisting of, the TR17 extracellular domain (predicted to constitute amino acid residues from about 1 to about 165 FIG. 1 (SEQ ID NO:2); (b) a polypeptide comprising or alternatively, consisting of, a TR17 cysteine rich domain (predicted to constitute amino acid residues from about 33 to about 104 FIG. 1 (SEQ ID NO:2); (c) a polypeptide comprising or alternatively, consisting of, the TR17 transmembrane domain (predicted to constitute amino acid residues from about 166 to about 186 FIG. 1 (SEQ ID NO:2); (d) a polypeptide comprising or alternatively, consisting of, the TR17 intracellular domain (predicted to constitute amino acid residues from about 187 to about 293 FIG. 1 (SEQ ID NO:2)); (e) a polypeptide comprising, or alternatively, consisting of, one, two, three, four or more, epitope bearing portions of the TR17 protein; or (f) any combination of polypeptides (a)–(e). Polynucleotides encoding these polypeptides are also encompassed by the invention.

As discussed above, it is believed that the extracellular cysteine rich motifs of TR17 are important for interactions between TR17 and its ligands. Accordingly, in preferred embodiments, polypeptide fragments of the invention comprise, or alternatively consist of amino acid residues 33 to 66 and/or 70 to 104 of FIG. 1 (SEQ ID NO:2). In a specific embodiment the polypeptides of the invention comprise, or alternatively consist of one or both of the extracellular cysteine rich motifs disclosed in FIG. 1. Proteins comprising or alternatively consisting of a polypeptide sequence which is at least 80%, 90%, 95%, 96%, 97%, 98% or 99% identical to the polypeptide sequences of one or both of these cysteine rich motifs are also encompassed by the invention. Polynucleotides encoding these polypeptides are also encompassed by the invention.

Among the especially preferred fragments of the invention are fragments characterized by structural or functional attributes of TR17. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) TR17 (FIG. 1 (SEQ ID NO:2)). Certain preferred regions are those set out in FIG. 2 and include, but are not limited to, regions of the aforementioned types identified by analysis of the amino acid sequence depicted in FIG. 1 (SEQ ID NO:2), such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic; Hopp-Woods predicted hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

As mentioned above, even if deletion of one or more amino acids from the N-terminus of a protein results in modification of loss of one or more biological functions of the protein, other functional activities (e.g., biological activities, ability to multimerize, ability to bind TR17 ligand (e.g., Neutrokine-alpha and APRIL)) may still be retained. For example, the ability of shortened TR17 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete full-length polypeptide retains such immunologic activities can readily be determined by routine methods described herein and otherwise known in the art. It is not unlikely that an TR17 mutein with a large number of deleted N-terminal amino acid residues may retain some biological or immunogenic activities. In fact, peptides composed of as few as six TR17 amino acid residues may often evoke an immune response.

Accordingly, the present invention further provides polypeptides having one or more residues deleted from the amino terminus of the TR17 amino acid sequence shown in FIG. 1, up to the glutamine residue at position number 288 and polynucleotides encoding such polypeptides. In particular, the present invention provides polypeptides comprising the amino acid sequence of residues $n^{1-293}$ of FIG. 1, where $n^1$ is an integer from 2 to 288 corresponding to the position of the amino acid residue in FIG. 1 (SEQ ID NO:2).

More in particular, the invention provides polynucleotides encoding polypeptides comprising, or alternatively consisting of, the amino acid sequence of residues: S-2 to A-293; G-3 to A-293; L-4 to A-293; G-5 to A-293; R-6 to A-293; S-7 to A-293; R-8 to A-293; R-9 to A-293; G-10 to A-293; G-11 to A-293; R-12 to A-293; S-13 to A-293; R-14 to A-293; V-15 to A-293; D-16 to A-293; Q-17 to A-293; E-18 to A-293; E-19 to A-293; R-20 to A-293; F-21 to A-293; P-22 to A-293; Q-23 to A-293; G-24 to A-293; L-25 to A-293; W-26 to A-293; T-27 to A-293; G-28 to A-293; V-29 to A-293; A-30 to A-293; M-31 to A-293; R-32 to A-293; S-33 to A-293; C-34 to A-293; P-35 to A-293; E-36 to A-293; E-37 to A-293; Q-38 to A-293; Y-39 to A-293; W-40 to A-293; D-41 to A-293; P-42 to A-293; L-43 to A-293; L-44 to A-293; G-45 to A-293; T-46 to A-293; C-47to A-293; M-48 to A-293; S-49 to A-293; C-50 to A-293; K-51 to A-293; T-52 to A-293; I-53 to A-293; C-54 to A-293; N-55 to A-293; H-56 to A-293; Q-57 to A-293; S-58 to A-293; Q-59 to A-293; R-60 to A-293; T-61 to A-293; C-62 to A-293; A-63 to A-293; A-64 to A-293; F-65 to A-293; C-66 to A-293; R-67 to A-293; S-68 to A-293; L-69 to A-293; S-70 to A-293; C-71 to A-293; R-72 to A-293; K-73 to A-293; E-74 to A-293; Q-75 to A-293; G-76 to A-293; K-77 to A-293; F-78 to A-293; Y-79 to A-293; D-80 to A-293; H-81 to A-293; L-82 to A-293; L-83 to A-293; R-84 to A-293; D-85 to A-293; C-86 to A-293; I-87 to A-293; S-88 to A-293; C-89 to A-293; A-90 to A-293; S-91 to A-293; I-92 to A-293; C-93 to A-293; G-94 to A-293; Q-95 to A-293; H-96 to A-293; P-97 to A-293; K-98 to A-293; Q-99 to A-293; C-100 to A-293; A-101 to A-293; Y-102 to A-293; F-103 to A-293; C-104 to A-293; E-105 to A-293; N-106 to A-293; K-107 to A-293; L-108 to A-293; R-109 to A-293; S-110 to A-293; P-111 to A-293; V-112 to A-293; N-113 to A-293; L-114 to A-293; P-115 to A-293; P-116 to A-293; E-117 to A-293; L-118 to A-293; R-119 to A-293; R-120 to A-293; Q-121 to A-293; R-122 to A-293; S-123 to A-293; G-124 to A-293; E-125 to A-293; V-126 to A-293; E-127 to A-293; N-128 to A-293; N-129 to A-293; S-130 to A-293; D-131 to A-293; N-132 to A-293; S-133 to A-293; G-134 to A-293; R-135 to A-293; Y-136 to A-293; Q-137 to A-293; G-138 to A-293; L-139 to A-293; E-140 to A-293; H-141 to A-293; R-142 to A-293; G-143 to A-293; S-144 to A-293; E-145 to A-293; A-146 to A-293; S-147 to A-293; P-148 to A-293; A-149 to A-293; L-150 to A-293; P-151 to A-293; G-152 to A-293; L-153 to A-293; K-154 to A-293; L-155 to A-293; S-156 to A-293; A-157 to A-293; D-158 to A-293; Q-159 to A-293; V-160 to A-293; A-161 to A-293; L-162 to A-293; V-163 to A-293; Y-164 to A-293; S-165 to A-293; T-166 to A-293; L-167 to A-293; G-168 to A-293; L-169 to A-293; C-170 to A-293; L-171 to A-293; C-172 to A-293; A-173 to A-293; V-174 to A-293; L-175 to A-293; C-176 to A-293; C-177 to A-293; F-178 to A-293; L-179 to A-293; V-180 to A-293; A-178 to A-293; V-182 to A-293; A-183 to A-293; C-184 to A-293; F-185 to A-293; L-186 to A-293; K-187 to A-293; K-188 to A-293; R-189 to A-293; G-190 to A-293; D-191 to A-293; P-192 to A-293; C-193 to A-293; S-194 to A-293; C-195 to A-293; Q-196 to A-293; P-197 to A-293; R-198 to A-293; S-199 to A-293; R-200 to A-293; P-201 to A-293; R-202 to A-293; Q-203 to A-293; S-204 to A-293; P-205 to A-293; A-206 to A-293; K-207 to A-293; S-208 to A-293; S-209 to A-293; Q-210 to A-293; D-211 to A-293; H-212 to A-293; A-213 to A-293; M-214 to A-293; E-215 to A-293; A-216 to A-293; G-217 to A-293; S-218 to A-293; P-219 to A-293; V-220 to A-293; S-221 to A-293; T-222 to A-293; S-223 to A-293; P-224 to A-293; E-225 to A-293; P-226 to A-293; V-227 to A-293; E-228 to A-293; T-229 to A-293; C-230 to A-293; S-231 to A-293; F-232 to A-293; C-233 to A-293; F-234 to A-293; P-235 to A-293; E-236 to A-293; C-237 to A-293; R-238 to A-293; A-239 to A-293; P-240 to A-293; T-241 to A-293; Q-242 to A-293; E-243 to A-293; S-244 to A-293; A-245 to A-293; V-246 to A-293; T-247 to A-293; P-248 to A-293; G-249 to A-293; T-250 to A-293; P-251 to A-293; D-252 to A-293; P-253 to A-293; T-254 to A-293; C-255 to A-293; A-256 to A-293; G-257 to A-293; R-258 to A-293; W-259 to A-293; G-260 to A-293; C-261 to A-293; H-262 to A-293; T-263 to A-293; R-264 to A-293; T-265 to A-293; T-266 to A-293; V-267 to A-293; L-268 to A-293; Q-269 to A-293; P-270 to A-293; C-271 to A-293; P-272 to A-293; H-273 to A-293; 1-274 to A-293; P-275 to A-293; D-276 to A-293; S-277 to A-293; G-278 to A-293; L-279 to A-293; G-280 to A-293; 1-281 to A-293; V-282 to A-293; C-283 to A-293; V-284 to A-293; P-285 to A-293; A-286 to A-293; Q-287 to A-293; and/or E-288 to A-293 of the TR17 sequence shown in FIG. 1. Polypeptides encoded by these polynucleotides are also encompassed by the invention.

In another embodiment, N-terminal deletions of the TR17 polypeptide can be described by the general formula $n^2$–165, where $n^2$ is a number from 2 to 161, corresponding to the position of amino acid identified in FIG. 1 (SEQ ID NO:2). Preferably, N-terminal deletions of the TR17 polypeptide of the invention shown as FIG. 1 (SEQ ID NO:2) include polypeptides comprising, or alternatively consisting of, the amino acid sequence of residues: S-2 to S-165; G-3 to S-165; L-4 to S-165; G-5 to S-165; R-6 to S-165; S-7 to S-165; R-8 to S-165; R-9 to S-165; G-10 to S-165; G-11 to S-165; R-12 to S-165; S-13 to S-165; R-14 to S-165; V-15 to S-165; D-16 to S-165; Q-17 to S-165; E-18 to S-165; E-19 to S-165; R-20 to S-165; F-21 to S-165; P-22 to S-165; Q-23 to S-165; G-24 to S-165; L-25 to S-165; W-26 to S-165; T-27 to S-165; G-28 to S-165; V-29 to S-165; A-30 to S-165; M-31 to S-165; R-32 to S-165; S-33 to S-165; C-34 to S-165; P-35 to S-165; E-36 to S-165; E-37 to S-165; Q-38 to S-165; Y-39 to S-165; W-40 to S-165; D-41 to S-165; P-42 to S-165; L-43 to S-165; L-44 to S-165; G-45 to S-165; T-46 to S-165; C-47 to S-165; M-48 to S-165; S-49 to S-165; C-50 to S-165; K-51 to S-165; T-52 to S-165; I-53 to S-165; C-54 to S-165; N-55 to S-165; H-56 to S-165; Q-57 to S-165; S-58 to S-165; Q-59 to S-165; R-60 to S-165; T-61 to S-165; C-62 to S-165; A-63 to S-165; A-64 to S-165; F-65 to S-165; C-66 to S-165; R-67 to S-165; S-68 to S-165; L-69 to S-165; S-70 to S-165; C-71 to S-165; R-72 to S-165; K-73 to S-165; E-74 to S-165; Q-75 to S-165; G-76 to S-165; K-77 to S-165; F-78 to S-165; Y-79 to S-165; D-80 to S-165; H-81 to S-165; L-82 to S-165; L-83 to S-165; R-84 to S-165; D-85 to S-165; C-86 to S-165; I-87 to S-165; S-88 to S-165; C-89 to S-165; A-90 to S-165; S-91 to S-165; 1-92 to S-165; C-93 to S-165; G-94 to S-165; Q-95 to S-165; H-96 to S-165; P-97 to S-165; K-98 to S-165; Q-99 to S-165; C-100 to S-165; A-101 to S-165; Y-102 to S-165; F-103 to S-165; C-104 to S-165; E-105 to S-165; N-106 to S-165; K-107 to S-165; L-108 to S-165; R-109 to S-165; S-110 to S-165; P-111 to S-165; V-112 to S-165; N-113 to S-165; L-114 to S-165; P-115 to S-165; P-116 to S-165; E-117 to S-165; L-118 to S-165; R-119 to S-165; R-120 to S-165; Q-121 to S-165; R-122 to S-165; S-123 to S-165; G-124 to S-165; E-125 to S-165; V-126 to S-165; E-127 to S-165; N-128 to S-165; N-129 to S-165; S-130 to S-165; D-131 to S-165; N-132 to S-165; S-133 to S-165; G-134 to S-165; R-135 to S-165; Y-136 to S-165; Q-137 to S-165; G-138 to S-165; L-139 to S-165; E-140 to S-165; H-141 to S-165; R-142 to S-165; G-143 to S-165; S-144 to S-165; E-145 to S-165; A-146 to S-165; S-147 to S-165; P-148 to S-165; A-149 to S-165; L-150 to S-165; P-151 to S-165; G-152 to S-165; L-153 to S-165; K-154 to S-165; L-155 to S-165; S-156 to S-165; A-157 to S-165; D-158 to S-165; Q-159 to S-165; V-160 to S-165; and/or A-161 to S-165 of the TR17 extracellular domain sequence shown in FIG. 1 (SEQ ID NO:2).

Also as mentioned above, even if deletion of one or more amino acids from the C-terminus of a protein results in modification of loss of one or more biological functions of the protein, other functional activities (e.g., biological activities, ability to multimerize, ability to bind TR17 ligand may still be retained). For example the ability of the shortened TR17 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TR17 mutein with a large number of deleted C-terminal amino acid residues may retain some biological or immunogenic activities. In fact, peptides composed of as few as six TR17 amino acid residues may often evoke an immune response.

Accordingly, the present invention further provides polypeptides having one or more residues deleted from the carboxy terminus of the amino acid sequence of the TR17 polypeptide shown in FIG. 1, up to the arginine residue at position number 6, and polynucleotides encoding such polypeptides. In particular, the present invention provides polypeptides comprising the amino acid sequence of residues 1-m$^1$ of FIG. 1, where m$^1$ is an integer from 6 to 292 corresponding to the position of the amino acid residue in FIG. 1 (SEQ ID NO:2).

More in particular, the invention provides polynucleotides encoding polypeptides comprising, or alternatively consisting of, the amino acid sequence of residues: M-1 to G-292; M-1 to P-291; M-1 to G-290; M-1 to G-289; M-1 to E-288; M-1 to Q-287; M-1 to A-286; M-1 to P-285; M-1 to V-284; M-1 to C-283; M-1 to V-282; M-1 to 1-281; M-1 to G-280; M-1 to L-279; M-1 to G-278; M-1 to S-277; M-1 to D-276; M-1 to P-275; M-1 to I-274; M-1 to H-273; M-1 to P-272; M-1 to C-271; M-1 to P-270; M-1 to Q-269; M-1 to L-268; M-1 to V-267; M-1 to T-266; M-1 to T-265; M-1 to R-264; M-1 to T-263; M-1 to H-262; M-1 to C-261; M-1 to G-260; M-1 to W-259; M-1 to R-258; M-1 to G-257; M-1 to A-256; M-1 to C-255; M-1 to T-254; M-1 to P-253; M-1 to D-252; M-1 to P-251; M-1 to T-250; M-1 to G-249; M-1 to P-248; M-1 to T-247; M-1 to V-246; M-1 to A-245; M-1 to S-244; M-1 to E-243; M-1 to Q-242; M-1 to T-241; M-1 to P-240; M-1 to A-239; M-1 to R-238; M-1 to C-237; M-1 to E-236; M-1 to P-235; M-1 to F-234; M-1 to C-233; M-1 to F-232; M-1 to S-231; M-1 to C-230; M-1 to T-229; M-1 to E-228; M-1 to V-227; M-1 to P-226; M-1 to E-225; M-1 to P-224; M-1 to S-223; M-1 to T-222; M-1 to S-221; M-1 to V-220; M-1 to P-219; M-1 to S-218; M-1 to G-217; M-1 to A-216; M-1 to E-215; M-1 to M-214; M-1 to A-213; M-1 to H-212; M-1 to D-21 1; M-1 to Q-210; M-1 to S-209; M-1 to S-208; M-1 to K-207; M-1 to A-206; M-1 to P-205; M-1 to S-204; M-1 to Q-203; M-1 to R-202; M-1 to P-201; M-1 to R-200; M-1 to S-199; M-1 to R-198; M-1 to P-197; M-1 to Q-196; M-1 to C-195; M-1 to S-194; M-1 to C-193; M-1 to P-192; M-1 to D-191; M-1 to G-190; M-1 to R-189; M-1 to K-188; M-1 to K-187; M-1 to L-186; M-1 to F-185; M-1 to C-184; M-1 to A-183; M-1 to V-182; M-1 to A-181; M-1 to V-180; M-1 to L-179; M-1 to F-178; M-1 to C-177; M-1 to C-176; M-1 to L-175; M-1 to V-174; M-1 to A-173; M-1 to C-172; M-1 to L-171; M-1 to C-170; M-1 to L-169; M-1 to G-168; M-1 to L-167; M-1 to T-166; M-1 to S-165; M-1 to Y-164; M-1 to V-163; M-1 to L-162; M-1 to A-161; M-1 to V-160; M-1 to Q-159; M-1 to D-158; M-1 to A-157; M-1 to S-156; M-1 to L-155; M-1 to K-154; M-1 to L-153; M-1 to G-152; M-1 to P-151; M-1 to L-150; M-1 to A-149; M-1 to P-148; M-1 to S-147; M-1 to A-146; M-1 to E-145; M-1 to S-144; M-1 to G-143; M-1 to R-142; M-1 to H-141; M-1 to E-140; M-1 to L-139; M-1 to G-138; M-1 to Q-137; M-1 to Y-136; M-1 to R-135; M-1 to G-134; M-1 to S-133; M-1 to N-132; M-1 to D-131; M-1 to S-130; M-1 to N-129; M-1 to N-128; M-1 to E-127; M-1 to V-126; M-1 to E-125; M-1 to G-124; M-1 to S-123; M-1 to R-122; M-1 to Q-121; M-1 to R-120; M-1 to R-119; M-1 to L-118; M-1 to E-117; M-1 to P-1 16; M-1 to P-1 15; M-1 to L-114; M-1 to N-113; M-1 to V-112; M-1 to P-111; M-1 to S-110; M-1 to R-109; M-1 to L-108; M-1 to K-107; M-1 to N-106; M-1 to E-105; M-1 to C-104; M-1 to F-103; M-1 to Y-102; M-1 to A-101; M-1 to C-100; M-1 to Q-99; M-1 to K-98; M-1 to P-97; M-1 to H-96; M-1 to Q-95; M-1 to G-94; M-1 to C-93; M-1 to I-92; M-1 to S-91; M-1 to A-90; M-1 to C-89; M-1 to S-88; M-1 to I-87; M-1 to C-86; M-1 to D-85; M-1 to R-84; M-1 to L-83; M-1 to L-82; M-1 to H-81; M-1 to D-80; M-1 to Y-79; M-1 to F-78; M-1 to K-77; M-1 to G-76; M-1 to Q-75; M-1 to E-74; M-1 to K-73; M-1 to R-72; M-1 to C-71; M-1 to S-70; M-1 to L-69; M-1 to S-68; M-1 to R-67; M-1 to C-66; M-1 to F-65; M-1 to A-64; M-1 to A-63; M-1 to C-62; M-1 to T-61; M-1 to R-60; M-1 to Q-59; M-1 to S-58; M-1 to Q-57; M-1 to H-56; M-1 to N-55; M-1 to C-54; M-1 to I-53; M-1 to T-52; M-1 to K-51; M-1 to C-50; M-1 to S-49; M-1 to M-48; M-1 to C-47; M-1 to T-46; M-1 to G-45; M-1 to L-44; M-1 to L-43; M-1 to P-42; M-1 to D-41; M-1 to W-40; M-1 to Y-39; M-1 to Q-38; M-1 to E-37; M-1 to E-36; M-1 to P-35; M-1 to C-34; M-1 to S-33; M-1 to R-32; M-1 to M-31; M-1 to A-30; M-1 to V-29; M-1 to G-28; M-1 to T-27; M-1 to W-26; M-1 to L-25; M-1 to G-24; M-1 to Q-23; M-1 to P-22; M-1 to F-21; M-1 to R-20; M-1 to E-19; M-1 to E-18; M-1 to Q-17; M-1 to D-16; M-1 to V-15; M-1 to R-14; M-1 to S-13; M-1 to R-12; M-1 to G-11; M-1 to G-10; M-1 to R-9; M-1 to R-8; and/or M-1 to S-7 of the TR17 sequence shown in FIG. 1. Polypeptides encoded by these polynucleotides are also encompassed by the invention.

The invention also provides polypeptides having one or more amino acids deleted from both the amino and the carboxyl termini, which may be described generally as having residues n$^1$-m$^1$ and/or n$^2$-m$^1$ of FIG. 1 (i.e., SEQ ID NO:2), where n$^1$, n$^2$, and m$^1$ are integers as described above. Thus, any of the above listed N- or C-terminal deletions can be combined to produce a N- and C-terminal deleted TR17 polypeptide.

The present invention encompasses TR17 polypeptides comprising, or alternatively consisting of, an epitope of the polypeptide having an amino acid sequence of FIG. 1 (SEQ ID NO:2), or an epitope of the polypeptide sequence encoded by a polynucleotide that hybridizes to the complement of the sequence of SEQ ID NO:1 under stringent hybridization conditions or lower stringency hybridization conditions as defined supra. The present invention further encompasses polynucleotide sequences encoding an epitope of a TR17 polypeptide sequence of the invention (such as, for example, the sequence disclosed in SEQ ID NO:2), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length.

Non-limiting examples of antigenic polypeptides or peptides that can be used to generate TR17-specific antibodies include: a polypeptide comprising, or alternatively consisting of, amino acid residues from about Gly-5 to about Gly-11 in FIG. 1 (SEQ ID NO:2); a polypeptide comprising, or alternatively consisting of, amino acid residues from about Ser-33 to about Glu-36 in FIG. 1 (SEQ ID NO:2); a polypeptide comprising, or alternatively consisting of, amino acid residues from about Gln-57 to about Arg-60 in FIG. 1 (SEQ ID NO:2); a polypeptide comprising, or alternatively consisting of, amino acid residues from about Arg-72 to about Phe-78 in FIG. 1 (SEQ ID NO:2); a polypeptide comprising, or alternatively consisting of, amino acid residues from about Glu-105 to about Ser-110 in FIG. 1 (SEQ ID NO:2); a polypeptide comprising, or alternatively consisting of, amino acid residues from about Pro-115 to about Gly-134 in FIG. 1 (SEQ ID NO:2); a polypeptide comprising, or alternatively consisting of, amino acid residues from about Glu-140 to about Pro-148 in FIG. 1 (SEQ ID NO:2); a polypeptide comprising, or alternatively consisting of, amino acid residues from about Leu-186 to about Ala-216 in FIG. 1 (SEQ ID NO:2); a polypeptide comprising, or alternatively consisting of, amino acid residues from about Thr-222 to about Glu-228 in FIG. 1 (SEQ ID NO:2); a polypeptide comprising, or alternatively consisting of, amino acid residues from about Arg-238 to about Ser-244 in FIG. 1 (SEQ ID NO:2); a polypeptide comprising, or alternatively consisting of, amino acid residues from about Asp-252 to about Cys-255 in FIG. 1 (SEQ ID NO:2); and a polypeptide comprising, or alternatively consisting of, amino acid residues from about Ala-286 to about Gly-290 in FIG. 1 (SEQ ID NO:2). In this context, "about" means the particularly recited ranges and ranges larger or smaller by several, a few, 5, 4, 3, 2 or 1 amino acid residues at either or both the amino- and carboxy-termini. These polypeptide fragments have been determined to bear antigenic epitopes of the TR17 polypeptide by the analysis of the Jameson-Wolf antigenic index, as shown in FIG. 2 and Table I, above. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued June 16, 1998, herein incorporated by reference in their entirety)) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2): 76–82 (1998); Hansson, et al., J. Mol. Biol. 287:265–76 (1999); and Lorenzo and Blasco, Biotechniques 24(2): 308–13 (1998) (each of these Patents and publications are hereby incorporated by reference in its entirety). In one embodiment, alteration of TR17 polynucleotides corresponding to FIG. 1 (SEQ ID NO:1) and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

It will be recognized in the art that some amino acid sequences of TR17 can be varied without significant effect on the structure or function of the protein. If such differences in sequence are contemplated, it should be remembered that there will be critical areas on the protein which determine activity. Thus, the invention further includes variations of the TR17 receptor, which show substantial TR17 receptor activity or which include regions of TR17 proteins, such as the protein portions discussed herein. Such mutants include deletions, insertions, inversions, repeats, and type substitutions. As indicated above, guidance concerning which amino acid changes are likely to be phenotypically silent can be found in J. U. Bowie et al., Science 247:1306–1310 (1990).

Thus, the fragment, derivative, or analog of the polypeptide of FIG. 1 (SEQ ID NO:2), may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR17 receptor protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993), describes certain mutations resulting in selective binding of TNF-α to only one of the two known types of TNF receptors. Thus, the TR17 polypeptides receptor of the present invention may include one or more amino acid substitutions, deletions, or additions, either from natural mutations or human manipulation.

As indicated, changes are preferably of a minor nature, such as conservative amino acid substitutions that do not significantly affect the folding or activity of the protein (see Table II).

TABLE II

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of FIG. 1 and/or any of the polypeptide fragments described herein (e.g., the extracellular domain or intracellular domain) is 75, 70, 60, 50, 40, 35, 30, 25, 20, 15, 10, 9, 8, 7, 6, 5, 4, 3, 2, 1 or 30–20, 20–15, 20–10, 15–10, 10–1, 5–10, 1–5, 1–3 or 1–2.

In another embodiment, site directed changes at the amino acid level of TR17 can be made by replacing a particular amino acid with a conservative substitution. Preferred conservative substitution mutations of the TR17 amino acid sequence provided in SEQ ID NO:2 include: M1 replaced with A, G, I, L, S, T, or V; S2 replaced with A, G, I, L, T, M, or V; G3 replaced with A, I, L, S, T, M, or V; L4 replaced with A, G, I, S, T, M, or V; G5 replaced with A, I, L, S, T, M, or V; R6 replaced with H, or K; S7 replaced with A, G, I, L, T, M, or V; R8 replaced with H, or K; R9 replaced with H, or K; G10 replaced with A, I, L, S, T, M, or V; G11 replaced with A, I, L, S, T, M, or V; R12 replaced with H, or K; S13 replaced with A, G, I, L, T, M, or V; R14 replaced with H, or K; V15 replaced with A, G, I, L, S, T, or M; D16 replaced with E; Q17 replaced with N; E18 replaced with D; E19 replaced with D; R20 replaced with H, or K; F21 replaced with W, or Y; Q23 replaced with N; G24 replaced with A, I, L, S, T, M, or V; L25 replaced with A, G, I, S, T, M, or V; W26 replaced with F, or Y; T27 replaced with A, G, I, L, S, M, or V; G28 replaced with A, I, L, S, T, M, or V; V29 replaced with A, G, I, L, S, T, or M; A30 replaced with G, I, L, S, T, M, or V; M31 replaced with A, G, I, L, S, T, or V; R32 replaced with H, or K; S33 replaced with A, G, I, L, T, M, or V; E36 replaced with D; E37 replaced with D; Q38 replaced with N; Y39 replaced with F, or W; W40 replaced with F, or Y; D41 replaced with E; L43 replaced with A, G, I, S, T, M, or V; L44 replaced with A, G, I, S, T, M, or V; G45 replaced with A, I, L, S, T, M, or V; T46 replaced with A, G, I, L, S, M, or V; M48 replaced with A, G, I, L, S, T, or V; S49 replaced with A, G, I, L, T, M, or V; K51 replaced with H, or R; T52 replaced with A, G, I, L, S, M, or V; 153 replaced with A, G, L, S, T, M, or V; N55 replaced with Q; H56 replaced with K, or R; Q57 replaced with N; S58 replaced with A, G, I, L, T, M, or V; Q59 replaced with N; R60 replaced with H, or K; T61 replaced with A, G, I, L, S, M, or V; A63 replaced with G, I, L, S, T, M, or V; A64 replaced with G, I, L, S, T, M, or V; F65 replaced with W, or Y; R67 replaced with H, or K; S68 replaced with A, G, I, L, T, M, or V; L69 replaced with A, G, I, S, T, M, or V; S70 replaced with A, G, I, L, T, M, or V; R72 replaced with H, or K; K73 replaced with H, or R; E74 replaced with D; Q75 replaced with N; G76 replaced with A, I, L, S, T, M, or V; K77 replaced with H, or R; F78 replaced with W, or Y; Y79 replaced with F, or W; D80 replaced with E; H81 replaced with K, or R; L82 replaced with A, G, I, S, T, M, or V; L83 replaced with A, G, I, S, T, M, or V; R84 replaced with H, or K; D85 replaced with E; 187 replaced with A, G, L, S, T, M, or V; S88 replaced with A, G, I, L, T, M, or V; A90 replaced with G, I, L, S, T, M, or V; S91 replaced with A, G, I, L, T, M, or V; 192 replaced with A, G, L, S, T, M, or V; G94 replaced with A, I, L, S, T, M, or V; Q95 replaced with N; H96 replaced with K, or R; K98 replaced with H, or R; Q99 replaced with N; A10 replaced with G, I, L, S, T, M, or V; Y102 replaced with F, or W; F103 replaced with W, or Y; E105 replaced with D; N106 replaced with Q; K107 replaced with H, or R; L108 replaced with A, G, I, S, T, M, or V; R109 replaced with H, or K; S11 replaced with A, G, I, L, T, M, or V; V112 replaced with A, G, I, L, S, T, or M; N113 replaced with Q; L114 replaced with A, G, I, S, T, M, or V; E117 replaced with D; L118 replaced with A, G, I, S, T, M, or V; R 119 replaced with H, or K; R120 replaced with H, or K; Q121 replaced with N; R122 replaced with H, or K; S123 replaced with A, G, I, L, T, M, or V; G124 replaced with A, I, L, S, T, M, or V; E125 replaced with D; V126 replaced with A, G, I, L, S, T, or M; E127 replaced with D; N128 replaced with Q; N129 replaced with Q; S130 replaced with A, G, I, L, T, M, or V; D131 replaced with E; N132 replaced with Q; S133 replaced with A, G, I, L, T, M, or V; G134 replaced with A, I, L, S, T, M, or V; R135 replaced with H, or K; Y136 replaced with F, or W; Q137 replaced with N; G138 replaced with A, I, L, S, T, M, or V; L139 replaced with A, G, I, S, T, M, or V; E140 replaced with D; H141 replaced with K, or R; R142 replaced with H, or K; G143 replaced with A, I, L, S, T, M, or V; S144 replaced with A, G, I, L, T, M, or V; E145 replaced with D; A146 replaced with G, I, L, S, T, M, or V; S147 replaced with A, G, I, L, T, M, or V; A149 replaced with G, I, L, S, T, M, or V; L150 replaced with A, G, I, S, T, M, or V; G152 replaced with A, I, L, S, T, M, or V; L153 replaced with A, G, I, S, T, M, or V; K154 replaced with H, or R; L155 replaced with A, G, I, S, T, M, or V; S156 replaced with A, G, I, L, T, M, or V; A157 replaced with G, I, L, S, T, M, or V; D158 replaced with E; Q159 replaced with N; V160 replaced with A, G, I, L, S, T, or M; A161 replaced with G, I, L, S, T, M, or V; L162 replaced with A, G, I, S, T, M, or V; V163 replaced with A, G, I, L, S, T, or M; Y164 replaced with F, or W; S165 replaced with A, G, I, L, T, M, or V; T166 replaced with A, G, I, L, S, M, or V; L167 replaced with A, G, I, S, T, M, or V; G168 replaced with A, I, L, S, T, M, or V; L169 replaced with A, G, I, S, T, M, or V; L171 replaced with A, G, I, S, T, M, or V; A173 replaced with G, I, L, S, T, M, or V; V174 replaced with A, G, I, L, S, T, or M; L175 replaced with A, G, I, S, T, M, or V; F178 replaced with W, or Y; L179 replaced with A, G, I, S, T, M, or V; V180 replaced with A, G, I, L, S, T, or M; A181 replaced with G, I, L, S, T, M, or V; V182 replaced with A, G, I, L, S, T, or M; A183 replaced with G, I, L, S, T, M, or V; F185 replaced with W, or Y; L186 replaced with A, G, I, S, T, M, or V; K187 replaced with H, or R; K188 replaced with H, or R; R189 replaced with H, or K; G190 replaced with A, I, L, S, T, M, or V; D191 replaced with E; S194 replaced with A, G, I, L, T, M, or V; Q196 replaced with N; R198 replaced with H, or K; S199 replaced with A, G, I, L, T, M, or V; R200 replaced with H, or K; R202 replaced with H, or K; Q203 replaced with N; S204 replaced with A, G, I, L, T, M, or V; A206 replaced with G, I, L, S, T, M, or V; K207 replaced with H, or R; S208 replaced with A, G, I, L, T, M, or V; S209 replaced with A, G, I, L, T, M, or V; Q210 replaced with N; D211 replaced with E; H212 replaced with K, or R; A213 replaced with G, I, L, S, T, M, or V; M214 replaced with A, G, I, L, S, T, or V; E215 replaced with D; A216 replaced with G, I, L, S, T, M, or V; G217 replaced with A, I, L, S, T, M, or V; S218 replaced with A, G, I, L, T, M, or V; V220 replaced with A, G, I, L, S, T, or M; S221 replaced with A, G, I, L, T, M, or V; T222 replaced with A, G, I, L, S, M, or V; S223 replaced with A, G, I, L, T, M, or V; E225 replaced with D; V227 replaced with A, G, I, L, S, T, or M; E228 replaced with D; T229 replaced with A, G, I, L, S, M, or V; S231 replaced with A, G, I, L, T, M, or V; F232 replaced with W, or Y; F234 replaced with W, or Y; E236 replaced with D; R238 replaced with H, or K; A239 replaced with G, I, L, S, T, M, or V; T241 replaced with A, G, I, L, S, M, or V; Q242 replaced with N; E243 replaced with D; S244 replaced with A, G, I, L, T, M, or V; A245 replaced with G, I, L, S, T, M, or V; V246 replaced with A, G, I, L, S, T, or M; T247 replaced with A, G, I, L, S, M, or V; G249 replaced with A, I, L, S, T, M, or V; T250 replaced with A, G, I, L, S, M, or V; D252 replaced with E; T254 replaced with A, G, I, L, S, M, or V; A256 replaced with G, I, L, S, T, M, or V; G257 replaced with A, I, L, S, T, M, or V; R258 replaced with H, or K; W259 replaced with F, or Y; G260 replaced with A, I, L, S, T, M, or V; H262 replaced with K, or R; T263 replaced with A, G, I, L, S, M, or V; R264 replaced with H, or K; T265 replaced with A, G, I, L, S, M, or V; T266 replaced with A, G, I, L, S, M, or V; V267 replaced with A, G, I, L, S, T, or M; L268 replaced with A, G, I, S, T, M, or V; Q269 replaced with N; H273 replaced with K, or R; 1274 replaced with A, G, L, S, T, M, or V; D276 replaced with E; S277 replaced with A, G, I, L, T, M, or V; G278 replaced with A, I, L, S, T, M, or V; L279 replaced with A, G, I, S, T, M, or V; G280 replaced with A, I, L, S, T, M, or V; I281 replaced with A, G, L, S, T, M, or V; V282 replaced with A, G, I, L, S, T, or M; V284 replaced with A, G, I, L, S, T, or M; A286 replaced with G, I, L, S, T, M, or V; Q287 replaced with N; E288 replaced with D; G289 replaced with A, I, L, S, T, M, or V; G290 replaced with A, I, L, S, T, M, or V; G292 replaced with A, I, L, S, T, M, or V; and/or A293 replaced with G, I, L, S, T, M, or V. Polynucleotides encoding these polypeptides are also encompassed by the invention. The resulting TR17 of the invention may be routinely screened for TR17 functional activity and/or physical properties (such as, for example, enhanced or reduced stability and/or solubility). Preferably, the resulting proteins of the invention have an increased and/or a decreased TR17 functional activity. More preferably, the resulting TR17 proteins of the invention have more than one increased and/or decreased TR17 functional activity and/or physical property.

Amino acids in the TR17 proteins of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331–340 (1967); Robbins et al., Diabetes 36: 838–845 (1987); Cleland et al., *Crit. Rev. Therapeutic Drug Carrier Systems* 10:307–377 (1993).

In another embodiment, the invention provides for polypeptides having amino acid sequences containing non-conservative substitutions of the amino acid sequence provided in SEQ ID NO:2. For example, non-conservative substitutions of the TR17 protein sequence provided in SEQ ID NO:2 include: M1 replaced with D, E, H, K, R, N, Q, F, W, Y, P, or C; S2 replaced with D, E, H, K, R, N, Q, F, W, Y, P, or C; G3 replaced with D, E, H, K, R, N, Q, F, W, Y, P, or C; L4 replaced with D, E, H, K, R, N, Q, F, W, Y, P, or C; G5 replaced with D, E, H, K, R, N, Q, F, W, Y, P, or C; R6 replaced with D, E, A, G, I, L, S, T, M, V, N, Q, F, W, Y, P, or C; S7 replaced with D, E, H, K, R, N, Q, F, W, Y, P, or C; R8 replaced with D, E, A, G, I, L, S, T, M, V, N, Q, F, W, Y, P, or C; R9 replaced with D, E, A, G, I, L, S, T, M, V, N, Q, F, W, Y, P, or C; G10 replaced with D, E, H, K, R, N, Q, F, W, Y, P, or C; G11 replaced with D, E, H, K, R, N, Q, F, W, Y, P, or C; R12 replaced with D, E, A, G, I, L, S, T, M, V, N, Q, F, W, Y, P, or C; S13 replaced with D, E, H, K, R, N, Q, F, W, Y, P, or C; R14 replaced with D, E, A, G, I, L, S, T, M, V, N, Q, F, W, Y, P, or C; V15 replaced with D, E, H, K, R, N, Q, F, W, Y, P, or C; D16 replaced with H, K, R, A, G, I, L, S, T, M, V, N, Q, F, W, Y, P, or C; Q17 replaced with D, E, H, K, R, A, G, I, L, S, T, M, V, F, W, Y, P, or C; E18 replaced with H, K, R, A, G, I, L, S, T, M, V, N, Q, F, W, Y, P, or C; E19 replaced with H, K, R, A, G, I, L, S, T, M, V, N, Q, F, W, Y, P, or C; R20 replaced with D, E, A, G, I, L, S, T, M, V, N, Q, F, W, Y, P, or C; F21 replaced with D, E, H, K, R, N, Q, A, G, I, L, S, T, M, V, P, or C; P22 replaced with D, E, H, K, R, A, G, I, L, S, T, M, V, N, Q, F, W, Y, or C; Q23 replaced with D, E, H, K, R, A, G, I, L, S, T, M, V, F, W, Y, P, or C; G24 replaced with D, E, H, K, R, N, Q, F, W, Y, P, or C; L25 replaced with D, E, H, K, R, N, Q, F, W, Y, P, or C; W26 replaced with D, E, H, K, R, N, Q, A, G, I, L, S, T, M, V, P, or C; T27 replaced with D, E, H, K, R, N, Q, F, W, Y, P, or C; G28 replaced with D, E, H, K, R, N, Q, F, W, Y, P, or C; V29 replaced with D, E, H, K, R, N, Q, F, W, Y, P, or C; A30 replaced with D, E, H, K, R, N, Q, F, W, Y, P, or C; M31 replaced with D, E, H, K, R, N, Q, F, W, Y, P, or C; R32 replaced with D, E, A, G, I, L, S, T, M, V, N, Q, F, W, Y, P, or C; S33 replaced with D, E, H, K, R, N, Q, F, W, Y, P, or C; C34 replaced with D, E, H, K, R, A, G, I, L, S, T, M, V, N, Q, F, W, Y, or P; P35 replaced with D, E, H, K, R, A, G, I, L, S, T, M, V, N, Q, F, W, Y, or C; E36 replaced with H, K, R, A, G, I, L, S, T, M, V, N, Q, F, W, Y, P, or C; E37 replaced with H, K, R, A, G, I, L, S, T, M, V, N, Q, F, W, Y, P, or C; Q38 replaced with D, E, H, K, R, A, G, I, L, S, T, M, V, F, W, Y, P, or C; Y39 replaced with D, E, H, K, R, N, Q, A, G, I, L, S, T, M, V, P, or C; W40 replaced with D, E, H, K, R, N, Q, A, G, I, L, S, T, M, V, P, or C; D41 replaced with H, K, R, A, G, I, L, S, T, M, V, N, Q, F, W, Y, P, or C; P42 replaced with D, E, H, K, R, A, G, I, L, S, T, M, V, N, Q, F, W, Y, or C; L43 replaced with D, E, H, K, R, N, Q, F, W, Y, P, or C; L44 replaced with D, E, H, K, R, N, Q, F, W, Y, P, or C; G45 replaced with D, E, H, K, R, N, Q, F, W, Y, P, or C; T46 replaced with D, E, H, K, R, N, Q, F, W, Y, P, or C; C47 replaced with D, E, H, K, R, A, G, I, L, S, T, M, V, N, Q, F, W, Y, or P; M48 replaced with D, E, H, K, R, N, Q, F, W, Y, P, or C; S49 replaced with D, E, H, K, R, N, Q, F, W, Y, P, or C; C50 replaced with D, E, H, K, R, A, G, I, L, S, T, M, V, N, Q, F, W, Y, or P; K51 replaced with D, E, A, G, I, L, S, T, M, V, N, Q, F, W, Y, P, or C; T52 replaced with D, E, H, K, R, N, Q, F, W, Y, P, or C; I53 replaced with D, E, H, K, R, N, Q, F, W, Y, P, or C; C54 replaced with D, E, H, K, R, A, G, I, L, S, T, M, V, N, Q, F, W, Y, or P; N55 replaced with D, E, H, K, R, A, G, I, L, S, T, M, V, F, W, Y, P, or C; H56 replaced with D, E, A, G, I, L, S, T, M, V, N, Q, F, W, Y, P, or C; Q57 replaced with D, E, H, K, R, A, G, I, L, S, T, M, V, F, W, Y, P, or C; S58 replaced with D, E, H, K, R, N, Q, F, W, Y, P, or C; Q59 replaced with D, E, H, K, R, A, G, I, L, S, T, M, V, F, W, Y, P, or C; R60 replaced with D, E, A, G, I, L, S, T, M, V, N, Q, F, W, Y, P, or C; T61 replaced with D, E, H, K, R, N, Q, F, W, Y, P, or C; C62 replaced with D, E, H, K, R, A, G, I, L, S, T, M, V, N, Q, F, W, Y, or P; A63 replaced with D, E, H, K, R, N, Q, F, W, Y, P, or C; A64 replaced with D, E, H, K, R, N, Q, F, W, Y, P, or C; F65 replaced with D, E, H, K, R, N, Q, A, G, I, L, S, T, M, V, P, or C; C66 replaced with D, E, H, K, R, A, G, I, L, S, T, M, V, N, Q, F, W, Y, or P; R67 replaced with D, E, A, G, I, L, S, T, M, V, N, Q, F, W, Y, P, or C; S68 replaced with D, E, H, K, R, N, Q, F, W, Y, P, or C; L69 replaced with D, E, H, K, R, N, Q, F, W, Y, P, or C; S70 replaced with D, E, H, K, R, N, Q, F, W, Y, P, or C; C71 replaced with D, E, H, K, R, A, G, I, L, S, T, M, V, N, Q, F, W, Y, or P; R72 replaced with D, E, A, G, I, L, S, T, M, V, N, Q, F, W, Y, P, or C; K73 replaced with D, E, A, G, I, L, S, T, M, V, N, Q, F, W, Y, P, or C; E74 replaced with H, K, R, A, G, I, L, S, T, M, V, N, Q, F, W, Y, P, or C; Q75 replaced with D, E, H, K, R, A, G, I, L, S, T, M, V, F, W, Y, P, or C; G76 replaced with D, E, H, K, R, N, Q, F, W, Y, P, or C; K77 replaced with D, E, A, G, I, L, S, T, M, V, N, Q, F, W, Y, P, or C; F78 replaced with D, E, H, K, R, N, Q, A, G, I, L, S, T, M, V, P, or C; Y79 replaced with D, E, H, K, R, N, Q, A, G, I, L, S, T, M, V, P, or C; D80 replaced with H, K, R, A, G, I, L, S, T, M, V, N, Q, F, W, Y, P, or C; H81 replaced with D, E, A, G, I, L, S, T, M, V, N, Q, F, W, Y, P, or C; L82 replaced with D, E, H, K, R, N, Q, F, W, Y, P, or C; L83 replaced with D, E, H, K, R, N, Q, F, W, Y, P, or C; R84 replaced with D, E, A, G, I, L, S, T, M, V, N, Q, F, W, Y, P, or C; D85 replaced with H, K, R, A, G, I, L, S, T, M, V, N, Q, F, W, Y, P, or C; C86 replaced with D, E, H, K, R, A, G, I, L, S, T, M, V, N, Q, F, W, Y, or P; 187 replaced with D, E, H, K, R, N, Q, F, W, Y, P, or C; S88 replaced with D, E, H, K, R, N, Q, F, W, Y, P, or C; C89 replaced with D, E, H, K, R, A, G, I, L, S, T, M, V, N, Q, F, W, Y, or P; A90 replaced with D, E, H, K, R, N, Q, F, W, Y, P, or C; S91 replaced with D, E, H, K, R, N, Q, F, W, Y, P, or C; 192 replaced with D, E, H, K, R, N, Q, F, W, Y, P, or C; C93 replaced with D, E, H, K, R, A, G, I, L, S, T, M, V, N, Q, F, W, Y, or P; G94 replaced with D, E, H, K, R, N, Q, F, W, Y, P, or C; Q95 replaced with D, E, H, K, R, A, G, I, L, S, T, M, V, F, W, Y, P, or C; H96 replaced with D, E, A, G, I, L, S, T, M, V, N, Q, F, W, Y, P, or C; P97 replaced with D, E, H, K, R, A, G, I, L, S, T, M, V, N, Q, F, W, Y, or C; K98 replaced with D, E, A, G, I, L, S, T, M, V, N, Q, F, W, Y, P, or C; Q99 replaced with D, E, H, K, R, A, G, I, L, S, T, M, V, F, W, Y, P, or C; C100 replaced with D, E, H, K, R, A, G, I, L, S, T, M, V, N, Q, F, W, Y, or P; A101 replaced with D, E, H, K, R, N, Q, F, W, Y, P, or C; Y102 replaced with D, E, H, K, R, N, Q, A, G, I, L, S, T, M, V, P, or C; F103 replaced with D, E, H, K, R, N, Q, A, G, I, L, S, T, M, V, P, or C; C104 replaced with D, E, H, K, R, A, G, I, L, S, T, M, V, N, Q, F, W, Y, or P; E105 replaced with H, K, R, A, G, I, L, S, T, M, V, N, Q, F, W, Y, P, or C; N106 replaced with D, E, H, K, R, A, G, I, L, S, T, M, V, F, W, Y, P, or C; K107 replaced with D, E, A, G, I, L, S, T, M, V, N, Q, F, W, Y, P, or C; L108 replaced with D, E, H, K, R, N, Q, F, W, Y, P, or C; R109 replaced with D, E, A, G, I, L, S, T, M, V, N, Q, F, W, Y, P, or C; S110 replaced with D, E, H, K, R, N, Q, F, W, Y, P, or C; P111 replaced with D, E, H, K, R, A, G, I, L, S, T, M, V, N, Q, F, W, Y, or C; V112 replaced with D, E, H, K, R, N, Q, F, W, Y, P, or C; N113 replaced with D, E, H, K, R, A, G, I, L, S, T, M, V, F, W, Y, P, or C; L 14 replaced with D, E, H, K, R, N, Q, F, W, Y, P, or C; P115 replaced with D, E, H, K, R, A, G, I, L, S, T, M, V, N, Q, F, W, Y, or C; P116 replaced with D, E, H, K, R, A, G, I, L, S, T, M, V, N, Q, F, W, Y, or C; E117 replaced with H, K, R, A, G, I, L, S, T, M, V, N, Q, F, W, Y, P, or C; L118 replaced with D, E, H, K, R, N, Q, F, W, Y, P, or C; R119 replaced with D, E, A, G, I, L, S, T, M, V, N, Q, F, W, Y, P, or C; R120 replaced with D, E, A, G, I, L, S, T, M, V, N, Q, F, W, Y, P, or C; Q121 replaced with D, E, H, K, R, A, G, I, L, S, T, M, V, F, W, Y, P, or C; R122 replaced with D, E, A, G, I, L, S, T, M, V, N, Q, F, W, Y, P, or C; S123 replaced with D, E, H, K, R, N, Q, F, W, Y, P, or C; G124 replaced with D, E, H, K, R, N, Q, F, W, Y, P, or C; E125 replaced with H, K, R, A, G, I, L, S, T, M, V, N, Q, F, W, Y, P, or C; V126 replaced with D, E, H, K, R, N, Q, F, W, Y, P, or C; E127 replaced with H, K, R, A, G, I, L, S, T, M, V, N, Q, F, W, Y, P, or C; N128 replaced with D, E, H, K, R, A, G, I, L, S, T, M, V, F, W, Y, P, or C; N 129 replaced with D, E, H, K, R, A, G, I, L, S, T, M, V, F, W, Y, P, or C; S130 replaced with D, E, H, K, R, N, Q, F, W, Y, P, or C; D131 replaced with H, K, R, A, G, I, L, S, T, M, V, N, Q, F, W, Y, P, or C; N132 replaced with D, E, H, K, R, A, G, I, L, S, T, M, V, F, W, Y, P, or C; S133 replaced with D, E, H, K, R, N, Q, F, W, Y, P, or C; G134 replaced with D, E, H, K, R, N, Q, F, W, Y, P, or C; R135 replaced with D, E, A, G, I, L, S, T, M, V, N, Q, F, W, Y, P, or C; Y136 replaced with D, E, H, K, R, N, Q, A, G, I, L, S, T, M, V, P, or C; Q137 replaced with D, E, H, K, R, A, G, I, L, S, T, M, V, F, W, Y, P, or C; G138 replaced with D, E, H, K, R, N, Q, F, W, Y, P, or C; L139 replaced with D, E, H, K, R, N, Q, F, W, Y, P, or C; E140 replaced with H, K, R, A, G, I, L, S, T, M, V, N, Q, F, W, Y, P, or C; H141 replaced with D, E, A, G, I, L, S, T, M, V, N, Q, F, W, Y, P, or C; R142 replaced with D, E, A, G, I, L, S, T, M, V, N, Q, F, W, Y, P, or C; G143 replaced with D, B, H, K, R, N, Q, F, W, Y, P, or C; S144 replaced with D, E, H, K, R, N, Q, F, W, Y, P, or C; E145 replaced with H, K, R, A, G, I, L, S, T, M, V, N, Q, F, W, Y, P, or C; A146 replaced with D, E, H, K, R, N, Q, F, W, Y, P, or C; S147 replaced with D, E, H, K, R, N, Q, F, W, Y, P, or C; P148 replaced with D, E, H, K, R, A, G, I, L, S, T, M, V, N, Q, F, W, Y, or C; A149 replaced with D, E, H, K, R, N, Q, F, W, Y, P, or C; L150 replaced with D, E, H, K, R, N, Q, F, W, Y, P, or C; P151 replaced with D, E, H, K, R, A, G, I, L, S, T, M, V, N, Q, F, W, Y, or C; G152 replaced with D, E, H, K, R, N, Q, F, W, Y, P, or C; L153 replaced with D, E, H, K, R, N, Q, F, W, Y, P, or C; K154 replaced with D, E, A, G, I, L, S, T, M, V, N, Q, F, W, Y, P, or C; L155 replaced with D, B, H, K, R, N, Q, F, W, Y, P, or C; S156 replaced with D, E, H, K, R, N, Q, F, W, Y, P, or C; A157 replaced with D, E, H, K, R, N, Q, F, W, Y, P, or C; D158 replaced with H, K, R, A, G, I, L, S, T, M, V, N, Q, F, W, Y, P, or C; Q159 replaced with D, E, H, K, R, A, G, I, L, S, T, M, V, F, W, Y, P, or C; V160 replaced with D, E, H, K, R, N, Q, F, W, Y, P, or C; A161 replaced with D, E, H, K, R, N, Q, F, W, Y, P, or C; L162 replaced with D, E, H, K, R, N, Q, F, W, Y, P, or C; V163 replaced with D, E, H, K, R, N, Q, F, W, Y, P, or C; Y164 replaced with D, E, H, K, R, N, Q, A, G, I, L, S, T, M, V, P, or C; S165 replaced with D, E, H, K, R, N, Q, F, W, Y, P, or C; T166 replaced with D, E, H, K, R, N, Q, F, W, Y, P, or C; L167 replaced with D, E, H, K, R, N, Q, F, W, Y, P, or C; G168 replaced with D, E, H, K, R, N, Q, F, W, Y, P, or C; L169 replaced with D, E, H, K, R, N, Q, F, W, Y, P, or C; C170 replaced with D, E, H, K, R, A, G, I, L, S, T, M, V, N, Q, F, W, Y, or P; L171 replaced with D, E, H, K, R, N, Q, F, W, Y, P, or C; C172 replaced with D, E, H, K, R, A, G, I, L, S, T, M, V, N, Q, F, W, Y, or P; A173 replaced with D, E, H, K, R, N, Q, F, W, Y, P, or C; V174 replaced with D, E, H, K, R, N, Q, F, W, Y, P, or C; L175 replaced with D, E, H, K, R, N, Q, F, W, Y, P, or C; C176 replaced with D, E, H, K, R, A, G, I, L, S, T, M, V, N, Q, F, W, Y, or P; C177 replaced with D, E, H, K, R, A, G, I, L, S, T, M, V, N, Q, F, W, Y, or P; F178 replaced with D, E, H, K, R, N, Q, A, G, I, L, S, T, M, V, P, or C; L179 replaced with D, E, H, K, R, N, Q, F, W, Y, P, or C; V180 replaced with D, E, H, K, R, N, Q, F, W, Y, P, or C; A181 replaced with D, E, H, K, R, N, Q, F, W, Y, P, or C; V182 replaced with D, E, H, K, R, N, Q, F, W, Y, P, or C; A183 replaced with D, E, H, K, R, N, Q, F, W, Y, P, or C; C184 replaced with D, E, H, K, R, A, G, I, L, S, T, M, V, N, Q, F, W, Y, or P; F185 replaced with D, E, H, K, R, N, Q, A, G, I, L, S, T, M, V, P, or C; L186 replaced with D, E, H, K, R, N, Q, F, W, Y, P, or C; K187 replaced with D, E, A, G, I, L, S, T, M, V, N, Q, F, W, Y, P, or C; K188 replaced with D, E, A, G, I, L, S, T, M, V, N, Q, F, W, Y, P, or C; R189 replaced with D, E, A, G, I, L, S, T, M, V, N, Q, F, W, Y, P, or C; G190 replaced with D, E, H, K, R, N, Q, F, W, Y, P, or C; D191 replaced with H, K, R, A, G, I, L, S, T, M, V, N, Q, F, W, Y, P, or C; P192 replaced with D, E, H, K, R, A, G, I, L, S, T, M, V, N, Q, F, W, Y, or C; C193 replaced with D, E, H, K, R, A, G, I, L, S, T, M, V, N, Q, F, W, Y, or P; S194 replaced with D, E, H, K, R, N, Q, F, W, Y, P, or C; C195 replaced with D, E, H, K, R, A, G, I, L, S, T, M, V, N, Q, F, W, Y, or P; Q196 replaced with D, E, H, K, R, A, G, I, L, S, T, M, V, F, W, Y, P, or C; P197 replaced with D, E, H, K, R, A, G, I, L, S, T, M, V, N, Q, F, W, Y, or C; R198 replaced with D, E, A, G, I, L, S, T, M, V, N, Q, F, W, Y, P, or C; S199 replaced with D, E, H, K, R, N, Q, F, W, Y, P, or C; R200 replaced with D, E, A, G, I, L, S, T, M, V, N, Q, F, W, Y, P, or C; P201 replaced with D, E, H, K, R, A, G, I, L, S, T, M, V, N, Q, F, W, Y, or C; R202 replaced with D, E, A, G, I, L, S, T, M, V, N, Q, F, W, Y, P, or C; Q203 replaced with D, E, H, K, R, A, G, I, L, S, T, M, V, F, W, Y, P, or C; S204 replaced with D, E, H, K, R, N, Q, F, W, Y, P, or C; P205 replaced with D, E, H, K, R, A, G, I, L, S, T, M, V, N, Q, F, W, Y, or C; A206 replaced with D, E, H, K, R, N, Q, F, W, Y, P, or C; K207 replaced with D, E, A, G, I, L, S, T, M, V, N, Q, F, W, Y, P, or C; S208 replaced with D, E, H, K, R, N, Q, F, W, Y, P, or C; S209 replaced with D, E, H, K, R, N, Q, F, W, Y, P, or C; Q210 replaced with D, E, H, K, R, A, G, I, L, S, T, M, V, F, W, Y, P, or C; D211 replaced with H, K, R, A, G, I, L, S, T, M, V, N, Q, F, W, Y, P, or C; H212 replaced with D, E, A, G, I, L, S, T, M, V, N, Q, F, W, Y, P, or C; A213 replaced with D, E, H, K, R, N, Q, F, W, Y, P, or C; M214 replaced with D, E, H, K, R, N, Q, F, W, Y, P, or C; E215 replaced with H, K, R, A, G, I, L, S, T, M, V, N, Q, F, W, Y, P, or C; A216 replaced with D, E, H, K, R, N, Q, F, W, Y, P, or C; G217 replaced with D, E, H, K, R, N, Q, F, W, Y, P, or C; S218 replaced with D, E, H, K, R, N, Q, F, W, Y, P, or C; P219 replaced with D, E, H, K, R, A, G, I, L, S, T, M, V, N, Q, F, W, Y, or C; V220 replaced with D, E, H, K, R, N, Q, F, W, Y, P, or C; S221 replaced with D, E, H, K, R, N, Q, F, W, Y, P, or C; T222 replaced with D, E, H, K, R, N, Q, F, W, Y, P, or C; S223 replaced with D, E, H, K, R, N, Q, F, W, Y, P, or C; P224 replaced with D, E, H, K, R, A, G, I, L, S, T, M, V, N, Q, F, W, Y, or C; E225 replaced with H, K, R, A, G, I, L, S, T, M, V, N, Q, F, W, Y, P, or C; P226 replaced with D, E, H, K, R, A, G, I, L, S, T, M, V, N, Q, F, W, Y, or C; V227 replaced with D, E, H, K, R, N, Q, F, W, Y, P, or C; E228 replaced with H, K, R, A, G, I, L, S, T, M, V, N, Q, F, W, Y, P, or C; T229 replaced with D, E, H, K, R, N, Q, F, W, Y, P, or C; C230 replaced with D, E, H, K, R, A, G, I, L, S, T, M, V, N, Q, F, W, Y, or P; S231 replaced with D, E, H, K, R, N, Q, F, W, Y, P, or C; F232 replaced with D, E, H, K, R, N, Q, A, G, I, L, S, T, M, V, P, or C; C233 replaced with D, E, H, K, R, A, G, I, L, S, T, M, V, N, Q, F, W, Y, or P; F234 replaced with D, E, H, K, R, N, Q, A, G, I, L, S, T, M, V, P, or C; P235 replaced with D, E, H, K, R, A, G, I, L, S, T, M, V, N, Q, F, W, Y, or C; E236 replaced with H, K, R, A, G, I, L, S, T, M, V, N, Q, F, W, Y, P, or C; C237 replaced with D, E, H, K, R, A, G, I, L, S, T, M, V, N, Q, F, W, Y, or P; R238 replaced with D, E, A, G, I, L, S, T, M, V, N, Q, F, W, Y, P, or C; A239 replaced with D, E, H, K, R, N, Q, F, W, Y, P, or C; P240 replaced with D, E, H, K, R, A, G, I, L, S, T, M, V, N, Q, F, W, Y, or C; T241 replaced with D, E, H, K, R, N, Q, F, W, Y, P, or C; Q242 replaced with D, E, H, K, R, A, G, I, L, S, T, M, V, F, W, Y, P, or C; E243 replaced with H, K, R, A, G, I, L, S, T, M, V, N, Q, F, W, Y, P, or C; S244 replaced with D, E, H, K, R, N, Q, F, W, Y, P, or C; A245 replaced with D, E, H, K, R, N, Q, F, W, Y, P, or C; V246 replaced with D, E, H, K, R, N, Q, F, W, Y, P, or C; T247 replaced with D, E, H, K, R, N, Q, F, W, Y, P, or C; P248 replaced with D, E, H, K, R, A, G, I, L, S, T, M, V, N, Q, F, W, Y, or C; G249 replaced with D, E, H, K, R, N, Q, F, W, Y, P, or C; T250 replaced with D, E, H, K, R, N, Q, F, W, Y, P, or C; P251 replaced with D, E, H, K, R, A, G, I, L, S, T, M, V, N, Q, F, W, Y, or C; D252 replaced with H, K, R, A, G, I, L, S, T, M, V, N, Q, F, W, Y, P, or C; P253 replaced with D, E, H, K, R, A, G, I, L, S, T, M, V, N, Q, F, W, Y, or C; T254 replaced with D, E, H, K, R, N, Q, F, W, Y, P, or C; C255 replaced with D, E, H, K, R, A, G, I, L, S, T, M, V, N, Q, F, W, Y, or P; A256 replaced with D, E, H, K, R, N, Q, F, W, Y, P, or C; G257 replaced with D, E, H, K, R, N, Q, F, W, Y, P, or C; R258 replaced with D, E, A, G, I, L, S, T, M, V, N, Q, F, W, Y, P, or C; W259 replaced with D, E, H, K, R, N, Q, A, G, I, L, S, T, M, V, P, or C; G260 replaced with D, E, H, K, R, N, Q, F, W, Y, P, or C; C261 replaced with D, E, H, K, R, A, G, I, L, S, T, M, V, N, Q, F, W, Y, or P; H262 replaced with D, E, A, G, I, L, S, T, M, V, N, Q, F, W, Y, P, or C; T263 replaced with D, E, H, K, R, N, Q, F, W, Y, P, or C; R264 replaced with D, E, A, G, I, L, S, T, M, V, N, Q, F, W, Y, P, or C; T265 replaced with D, E, H, K, R, N, Q, F, W, Y, P, or C; T266 replaced with D, E, H, K, R, N, Q, F, W, Y, P, or C; V267 replaced with D, E, H, K, R, N, Q, F, W, Y, P, or C; L268 replaced with D, E, H, K, R, N, Q, F, W, Y, P, or C; Q269 replaced with D, E, H, K, R, A, G, I, L, S, T, M, V, F, W, Y, P, or C; P270 replaced with D, E, H, K, R, A, G, I, L, S, T, M, V, N, Q, F, W, Y, or C; C271 replaced with D, E, H, K, R, A, G, I, L, S, T, M, V, N, Q, F, W, Y, or P; P272 replaced with D, E, H, K, R, A, G, I, L, S, T, M, V, N, Q, F, W, Y, or C; H273 replaced with D, E, A, G, I, L, S, T, M, V, N, Q, F, W, Y, P, or C; 1274 replaced with D, E, H, K, R, N, Q, F, W, Y, P, or C; P275 replaced with D, E, H, K, R, A, G, I, L, S, T, M, V, N, Q, F, W, Y, or C; D276 replaced with H, K, R, A, G, I, L, S, T, M, V, N, Q, F, W, Y, P, or C; S277 replaced with D, E, H, K, R, N, Q, F, W, Y, P, or C; G278 replaced with D, E, H, K, R, N, Q, F, W, Y, P, or C; L279 replaced with D, E, H, K, R, N, Q, F, W, Y, P, or C; G280 replaced with D, E, H, K, R, N, Q, F, W, Y, P, or C; 1281 replaced with D, E, H, K, R, N, Q, F, W, Y, P, or C; V282 replaced with D, E, H, K, R, N, Q, F, W, Y, P, or C; C283 replaced with D, E, H, K, R, A, G, I, L, S, T, M, V, N, Q, F, W, Y, or P; V284 replaced with D, E, H, K, R, N, Q, F, W, Y, P, or C; P285 replaced with D, E, H, K, R, A, G, I, L, S, T, M, V, N, Q, F, W, Y, or C; A286 replaced with D, E, H, K, R, N, Q, F, W, Y, P, or C; Q287 replaced with D, E, H, K, R, A, G, I, L, S, T, M, V, F, W, Y, P, or C; E288 replaced with H, K, R, A, G, I, L, S, T, M, V, N, Q, F, W, Y, P, or C; G289 replaced with D, E, H, K, R, N, Q, F, W, Y, P, or C; G290 replaced with D, E, H, K, R, N, Q, F, W, Y, P, or C; P291 replaced with D, E, H, K, R, A, G, I, L, S, T, M, V, N, Q, F, W, Y, or C; G292 replaced with D, E, H, K, R, N, Q, F, W, Y, P, or C; and/or A293 replaced with D, E, H, K, R, N, Q, F, W, Y, P, or C. Polynucleotides encoding these polypeptides are also encompassed by the invention. The resulting TR17 proteins of the invention may be routinely screened for TR17 functional activities and/or physical properties (such as, for example, enhanced or reduced stability and/or solubility) described throughout the specification and known in the art. Preferably, the resulting proteins of the invention have an increased and/or a decreased TR17 functional activity. More preferably, the resulting TR17 proteins of the invention have more than one increased and/or decreased TR17 functional activity and/or physical property.

To improve or alter the characteristics of TR17 polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al, *Gene* 34:315 (1985)), restriction selection mutagenesis (see e.g., Wells et al, *Philos. Trans. R. Soc. London SerA* 317:415 (1986)).

Thus, the invention also encompasses TR17 derivatives and analogs that have one or more amino acid residues deleted, added, or substituted to generate TR17 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the TR17 polypeptides of the invention, and/or an amino acid deletion at the second position of any one or more such recognition sequences will prevent glycosylation of the TR17 at the modified tripeptide sequence (see, e.g., Miyajimo et al., *EMBO J* 5(6):1193–1197). Additionally, one or more of the amino acid residues of the polypeptides of the invention (e.g., arginine and lysine residues) may be deleted or substituted with another residue to eliminate undesired processing by proteases such as, for example, furins or kexins.

The polypeptides of the present invention include a polypeptide comprising, or alternatively, consisting of a polypeptide comprising, or alternatively, consisting of amino acids from about 1 to about 293 in FIG. 1 (SEQ ID NO:2); a polypeptide comprising, or alternatively, consisting of amino acids from about 2 to about 293 in FIG. 1 (SEQ ID NO:2); a polypeptide comprising, or alternatively, consisting of the TR17 extracellular domain; a polypeptide comprising, or alternatively, consisting of the TR17 cysteine rich domain; a polypeptide comprising, or alternatively, consisting of the TR17 transmembrane domain; a polypeptide comprising, or alternatively, consisting of the intracellular domain of TR17; and a polypeptide comprising, or alternatively, consisting of the TR17 extracellular domain and one of the TR17 intracellular domains with all or part of the transmembrane domain deleted; as well as polypeptides which are at least 80% identical, more preferably at least 90% or 95% identical, still more preferably at least 96%, 97%, 98%, 99% or 100% identical to the polypeptides described above (e.g., the polypeptide of FIG. 1 (SEQ ID NO:2)), and also include portions of such polypeptides with at least 30 amino acids and more preferably at least 50 or at least 100 amino acids. Polynucleotides encoding these polypeptides are also encompassed by the invention.

By a polypeptide having an amino acid sequence at least, for example, 95% "identical" to a reference amino acid sequence of a TR17 polypeptide is intended that the amino acid sequence of the polypeptide is identical to the reference sequence except that the polypeptide sequence may include up to five amino acid alterations per each 100 amino acids of the reference amino acid of the TR17 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98%, or 99% identical to, for instance, the amino acid sequence shown in FIG. 1 (SEQ ID NO:2), can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

In additional embodiments, polynucleotides of the invention comprise, or alternatively consist of, a polynucleotide sequence at least 90%, 95%, 96%, 97%, 98%, 99% or 100% identical to the polynucleotide sequence encoding one or more of the extracellular cysteine rich motifs of TR17 disclosed in FIG. 1 (amino acid residues from 33 to 66 and/or 70 to 104). In another embodiment, the invention provides an isolated nucleic acid molecule comprising a polynucleotide which hybridizes under stringent hybridization conditions to DNA complementary to the polynucleotide sequence encoding one, or both of the TR17 extracellular cysteine rich motifs. The present invention also encompasses the above polynucleotide/nucleic acid sequences fused to a heterologous polynucleotide sequence. Polypeptides encoded by these nucleic acids and/or polynucleotide sequences are also encompassed by the invention.

The present application is also directed to proteins cotaining polypeptides at least 90%, 95%, 96%, 97%, 98% or 99% identical to the TR17 polypeptide sequence set forth as $n^1$–$m^1$, and/or $n^2$–$m^-$ herein. In preferred embodiments, the application is directed to proteins containing polypeptides at least 90%, 95%, 96%, 97%, 98% or 99% identical to polypeptides having the amino acid sequence of the specific TR17 N- and C-terminal deletions recited herein. Polynucleotides encoding these polypeptides are also encompassed by the invention.

In certain preferred embodiments, TR17 proteins of the invention comprise fusion proteins as described above wherein the TR17 polypeptides are those described as $n^1$–$m^1$, and/or $n^2$–$m^1$ herein. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

Antibodies

Further polypeptides of the invention relate to antibodies and T-cell antigen receptors (TCR) which immunospecifically bind a TR17 polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In specific embodiments, the immunoglobulin molecules of the invention are IgG1. In other specific embodiments, the immunoglobulin molecules of the invention are IgG4.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$M, $5 \times 10^{-7}$ M, $10^{-7}$ M, $5 \times 10^{-8}$ M, or $10^{-8}$ M. Even more preferred binding affinities include those with a dissociation constant or Kd less than $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein (e.g., amino acid residues 5 to 11, 33 to 36, 57 to 60, 72 to 78, 105 to 110, 115 to 134, 140 to 148, 186 to 216, 222 to 228, 238 to 244, 252 to 255 and 286 to 290), or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting activation of the transcription factors NF-AT, AP-1, and/or NF-kappaB using techniques known in the art, and/or the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody. In other specific embodiments, antibodies are provided that promote ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization and/or aggregation (i.e., via antibody cross-linking) of the receptor (i.e., TR17). The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161(4):1786–1794 (1998); Zhu et al., Cancer Res. 58(15):3209–3214 (1998); Yoon et al., J. Immunol. 160(7):3170–3179 (1998); Prat et al., J. Cell. Sci. 111(Pt2):237–247 (1998); Pitard et al., J. Immunol. Methods 205(2):177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

By way of another non-limiting example, antibodies of the invention may be administered to individuals as a form of passive immunization. Alternatively, antibodies of the present invention may be used for epitope mapping to identify the epitope(s) bound by the antibody. Epitopes identified in this way may, in turn, for example, be used as vaccine candidates, i.e., to immunize an individual to elicit antibodies against the naturally occuring forms of TR17.

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum.* Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 2). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Protocols for generating EBV-transformed B cell lines are commonly known in the art, such as, for example, the protocol outlined in Chapter 7.22 of Current Protocols in Immunology, Coligan et al., Eds., 1994, John Wiley & Sons, NY, which is hereby incorporated in its entirety by reference herein. The source of B cells for transformation is commonly human peripheral blood, but B cells for transformation may also be derived from other sources including, but not limited to, lymph nodes, tonsil, spleen, tumor tissue, and infected tissues. Tissues are generally made into single cell suspensions prior to EBV transformation. Investigators may also choose to perform selection procedures that will enrich the sample for B cells that are antigen-reactive. For example, one method of enriching for antigen-reactive B cells is panning on a plastic dish that has been coated with antigen. Antigen reactive B cells may then be eluted from the plastic dish and used for transformation. Alternatively, it is possible to enrich for antigen-reactive B cells using fluorescence activated cells sorting (FACS). In this method, one might use fluorescently labelled antigen to sort out a population of antigen reactive B-cells from non-antigen reactive B cells an other cells types. Both FACS analysis and panning, may also be performed ina manner so as to enrich for B cells as opposed to antigen-reactive B cells. The advantage of selecting for total B cells populations is that one is more likely to include plasma cells, or B cells actively secreteing immunoglobulin, that might be missed in procedures that require the presence of cell-surface immunoglobulin for detection. Growth of EBV-infected cells is promoted by monocytes, so investigators may wish to take care not to exclude these form culture, or to resupply monocytes after selection procedures. Additionally, steps may be taken to either physically remove or inactivate T cells (e.g., by treatment with cyclosporin A) in B cell-containing samples, because T cells from individuals seropositive for anti-EBV antibodies can suppress B cell immortalization by EBV.

In general, the sample containing human B cells is innoculated with EBV, and cultured for 3–4 weeks. A typical source of EBV is the culture supernatant of the B95-8 cell line (ATCC #VR-1492). Physical signs of EBV transformation can generally be seen towards the end of the 3–4 week culture period. By phase-contrast microscopy, transformed cells may appear large, clear, hairy and tend to aggregate in tight clusters of cells. Initially, EBV lines are generally polyclonal. However, over prolonged periods of cell cultures, EBV lines may become monoclonal or polyclonal as a result of the selective outgrowth of particular B cell clones. Alternatively, polyclonal EBV transformed lines may be subcloned (e.g., by limiting dilution culture) or fused with a suitable fusion partner and plated at limiting dilution to obtain monoclonal B cell lines. Suitable fusion partners for EBV transformed cell lines include mouse myeloma cell lines (e.g., SP2/0, X63-Ag8.653), heteromyeloma cell lines (human x mouse; e.g, SPAM-8, SBC-H20, and CB-F7), and human cell lines (e.g., GM 1500, SKO-007, RPMI 8226, and KR-4). Thus, the present invention also provides a method of generating polyclonal or monoclonal human antibodies against polypeptides of the invention or fragments thereof, comprising EBV-transformation of human B cells.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5):4 89–498 (1991); Studnicka et al., Protein Engineering 7(6): 805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby activate or block its biological activity.

Intrabodies of the invention can be produced using methods known in the art, such as those disclosed and reviewed in Chen et al., *Hum. Gene Ther.* 5:595–601 (1994); Marasco, W. A., *Gene Ther.* 4:11–15 (1997); Rondon and Marasco, *Annu. Rev. Microbiol.* 51:257–283 (1997); Proba et al., *J. Mol. Biol.* 275:245–253 (1998); Cohen et al., *Oncogene* 17:2445–2456 (1998); Ohage and Steipe, *J. Mol. Biol.* 291:1119–1128 (1999); Ohage et al., *J. Mol. Biol.* 291:1129–1134 (1999); Wirtz and Steipe, *Protein Sci.* 8:2245–2250 (1999); Zhu et al., *J. Immunol. Methods* 231:207–222 (1999); and references cited therein. In particular, a CCR5 intrabody has been produced by Steinberger et al., *Proc. Natl. Acad. Sci. USA* 97:805–810 (2000).

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a TR17 polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608

(1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques. Methods of producing antibodies include, but are not limited to, hybridoma technology, EBV transformation, and other methods discussed herein as well as through the use recombinant DNA technology, as discussed below.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli*, *B. subtilis*) transformed with recombinant bacteriophage DNA, plasmid DNA or cosmid DNA expression vectors containing antibody coding sequences; yeast (e.g., *Saccharomyces*, *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (ACNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt- cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5) :155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availabilty of cell lines (e.g., the murine myeloma cell line, NS0) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. Vectors that use glutamine synthase as the selectable marker include, but are not limited to, the pEE6 expression vector described in Stephens and Cockett, Nucl. Acids. Res 17:7110 (1989). A glutamine synthase expression system and components thereof are detailed in PCT publications: WO87/04462; WO86/05807; WO89/01036; WO89/10404; and WO91/06657 which are incorporated in their entireties by reference herein. Additionally, glutamine synthase expression vectors that may be used according to the present invention are commercially available from suplliers, including, for example Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are incorporated in their entirities by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a TR17 polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon (133Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators useful for conjugating radiometal ions, including but not limited to, $^{177}$Lu, $^{90}$Y, $^{166}$Ho, $^{111}$In and $^{153}$Sm, to polypeptides. In a preferred embodiment, the radiometal ion associated with the macrocyclic chelators attached to polypeptides of the invention is $^{111}$In. In another preferred embodiment, the radiometal ion associated with the macrocyclic chelator attached to polypeptides of the invention is $^{90}$Y. In specific embodiments, the macrocyclic chelator is 1,4,7,10-tetraazacyclododecane-N,N',N",N'"-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483–90, 1998; Peterson et al., Bioconjug. Chem. 10(4):553–7, 1999; and Zimmerman et al, Nucl. Med. Biol. 26(8):943–50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), CD40-ligand, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein).

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein.

For example, antibody antagonists of the invention may be used to treat, inhibit or prevent autoimmune diseases, disorders, or conditions associated with such diseases or disorders, including, but not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders).

In a specific embodiment, antibodies of the invention are be used to treat, inhibit, prognose, diagnose or prevent rheumatoid arthritis. In another embodiment, antibodies of the invention are be used to treat, inhibit, prognose, diagnose or prevent advanced rheumatoid arthritis.

In another specific embodiment, antibodies of the invention are used to treat, inhibit, prognose, diagnose or prevent systemic lupus erythematosis.

In other embodiments, antibody agonists of the invention are be used to treat, inhibit or prevent immunodeficiencies, and/or disorders, or conditions associated with immunodeficiencies. Such immunodeficiencies include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

In another specific embodiment, antibodies of the invention are used to treat, inhibit, prognose, diagnose or prevent CVID, or a subgroup of individuals having CVID.

In another specific embodiment, antibody agonists of the invention are used as an adjuvant to stimulate B cell proliferation, immunoglobulin production, and/or to enhance B cell survival.

The treatment and/or prevention of diseases, disorders, or conditions associated with aberrant expression and/or activity of a polypeptide of the invention includes, but is not limited to, alleviating symptoms associated with those diseases, disorders or conditions. The antibodies of the invention may also be used to target and kill cells expressing TR17 on their surface (e.g., cells of B cell and/or T cell lineage) and/or cells having TR17 bound to their surface (e.g., cells of monocytic lineage). Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{8}$ M, $10^{-8}$ M, $5\times10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5) :155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an inununoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. Diagnosis and Imaging Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell . Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the Patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Immune System-Related Disorder Diagnosis

TR17 is expressed in spleen, small intestine, thymus, and peripheral blood lymphocytes. For a number of immune system-related disorders, substantially altered (increased or decreased) levels of TR17 gene expression can be detected in immune system tissue or other cells or bodily fluids (e.g., sera, plasma, urine, synovial fluid or spinal fluid) taken from an individual having such a disorder, relative to a "standard" TR17 gene expression level, that is, the TR17 expression level in immune system tissues or bodily fluids from an individual not having the immune system disorder. Thus, the invention provides a diagnostic method useful during diagnosis of an immune system disorder, which involves measuring the expression level of the gene encoding the TR17 polypeptide in immune system tissue or other cells or body fluid from an individual and comparing the measured gene expression level with a standard TR17 gene expression level, whereby an increase or decrease in the gene expression level compared to the standard is indicative of an immune system disorder or normal activation, proliferation, differentiation, and/or death.

In particular, it is believed that certain tissues in mammals with cancer of cells or tissue of the immune system express significantly enhanced or reduced levels of the TR17 polypeptide and mRNA encoding the TR17 polypeptide when compared to a corresponding "standard" level. Further, it is believed that enhanced or depressed levels of the TR17 polypeptide can be detected in certain body fluids (e.g., sera, plasma, urine, and spinal fluid) or cells or tissue from mammals with such a cancer when compared to sera from mammals of the same species not having the cancer.

For example, as disclosed herein, TR17 is highly expressed primarily in cells of B cell lineage. Accordingly, polynucleotides of the invention (e.g., polynucleotide sequences complementary to all or a portion of TR17 mRNA) and antibodies (and antibody fragments) directed against the polypeptides of the invention may be used to quantitate or qualitate concentrations of cells of B cell lineage (e.g., B cell leukemia and lymphoma cells) expressing TR17 on their cell surfaces. These antibodies additionally have diagnostic applications in detecting abnormalities in the level of TR17 gene expression, or abnormalities in the structure and/or temporal, tissue, cellular, or subcellular location of TR17. These diagnostic assays may be performed in vivo or in vitro, such as, for example, on blood samples, biopsy tissue or autopsy tissue.

Additionally, as disclosed herein, the TR17 ligand, Neutrokine-alpha, is expressed primarily on cells of monocytic lineage. Accordingly, TR17 polypeptides of the invention (including labeled TR17 polypeptides and TR17 fusion proteins), and anti-TR17 antibodies (including anti-TR17 antibody fragments) against the polypeptides of the invention may be used to quantitate or qualitate concentrations of cells of monocytic lineage (e.g., monocyte cell lineage related leukemias or lymphomas) expressing Neutrokine-alpha on their cell surfaces. These TR17 polypeptides and antibodies additionally have diagnostic applications in detecting abnormalities in the level of Neutrokine-alpha gene expression, or abnormalities in the structure and/or temporal, tissue, cellular, or subcellular location of Neutrokine-allpha and/or diagnosing activity/defects in signalling pathways associated with TR17. These diagnostic assays may be performed in vivo or in vitro, such as, for example, on blood samples or biopsy tissue using techniques described herein or otherwise known in the art.

In one embodiment, TR17 polynucleotides or polypeptides or TR17 agonists (e.g., anti-TR17 antibodies) or antagonists (e.g., anti-TR17 antibodies) of the invention are used to treat, prevent, diagnose, or prognose an individual having an immunodeficiency.

Immunodeficiencies that may be treated, prevented, diagnosed, and/or prognosed with the TR17 polynucleotides or polypeptides or TR17 agonists (e.g., anti-TR17 antibodies) or antagonists (e.g., anti-TR17 antibodies) of the invention, include, but are not limited to, one or more immunodeficiencies selected from: severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), chronic granulomatous disease, Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

According to this embodiment, an individual having an immunodeficiency expresses aberrantly low levels of TR17 when compared to an individual not having an immunodeficiency. Any means described herein or otherwise known in the art may be applied to detect TR17 polynucleotides or polypeptides of the invention (e.g., FACS analysis or ELISA detection of TR17 polypeptides of the invention and hybridization or PCR detection of TR17 polynucleotides of the invention) and to determine the expression profile of TR17, polynucleotides and/or polypeptides of the invention in a biological sample.

A biological sample of a person afflicted with an immunodeficiency is characterized by low levels of expression of TR17 when compared to that observed in individuals not having an immunodeficiency. Thus, TR17 polynucleotides and/or polypeptides of the invention, and/or agonists or antagonists thereof, may be used according to the methods of the invention in the diagnosis and/or prognosis of an immunodeficiency. For example, a biological sample obtained from a person suspected of being afflicted with an immunodeficiency ("the subject") may be analyzed for the relative expression level(s) of TR17 polynucleotides and/or polypeptides of the invention. The expression level(s) of one or more of these molecules of the invention is (are) then compared to the expression level(s) of the same molecules of the invention as expressed in a person known not to be afflicted with an immunodeficiency. A significant difference in expression level(s) of TR17, polynucleotides and/or polypeptides of the invention, and/or agonists and/or antagonists thereof, between samples obtained from the subject and the control suggests that the subject is afflicted with an immunodeficiency.

In another embodiment, TR17 polynucleotides or polypeptides or TR17 agonists (e.g., anti-TR17 antibodies) or antagonists (e.g., anti-TR17 antibodies) of the invention are used to treat, diagnose and/or prognose an individual having common variable immunodeficiency disease ("CVID"; also known as "acquired agammaglobulinemia" and "acquired hypogammaglobulinemia") or a subset of this disease. According to this embodiment, an individual having CVID or a subset of individuals having CVID expresses aberrant levels of Neutrokine-alpha, APRIL, and/or TR17 on their B cells and/or monocytes, when compared to individuals not having CVID. Any means described herein or otherwise known in the art may be applied to detect TR17 polynucleotides or polypeptides of the invention (e.g., FACS analysis or ELISA detection of TR17 polypeptides of the invention and hybridization or PCR detection of TR17 polynucleotides of the invention) and to determine differentially the expression profile of TRl7 polynucleotides or polypeptides of the invention in a sample containing at least monocyte cells or some component thereof (e.g., RNA) as compared to a sample containing at least B cells or a component thereof (e.g., RNA). In the instance where a sample containing at least monocyte cells or some component thereof (e.g., RNA) is determined to reflect TR17 ligand (e.g., Neutrokine-alpha and/or APRIL) polynucleotide or polypeptide expression and a sample containing at least B cells or a component thereof (e.g., RNA) is determined to reflect less than normal levels of TR17 polynucleotide or polypeptide expression, the samples may be correlated with the occurrence of CVID (i.e., "acquired agammaglobulinemia" or "acquired hypogammaglobulinemia").

A subset of persons afflicted with CVID are characterized by high levels of expression of both TR17 ligand (e.g., Neutrokine-alpha and/or APRIL) and TR17 in peripheral or circulating B cells when compared to that observed in individuals not having CVID. In contrast, persons who are not afflicted with CVID are typically characterized by low levels of TR17 ligand (e.g., Neutrokine-alpha and/or APRIL) expression and high levels of TR17 expression in peripheral or circulating B cells. Thus, TR17 polypeptides, polynucleotides and/or polypeptides of the invention, and/or agonists or antagonists thereof, may be used according to the methods of the invention in the differential diagnosis of this subset of CVID. For example, a sample of peripherial B cells obtained from a person suspected of being afflicted with CVID ("the subject") may be analyzed for the relative expression level(s) of TR17 ligand (e.g., Neutrokine-alpha and/or APRIL), and/or TR17 polynucleotides and/or polypeptides of the invention. The expression level(s) of one or more of these molecules of the invention is (are) then compared to the expression level(s) of the same molecules of the invention as expressed in a person known not to be afflicted with CVID ("the control"). A significant difference in expression level(s) of TR17 ligand (e.g., Neutrokine-alpha and/or APRIL) and/or TR17 polynucleotides or polypeptides of the invention, and/or agonists and/or antagonists thereof, between samples obtained from the subject and the control suggests that the subject is afflicted with this subset of CVID.

Cunningham-Rundles and Bodian followed 248 CVID patients over a period of 1–25 years and discovered that a number of associated diseases or conditions appear with increased frequency in CVID patients (Cunningham-Rundles and Bodian, *J. Clin. Immunol.*, 92:34–48 (1999) which is herein incorporated by reference in its entirety.) The most important clinical events include infections, autoimmunity, inflammatory disorders, marked by gastrointestinal and granulomatous disease, cancer and hepatitis. Most CVID patients are at increased risk of recurrent infections particularly of the respiratory tract. The types of acute and recurring bacterial infections exhibited in most patients include pneumonia, bronchitis and sinusitis. Children with CVID have a marked increased risk of otitis media. Additionally, blood borne infections including sepsis, meningitis, septic arthritis, and osteomyelitis are seen with increased frequency in these patients.

In another specific embodiment, TR17 polynucleotides or polypeptides, or agonists or antagonists thereof (e.g., anti-TR17 antibodies) are used to diagnose, prognose, treat, or prevent conditions associated with CVID, including, but not limited to, conditions associated with acute and recurring infections (e.g., pneumonia, bronchitis, sinusitis, otitis media, sepsis, meningitis, septic arthritis, and osteomyelitis), chronic lung disease, autoimmunity, granulomatous disease, lymphoma, cancers (e.g., cancers of the breast, stomach, colon, mouth, prostate, lung, vagina, ovary, skin, and melanin forming cells (i.e. melanoma), inflammatory bowel disease (e.g., Crohn's disease, ulcerative colitis, and ulcerative proctitis), malabsoption, Hodgkin's disease, and Waldenstrom's macroglobulinemia.

In a specific embodiment, TR17 polynucleotides or polypeptides, or agonists or antagonists thereof (e.g., anti-TR17 antibodies) are used to diagnose, prognose, treat, or prevent a disorder characterized by deficient serum immunoglobulin production, recurrent infections, and/or immune system dysfunction. Moreover, TR17 polynucleotides or polypeptides, or agonists or antagonists thereof (e.g., anti-TR17 antibodies) may be used to diagnose, prognose, treat, or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pneumocystis carnii.

In another embodiment, TR17 polynucleotides or polypeptides or TR17 agonists (e.g., anti-TR17 antibodies) or antagonists (e.g., anti-TR17 antibodies) of the invention are used to treat, diagnose, or prognose an individual having an autoimmune disease or disorder.

Autoimmune diseases or disorders that may be treated, diagnosed, or prognosed using TR17 polynucleotides or polypeptides or TR17 agonists (e.g., anti-TR17 antibodies) or antagonists (e.g., anti-TR17 antibodies) of the invention include, but are not limited to, one or more of the following: autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitus, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dernatitis, asthma, inflammatory myopathies, and other inflammatory, granulamatous, degenerative, and atrophic disorders.

According to this embodiment, an individual having an autoimmune disease or disorder expresses aberrantly high levels of TR17 ligand (e.g., Neutrokine-alpha), and/or TR17 when compared to an individual not having an autoimmune disease or disorder. Any means described herein or otherwise known in the art may be applied to detect TR17 polynucleotides or polypeptides of the invention (e.g., FACS analysis or ELISA detection of TR17 polypeptides of the invention and hybridization or PCR detection of TR17 polynucleotides of the invention) and to determine the expression profile of TR17, polynucleotides and/or polypeptides of the invention in a biological sample.

A biological sample of persons afflicted with an autoimmune disease or disorder is characterized by high levels of expression of TR17 when compared to that observed in individuals not having an autoimmune disease or disorder. Thus, TR17 polynucleotides and/or polypeptides of the invention, and/or agonists or antagonists thereof, may be used according to the methods of the invention in the diagnosis and/or prognosis of an autoimmune disease or disorder. For example, a biological sample obtained from a person suspected of being afflicted with an autoimmune disease or disorder ("the subject") may be analyzed for the relative expression level(s) of TR17 polynucleotides and/or polypeptides of the invention. The expression level(s) of one or more of these molecules of the invention is (are) then compared to the expression level(s) of the same molecules of the invention as expressed in a person known not to be afflicted with an autoimmune disease or disorder. A significant difference in expression level(s) of TR17, polynucleotides and/or polypeptides of the invention, and/or agonists and/or antagonists thereof, between samples obtained from the subject and the control suggests that the subject is afflicted with an autoimmune disease or disorder.

In another embodiment, TR17 polynucleotides or polypeptides or TR17 agonists (e.g., anti-TR17 antibodies)

or antagonists (e.g., anti-TR17 antibodies) of the invention are used to treat, diagnose, or prognose an individual having systemic lupus erythematosus or a subset of this disease. According to this embodiment, an individual having systemic lupus erythematosus or a subset of individuals having systemic lupus erythematosus expresses aberrantly high levels of TR17 when compared to an individual not having systemic lupus erythematosus or this subset of systemic lupus erythematosus. Any means described herein or otherwise known in the art may be applied to detect TR17 polynucleotides or polypeptides of the invention (e.g., FACS analysis or ELISA detection of TR17 polypeptides of the invention and hybridization or PCR detection of TR17 polynucleotides of the invention) and to determine the expression profile of TR17, polynucleotides and/or polypeptides of the invention in a biological sample.

A biological sample of persons afflicted with systemic lupus erythematosus is characterized by high levels of expression of TR17 when compared to that observed in individuals not having systemic lupus erythematosus. Thus, TR17 polynucleotides and/or polypeptides of the invention, and/or agonists or antagonists thereof, may be used according to the methods of the invention in the diagnosis and/or prognosis of systemic lupus erythematosus or a subset of systemic lupus erythematosus. For example, a biological sample obtained from a person suspected of being afflicted with systemic lupus erytheamatosus ("the subject") may be analyzed for the relative expression level(s) of TR17 polynucleotides and/or polypeptides of the invention. The expression level(s) of one or more of these molecules of the invention is (are) then compared to the expression level(s) of the same molecules of the invention as expressed in a person known not to be afflicted with systemic lupus erythematosus. A significant difference in expression level(s) of TR17, polynucleotides and/or polypeptides of the invention, and/or agonists (e.g., agonistic antibodies) and/or antagonists thereof, between samples obtained from the subject and the control suggests that the subject is afflicted with systemic lupus erythematosus or a subset thereof.

Furthermore, there is a direct correlation between the severity of systemic lupus erythematosus, or a subset of this disease, and the concentration of TR17 polynucleotides (RNA) and/or polypeptides of the invention. Thus, TR17 polynucleotides, (RNA), polypeptides and/or agonists or antagonists of the invention, may be used according to the methods of the invention in prognosis of the severity of systemic lupus erythematosus or a subset of systemic lupus erythematosus. For example, a biological sample obtained from a person suspected of being afflicted with systemic lupus erythematosus ("the subject") may be analyzed for the relative expression level(s) of TR17 polynucleotides and/or polypeptides of the invention. The expression level(s) of one or more of these molecules of the invention is (are) then compared to the expression level(s) of the same molecules of the invention as expressed in a panel of persons known to represent a range in severities of this disease. According to this method, the match of expression level witht a characterized member of the panel indicates the severity of the disease.

In another embodiment, TR17 polynucleotides or polypeptides or TR17 agonists (e.g., anti-TR17 antibodies) or antagonists (e.g., anti-TR17 antibodies) of the invention are used to treat, diagnose, or prognose an individual having rheumatoid arthritis or a subset of this disease. According to this embodiment, an individual having rheumatoid arthritis or a subset of individuals having rheumatoid arthritis expresses aberrantly high levels of TR17 when compared to an individual not having rheumatoid arthritis or this subset of rheumatoid arthritis. Any means described herein or otherwise known in the art may be applied to detect TR17 polynucleotides or polypeptides of the invention (e.g., FACS analysis or ELISA detection of TR17 polypeptides of the invention and hybridization or PCR detection of TR17 polynucleotides of the invention) and to determine the expression profile of TR17, polynucleotides and/or polypeptides of the invention in a biological sample.

A biological sample of persons afflicted with rheumatoid arthritis is characterized by high levels of expression of TR17 when compared to that observed in individuals not having rheumatoid arthritis. Thus, TR17 polynucleotides and/or polypeptides of the invention, and/or agonists or antagonists thereof, may be used according to the methods of the invention in the diagnosis and/or prognosis of rheumatoid arthritis or a subset of rheumatoid arthritis. For example, a biological sample obtained from a person suspected of being afflicted with rheumatoid arthritis ("the subject") may be analyzed for the relative expression level(s) of TR17 polynucleotides and/or polypeptides of the invention. The expression level(s) of one or more of these molecules of the invention is (are) then compared to the expression level(s) of the same molecules of the invention as expressed in a person known not to be afflicted with rheumatoid arthritis. A significant difference in expression level(s) of TR17, polynucleotides and/or polypeptides of the invention, and/or agonists and/or antagonists thereof, between samples obtained from the subject and the control suggests that the subject is afflicted with rheumatoid arthritis or a subset thereof.

Thus, the invention provides a diagnostic method usefull during diagnosis of a immune system disorder, including cancers of this system, and immunodeficiencies and/or autoimmune diseases which involves measuring the expression level of the gene encoding the TR17 polypeptide in immune system tissue or other cells or body fluid from an individual and comparing the measured gene expression level with a standard TR17 gene expression level, whereby an increase or decrease in the gene expression level compared to the standard is indicative of an immune system disorder.

Where a diagnosis of a disorder in the immune system, including, but not limited to, diagnosis of a tumor, diagnosis of an immunodeficiency, and/or diagnosis of an autoimmune disease, has already been made according to conventional methods, the present invention is useful as a prognostic indicator, whereby patients exhibiting enhanced or depressed TR17 gene expression will experience a worse clinical outcome relative to patients expressing the gene at a level nearer the standard level.

By analyzing or determining the expression level of the gene encoding the TR17 polypeptide is intended qualitatively or quantitatively measuring or estimating the level of the TR17 polypeptide or the level of the mRNA encoding the TR17 polypeptide in a first biological sample either directly (e.g., by determining or estimating absolute protein level or mRNA level) or relatively (e.g., by comparing to the TR17 polypeptide level or mRNA level in a second biological sample). Preferably, the TR17 polypeptide level or mRNA level in the first biological sample is measured or estimated and compared to a standard TR17 polypeptide level or mRNA level, the standard being taken from a second biological sample obtained from an individual not having the disorder or being determined by averaging levels from a population of individuals not having a disorder of the immune system. As will be appreciated in the art, once a standard TR17 polypeptide level or mRNA level is known, it can be used repeatedly as a standard for comparison.

By "biological sample" is intended any biological sample obtained from an individual, body fluid, cell line, tissue culture, or other source which contains TR17 polypeptide or mRNA. As indicated, biological samples include body fluids (such as sera, plasma, urine, synovial fluid and spinal fluid) which contain free extracellular domains of the TR17 polypeptide, immune system tissue, and other tissue sources found to express complete or free extracellular domain of the TR17. Methods for obtaining tissue biopsies and body fluids from mammals are well known in the art. Where the biological sample is to include mRNA, a tissue biopsy is the preferred source.

The compounds of the present invention are useful for diagnosis, prognosis, or treatment of various immune system-related disorders in mammals, preferably humans. Such disorders include, but are not limited to tumors (e.g., B cell and monocytic cell leukemias and lymphomas) and tumor metastasis, infections by bacteria, viruses and other parasites, immunodeficiencies, inflammatory diseases, lymphadenopathy, autoimmune diseases (e.g., rheumatoid arhtritis, systemic lupus erythamatosus, Sjogren syndrome, mixed connective tissue disease, and inflammatory myopathies), and graft versus host disease.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the TR17 polypeptide are then assayed using any appropriate method. These include Northern blot analysis, SI nuclease mapping, the polymerase chain reaction (PCR), reverse transcription in combination with the polymerase chain reaction (RT-PCR), and reverse transcription in combination with the ligase chain reaction (RT-LCR).

Assaying TR17 polypeptide levels in a biological sample can occur using antibody-based techniques. For example, TR17 polypeptide expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting TR17 polypeptide gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, 90Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

The tissue or cell type to be analyzed will generally include those which are known, or suspected, to express the TR17 (such as, for example, cells of B cell lineage and the spleen). The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the TR17 gene.

For example, antibodies, or fragments of antibodies, such as those described herein, may be used to quantitatively or qualitatively detect the presence of TR17 gene products or conserved variants or peptide fragments thereof. This can be accomplished, for example, by immunofluorescence techniques employing a fluorescently labeled antibody coupled with light microscopic, flow cytometric, or fluorimetric detection.

The antibodies (or fragments thereof) or TR17 polypeptides or polypeptides of the present invention may, additionally, be employed histologically, as in immunofluorescence, immunoelectron microscopy or non-immunological assays, for in situ detection of TR17 gene products or conserved variants or peptide fragments thereof, or for TR17 ligand (e.g., Neutrokine-alpha) binding to TR17. In situ detection may be accomplished by removing a histological specimen from a patient, and applying thereto a labeled antibody or TR17 polypeptide of the present invention. The antibody (or fragment) or TR17 polypeptide is preferably applied by overlaying the labeled antibody (or fragment) onto a biological sample. Through the use of such a procedure, it is possible to determine not only the presence of the TR17 gene product, or conserved variants or peptide fragments, or TR17 polypeptide binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for TR17 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying TR17 gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-TR17 antibody or detectable TR17 polypeptide. The solid phase support may then be washed with the buffer a second time to remove unbound antibody or polypeptide. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-TR17 antibody or TR17 polypeptide may be determined according to well-known methods. Those skilled in the art will be able to determine operative and optimal assay conditions for each determination by employing routine experimentation.

In addition to assaying TR17 polypeptide levels or polynucleotide levels in a biological sample obtained from an individual, TR17 polypeptides or polynucleotides can also be detected in vivo by imaging. For example, in one embodiment of the invention, TR17 polypeptide and/or anti-TR17 antibody is used to image B cell lymphomas. In another embodiment, TR17 polypepitdes and/or anti-TR17 antibodies and/or TR17 polynucleotides of the invention (e.g., polynucleotides complementary to all or a portion of TR17 mRNA) is used to image lymphomas (e.g., monocyte and B cell lymphomas).

Antibody labels or markers for in vivo imaging of TR17 polypeptide include those detectable by X-radiography, NMR, MRI, CAT-scans or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. Where in vivo imaging is used to detect enhanced levels of TR17 polypeptide for diagnosis in humans, it may be preferable to use human antibodies or "humanized" chimeric monoclonal antibodies. Such antibodies can be produced using techniques described herein or otherwise known in the art. For example methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al, *Nature* 314:268 (1985).

Additionally, any TR17 polypeptide whose presence can be detected, can be administered. For example, TR17 polypeptides labeled with a radio-opaque or other appropriate compound can be administered and visualized in vivo, as discussed, above for labeled antibodies. Further such TR17 polypeptides can be utilized for in vitro diagnostic procedures.

A TR17 polypeptide-specific antibody or antibody fragment which has been labeled with an appropriate detectable imaging moiety, such as a radioisotope (for example, $^{131}$I, $^{112}$In, $^{99m}$Tc, ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, 112In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TR17 protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

With respect to antibodies, one of the ways in which the anti-TR17 antibody can be detectably labeled is by linking the same to an enzyme and using the linked product in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller et al., *J. Clin. Pathol.* 31:507–520 (1978); Butler, J. E., *Meth. Enzymol.* 73:482–523 (1981); Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect TR17 through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by means including, but not limited to, a gamma counter, a scintillation counter, or autoradiography.

It is also possible to label the antibody with a fluorescent compound. When the fluorescently labeled antibody is exposed to light of the proper wave-length, its presence can then be detected due to fluorescence. Among the most commonly used fluorescent labeling compounds are fluorescein isothiocyanate, rhodamine, phycoerythrin, phycocyanin, allophycocyanin, ophthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling include, but are not limited to, luciferin, luciferase and aequorin.

Treatment of Immune System-Related Disorders

As noted above, TR17 polynucleotides and polypeptides, and anti-TR17 antibodies, are useful for diagnosis of conditions involving abnormally high or low expression of TR17 activities. Given the cells and tissues where TR17 is expressed as well as the activities modulated by TR17, it is readily apparent that a substantially altered (increased or decreased) level of expression of TR17 in an individual compared to the standard or "normal" level produces pathological conditions related to the bodily system(s) in which TR17 is expressed and/or is active.

It will also be appreciated by one of ordinary skill that, since the TR17 polypeptides of the invention are members of the TNFR family, the extracellular domains of the respective proteins may be released in soluble form from the cells which express TR17 by proteolytic cleavage and therefore, when TR17 polypeptide (particularly a soluble form of the respective extracellular domains) is added from an exogenous source to cells, tissues or the body of an individual, the polypeptide may inhibit the modulating activities of it's ligands (e.g., Neutrokine-alpha and/or APRIL) on any of its target cells of that individual. Also, cells expressing this type III transmembrane protein may be added to cells, tissues or the body of an individual whereby the added cells will bind to cells expressing the TR17 ligands (e.g., Neutrokine-alpha and/or APRIL) whereby the cells expressing the TR17 ligand (e.g., Neutrokine-alpha and/or APRIL) can cause actions (e.g., proliferation or cytotoxicity) on the ligand-bearing target cells.

The present invention is further directed to TR-17 based therapies which involve administering TR-17 based therapeutic compounds of the invention to an animal, preferably a mammal, and most preferably a human, patient for treating one or more of the diseases, disorders, or conditions disclosed herein. Therapeutic compounds of the invention include, but are not limited to, TR17 polypeptides (including fragments and variants of TR17 polypeptides), polynucleotides encoding these polypeptides, and antibodies that bind these polypeptides. The TR17 polypeptides, polynucleotides, and antibodies of the invention can be used to treat, ameliorate or prevent diseases, disorders or conditions associated with aberrant expression and/or activity of Neutrokine-alpha, APRIL, BCMA, and/or TR17, including, but not limited to, any one or more of the diseases, disorders, or conditions described herein. The treatment and/or prevention of diseases, disorders, or conditions associated with aberrant expression and/or activity of Neutrokine-alpha, APRIL, BCMA, and/or TR17, includes, but is not limited to, alleviating symptoms associated with those diseases, disorders or conditions. TR17 compositions of the invention may be provided in pharmaceutically acceptable compositions as known in the art or as described herein.

The TR17 polypeptides, polynucleotides, and antibodies of the invention that function as agonists or antagonists of Neutrokine alpha and/or APRIL, preferably of Neutrokine alpha-induced signal transduction and/or APRIL-induced signal transduction, can be administered to an animal to treat, prevent or ameliorate a disease or disorder associated with aberrant Neutrokine alpha expression, aberrant APRIL expression, lack of Neutrokine alpha function, lack of APRIL function, aberrant TR17 expression, aberrant BCMA expression, lack of TR17 function and/or lack of BCMA function. For example, TR17 polypeptides of the invention which disrupt the interaction between TR17 and one or more of its ligands may be administered to an animal to treat, prevent or ameliorate a disease or disorder associated with aberrant Neutrokine alpha expression, aberrant APRIL expression, excessive Neutrokine alpha function, excessive APRIL function, aberrant TR17 expression, aberrant BCMA expression, excessive TR17 function or excessive BCMA function.

In a preferred embodiment, TR17 polypeptides of the invention neutralize Neutrokine alpha activity. In another preferred embodiment, TR17 polypeptides of the invention neutralize APRIL activity. In another preferred embodiment, TR17 polypeptides of the invention inhibit B cell proliferation. In another preferred embodiment, TR17 polypeptides of the invention inhibit immunoglobulin production by B cells.

In a preferred embodiment, TR17 polypeptides of the invention (including TR17 fragments and variants, and anti-TR17 antibodies) inhibit or reduce binding of the soluble form of Neutrokine-alpha to a Neutrokine alpha receptor (e.g., TR17 and BCMA). In another preferred embodiment, TR17 polypeptides of the invention (including TR17 fragments and variants, and anti-TR17 antibodies) inhibit or reduce binding of the soluble form of APRIL to an APRIL receptor (e.g., TR17 and BCMA). In another preferred embodiment TR17 polypeptides of the invention (including TR17 fragments and variants, and anti-TR17 antibodies) inhibit or reduce B cell proliferation induced by the soluble form of Neutrokine-alpha. In another preferred embodiment TR17 polypeptides of the invention (including TR17 fragments and variants, and anti-TR17 antibodies) inhibit or reduce B cell proliferation induced by the membrane or soluble form of APRIL. In another preferred embodiment TR17 polypeptides of the invention (including TR17 fragments and variants, and anti-TR17 antibodies) inhibit or reduce immunoglobulin production induced by the soluble form of Neutrokine alpha. In another preferred embodiment TR17 polypeptides of the invention (including TR17 fragments and variants, and anti-TR17 antibodies) inhibit or reduce immunoglobulin production induced by the membrane bound or soluble form of APRIL.

In one embodiment, the invention provides a method of delivering radiolabelled TR17 (including TR17 fragments and variants, and anti-TR17 antibodies) polypeptide conjugates of the invention to targeted cells, such as, for example, monocytic cells expressing the membrane-bound form of Neutrokine alpha.

In one embodiment, the invention provides methods and compositions for inhibiting or reducing immunoglobulin production (e.g. IgM, IgG, and/or IgA production), comprising, or alternatively consisting of, contacting an effective amount of TR17 polypeptides of the invention (including TR17 fragments and variants, and anti-TR17 antibodies) with Neutrokine alpha and/or APRIL, wherein the effective amount of TR17 polypeptide inhibits or reduces Neutrokine alpha-and/or APRIL-mediated immunoglobulin production. In another embodiment, the invention provides methods and compositions for inhibiting or reducing immunoglobulin production (e.g. IgM, IgG, and/or IgA production), comprising, or alternatively consisting of, administering to an animal in which such inhibition or reduction is desired, TR17 polypeptides of the invention (including TR17 fragments and variants, and anti-TR17 antibodies) in an amount effective to inhibit or reduce immunoglobulin production.

In another embodiment, the invention provides methods and compositions for stimulating immunoglobulin production (e.g. IgM, IgG, and/or IgA production), comprising, or alternatively consisting of, contacting an effective amount of TR17 polypeptides of the invention (including TR17 fragments and variants, and anti-TR17 antibodies) with Neutrokine alpha and/or APRIL, wherein the effective amount of the TR17 polypeptide stimulates Neutrokine alpha and/or APRIL mediated immunoglobulin production. In another embodiment, the invention provides methods and compositions for stimulating immunoglobulin production (e.g. IgM, IgG, and/or IgA production) comprising, or alternatively consisting of, administering to an animal in which such stimulation is desired, a TR17 polypeptide of the invention (including TR17 fragments and variants, and anti-TR17 antibodies) in an amount effective to stimulate immunoglobulin production. Determination of immunoglobulin levels are most often performed by comparing the level of immunoglobulin in a sample to a standard containing a known amount of immunoglobulin using ELISA assays. Determination of immunoglobulin levels in a given sample, can readily be determined using ELISA or other method known in the art.

Investigation of Neutrokine alpha induced signaling in human tonsillar B cells co-stimulated with Staph. Aureus Cowan consistently revealed that mRNA for ERK-1 and PLK were upregulated by Neutrokine alpha+SAC treatment (data not shown). Polo like kinases (PLK) belong to a sub family of serine/threonine kinases related to *Saccharomyces cerevisiae* cell cycle protein CDC5. The expression of PLK is induced during G2 and S phase of the cell cycle. PLK is reported to play a role in cell proliferation (Lee et al., Proc. Natl. Acad. Sci. 95:9301–9306). The role or extracellular-signal related kinases (ERK1/2) in cell survival and proliferative effects of growth factors and other agonists has been extensively studied. The induced expression of PLK and ERK-1 is consistent with the survival and proliferative effects of Neutrokine alpha on B cells.

Additionally, in some samples of human tonsillar B cells stimulated with Neutrokine alpha and SAC, mRNA for CD25 (IL-2Ralpha) was upregulated. Nuclear extracts from Human tonsillar B cells treated with Neutrokine alpha and from IM-9 cells treated with Neutrokine alpha were able to shift probes from the CD25 promoter region containing sites for NF-kappaB, SRF, ELF-1 and HMGI/Y in an electromobility shift assay. ELF-1 for example, is a transcription factor that is part of the ETS family of proteins and whose expression appears to be restricted to T and B cells. Binding sites for ELF-1 have been described in the promoters of a number of proteins that are important in the regulation of the immune response.

Thus Neutrokine alpha induced signaling has been shown to be consistent with the activation of cellular activation and cellular proliferation pathways as well as with cellular signaling pathways that regulate B cell lifespan. Further, Neutrokine alpha treatment of B cells induces cellular proliferation immunoglobulin secretion, a characteristic of activated B cells (Moore et al., Science 285:260–263, 1999). TR17 polypeptides complexed with Neutrokine alpha may inhibit, stimulate, or not significantly alter these Neutrokine alpha mediated activities.

In one embodiment, the invention provides methods and compositions for inhibiting or reducing B cell proliferation, comprising, or alternatively consisting of, contacting an effective amount of TR17 polypeptides of the invention (including TR17 fragments and variants, and anti-TR17 antibodies) with Neutrokine alpha, wherein the effective amount of TR17 polypeptide inhibits or reduces Neutrokine alpha mediated B cell proliferation. In another embodiment, the invention provides methods and compositions for inhibiting or reducing B cell proliferation comprising, or alternatively consisting of, administering to an animal in which such inhibition or reduction is desired, a TR17 polypeptide in an amount effective to inhibit or reduce B cell proliferation.

In another embodiment, the invention provides methods and compositions for inhibiting or reducing B cell proliferation, comprising, or alternatively consisting of, contacting an effective amount of TR17 polypeptides of the invention (including TR17 fragments and variants, and anti-TR17 antibodies) with APRIL, wherein the effective amount of TR17 polypeptide inhibits or reduces APRIL mediated B cell proliferation. In another embodiment, the invention provides methods and compositions for inhibiting or reducing B cell proliferation comprising, or alternatively consisting of, administering to an animal in which such inhibition or reduction is desired, a TR17 polypeptide in an amount effective to inhibit or reduce B cell proliferation.

In one embodiment, the invention provides methods and compositions for stimulating B cell proliferation, comprising, or alternatively consisting of, contacting an effective amount of TR17 polypeptides of the invention (including TR17 fragments and variants, and anti-TR17 antibodies) with Neutrokine alpha, wherein the effective amount of TR17 polypeptide stimulates Neutrokine alpha mediated B cell proliferation. In one embodiment, the invention provides methods and compositions for stimulating B cell proliferation, comprising, or alternatively consisting of, administering to an animal in which such stimulation is desired, a TR17 polypeptide in an amount effective to stimulate B cell proliferation.

In another embodiment, the invention provides methods and compositions for stimulating B cell proliferation, comprising, or alternatively consisting of, contacting an effective amount of TR17 polypeptides of the invention (including TR17 fragments and variants, and anti-TR17 antibodies) with APRIL, wherein the effective amount of TR17 polypeptide stimulates APRIL mediated B cell proliferation. In one embodiment, the invention provides methods and compositions for stimulating B cell proliferation, comprising, or alternatively consisting of, administering to an animal in which such stimulation is desired, a TR17 polypeptide (e.g., an anti-TR17 antibody) in an amount effective to stimulate B cell proliferation. B cell proliferation is most commonly assayed in the art by measuring tritiated thymidine incorporation. This and other assays are commonly known in the art and could be routinely adapted for the use of determining the effect of TR17 polypeptides on B cell proliferation.

In one embodiment, the invention provides methods and compositions for inhibiting or reducing activation of B cells, comprising, or alternatively consisting of, contacting an effective amount of TR17 polypeptides of the invention (including TR17 fragments and variants, and anti-TR17 antibodies) with Neutrokine alpha, wherein the effective amount TR17 polypeptides inhibits or reduces Neutrokine alpha mediated B cell activation. In one embodiment, the invention provides methods and compositions for inhibiting or reducing activation of B cells, comprising, or alternatively consisting of, administering to an animal in which such inhibition or reduction is desired, a TR17 polypeptide in an amount effective to inhibit or reduce B cell activation.

In another embodiment, the invention provides methods and compositions for inhibiting or reducing activation of B cells, comprising, or alternatively consisting of, contacting an effective amount of TR17 polypeptides of the invention (including TR17 fragments and variants, and anti-TR17 antibodies) with APRIL, wherein the effective amount TR17 polypeptides inhibits or reduces APRIL mediated B cell activation. In one embodiment, the invention provides methods and compositions for inhibiting or reducing activation of B cells, comprising, or alternatively consisting of, administering to an animal in which such inhibition or reduction is desired, a TR17 polypeptide in an amount effective to inhibit or reduce B cell activation.

In one embodiment, the invention provides methods and compositions for increasing activation of B cells, comprising, or alternatively consisting of, contacting an effective amount of TR17 polypeptides of the invention (including TR17 fragments and variants, and anti-TR17 antibodies) with Neutrokine alpha, wherein the effective amount of TR17 polypeptides increase Neutrokine alpha mediated activation of B cells. In one embodiment, the invention provides methods and compositions for increasing activation of B cells, comprising, or alternatively consisting of, administering to an animal in which such increase is desired, a TR17 polypeptide (e.g., an anti-TR17 antibody) in an amount effective to increase B cell activation.

In another embodiment, the invention provides methods and compositions for increasing activation of B cells, comprising, or alternatively consisting of, contacting an effective amount of TR17 polypeptides of the invention (including TR17 fragments and variants, and anti-TR17 antibodies) with APRIL, wherein the effective amount of TR17 polypeptides increase APRIL mediated activation of B cells. In one embodiment, the invention provides methods and compositions for increasing activation of B cells, comprising, or alternatively consisting of, administering to an animal in which such increase is desired, a TR17 polypeptide (e.g., an anti-TR17 antibody) in an amount effective to increase B cell activation.

B cell activation can measured in a variety of ways, such as FACS analysis of activation markers expressed on B cells. B cells activation markers include, but are not limited to, CD26, CD28, CD30, CD38, CD39, CD69, CD70 CD71, CD77, CD83, CD126, CDw130, and B220. Additionally, B cell activation may be measured by analysis of the activation of signaling molecules involved in B cell activation. By way of non-limiting example, such analysis may take the form of analyzing mRNA levels of signaling molecules by Northern analysis or real time PCR. One can also measure, for example, the phosphorylation of signaling molecules using anti-phosphotyrosine antibodies in a Western blot. B cell activation may also be measured by measuring the calcium levels in B cells. These and other methods of determining B cell activation are commonly known in the art and could be routinely adapted for the use of determining the effect of TR17 polypeptides of the invention on B cell activation.

In one embodiment, the invention provides methods and compositions for decreasing lifespan of B cells, comprising, or alternatively consisting of, contacting an effective amount of TR17 polypeptides of the invention (including TR17 fragments and variants, and anti-TR17 antibodies) with Neutrokine alpha, wherein the effective amount of TR17 polypeptide inhibits or reduces Neutrokine alpha regulated lifespan of B cells. In one embodiment, the invention provides methods and compositions for decreasing lifespan of B cells, comprising, or alternatively consisting of, administering to an animal in which such decrease is desired, a TR17 polypeptide of the invention in an amount effective to decrease B cell lifespan.

In another embodiment, the invention provides methods and compositions for decreasing lifespan of B cells, comprising, or alternatively consisting of, contacting an effective amount of TR17 polypeptides of the invention (including TR17 fragments and variants, and anti-TR17 antibodies) with APRIL, wherein the effective amount of TR17 polypeptide inhibits or reduces APRIL regulated lifespan of B cells. In one embodiment, the invention provides methods and compositions for decreasing lifespan of B cells, comprising, or alternatively consisting of, administering to an animal in which such decrease is desired, a TR17 polypeptide of the invention in an amount effective to decrease B cell lifespan.

In one embodiment, the invention provides methods and compositions for increasing lifespan of B cells, comprising, or alternatively consisting of, contacting an effective amount of TR17 polypeptides of the invention (including TR17 fragments and variants, and anti-TR17 antibodies) with Neutrokine alpha, wherein the effective amount of TR17 polypeptides increases Neutrokine alpha regulated lifespan of B cells. In one embodiment, the invention provides methods and compositions for increasing lifespan of B cells, comprising, or alternatively consisting of, administering to an animal in which such increase is desired, a TR17 polypeptide of the invention (e.g., anti-TR17 antibody) in an amount effective to increase lifespan of B cells.

In another embodiment, the invention provides methods and compositions for increasing lifespan of B cells, comprising, or alternatively consisting of, contacting an effective amount of TR17 polypeptides of the invention (including TR17 fragments and variants, and anti-TR17 antibodies) with APRIL, wherein the effective amount of TR17 polypeptides increases APRIL regulated lifespan of B cells. In one embodiment, the invention provides methods and compositions for increasing lifespan of B cells, comprising, or alternatively consisting of, administering to an animal in which such increase is desired, a TR17 polypeptide of the invention (e.g., anti-TR17 antibody) in an amount effective to increase lifespan of B cells.

B cell life span in vivo may be measured by 5-bromo-2'-deoxyuridine (BrdU) labeling experiments which are well known to one skilled in the art. BrdU is a thymidine analogue that gets incorporated into the DNA of dividing cells. Cells containing BrdU in their DNA can be detected using, for example fluorescently labeled anti-BrdU antibody and flow cytometry. Briefly, an animal is injected with BrdU in an amount sufficient to label developing B cells. Then, a sample of B cells is withdrawn from the animal, for example, from peripheral blood, and analyzed for the percentage of cells that contain BrdU. Such an analysis performed at several time points can be used to calculate the half life of B cells. Alternatively, B cell survival may be measured in vitro. For example, B cells may be cultured under conditions where proliferation does not occur, (for example the media should contain no reagents that crosslink the immunoglobulin receptor, such as anti-IgM antibodies) for a period of time (usually 2–4 days). At the end of this time, the percent of surviving cells is determined, using for instance, the vital dye Trypan Blue, or by staining cells with propidium iodide or any other agent designed to specifically stain apoptotic cells and analyzing the percentage of cells stained using flow cytometry. One could perform this experiment under several conditions, such as B cells treated with Neutrokine alpha, B cells treated with APRIL, B cells treated with Neutrokine-alpha—TR17 complexes, B cells treated with APRIL—TR17 complexes, and untreated B cells in order to determine the effects of Neutrokine alpha and TR17 polypeptides on B cells survival. These and other methods for determining B cell lifespan are commonly known in the art and could routinely be adapted to determining the effect of TR17 polypeptides on Neutrokine alpha-and/or APRIL-regulated B cell lifespan.

In a further embodiment, the invention provides a method of delivering compositions containing the polypeptides of the invention (e.g., compositions containing TR17 polypeptides or anti-TR17 antibodies associated with heterologous polypeptides, heterologous nucleic acids, toxins, or prodrugs) to targeted cells, such as, for example, monocytic cells expressing TR17 ligand (e.g., Neutrokine-alpha), or B cells expressing TR17. TR17 polypeptides (e.g., soluble TR17 extracellular domain) or anti-TR17 antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., TR17 polypeptides or anti-TR17 antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., TR17 polypeptides or anti-TR17 antibodies) in association with toxins or cytotoxic prodrugs.

In a specific embodiment, the invention provides a method for the specific destruction of cells of monocytic lineage (e.g., monocyric cell related leukemias or lymphomas) by administering TR17 polypeptides (e.g,. a soluble fragment of the TR17 extracellular domain) and/or anti-TR17 antibodies in association with toxins or cytotoxic prodrugs.

In another specific embodiment, the invention provides a method for the specific destruction of cells of B cell and/or T cell lineage (e.g., B cell related leukemias or lymphomas and or T cell related leukemias or lymphomas) by administering anti-TR17 antibodies in association with toxins or cytotoxic prodrugs.

By "toxin" is meant compounds that bind and activate endogenous cytotoxic effector systems, radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

In specific embodiments, TR17 and/or anti-TR17 polypeptides in association with radioisotopes, toxins or cytotoxic prodrugs are used to treat or ameliorate the symptoms of autoimmune diseases. In preferred emodiments, TR17 and/or anti-TR17 polypeptides in association with radioisotopes, toxins or cytotoxic prodrugs are used to treat or ameliorate the symptoms of systemic lupus erythematosus. TR17 and/or anti-TR17 polypeptides in association with radioisotopes, toxins or cytotoxic prodrugs are used to treat or ameliorate the symptoms of rheumatoid arthritis including advanced rheumatoid arthritis. In preferred emodiments, TR17 and/or anti-TR17 polypeptides in association with radioisotopes, toxins or cytotoxic prodrugs are used to treat or ameliorate the symptoms of idiopathic thrombocytopenic purpura (ITP).

In other preferred embodiments TR17 and/or anti-TR17 polypeptides in association with radioisotopes, toxins or cytotoxic prodrugs are used to treat or ameliorate the symptoms of Sjogren's syndrome. In other preferred embodiments, TR17 and/or anti-TR17 polypeptides in association with radioisotopes, toxins or cytotoxic prodrugs are used to treat or ameliorate the symptoms of IgA nephropathy. In other preferred embodiments, TR17 and/or anti-TR17 polypeptides in association with radioisotopes, toxins or cytotoxic prodrugs are used to treat or ameliorate the symptoms of Myasthenia gravis. In preferred emodiments, TR17 and/or anti-TR17 polypeptides in association with radioisotopes, toxins or cytotoxic prodrugs are used to treat or ameliorate the symptoms of multiple sclerosis.

It will be appreciated that conditions caused by a decrease in the standard or normal level of TR17 activity in an individual, particularly disorders of the immune system, can be treated by administration of TR17 polypeptide (in the form of soluble extracellular domain or cells expressing the complete protein) or agonist. Thus, the invention also provides a method of treatment of an individual in need of an increased level of TR17 activity comprising administering to such an individual a pharmaceutical composition comprising an amount of an isolated TR17 polypeptide of the invention, or agonist thereof, effective to increase the TR17 activity level in such an individual.

It will also be appreciated that conditions caused by a increase in the standard or normal level of TR17 activity in an individual, particularly disorders of the immune system, can be treated by administration of TR17 polypeptides (in the form of soluble extracellular domain or cells expressing the complete protein) or antagonist (e.g, an anti-TR17 antibody). Thus, the invention also provides a method of treatment of an individual in need of an dereased level of TR17 activity comprising administering to such an individual a pharmaceutical composition comprising an amount of an isolated TR17 polypeptide of the invention, or antagonist thereof, effective to decrease the TR17 activity level in such an individual.

Autoantibody production is common to several autoimmune diseases and contributes to tissue destruction and exacerbation of disease. Autoantibodies can also lead to the occurrence of immune complex deposition complications and lead to many symptoms of systemic lupus erythomatosis, including kidney failure, neuralgic symptoms and death. Modulating antibody production independent of cellular response would also be beneficial in many disease states. B cells have also been shown to play a role in the secretion of arthritogenic immunoglobulins in rheumatoid arthritis, (Korganow et al., *Immunity* 10:451–61, 1999). As such, inhibition of Neutrokine alpha-mediated antibody production would be beneficial in treatment of autoimmune diseases such as myasthenia gravis and rheumatoid arthritis. Compunds of the invetion that selectively block or neutralize the action of B-lymphocytes would be useful for such purposes. To verify these capabilities in compositions of the present invention, such compositions are evaluated using assays known in the art and described herein.

The invention provides methods employing compositions of the invention (e.g., TR17 polynucleotides or polypeptides of the invention and/or agonists and/or antagonists thereof) for selectively blocking or neutralizing the actions of B-cells in association with end stage renal diseases, which may or may not be associated with autoimmune diseases. Such methods would also be useful for treating immunologic renal diseases. Such methods would be would be useful for treating glomerulonephritis associated with diseases such as membranous nephropathy, IgA nephropathy or Berger's Disease, IgM nephropathy, Goodpasture's Disease, post-infectious glomerulonephritis, mesangioproliferative disease, minimal-change nephrotic syndrome. Such methods would also serve as therapeutic applications for treating secondary glomerulonephritis or vasculitis associated with such diseases as lupus, polyarteritis, Henoch-Schonlein, Scleroderma, HIV-related diseases, amyloidosis or hemolytic uremic syndrome. The methods of the present invention would also be useful as part of a therapeutic application for treating interstitial nephritis or pyelonephritis associated with chronic pyelonephritis, analgesic abuse, nephrocalcinosis, nephropathy caused by other agents, nephrolithiasis, or chronic or acute interstitial nephritis.

The methods of the present invention also include use of compositions of the invention in the treatment of hypertensive or large vessel diseases, including renal artery stenosis or occlusion and cholesterol emboli or renal emboli.

The present invention also provides methods for diagnosis and treatment of renal or urological neoplasms, multiple mylelomas, lymphomas, light chain neuropathy or amyloidosis.

The invention also provides methods for blocking or inhibiting activated B cells using compositions of the invention for the treatment of asthma and other chronic airway diseases such as bronchitis and emphysema.

TR17 polynucleotides or polypeptides of the invention, or agonists of TR17 (e.g., agonistic antibodies), can be used in the treatment of infectious agents. For example, by increasing the immune response, particularly increasing the proliferation and differentiation of B cells, infectious diseases may be treated. The immune response may be increased by either enhancing an existing immune response, or by initiating a new immune response. Alternatively, TR17 polynucleotides or polypeptides, or agonists of TR17 (e.g., agonistic antibodies), may also directly inhibit the infectious agent, without necessarily eliciting an immune response.

Viruses are one example of an infectious agent that can cause disease or symptoms that can be treated by TR17 polynucleotides or polypeptides, or agonists of TR17 (e.g., agonistic antibodies). Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. TR17 polynucleotides or polypeptides, or agonists or antagonists of TR17, can be used to treat, prevent, diagnose, and/or detect any of these symptoms or diseases. In specific embodiments, TR17 polynucleotides, polypeptides, or agonists are used to treat, prevent, and/or diagnose: meningitis, Dengue, EBV, and/or hepatitis (e.g., hepatitis B). In an additional specific embodiment TR17 polynucleotides, polypeptides, or agonists are used to treat patients nonresponsive to one or more other commercially available hepatitis vaccines. In a further specific embodiment, TR17 polynucleotides, polypeptides, or agonists are used to treat, prevent, and/or diagnose AIDS. In an additional specific embodiment TR17 polynucleotides, polypeptides, agonists, and/or antagonists are used to treat, prevent, and/or diagnose patients with cryptosporidiosis.

Similarly, bacterial or fungal agents that can cause disease or symptoms and that can be treated by TR17 polynucleotides or polypeptides, or agonists or antagonists of TR17, include, but not limited to, the following Gram-Negative and Gram-positive bacteria and bacterial families and fungi: Actinomycetales (e.g., *Corynebacterium, Mycobacterium, Norcardi*a), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*, Brucellosis, Candidiasis, *Campylobacter*, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter*, Legionellosis, Leptospirosis, *Listeria* (e.g, *Listeria monocytogenes*), Mycoplasmatales, *Mycobacterium leprae, Vibrio cholerae*, Neisseriaceae (e.g., *Acinetobacter*, Gonorrhea, Menigococcal), *Meisseria meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. TR17 polynucleotides or polypeptides, or agonists or antagonists of TR17, can be used to treat, prevent, diagnose, and/or detect any of these symptoms or diseases. In specific embodiments, TR17 polynucleotides, polypeptides, or agonists thereof are used to treat, prevent, and/or diagnose: tetanus, Diptheria, botulism, and/or meningitis type B.

Moreover, parasitic agents causing disease or symptoms that can be treated by TR17 polynucleotides or polypeptides, or agonists of TR17, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and *Trichomonas* and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. TR17 polynucleotides or polypeptides, or agonists or antagonists of TR17, can be used to treat, prevent, diagnose, and/or detect any of these symptoms or diseases. In specific embodiments, TR17 polynucleotides, polypeptides, or agonists thereof are used to treat, prevent, and/or diagnose malaria.

In another embodiment, TR17 polynucleotides or polypeptides of the invention and/or agonists and/or antagonists thereof, are used to treat, prevent, and/or diagnose inner ear infection (such as, for example, otitis media), as well as other infections characterized by infection with *Streptococcus pneumoniae* and other pathogenic organisms.

In a specific embodiment, TR17 polynucleotides or polypeptides, or agonists or antagonists thereof (e.g., anti-TR17 antibodies) are used to treat or prevent a disorder characterized by deficient serum immunoglobulin production, recurrent infections, and/or immune system dysfunction. Moreover, TR17 polynucleotides or polypeptides, or agonists or antagonists thereof (e.g., anti-TR17 antibodies) may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, multiple myeloma, recurrent bronchitis, sinusitis, otitis media, conjunctivitis, pneumonia, hepatitis, meningitis, herpes zoster (e.g., severe herpes zoster), and/or pheumocystis camii.

TR17 polynucleotides or polypeptides of the invention, or agonists or antagonists thereof, may be used to diagnose, prognose, treat or prevent one or more of the following diseases or disorders, or conditions associated therewith: primary immuodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

Additionally, TR17 polynucleotides or polypeptides of the invention, or agonists or antagonists thereof, may be used to diagnose, prognose, treat or prevent one or more of the following diseases, disorders, or conditions associated therewith, Guillain-Barre syndrome, anemia (e.g., anemia associated with parvovirus B19, patients with stable mutliple myeloma who are at high risk for infection (e.g., recurrent infection), autoimmune hemolytic anemia (e.g., warm-type autoimmune hemolytic anemia), thrombocytopenia (e.g, neonatal thrombocytopenia), and immune-mediated neutropenia), transplantation (e.g, cytamegalovirus (CMV)-negative recipients of CMV-positive organs), hypogammaglobulinemia (e.g., hypogammaglobulinemic neonates with risk factor for infection or morbidity), epilepsy (e.g, intractable epilepsy), systemic vasculitic syndromes, myasthenia gravis (e.g, decompensation in myasthenia gravis), dermatomyositis, and polymyositis.

Additional preferred embodiments of the invention include, but are not limited to, the use of TR17 polypeptides, TR17 polynucleotides, and functional agonists thereof, in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response. In a specific nonexclusive embodiment, TR17 polypeptides of the invention, and/or agonists thereof, are administered to boost the immune system to produce increased quantities of IgG. In another specific nonexclusive embodiment, TR17 polypeptides of the invention and/or agonists thereof, are administered to boost the immune system to produce increased quantities of IgA. In another specific nonexclusive embodiment, TR17 polypeptides of the invention and/or agonists thereof, are administered to boost the immune system to produce increased quantities of IgM.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741).

A vaccine adjuvant that enhances immune responsiveness to specific antigen. In a specific embodiment, the vaccine adjuvant is a TR17 polypeptide described herein. In another specific embodiment, the vaccine adjuvant is a polynucleotide described herein (i.e., the TR17 polynucleotide is a genetic vaccine adjuvant). As discussed herein, TR17 polynucleotides may be administered using techniques known in the art, including but not limited to, liposomal delivery, recombinant vector delivery, injection of naked DNA, and gene gun delivery.

An adjuvant to enhance tumor-specific immune responses.

An adjuvant to enhance anti-viral immune responses. Anti-viral immune responses that may be enhanced using the compositions of the invention as an adjuvant, include, but are not limited to, virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions of the invention are used as an adjuvant to enhance an immune response to the HIV gp120 antigen.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B *streptococcus, Shigella* spp., Enterotoxigenic *Escherichia coli*, Enterohemorrhagic *E. coli, Borrelia burgdorferi*, and *Plasmodium* (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria).

As a stimulator of B cell responsiveness to pathogens.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among B cell immunodeficient individuals, such as, for example, an individual who has undergone a partial or complete splenectomy. B cell immunodeficiencies that may be ameliorated or treated by administering the TR17 polypeptides or polynucleotides of the invention, or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified bypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

As an agent to boost immunoresponsiveness among individuals having an acquired loss of B cell function. Conditions resulting in an acquired loss of B cell function that may be ameliorated or treated by administering the TR17 polypeptides or polynucleotides of the invention, or agonists thereof, include, but are not limited to, HIV Infection, AIDS, bone marrow transplant, multiple myeloma and B cell chronic lymphocytic leukemia (CLL).

Patients with CLL and myeloma are at risk for increased infections. Thus, one aspect of the present invention provides for the use of TR17 and/or anti-TR17 polynucletides and/or polypeptides as an agent to boost immunoresponsiveness in CLL and myeloma patients.

As an agent to boost immunoresponsiveness among individuals having a temporary immune deficiency or compromised immune system. Conditions resulting in a temporary immune deficiency/compromised immune system that may be ameliorated or treated by administering the TR17 polypeptides or polynucleotides of the invention, or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery and recovery from burns.

As a regulator of antigen presentation by monocytes, dendritic cells, T cells and/or B-cells. In one embodiment, TR17 polypeptides (in soluble, membrane-bound or transmembrane forms) or polynucleotides enhance antigen presentation or antagonize antigen presentation in vitro or in vivo. Moreover, in related embodiments, this enhancement or antagonization of antigen presentation may be useful in anti-tumor treatment or to modulate the immune system.

As a mediator of mucosal immune responses. The expression of TR17 ligand (Neutrokine-alpha) on monocytes, the expression of TR17 on B cells, and the responsiveness of B cells to Neutrokine-alpha suggests that it may be involved in exchange of signals between B cells and monocytes or their differentiated progeny. This activity is in many ways analogous to the CD40-CD154 signaling between B cells and T cells. TR17 may therefore be an important regulator of T cell independent immune responses to environmental pathogens. In particular, the unconventional B cell populations (CD5+) that are associated with mucosal sites and responsible for much of the innate immunity in humans may respond to TR17 thereby enhancing an individual's protective immune status.

As an agent to direct an individual's immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a B cell specific binding protein to which specific activators or inhibitors of cell growth may be attached. The result would be to focus the activity of such activators or inhibitors onto normal, diseased, or neoplastic B cell populations.

As a means of detecting B-lineage cells by virtue of its specificity. This application may require labeling the protein with biotin or other agents (e.g., as described herein) to afford a means of detection.

As a stimulator of B cell production in pathologies such as AIDS, chronic lymphocyte disorder and/or Common Variable Immunodificiency.

As part of a B cell selection device the function of which is to isolate B cells from a heterogenous mixture of cell types. TR17 could be coupled to a solid support to which B cells would then specifically bind. Unbound cells would be washed out and the bound cells subsequently eluted. A nonlimiting use of this selection would be to allow purging of tumor cells from, for example, bone marrow or peripheral blood prior to transplant.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance TR17 mediated responses.

As a means of activating monocytes/macrophages to defend against parasitic diseases that effect monocytes such as *Leshmania*.

As pretreatment of bone marrow samples prior to transplant. Such treatment would increase B cell representation and thus accelerate recover.

As a means of regulating secreted cytokines that are elicited by TR17.

TR17 polypeptides or polynucleotides of the invention, or agonists may be used to modulate IgE concentrations in vitro or in vivo.

Additionally, TR17 polypeptides or polynucleotides of the invention, or agonists thereof, may be used to treat, prevent, and/or diagnose IgE-mediated allergic reactions. Such allergic reactions include, but are not limited to, asthma, rhinitis, and eczema.

In a specific embodiment, TR17 polypeptides or polynucleotides of the invention, or agonists thereof, is administered to treat, prevent, diagnose, and/or ameliorate selective IgA deficiency.

In another specific embodiment, TR17 polypeptides or polynucleotides of the invention, or agonists thereof, is administered to treat, prevent, diagnose, and/or ameliorate ataxia-telangiectasia.

In another specific embodiment, TR17 polypeptides or polynucleotides of the invention, or agonists thereof, is administered to treat, prevent, diagnose, and/or ameliorate common variable immunodeficiency.

In another specific embodiment, TR17 polypeptides or polynucleotides of the invention, or agonists thereof, is administered to treat, prevent, diagnose, and/or ameliorate X-linked agammaglobulinemia.

In another specific embodiment, TR17 polypeptides or polynucleotides of the invention, or agonists thereof, is administered to treat, prevent, diagnose, and/or ameliorate severe combined immunodeficiency (SCID).

In another specific embodiment, TR17 polypeptides or polynucleotides of the invention, or agonists thereof, is administered to treat, prevent, diagnose, and/or ameliorate Wiskott-Aldrich syndrome.

In another specific embodiment, TR17 polypeptides or polynucleotides of the invention, or agonists thereof, is administered to treat, prevent, diagnose, and/or ameliorate X-linked Ig deficiency with hyper IgM.

In another specific embodiment, TR17 polypeptides or polynucleotides of the invention, or agonists or antagonists (e.g., anti-TR17 antibodies) thereof, is administered to treat, prevent, and/or diagnose chronic myelogenous leukemia, acute myelogenous leukemia, leukemia, hysticytic leukemia, monocytic leukemia (e.g., acute monocytic leukemia), leukemic reticulosis, Shilling Type monocytic leukemia, and/or other leukemias derived from monocytes and/or monocytic cells and/or tissues.

In another specific embodiment, TR17 polypeptides or polynucleotides of the invention, or agonists thereof, is administered to treat, prevent, diagnose, and/or ameliorate monocytic leukemoid reaction, as seen, for example, with tuberculosis.

In another specific embodiment, TR17 polypeptides or polynucleotides of the invention, or agonists thereof, is administered to treat, prevent, diagnose, and/or ameliorate monocytic leukocytosis, monocytic leukopenia, monocytopenia, and/or monocytosis.

In a specific embodiment, TR17 polynucleotides or polypeptides of the invention, and/or anti-TR17 antibodies and/or agonists or antagonists thereof, are used to treat, prevent, detect, and/or diagnose primary B lymphocyte disorders and/or diseases, and/or conditions associated therewith. In one embodiment, such primary B lymphocyte disorders, diseases, and/or conditions are characterized by a complete or partial loss of humoral immunity. Primary B lymphocyte disorders, diseases, and/or conditions associated therewith that are characterized by a complete or partial loss of humoral immunity and that may be prevented, treated, detected and/or diagnosed with compositions of the invention include, but are not limited to, X-Linked Agammaglobulinemia (XLA), severe combined immunodeficiency disease (SCID), and selective IgA deficiency.

In a preferred embodiment, TR17 polynucleotides, polypeptides, and/or agonists and/or antagonists thereof are used to treat, prevent, and/or diagnose diseases or disorders affecting or conditions associated with any one or more of the various mucous membranes of the body. Such diseases or disorders include, but are not limited to, for example, mucositis, mucoclasis, mucocolitis, mucocutaneous leishmaniasis (such as, for example, American leishmaniasis, leishmaniasis americana, nasopharyngeal leishmaniasis, and New World leishmaniasis), mucocutaneous lymph node syndrome (for example, Kawasaki disease), mucoenteritis, mucoepidermoid carcinoma, mucoepidermoid tumor, mucoepithelial dysplasia, mucoid adenocarcinoma, mucoid degeneration, myxoid degeneration; myxomatous degeneration; myxomatosis, mucoid medial degeneration (for example, cystic medial necrosis), mucolipidosis (including, for example, mucolipidosis I, mucolipidosis II, mucolipidosis III, and mucolipidosis IV), mucolysis disorders, mucomembranous enteritis, mucoenteritis, mucopolysaccharidosis (such as, for example, type I mucopolysaccharidosis (i.e., Hurler's syndrome), type IS mucopolysaccharidosis (i.e., Scheie's syndrome or type V mucopolysaccharidosis), type II mucopolysaccharidosis (i.e., Hunter's syndrome), type III mucopolysaccharidosis (i.e., Sanfilippo's syndrome), type IV mucopolysaccharidosis (i.e., Morquio's syndrome), type VI mucopolysaccharidosis (i.e., Maroteaux-Lamy syndrome), type VII mucopolysaccharidosis (i.e, mucopolysaccharidosis due to beta-glucuronidase deficiency), and mucosulfatidosis), mucopolysacchariduria, mucopurulent conjunctivitis, mucopus, mucormycosis (i.e., zygomycosis), mucosal disease (i.e., bovine virus diarrhea), mucous colitis (such as, for example, mucocolitis and myxomembranous colitis), and mucoviscidosis (such as, for example, cystic fibrosis, cystic fibrosis of the pancreas, Clarke-Hadfield syndrome, fibrocystic disease of the pancreas, mucoviscidosis, and viscidosis). In a highly preferred embodiment, TR17 polynucleotides, polypeptides, and/or agonists and/or antagonists thereof are used to treat, prevent, and/or diagnose mucositis, especially as associated with chemotherapy.

In a preferred embodiment, TR17 polynucleotides, polypeptides, and/or agonists and/or antagonists thereof are used to treat, prevent, and/or diagnose diseases or disorders affecting or conditions associated with sinusitis.

An additional condition, disease or symptom that can be treated, prevented, and/or diagnosed by TR17 polynucleotides or polypeptides, or agonists of TR17 (e.g., agonistic antibodies), is osteomyelitis.

An additional condition, disease or symptom that can be treated, prevented, and/or diagnosed by TR17 polynucleotides or polypeptides, or agonists of TR17, is endocarditis.

All of the above described applications as they may apply to veterinary medicine.

Antagonists of TR17 include binding and/or inhibitory antibodies, antisense nucleic acids, ribozymes, and TR17 polypeptides of the invention. These would be expected to reverse many of the activities of the ligand described above as well as find clinical or practical application as:

A means of blocking various aspects of immune responses to foreign agents or self. Examples include autoimmune disorders such as lupus, and arthritis, as well as immuno-responsiveness to skin allergies, inflammation, bowel disease, injury and pathogens. Although our current data speaks directly to the potential role of TR17 in B cell and monocyte related pathologies, it remains possible that other cell types may gain expression or responsiveness to TR17. Thus, TR17 may, like CD40 and its ligand, be regulated by the status of the immune system and the microenvironment in which the cell is located.

A therapy for preventing the B cell proliferation and Ig secretion associated with autoimmune diseases such as idiopathic thrombocytopenic purpura, systemic lupus erythematosus and MS.

An inhibitor of graft versus host disease or transplant rejection.

A therapy for B cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

TR17 polypeptides or polynucleotides of the invention, or antagonists may be used to modulate IgE concentrations in vitro or in vivo.

In another embodiment, administration of TR17 polypeptides or polynucleotides of the invention, or antagonists thereof, may be used to treat, prevent, and/or diagnose IgE-mediated allergic reactions including, but not limited to, asthma, rhinitis, and eczema.

An inhibitor of signaling pathways involving ERKI, COX2 and Cyclin D2 which have been associated with TR17 induced B cell activation.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

The agonists and antagonists may be employed in a composition with a pharmaceutically acceptable carrier, e.g., as described herein.

The antagonists may be employed for instance to inhibit TR17-mediated chemotaxis and activation of macrophages and their precursors, and of neutrophils, basophils, B lymphocytes and some T-cell subsets, e.g., activated and CD8 cytotoxic T cells and natural killer cells, in certain autoimmune and chronic inflammatory and infective diseases. Examples of auto-immune diseases include multiple sclerosis, and insulin-dependent diabetes. The antagonists may also be employed to treat, prevent, and/or diagnose infectious diseases including silicosis, sarcoidosis, idiopathic pulmonary fibrosis by preventing the recruitment and activation of mononuclear phagocytes. They may also be employed to treat, prevent, and/or diagnose idiopathic hyper-eosinophilic syndrome by preventing eosinophil production and migration. Endotoxic shock may also be treated by the antagonists by preventing the migration of macrophages and their production of the TR17 polypeptides of the present invention. The antagonists may also be employed for treating atherosclerosis, by preventing monocyte infiltration in the artery wall. The antagonists may also be employed to treat, prevent, and/or diagnose histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat, prevent, and/or diagnose chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat, prevent, and/or diagnose rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by TR17. The antagonists may also be employed to treat, prevent, and/or diagnose cases of bone marrow failure, for example, aplastic anemia and myelodysplastic syndrome. The antagonists may also be employed to treat, prevent, and/or diagnose asthma and allergy by preventing eosinophil accumulation in the lung. The antagonists may also be employed to treat, prevent, and/or diagnose subepithelial basement membrane fibrosis which is a prominent feature of the asthmatic lung. The antagonists may also be employed to treat, prevent, and/or diagnose lymphomas (e.g., one or more of the extensive, but not limiting, list of lymphomas provided herein).

All of the above described applications as they may apply to veterinary medicine. Moreover, all applications described herein may also apply to veterinary medicine.

TR17 polynucleotides or polypeptides of the invention and/or agonists and/or antagonists thereof, may be used to treat, prevent, and/or diagnose various immune system-related disorders and/or conditions associated with these disorders, in mammals, preferably humans. Many autoimmune disorders result from inappropriate recognition of self as foreign material by immune cells. This inappropriate recognition results in an immune response leading to the destruction of the host tissue. Therefore, the administration of TR17 polynucleotides or polypeptides of the invention and/or agonists and/or antagonists thereof that can inhibit an immune response, particularly the proliferation of B cells and/or the production of immunoglobulins, may be an effective therapy in treating and/or preventing autoimmune disorders. Thus, in preferred embodiments, and/or TR17 antagonists of the invention (e.g., polypeptide fragments of TR17 and anti-TR17 antibodies) are used to treat, prevent, and/or diagnose an autoimmune disorder.

Autoimmune disorders and conditions associated with these disorders that may be treated, prevented, and/or diagnosed with the TR17 polynucleotides, polypeptides, and/or antagonist of the invention (e.g,. anti-TR17 antibodies), include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitus, and autoimmune inflammatory eye disease.

Additional autoimmune disorders (that are highly probable) that may be treated, prevented, and/or diagnosed with the compositions of the invention include, but are not limited to, autoimmune thyroiditis, hypothyroidism (i.e., Hashimoto's thyroiditis) (often characterized, e.g., by cell-mediated and humoral thyroid cytotoxicity), systemic lupus erhythematosus (often characterized, e.g., by circulating and locally generated immune complexes), Goodpasture's syndrome (often characterized, e.g., by anti-basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.

Additional autoimmune disorders (that are probable) that may be treated, prevented, and/or diagnosed with the compositions of the invention include, but are not limited to, rheumatoid arthritis (often characterized, e.g., by immune complexes in joints), schleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis/dermatomyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by anti-spermatozoal antibodies), glomerulonephritis (often characterized, e.g., by glomerular basement membrane antibodies or immune complexes) such as primary glomerulonephritis and IgA nephropathy, bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), inflammatory myopathies, and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using anti-TR17.

In a specific preferred embodiment, rheumatoid arthritis is treated, prevented, and/or diagnosed using anti-TR1 7 antibodies and/or other antagonist of the invention.

In a specific preferred embodiment, lupus is treated, prevented, and/or diagnosed using anti-TR17 antibodies and/or other antagonist of the invention.

In a specific preferred embodiment, nephritis associated with lupus is treated, prevented, and/or diagnosed using anti-TR17 antibodies and/or other antagonist of the invention.

In a specific embodiment, TR17 polynucleotides or polypeptides, or antagonists thereof (e.g., anti-TR17 antibodies) are used to treat or prevent systemic lupus erythematosus and/or diseases, disorders or conditions associated therewith. Lupus-associated diseases, disorders, or conditions that may be treated or prevented with TR17 polynucleotides or polypeptides, or antagonists of the invention, include, but are not limited to, hematologic disorders (e.g., hemolytic anemia, leukopenia, lymphopenia, and thrombocytopenia), immunologic disorders (e.g., anti-DNA antibodies, and anti-Sm antibodies), rashes, photosensitivity, oral ulcers, arthritis, fever, fatigue, weight loss, serositis (e.g., pleuritus (pleuricy)), renal disorders (e.g., nephritis), neurological disorders (e.g., seizures, peripheral neuropathy, CNS related disorders), gastroinstestinal disorders, Raynaud phenomenon, and pericarditis. In a preferred embodiment, the TR17 polynucleotides or polypeptides, or antagonists thereof (e.g., anti-TR17 antibodies) are used to treat or prevent renal disorders associated with systemic lupus erythematosus. In a most preferred embodiment, TR17 polynucleotides or polypeptides, or antagonists thereof (e.g., anti-TR17 antibodies) are used to treat or prevent nephritis associated with systemic lupus erythematosus.

Similarly, allergic reactions and conditions, such as asthma (particularly allergic asthma) or other respiratory problems, may also be treated by TR17 polynucleotides or polypeptides of the invention and/or agonists and/or antagonists thereof. Moreover, these molecules can be used to treat, prevent, and/or diagnose anaphylaxis, hypersensitivity to an antigenic molecule, or blood group incompatibility.

TR17 polynucleotides or polypeptides of the invention and/or agonists and/or antagonists thereof, may also be used to treat, prevent, and/or diagnose organ rejection or graft-versus-host disease (GVHD) and/or conditions associated therewith. Organ rejection occurs by host immune cell destruction of the transplanted tissue through an immune response. Similarly, an immune response is also involved in GVHD, but, in this case, the foreign transplanted immune cells destroy the host tissues. The administration of TR17 polynucleotides or polypeptides of the invention and/or agonists and/or antagonists thereof, that inhibits an immune response, particularly the proliferation, differentiation, or chemotaxis of T-cells, may be an effective therapy in preventing organ rejection or GVHD.

Similarly, TR17 polynucleotides or polypeptides of the invention and/or agonists and/or antagonists thereof, may also be used to modulate inflammation. For example, TR17 polynucleotides or polypeptides of the invention and/or agonists and/or antagonists thereof, may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

In a specific embodiment, anti-TR17 antibodies of the invention are used to treat, prevent, modulate, detect, and/or diagnose inflammation.

In a specific embodiment, anti-TR17 of the invention are used to treat, prevent, modulate, detect, and/or diagnose inflamatory disorders.

In another specific embodiment, anti-TR17 of the invention are used to treat, prevent, modulate, detect, and/or diagnose allergy and/or hypersensitivity.

Antibodies against TR17 may be employed to bind to and inhibit TR17 activity to treat, prevent, and/or diagnose ARDS, by preventing infiltration of neutrophils into the lung after injury. The agonists and antagonists of the instant may be employed in a composition with a pharmaceutically acceptable carrier, e.g., as described hereinafter.

TR17 polynucleotides or polypeptides of the invention and/or agonists and/or antagonists thereof, are used to treat, prevent, and/or diagnose diseases and disorders of the pulmonary system (e.g., bronchi such as, for example, sinopulmonary and bronchial infections and conditions associated with such diseases and disorders and other respiratory diseases and disorders. In specific embodiments, such diseases and disorders include, but are not limited to, bronchial adenoma, bronchial asthma, pneumonia (such as, e.g., bronchial pneumonia, bronchopneumonia, and tuberculous bronchopneumonia), chronic obstructive pulmonary disease (COPD), bronchial polyps, bronchiectasia (such as, e.g., bronchiectasia sicca, cylindrical bronchiectasis, and saccular bronchiectasis), bronchiolar adenocarcinoma, bronchiolar carcinoma, bronchiolitis (such as, e.g., exudative bronchiolitis, bronchiolitis fibrosa obliterans, and proliferative bronchiolitis), bronchioloalveolar carcinoma, bronchitic asthma, bronchitis (such as, e.g., asthmatic bronchitis, Castellani's bronchitis, chronic bronchitis, croupous bronchitis, fibrinous bronchitis, hemorrhagic bronchitis, infectious avian bronchitis, obliterative bronchitis, plastic bronchitis, pseudomembranous bronchitis, putrid bronchitis, and verminous bronchitis), bronchocentric granulomatosis, bronchoedema, bronchoesophageal fistula, bronchogenic carcinoma, bronchogenic cyst, broncholithiasis, bronchomalacia, bronchomycosis (such as, e.g., bronchopulmonary aspergillosis), bronchopulmonary spirochetosis, hemorrhagic bronchitis, bronchorrhea, bronchospasm, bronchostaxis, bronchostenosis, Biot's respiration, bronchial respiration, Kussmaul respiration, Kussmaul-Kien respiration, respiratory acidosis, respiratory alkalosis, respiratory distress syndrome of the newborn, respiratory insufficiency, respiratory scleroma, respiratory syncytial virus, and the like.

In a specific embodiment, TR17 polynucleotides or polypeptides of the invention and/or agonists and/or antagonists thereof, are used to treat, prevent, and/or diagnose chronic obstructive pulmonary disease (COPD).

In another embodiment, TR17 polynucleotides or polypeptides of the invention and/or agonists and/or antagonists thereof, are used to treat, prevent, and/or diagnose fibroses and conditions associated with fibroses, such as, for example, but not limited to, cystic fibrosis (including such fibroses as cystic fibrosis of the pancreas, Clarke-Hadfield syndrome, fibrocystic disease of the pancreas, mucoviscidosis, and viscidosis), endomyocardial fibrosis, idiopathic retroperitoneal fibrosis, leptomeningeal fibrosis, mediastinal fibrosis, nodular subepidermal fibrosis, pericentral fibrosis, perimuscular fibrosis, pipestem fibrosis, replacement fibrosis, subadventitial fibrosis, and Symmers' clay pipestem fibrosis.

The TNF family ligands are known to be among the most pleiotropic cytokines, inducing a large number of cellular responses, including cytotoxicity, anti-viral activity, immunoregulatory activities, and the transcriptional regulation of several genes (D. V. Goeddel et al., "Tumor Necrosis Factors: Gene Structure and Biological Activities," *Symp. Quant. Biol.* 51:597–609 (1986), Cold Spring Harbor; B. Beutler and A. Cerami, *Annu. Rev. Biochem.* 57:505–518 (1988); L. J. Old, *Sci. Am.* 258:59–75 (1988); W. Fiers, *FEBS Lett.* 285:199–224 (1991)). The TNF-family ligands, including the TR17 ligands (e.g., Neutrokine-alpha and/or APRIL), induce such various cellular responses by binding to TNF-family receptors, including TR17. Neutrokine-alpha polypeptides and APRIL polypeptides are believed to elicit a potent cellular response including any genotypic, phenotypic, and/or morphologic change to the cell, cell line, tissue, tissue culture or patient. As indicated, such cellular responses include not only normal physiological responses to TNF-family ligands, but also diseases associated with increased apoptosis or the inhibition of apoptosis. Apoptosis-programmed cell death-is a physiological mechanism involved in the deletion of peripheral B and/or T lymphocytes of the immune system, and its disregulation can lead to a number of different pathogenic processes (J. C. Ameisen, *AIDS* 8:1197–1213 (1994); P. H. Krammer et al., *Curr. Opin. Immunol.* 6:279–289 (1994)).

Diseases associated with increased cell survival, or the inhibition of apoptosis that may be diagnosed, treated, or prevented with the TR17 polynucleotides or polypeptides of the invention, and agonists and antagonists thereof, include cancers (such as follicular lymphomas, carcinomas with p53 mutations, and hormone-dependent tumors, including, but not limited to, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. Thus, in preferred embodiments TR17 polynucleotides or polypeptides of the invention abd/or agonists or antagonists thereof, are used to treat, prevent, and/or diagnose autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment TR17 polynucleotides or polypeptides of the invention are used to activate, differentiate or proliferate cancerous cells or tissue (e.g., B cell lineage related cancers (e.g., CLL and MLL), lymphocytic leukemia, or lymphoma) and thereby render the cells more vulnerable to cancer therapy (e.g., chemotherapy or radiation therapy).

Moreover, in other embodiments, TR17 polynucleotides or polypeptides of the invention or agonists or antagonists thereof, are used to inhibit the growth, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis apoptosis that may be diagnosed, treated, or prevented with the TR17 polynucleotides or polypeptides of the invention, and agonists and antagonists thereof, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia. Thus, in preferred embodiments TR17 polynucleotides or polypeptides of the invention and/or agonists or antagonists thereof, are used to treat, prevent, and/or diagnose the diseases and disorders listed above.

In preferred embodiments, TR17 polypeptides of the invention and/or agonists or antagonists thereof (e.g., anti-TR17 antibodies) inhibit the growth of human histiocytic lymphoma U-937 cells in a dose-dependent manner. In additional preferred embodiments, TR17 polypeptides of the invention and/or agonists or antagonists thereof (e.g., anti-TR17 antibodies) inhibit the growth of PC-3 cells, HT-29 cells, HeLa cells, MCF-7 cells, and A293 cells. In highly preferred embodiments, TR17 polynucleotides or polypeptides of the invention and/or agonists or antagonists thereof (e.g., anti-TR17 antibodies) are used to inhibit growth, progression, and/or metastasis of prostate cancer, colon cancer, cervical carcinoma, and breast carcinoma.

Thus, in additional preferred embodiments, the present invention is directed to a method for enhancing apoptosis induced by a TNF-family ligand, which involves administering to a cell which expresses TR17 an effective amount of TR17 ligand (e.g., Neutrokine-alpha and/or APRIL), or an agonist or antagonist thereof, capable of increasing or decreasing TR17 mediated signaling. Preferably, TR17 mediated signaling is increased or decreased to treat, prevent, and/or diagnose a disease wherein decreased apoptosis or decreased cytokine and adhesion molecule expression is exhibited. An agonist or antagonist can include soluble forms of TR17 and monoclonal antibodies directed against the TR17 polypeptide.

In a further aspect, the present invention is directed to a method for inhibiting apoptosis induced by a TNF-family ligand, which involves administering to a cell which expresses the TR17 an effective amount of an agonist or antagonist capable of increasing or decreasing TR17 mediated signaling. Preferably, TR17 mediated signaling is increased or decreased to treat, prevent, and/or diagnose a disease wherein increased apoptosis or NF-kappaB expression is exhibited. An agonist or antagonist can include soluble forms of TR17 and monoclonal antibodies directed against the TR17 polypeptide.

Because TR17 belong to the TNFR superfamily, the polypeptides should also modulate angiogenesis. In addition, since TR17 inhibit immune cell functions, the polypeptides will have a wide range of anti-inflammatory activities. TR17 may be employed as an anti-neovascularizing agent to treat, prevent, and/or diagnose solid tumors by stimulating the invasion and activation of host defense cells, e.g., cytotoxic T cells and macrophages and by inhibiting the angiogenesis of tumors. Those of skill in the art will recognize other non-cancer indications where blood vessel proliferation is not wanted. They may also be employed to enhance host defenses against resistant chronic and acute infections, for example, myobacterial infections via the attraction and activation of microbicidal leukocytes. TR17 may also be employed to inhibit T-cell proliferation by the inhibition of IL-2 biosynthesis for the treatment of T-cell mediated auto-immune diseases and lymphocytic leukemias (including, for example, chronic lymphocytic leukemia (CLL)). TR17 may also be employed to stimulate wound healing, both via the recruitment of debris clearing and connective tissue promoting inflammatory cells. In this same manner, TR17 may also be employed to treat, prevent, and/or diagnose other fibrotic disorders, including liver cirrhosis, osteoarthritis and pulmonary fibrosis. TR17 also increases the presence of eosinophils that have the distinctive function of killing the larvae of parasites that invade tissues, as in schistosomiasis, trichinosis and ascariasis. It may also be employed to regulate hematopoiesis, by regulating the activation and differentiation of various hematopoietic progenitor cells, for example, to release mature leukocytes from the bone marrow following chemotherapy, i.e., in stem cell mobilization. TR17 may also be employed to treat, prevent, and/or diagnose sepsis.

Polynucleotides and/or polypeptides of the invention and/or agonists and/or antagonists thereof are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), Helicobacter pylori infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, wound healing (e.g., wounds, burns, and bone fractures). Polynucleotides and/or polypeptides of the invention and/or agonists and/or antagonists thereof are also useful as an adjuvant to enhance immune responsiveness to specific antigen, anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

Preferably, treatment using TR17 polynucleotides or polypeptides, and/or agonists or antagonists of TR17 (e.g., anti-TR17 antibody), could either be by administering an effective amount of TR17 polypeptide of the invention, or agonist or antagonist thereof, to the patient, or by removing cells from the patient, supplying the cells with TR17 polynucleotide, and returning the engineered cells to the patient (ex vivo therapy). Moreover, as further discussed herein, the TR17 polypeptide or polynucleotide can be used as an adjuvant in a vaccine to raise an immune response against infectious disease.

Formulations and Administration

The TR17 polypeptide composition (preferably containing a polypeptide which is a soluble form of the TR17 extracellular domains) will be formulated and dosed in a fashion consistent with good medical practice, taking into account the clinical condition of the individual patient (especially the side effects of treatment with TR17 polypeptide alone), the site of delivery of the TR17 polypeptide composition, the method of administration, the scheduling of administration, and other factors known to practitioners. The "effective amount" of TR17 polypeptide for purposes herein is thus determined by such considerations.

As a general proposition, the total pharmaceutically effective amount of TR17 polypeptide administered parenterally per dose will be in the range of about 1 microgram/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day.

In another embodiment, the TR17 polypeptide of the invention is administered to a human at a dose between 0.0001 and 0.045 mg/kg/day, preferably, at a dose between 0.0045 and 0.045 mg/kg/day, and more preferably, at a dose of about 45 microgram/kg/day in humans; and at a dose of about 3 mg/kg/day in mice.

If given continuously, the TR17 polypeptide is typically administered at a dose rate of about 1 microgram/kg/hour to about 50 micrograms/kg/hour, either by 1–4 injections per day or by continuous subcutaneous infusions, for example, using a mini-pump. An intravenous bag solution may also be employed.

The length of treatment needed to observe changes and the interval following treatment for responses to occur appears to vary depending on the desired effect.

In a specific embodiment, the total pharmaceutically effective amount of TR17 polypeptide administered parenterally per dose will be in the range of about 0.1 microgram/kg/day to 45 micrograms/kg/day of patient body weight, although, as noted above, this will be subject to therapeutic discretion. More preferably, this dose is at least 0.1 microgram/kg/day, and most preferably for humans between about 0.01 and 50 micrograms/kg/day for the protein. N TR17 may be administered as a continuous infusion, multiple dicreet injections per day (e.g., three or more times daily, or twice daily), single injection per day, or as discreet injections given intermitently (e.g., twice daily, once daily, every other day, twice weekly, weekly, biweekly, monthly, bimonthly, and quarterly). If given continuously, the TR17 polypeptide is typically administered at a dose rate of about 0.001 to 10 microgram/kg/hour to about 50 micrograms/kg/hour, either by 1–4 injections per day or by continuous subcutaneous infusions, for example, using a mini-pump.

Effective dosages of the compositions of the present invention to be administered may be determined through procedures well known to those in the art which address such parameters as biological half-life, bioavailability, and toxicity. Such determination is well within the capability of those skilled in the art, especially in light of the detailed disclosure provided herein.

Bioexposure of an organism to TR17 polypeptide during therapy may also play an important role in determining a therapeutically and/or pharmacologically effective dosing regime. Variations of dosing such as repeated administrations of a relatively low dose of TR17 polypeptide for a relatively long period of time may have an effect which is therapeutically and/or pharmacologically distinguishable from that achieved with repeated administrations of a relatively high dose of TR17 for a relatively short period of time.

Using the equivalent surface area dosage conversion factors supplied by Freireich, E. J., et al. (*Cancer Chemotherapy Reports* 50(4):219–44 (1966)), one of ordinary skill in the art is able to conveniently convert data obtained from the use of TR17 in a given experimental system into an accurate estimation of a pharmaceutically effective amount of TR17 polypeptide to be administered per dose in another experimental system. Experimental data obtained through the administration of TR17 in mice may converted through the conversion factors supplied by Freireich, et al., to accurate estimates of pharmaceutically effective doses of TR17 in rat, monkey, dog, and human. The following conversion table (Table III) is a summary of the data provided by Freireich, et al. Table III gives approximate factors for converting doses expressed in terms of mg/kg from one species to an equivalent surface area dose expressed as mg/kg in another species tabulated.

TABLE III

Equivalent Surface Area Dosage Conversion Factors.

| | --TO-- | | | | |
|---|---|---|---|---|---|
| --FROM-- | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 5/3 | 1 | 1/2 |
| Human | 12 | 7 | 3 | 2 | 1 |

Thus, for example, using the conversion factors provided in Table III, a dose of 50 mg/kg in the mouse converts to an appropriate dose of 12.5 mg/kg in the monkey because (50 mg/kg)×(1/4)=12.5 mg/kg. As an additional example, doses of 0.02, 0.08, 0.8, 2, and 8 mg/kg in the mouse equate to effect doses of 1.667 micrograms/kg, 6.67 micrograms/kg, 66.7 micrograms/kg, 166.7 micrograms/kg, and 0.667 mg/kg, respectively, in the human.

Pharmaceutical compositions containing TR17 polypeptides of the invention may be administered orally, rectally, parenterally, subcutaneously, intracistemally, intravaginally, intraperitoneally, topically (as by powders, ointments, drops or transdermal patch), bucally, or as an oral or nasal spray (e.g., via inhalation of a vapor or powder). In one embodiment, "pharmaceutically acceptable carrier" means a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can be employed as liquid carriers, particularly for injectable solutions. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The term "parenteral" as used herein refers to modes of administration which include intravenous, intramuscular, intraperitoneal, intrastemal, subcutaneous and intraarticular injection and infusion.

In a preferred embodiment, TR17 compositions of the invention (including polypeptides, polynucleotides, and antibodies, and agonists and/or antagonists thereof) are administered subcutaneously.

In another preferred embodiment, TR17 compositions of the invention (including polypeptides, polynucleotides, and antibodies, and agonists and/or antagonists thereof) are administered intravenously.

TR17 compositions of the invention are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988).

In a preferred embodiment, TR17 compositions of the invention are formulated in a biodegradable, polymeric drug delivery system, for example as described in U.S. Pat. Nos. 4,938,763; 5,278,201; 5,278,202; 5,324,519; 5,340,849; and 5,487,897 and in International Publication Numbers WO01/35929, WO00/24374, and WO00/06117 which are hereby incorporated by reference in their entirety. In specific preferred embodiments the TR17 compositions of the invention are formulated using the ATRIGEL® Biodegradable System of Atrix Laboratories, Inc. (Fort Collins, Colo.).

Examples of biodegradable polymers which can be used in the formulation of TR17 compositions, include but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), poly(methyl vinyl ether), poly(maleic anhydride), polyvinylpyrrolidone, polyethylene glycol, polyhydroxycellulose, chitin, chitosan, and copolymers, terpolymers, or combinations or mixtures of the above materials. The preferred polymers are those that have a lower degree of crystallization and are more hydrophobic. These polymers and copolymers are more soluble in the biocompatible solvents than the highly crystalline polymers such as polyglycolide and chitin which also have a high degree of hydrogen-bonding. Preferred materials with the desired solubility parameters are the polylactides, polycaprolactones, and copolymers of these with glycolide in which there are more amorphous regions to enhance solubility. In specific preferred embodiments, the biodegradable polymers which can be used in the formulation of TR17 compositions are poly(lactide-co-glycolides). Polymer properties such as molecular weight, hydrophobicity, and lactide/glycolide ratio may be modified to obtain the desired drug TR17 release profile (See, e.g., Ravivarapu et al., Journal of Pharmaceutical Sciences 89:732–741 (2000), which is hereby incorporated by reference in its entirety).

It is also preferred that the solvent for the biodegradable polymer be non-toxic, water miscible, and otherwise biocompatible. Examples of such solvents include, but are not limited to, N-methyl-2-pyrrolidone, 2-pyrrolidone, C2 to C6 alkanols, C1 to C15 alchohols, dils, triols, and tetraols such as ethanol, glycerine propylene glycol, butanol; C3 to C15 alkyl ketones such as acetone, diethyl ketone and methyl ethyl ketone; C3 to C15 esters such as methyl acetate, ethyl acetate, ethyl lactate; alkyl ketones such as methyl ethyl ketone, C1 to C15 amides such as dimethylformamide, dimethylacetamide and caprolactam; C3 to C20 ethers such as tetrahydrofuran, or solketal; tweens, triacetin, propylene carbonate, decylmethylsulfoxide, dimethyl sulfoxide, oleic acid, 1-dodecylazacycloheptan-2-one, Other preferred solvents are benzyl alchohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of the solvating ability and their compatibility.

Additionally, formulations comprising TR17 compositions and a biodegradable polymer may also include release-rate modification agents and/or pore-forming agents. Examples of release-rate modification agents include, but are not limited to, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as C.sub.6-C.sub.12 alkanols, 2-ethoxyethanol. The release rate modification agent may be used singly or in combination with other such agents. Suitable combinations of release rate modification agents include, but are not limited to, glycerin/propylene glycol, sorbitol/glycerine, ethylene oxide/propylene oxide, butylene glycol/adipic acid, and the like. Preferred release rate modification agents include, but are not limited to, dimethyl citrate, triethyl citrate, ethyl heptanoate, glycerin, and hexanediol. Suitable pore-forming agents that may be used in the polymer composition include, but are not limited to, sugars such as sucrose and dextrose, salts such as sodium chloride and sodium carbonate, polymers such as hydroxylpropylcellulose, carboxymethylcellulose, polyethylene glycol, and polyvinylpyrrolidone. Solid crystals that will provide a defined pore size, such as salt or sugar, are preferred.

In specific preferred embodiments the TR17 compositions of the invention are formulated using the BEMA™ Bio-Erodible Mucoadhesive System, MCA™ MucoCutaneous Absorption System, SMP™ Solvent MicroParticle System, or BCP™ BioCompatible Polymer System of Atrix Laboratories, Inc. (Fort Collins, Colo.).

Sustained-release compositions also include liposomally entrapped compositions of the invention (see generally, Langer, *Science* 249:1527–1533 (1990); Treat et al., in *Liposomes in the Therapy of Infectious Disease and Cancer*, Lopez-Berestein and Fidler (eds.), Liss, N.Y., pp. 317–327 and 353–365 (1989)). Liposomes containing TR17 polypeptide my be prepared by methods known per se: DE 3,218, 121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal TR17 polypeptide therapy.

In another embodiment systained release compositions of the invention include crystal formulations known in the art.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

For parenteral administration, in one embodiment, the TR17 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the TR17 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, sucrose, or dextrins; chelating agents such as EDTA; sugar alcohols such as mannitol or sorbitol; counterions such as sodium; preservatives, such as cresol, phenol, chlorobutanol, benzyl alcohol and parabens, and/or nonionic surfactants such as polysorbates, poloxamers, or PEG.

The TR17 polypeptide is typically formulated in such vehicles at a concentration of about 0.001 mg/ml to 100 mg/ml, or 0.1 mg/ml to 100 mg/ml, preferably 1–10 mg/ml or 1–10 mg/ml, at a pH of about 3 to 10, or 3 to 8, more preferably 5–8, preferably 6–7. It will be understood that the use of certain of the foregoing excipients, carriers, or stabilizers will result in the formation of TR17 polypeptide salts.

TR17 polypeptide to be used for therapeutic administration must be sterile. Sterility is readily accomplished by filtration through sterile filtration membranes (e.g., 0.2 micron membranes). Therapeutic TR17 polypeptide compositions generally are placed into a container having a sterile access port, for example, an intravenous solution bag or vial having a stopper pierceable by a hypodermic injection needle.

TR17 polypeptide ordinarily will be stored in unit or multi-dose containers, for example, sealed ampoules or vials, as an aqueous solution or as a lyophilized formulation for reconstitution. As an example of a lyophilized formulation, 1 0-ml vials are filled with 5 ml of sterile-filtered 1% (w/v) aqueous TR17 polypeptide solution, and the resulting mixture is lyophilized. The infusion solution is prepared by reconstituting the lyophilized TR17 polypeptide using bacteriostatic Water-for-Injection.

Alternatively, TR17 polypeptide is stored in single dose containers in lyophilized form. The infusion selection is reconstituted using a sterile carrier for injection.

The invention also provides a pharmaceutical pack or kit comprising one or more containers filled with one or more of the ingredients of the pharmaceutical compositions of the invention. Optionally, associated with such container(s) is a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In another specific embodiment, compositions of the invention are used in combination with PNELMOVAX-23™ to treat, prevent, and/or diagnose infection and/or any disease, disorder, and/or condition associated therewith. In one embodiment, compositions of the invention are used in combination with PNEUMOVAX-23™ to treat, prevent, and/or diagnose any Gram positive bacterial infection and/or any disease, disorder, and/or condition associated therewith. In another embodiment, compositions of the invention are used in combination with PNEUMOVAX-23™ to treat, prevent, and/or diagnose infection and/or any disease, disorder, and/or condition associated with one or more members of the genus *Enterococcus* and/or the genus *Streptococcus*. In another embodiment, compositions of the invention are used in any combination with PNEUMOVAX-23™ to treat, prevent, and/or diagnose infection and/or any disease, disorder, and/or condition associated with one or more members of the Group B streptococci. In another embodiment, compositions of the invention are used in combination with PNEUMOVAX-23™ to treat, prevent, and/or diagnose infection and/or any disease, disorder, and/ or condition associated with *Streptococcus pneumoniae*.

The compositions of the invention may be administered alone or in combination with other therapeutic agents, including but not limited to, chemotherapeutic agents, antibiotics, antivirals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-IBBL, DcR3, OX40L, TNF-gamma (International Publication No. WO 96/14328), AIM-I (International Publication No. WO 97/33899), AIM-II (International Publication No. WO 97/34911), APRIL (International Publication Number WO 97/33902; J. Exp. Med. 188(6):1185–1190 (1998)), endokine-alpha (International Publication No. WO 98/07880), OPG, and neutrokine-alpha (International Publication No. WO 98/18921), OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), BCMA (See e.g., Laabis et al., Nucleic acids research, 22(7) 1147–1154 (1994); Genbank Accession Number Z29574), and TR12.

In a preferred embodiment, the compositions of the invention are administered in combination with CD40 ligand (CD40L), a soluble form of CD40L (e.g., AVREND™), bioloigically active fragments, variants, or derivatives of CD40L, anti-CD40L antibodies (e.g., agonistic or antagonistic antibodies), and/or anti-CD40 antibodies (e.g., agonistic or antagonistic antibodies).

In a preferred embodiment, the compositions of the invention are administered in combination with BCMA (See e.g., Laabis et al., Nucleic acids research, 22(7) 1147–1154 (1994); Genbank Accession Number Z29574), a soluble form of BCMA, biologically active fragments, variants, or derivatives of BCMA (e.g., BCMA-Fc), and/or anti-BCMA antibodies (e.g., agonistic or antagonistic antibodies).

In a preferred embodiment, the compositions of the invention are administered in combination with Neutrokine-alpha (International Publication No. WO 98/18921), a soluble form of Neutrokine alpha, biologically active fragments, variants, or derivatives of Neutrokine-alpha, and/or anti-Neutrokine alpha antibodies (e.g., agonistic or antagonistic antibodies).

In a preferred embodiment, the compositions of the invention are administered in combination with APRIL (International Publication Number WO 97/33902; J. Exp. Med. 188(6):1185–1190 (1998)), a soluble form of APRIL, biologically active fragments, variants, or derivatives of APRIL, and/or anti-APRIL antibodies (e.g., agonistic or antagonistic antibodies).

In an additional embodiment, the compositions of the invention are administered alone or in combination with an anti-angiogenic agent(s). Anti-angiogenic agents that may be administered with the compositions of the invention include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitory, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono-and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; (Takeuchi et al., Agents Actions 36:312–316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. Brem and J. Folkman *J. Pediatr. Surg.* 28:445–51 (1993)); an integrin alpha v beta 3 antagonist (C. Storgard et al., *J Clin. Invest.* 103:47–54 (1999)); carboxynaminolmidazole; Carboxyamidotriazole (CAI) (National Cancer Institute, Bethesda, Md.); Conbretastatin A-4 (CA4P) (OXiGENE, Boston, Mass.); Squalamine (Magainin Pharmaceuticals, Plymouth Meeting, Pa.); TNP-470, (Tap Pharmaceuticals, Deerfield, Ill.); ZD-0101 Astra-Zeneca (London, UK); APRA (CT2584); Benefin, Byrostatin-1 (SC339555); CGP-41251 (PKC 412); CM101; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3340) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the compounds of the invention may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the compositions of the invention include, but are not limited to, AG-3340 (Agouron, La Jolla, Calif.), BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aetema, St-Foy, Quebec). Examples of anti-angiogenic inhibitors that act by blocking the function of endothelial cell-extracellular matrix adhesion molecules and which may be administered in combination with the compositions of the invention include, but are not limited to, EMD-121974 (Merck KcgaA Darmstadt, Germany) and Vitaxin (Ixsys, La Jolla, Calif./Medimmune, Gaithersburg, Md.). Examples of anti-angiogenic agents that act by directly antagonizing or inhibiting angiogenesis inducers and which may be administered in combination with the compositions of the invention include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with the compositions of the invention include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In particular embodiments, the use of compositions of the invention in combination with anti-angiogenic agents is contemplated for the treatment, prevention, and/or amelioration of an autoimmune disease, such as for example, an autoimmune disease described herein.

In a particular embodiment, the use of compositions of the invention in combination with anti-angiogenic agents is contemplated for the treatment, prevention, and/or amelioration of arthritis. In a more particular embodiment, the use of compositions of the invention in combination with anti-angiogenic agents is contemplated for the treatment, prevention, and/or amelioration of rheumatoid arthritis or conditions associated therewith.

In a particular embodiment, the use of compositions of the invention in combination with anti-angiogenic agents is contemplated for the treatment, prevention, and/or amelioration of arthritis. In a more particular embodiment, the use of compositions of the invention in combination with anti-angiogenic agents is contemplated for the treatment, prevention, and/or amelioration of systemic lupus erythematosus, or conditions associated therewith.

In another embodiment, the compositions of the invention are administered in combination with an anticoagulant. Anticoagulants that may be administered with the compositions of the invention include, but are not limited to, heparin, warfarin, and aspirin. In a specific embodiment, compositions of the invention are administered in combination with heparin and/or warfarin. In another specific embodiment, compositions of the invention are administered in combination with warfarin. In another specific embodiment, compositions of the invention are administered in combination with warfarin and aspirin. In another specific embodiment, compositions of the invention are administered in combination with heparin. In another specific embodiment, compositions of the invention are administered in combination with heparin and aspirin.

In another embodiment, compositions of the invention are administered in combination with an agent that suppresses the production of anticardiolipin antibodies. In specific embodiments, the polynucleotides of the invention are administered in combination with an agent that blocks and/or reduces the ability of anticardiolipin antibodies to bind phospholipid-binding plasma protein beta 2-glycoprotein I (b2GPI).

In another embodiment, therapeutic or pharmaceutical compositions of the invention are administered to an animal to treat, prevent or ameliorate ischemia and arteriosclerosis. Examples of such disorders include, but are not limited to, reperfusion damage (e.g., in the heart and/or brain) and cardiac hypertrophy.

Therapeutic or pharmaceutical compositions of the invention, may also be administered to to modulate blood clotting and to treat or prevent blood clotting disorders, such as, for example, antibody-mediated thrombosis (i.e., antiphospholipid antibody syndrome (APS)). For example, therapeutic or pharmaceutical compositions of the invention, may inhibit the proliferation and differentiation of cells involved in producing anticardiolipin antibodies. These compositions of the invention can be used to treat, prevent, ameliorate, diagnose, and/or prognose thrombotic related events including, but not limited to, stroke (and recurrent stroke), heart attack, deep vein thrombosis, pulmonary embolism, myocardial infarction, coronary artery disease (e.g., antibody-mediated coronary artery disease), thrombosis, graft reocclusion following cardiovascular surgery (e.g., coronary arterial bypass grafts, recurrent fetal loss, and recurrent cardiovascular thromboembolic events.

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat, prevent, and/or diagnose AIDS and/or to treat, prevent, and/or diagnose HIV infection.

Additional NRTIs include LODENOSINE™ (F-ddA; an acid-stable adenosine NRTI; Triangle/Abbott; COVIRACIL™ (emtricitabine/FTC; structurally related to lamivudine (3TC) but with 3-to 10-fold greater activity in vitro; Triangle/Abbott); dOTC (BCH-10652, also structurally related to lamivudine but retains activity against a substantial proportion of lamivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/Abbott); D-D4FC (related to 3TC, with activity against AZT/3TC-resistant virus); GW420867X (Glaxo Wellcome); ZIAGEN™ (abacavir/159U89; Glaxo Wellcome Inc.); CS-87 (3'azido-2',3'-dideoxyuridine; WO 99/66936); and S-acyl-2-thioethyl (SATE)-bearing prodrug forms of β-L-FD4C and β-L-FddC (WO 98/17281).

Additional NNRTIs include COACTINON™ (Emivirine/MKC-442, potent NNRTI of the HEPT class; Triangle/Abbott); CAPRAVIRINE™ (AG-1549/S-1153, a next generation NNRTI with activity against viruses containing the K103N mutation; Agouron); PNU-142721 (has 20-to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW-420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; Abbott Laboratories); BMS-232632 (an azapeptide; Bristol-Myres Squibb); TIPRANAVIR™ (PNU-140690, a non-peptic dihydropyrone; Pharmacia & Upjohn); PD-178390 (a nonpeptidic dihydropyrone; Parke-Davis); BMS 232632 (an azapeptide; Bristol-Myers Squibb); L-756, 423 (an indinavir analog; Merck); DMP-450 (a cyclic urea compound; Avid & DuPont); AG-1776 (a peptidomimetic with in vitro activity against protease inhibitor-resistant viruses; Agouron); VX-175/GW-433908 (phosphate prodrug of amprenavir; Vertex & Glaxo Welcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643–678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX40–4C (a cationic peptide), T22 (an 18 amino acid peptide; Trimeris) and the T22 analogs T 134 and T140; CCR5 antagonists such as RANTES (9–68), AOP-RANTES, NNY-RANTES, and TAK-779; and CCR5/CXCR4 antagonists such as NSC 651016 (a distamycin analog). Also included are CCR2B, CCR3, and CCR6 antagonists. Chemokine recpetor agonists such as RANTES, SDF-1, MIP-1α, MIP-1β, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compunds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors such as VX-497 (Vertex); and myvopholic acids such as CellCept (mycophenolate mofetil; Roche).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1α, MIP-1β, SDF-1α, IL-2, PROLEUKIN™ (aldesleukin/L2–7001; Chiron), IL-4, IL-10, IL-12, and IL-13; interferons such as IFN-α2a; antagonists of TNFs, NFκB, GM-CSF, M-CSF, and IL-10; agents that modulate immune activation such as cyclosporin and prednisone; vaccines such as Remune™ (HIV Immunogen), APL 400–003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targetted to the ER to block surface expression of newly synthesized CCR5 (Yang et al., *PNAS* 94:11567–72 (1997); Chen et al., *Nat. Med.* 3:1110–16 (1997)); antibodies such as the anti-CXCR4 antibody 12G5, the anti-CCR5 antibodies 2D7, 5C7, PA8, PA9, PA10, PA11, PA12, and PA14, the anti-CD4 antibodies Q4120 and RPA-T4, the anti-CCR3 antibody 7B11, the anti-gp120 antibodies 17b, 48d, 447–52D, 257-D, 268-D and 50.1, anti-Tat antibodies, anti-TNF-α antibodies, and monoclonal antibody 33A; aryl hydrocarbon (AH) receptor agonists and antagonists such as TCDD, 3,3',4,4',5-pentachlorobiphenyl, 3,3',4,4'-tetrachlorobiphenyl, and α-naphthoflavone (WO 98/30213); and antioxidants such as γ-L-glutamyl-L-cysteine ethyl ester (γ-GCE; WO 99/56764).

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTJN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, compositions of the invention are used in any combination with LEUCOVORIN™ and/or NEUPOGEN™ to prophylactically treat, prevent, and/or diagnose an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells.

Other immunosuppressive agents, that may be administered in combination with the compositions of the invention include, but are not limited to, prednisolone, methotrexate, thalidomide, methoxsalen, rapamycin, leflunomide, mizoribine (BREDININ™), brequinar, deoxyspergualin, and azaspirane (SKF 105685).

In specific embodiments, compositions of the invention are administered in combination with immunosuppressants. Immunosuppressant preparations that may be administered with the Therapeutics of the invention include, but are not limited to, ORTHOCLONE OKT® 3 (muromonab-CD3), SANDIMMUNE™, NEORAL™, SANGDYA™ (cyclosporine), PROGRAF® (FK506, tacrolimus), CELLCEPT(® (mycophenolate motefil, of which the active metabolite is mycophenolic acid), IMURAN™ (azathioprine), glucorticosteroids, adrenocortical steroids such as DELTASONE™ (prednisone) and HYDELTRASOL™ (prednisolone), FOLEX™ and MEXATE™ (methotrxate), OXSORALEN-ULTRA™ (methoxsalen) and RAPAMUNE™ (sirolimus). In a specific embodiment, immunosuppressants may be used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine.

In a preferred embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In one embodiment, the compositions of the invention are administered in combination with one or more of the following drugs: infliximab (also known as Remicade™ Centocor, Inc.), Trocade (Roche, RO-32–3555), Leflunomide (also known as Arava™ from Hoechst Marion Roussel), Kineret™ (an IL-1 Receptor antagonist also known as Anakinra from Amgen, Inc.), SCIO-469 (p38 kinase inhibitor from Scios, Inc), and/or ASLERA™ (prasterone, dehydroepiandrosterone, GL701) from Genelabs Technologies Inc.

In a preferred embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, and prednisolone.

In a more preferred embodiment, the compositions of the invention are administered in combination with an antimalarial, methotrexate, anti-TNF antibody, ENBREL™ and/or suflasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another specific embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, methotrexate and suflasalazine. In other embodiments, one or more antimalarials is combined with one of the above-recited combinations. In a specfic embodiment, the compositions of the invention are administered in combination with an antimalarial (e.g., hydroxychloroquine), ENBREL™, methotrexate and suflasalazine. In another specfic embodiment, the compositions of the invention are administered in combination with an antimalarial (e.g., hydroxychloroquine), sulfasalazine, anti-TNF antibody, and methotrexate.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIM™, GAMMAGARD S/D™, and GAMIMUNE™. In a specific embodiment, compositions of the invention are administered in combination with intravenous immune globulin preparations in transplantation therapy (e.g., bone marrow transplant).

CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In one embodiment, the compositions of the invention are administered in combination with anti-CD20 antibodies, human monoclonal anti-CD20 antibodies. In another embodiment, the compositions of the invention are administered in combination with anti-CD20 antibodies and CHOP, or anti-CD20 antibodies and any combination of one or more of the components of CHOP, particularly cyclophosphamide and/or prednisone. In a specific embodiment, compositions of the invention are administered in combination with Rituximab. In a further embodiment, compositions of the invention are administered with Rituximab and CHOP, or Rituximab and any combination of one or more of the components of CHOP, particularly cyclophosphamide and/or prednisone. In a specific embodiment, compositions of the invention are administered in combination with tositumomab (anti-CD20 antibody from Coulter Pharmaceuticals, San Francisco, Calif.). In a further embodiment, compositions of the invention are administered with tositumomab and CHOP, or tositumomab and any combination of one or more of the components of CHOP, particularly cyclophosphamide and/or prednisone. Tositumomab may optionally be associated with $^{131}$I. The anti-CD20 antibodies may optionally be associated with radioisotopes, toxins or cytotoxic prodrugs.

In another specific embodiment, the compositions of the invention are administered in combination Zevalin™. In a further embodiment, compositions of the invention are administered with Zevalin™ and CHOP, or Zevalin™ and any combination of one or more of the components of CHOP, particularly cyclophosphamide and/or prednisone. Zevalin™ may be associated with one or more radisotopes. Particularly preferred isotopes are $^{90}$Y and $^{111}$In.

In an additional embodiment, the compositions of the invention are administered in combination with cytokines. Cytokines that may be administered with the compositions of the invention include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In another embodiment, compositions of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, the compositions of the invention are administered in combination with IL4 and IL10.

In one embodiment, the compositions of the invention are administered in combination with one or more chemokines. In specific embodiments, the compositions of the invention are administered in combination with an α(CxC) chemokine selected from the group consisting of gamma-interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B cell stimulatory factor (PBSF)); and/or a β(CC) chemokine selected from the group consisting of: RANTES (regulated on activation, normal T expressed and secreted), macrophage inflammatory protein-1 alpha (MIP-1α), macrophage inflammatory protein-1 beta (MIP-1β), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1γ), macrophage inflammatory protein-3 alpha (MIP-3α), macrophage inflammatory protein-3 beta (MIP-3β), macrophage inflammatory protein-4 (MIP-4/DC-CK-1/PARC), eotaxin, Exodus, and I-309; and/or the γ(C) chemokine, lymphotactin.

In an additional embodiment, the compositions of the invention are administered with a chemokine. In another embodiment, the compositions of the invention are administered with chemokine beta-8, chemokine beta-1, and/or macrophage inflammatory protein-4. In a preferred embodiment, the compositions of the invention are administered with chemokine beta-8.

In an additional embodiment, the compositions of the invention are administered in combination with an IL-4 antagonist. IL-4 antagonists that may be administered with the compositions of the invention include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, the compositions of the invention are administered in combination with an IL-13 antagonist. IL-13 antagonists that may be administered with the compositions of the invention include, but are not limited to: soluble IL-13 receptor polypeptides, multimeric forms of soluble IL-13 receptor polypeptides; anti-IL-13 receptor antibodies that bind the IL-13 receptor without transducing the biological signal elicited by IL-13, anti-IL-13 antibodies that block binding of IL-13 to one or more IL-13 receptors, and muteins of IL-13 that bind IL-13 receptors but do not transduce the biological signal elicited by IL-13. Preferably, the antibodies employed according to this method are monoclonal antibodies (including antibody fragments, such as, for example, those described herein).

In an additional embodiment, the compositions of the invention are administered in combination with hematopoietic growth factors. Hematopoietic growth factors that may be administered with the compositions of the invention include, but are not limited to, LEUKINE™ (SARGRAMOSTIM™) and NEUPOGEN™ (FILGRASTIM™).

The invention also encompasses combining the polynucleotides and/or polypeptides of the invention (and/or agonists or antagonists thereof) with other proposed or conventional hematopoietic therapies. Thus, for example, the polynucleotides and/or polypeptides of the invention (and/or agonists or antagonists thereof) can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations of the compositions of the invention with compounds generally used to treat aplastic anemia, such as, for example, methenolene, stanozolol, and nandrolone; to treat iron-deficiency anemia, such as, for example, iron preparations; to treat malignant anemia, such as, for example, vitamin $B_{12}$ and/or folic acid; and to treat hemolytic anemia, such as, for example, adrenocortical steroids, e.g., corticoids. See e.g., Resegotti et al., Panminerva Medica, 23:243–248 (1981); Kurtz, FEBS Letters, 14a:105–108 (1982); McGonigle et al., Kidney Int., 25:437–444 (1984); and Pavlovic-Kantera, Expt. Hematol., 8(supp. 8) 283–291 (1980), the contents of each of which are hereby incorporated by reference in their entireties.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins, See for e.g., Dunn, "Current Concepts in Erythropoiesis", John Wiley and Sons (Chichester, England, 1983); Kalmani, Kidney Int., 22:383–391 (1982); Shahidi, New Eng. J. Med., 289:72–80 (1973); Urabe et al., J. Exp. Med., 149:1314–1325 (1979); Billat et al., Expt. Hematol., 10:133–140 (1982); Naughton et al., Acta Haemat, 69:171–179 (1983); Cognote et al. in abstract 364, Proceedings 7th Intl. Cong. of Endocrinology (Quebec City, Quebec, Jul. 1–7, 1984); and Rothman et al., 1982, J. Surg. Oncol., 20:105–108 (1982). Methods for stimulating hematopoiesis comprise administering a hematopoietically effective amount (i.e., an amount which effects the formation of blood cells) of a pharmaceutical composition containing polynucleotides and/or poylpeptides of the invention (and/or agonists or antagonists thereof) to a patient. The polynucleotides and/or polypeptides of the invention and/or agonists or antagonists thereof is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin $B_{12}$, folic acid and/or adrenocortical steroids.

In an additional embodiment, the compositions of the invention are administered in combination with fibroblast growth factors. Fibroblast growth factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Additionally, the compositions of the invention may be administered alone or in combination with other therapeutic regimens, including but not limited to, radiation therapy. Such combinatorial therapy may be administered sequentially and/or concomitantly.

Agonists and Antagonists—Assays and Molecules

The invention also provides a method of screening compounds to identify those which enhance or block the action of TR17 polypeptide on cells, such as its interaction with TR17 binding molecules such as ligand molecules. An agonist is a compound which increases the natural biological functions of TR17 or which functions in a manner similar to TR17 while antagonists decrease or eliminate such functions.

In another embodiment, the invention provides a method for identifying a ligand protein or other ligand-binding protein which binds specifically to TR17 polypeptide. For example, a cellular compartment, such as a membrane or a preparation thereof, may be prepared from a cell that expresses a molecule that binds TR17 ligand (e.g., Neutrokine-alpha and/or APRIL). The preparation is incubated with labeled TR17 ligand and complexes of TR17 ligand bound to TR17 or other binding protein are isolated and characterized according to routine methods known in the art. Alternatively, the TR17 ligand polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds TR17 such as a molecule of a signaling or regulatory pathway modulated by TR17. The preparation is incubated with labeled TR17 in the absence or the presence of a candidate molecule which may be a TR17 agonist or antagonist. The ability of the candidate molecule to bind the binding molecule is reflected in decreased binding of the labeled ligand. Molecules which bind gratuitously, i.e., without inducing the effects of TR17 on binding the TR17 binding molecule, are most likely to be good antagonists. Molecules that bind well and elicit effects that are the same as or closely related to TR17 are agonists.

TR17-like effects of potential agonists and antagonists may by measured, for instance, by determining activity of a second messenger system following interaction of the candidate molecule with a cell or appropriate cell preparation, and comparing the effect with that of TR17 or molecules that elicit the same effects as TR17. Second messenger systems that may be useful in this regard include but are not limited to AMP guanylate cyclase, ion channel or phosphoinositide hydrolysis second messenger systems.

Another example of an assay for TR17 antagonists is a competitive assay that combines TR17 and a potential antagonist with membrane-bound ligand molecules or recombinant TR17 ligang molecules under appropriate conditions for a competitive inhibition assay. TR17 can be labeled, such as by radioactivity, such that the number of TR17 molecules bound to a ligand molecule can be determined accurately to assess the effectiveness of the potential antagonist.

Potential antagonists include small organic molecules, peptides, polypeptides (e.g., IL-13), and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a ligand molecule, without inducing TR17 induced activities, thereby preventing the action of TR17 by excluding TR17 from binding.

Other potential antagonists include antisense molecules. Antisense technology can be used to control gene expression through antisense DNA or RNA or through triple-helix formation. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the extracellular domain of the polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of TR17. The antisense RNA oligonucleotide hybridizes to the mRNA in vivo and blocks translation of the mRNA molecule into TR17 polypeptide. The oligonucleotides described above can also be delivered to cells such that the antisense RNA or DNA may be expressed in vivo to inhibit production of TR17.

In one embodiment, the TR17 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TR17 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding TR17, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a TR17 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TR17 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a TR17 RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'- non-translated, non-coding regions of TR17 shown in FIG. 1, respectively, could be used in an antisense approach to inhibit translation of endogenous TR17 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of TR17 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., Proc. Natl. Acad. Sci. 84:648–652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., BioTechniques 6:958–976 (1988)) or intercalating agents. (See, e.g., Zon, Pharm. Res. 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al., Nucl. Acids Res. 15:6625–6641 (1987)). The oligonucleotide is a 2-0-methylribonucleotide (Inoue et al., Nucl. Acids Res. 15:6131–6148 (1987)), or a chimeric RNA-DNA analogue (Inoue et al., FEBS Lett. 215:327–330 (1997)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448–7451 (1988)), etc.

While antisense nucleotides complementary to the TR17 coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy TR17 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of TR17 (FIG. 1). Preferably, the ribozyme is engineered so that the cleavage recognition site is located near the 5' end of the TR17 mRNA; i.e., to increase efficiency and minimize the intracellular accumulation of non-functional MRNA transcripts.

As in the antisense approach, the ribozymes of the invention can be composed of modified oligonucleotides (e.g. for improved stability, targeting, etc.) and should be delivered to cells which express TR17 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TR17 messages and inhibit translation. Since ribozymes unlike antisense molecules, are catalytic, a lower intracellular concentration is required for efficiency.

Endogenous gene expression can also be reduced by inactivating or "knocking out" the TR17 gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In other embodiments, antagonists according to the present invention include soluble forms of TR17 (e.g., fragments of TR17 shown in FIG. 1 that include the ligand binding domain, TNFR conserved domain, and/or extracellular domain of TR17). Such soluble forms of the TR17, which may be naturally occurring or synthetic, antagonize TR17 mediated signaling by competing with native TR17 for binding to TR17 ligand (e.g., Neutrokine-alpha (International Publication No. WO 98/18921), and/or APRIL (International Publication Number WO 97/33902; J. Exp. Med. 188(6):1185–1190), and/or by forming a multimer that may or may not be capable of binding the receptor, but which is incapable of inducing signal transduction. Preferably, these antagonists inhibit TR17 mediated stimulation of lymphocyte (e.g., B-cell) proliferation, differentiation, and/or activation. Antagonists of the present invention also include antibodies specific for TNFR-family receptors and TR17-Fc fusion proteins.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-alpha, lymphotoxin-alpha (LT-alpha, also known as TNF-beta), LT-beta (found in complex heterotrimer LT-alpha2-beta), FasL, CD40L, (TNF-gamma (International Publication No. WO 96/14328), AIM-I (International Publication No. WO 97/33899), AIM-II (International Publication No. WO 97/34911), APRIL (International Publication Number WO 97/33902; J. Exp. Med. 188(6):1185–1190), endokine-alpha (International Publication No. WO 98/07880), neutrokine-alpha (International Publication No. WO 98/18921), CD27L, CD30L, 4-1BBL, OX40L, CD27, CD30, 4-1BB, OX40, and nerve growth factor (NGF). In specific embodiments, the TNF-family ligand is Neutrokine-alpha, or fragments or variants thereof. In other specific embodiments, the TNF-family ligand is APRIL, or fragments or variants thereof.

Antagonists of the present invention also include antibodies specific for TNF-family ligands (e.g., Neutrokine alpha and APRIL) or the TR17 polypeptides of the invention. Antibodies according to the present invention may be prepared by any of a variety of standard methods using TR17 immunogens of the present invention. As indicated, such TR17 immunogens include the complete TR17 polypeptides depicted in FIG. 1 (SEQ ID NO:2) and TR17 polypeptide fragments comprising, for example, one or both of the cysteine rich domains, extracellular domain, transmembrane domain, and/or intracellular domain, or any combination thereof.

Polyclonal and monoclonal antibody agonists or antagonists according to the present invention can be raised according to the methods disclosed in Tartaglia and Goeddel, *J. Biol. Chem.* 267(7):4304–4307(1992)); Tartaglia et al., *Cell* 73:213–216 (1993)), and PCT Application WO 94/09137 and are preferably specific to (i.e., bind uniquely to polypeptides of the invention having the amino acid sequence of SEQ ID NO:2. The term "antibody" (Ab) or "monoclonal antibody" (mAb) as used herein is meant to include intact molecules as well as fragments thereof (such as, for example, Fab and F(ab') fragments) which are capable of binding an antigen. Fab, Fab' and F(ab') fragments lack the Fc fragment intact antibody, clear more rapidly from the circulation, and may have less non-specific tissue binding of an intact antibody (Wahl et al., *J. Nucl. Med.*, 24:316–325 (1983)).

In a preferred method, antibodies according to the present invention are mAbs. Such mAbs can be prepared using hybridoma technology (Kohler and Millstein, *Nature* 256:495–497 (1975) and U.S. Pat. No. 4,376,110; Harlow et al., *Antibodies: A Laboratory Manual,* Cold Spring Harbor Laboratory Press, Cold Spring Harbor, N.Y., 1988; *Monoclonal Antibodies and Hybridomas: A New Dimension in Biological Analyses,* Plenum Press, New York, N.Y., 1980; Campbell, "Monoclonal Antibody Technology," In: *Laboratory Techniques in Biochemistry and Molecular Biology,* Volume 13 (Burdon et al., eds.), Elsevier, Amsterdam (1984)).

Proteins and other compounds which bind the TR17 domains are also candidate agonists and antagonists according to the present invention. Such binding compounds can be "captured" using the yeast two-hybrid system (Fields and Song, *Nature* 340:245–246 (1989)). A modified version of the yeast two- hybrid system has been described by Roger Brent and his colleagues (Gyuris, *Cell* 75:791–803 (1993); Zervos et al., *Cell* 72:223–232 (1993)). Preferably, the yeast two-hybrid system is used according to the present invention to capture compounds which bind to the extracellular domain, intracellular, transmembrane, and one or both of the cysteine rich domains of the TR17. Such compounds are good candidate agonists and antagonists of the present invention.

For example, using the two-hybrid assay described above, the extracellular or intracellular domain of the TR17, or a portion thereof (e.g., one or both of the cysteine rich domains), may be used to identify cellular proteins which interact with TR17 the receptor in vivo. Such an assay may also be used to identify ligands with potential agonistic or antagonistic activity of TR17 receptor function. This screening assay has previously been used to identify protein which interact with the cytoplasmic domain of the murine TNF-RII and led to the identification of two receptor associated proteins. Rothe et al., *Cell* 78:681 (1994). Such proteins and amino acid sequences which bind to the cytoplasmic domain of the TR17 are good candidate agonist and antagonist of the present invention.

Other screening techniques include the use of cells which express the polypeptide of the present invention (for example, transfected CHO cells) in a system which measures extracellular pH changes caused by receptor activation, for example, as described in *Science,* 246:181–296 (1989). In another example, potential agonists or antagonists may be contacted with a cell which expresses the polypeptide of the present invention and a second messenger response, e.g., signal transduction may be measured to determine whether the potential antagonist or agonist is effective.

Agonists according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457–1458 (1995)).

Preferred agonists are fragments of TR17 polypeptides of the invention which stimulate lymphocyte (e.g., B cell) proliferation, differentiation and/or activation. Further preferred agonists include polyclonal and monoclonal antibodies raised against the TR17 polypeptides of the invention, or a fragment thereof. Such agonist antibodies raised against a TNF-family receptor are disclosed in Tartaglia et al., *Proc. Natl. Acad. Sci. USA* 88:9292–9296 (1991); and Tartaglia et al., *J. Biol. Chem.* 267:4304–4307(1992). See, also, PCT Application WO 94/09137.

In an additional embodiment, immunoregulatory molecules such as, for example, IL2, IL3, IL4, IL5, IL6, IL7, IL10, IL12, IL13, IL15, anti-CD40, CD40L, IFN-gamma and TNF-alpha, may be used as agonists of TR17 polypeptides of the invention which stimulate lymphocyte (e.g., B cell) proliferation, differentiation and/or activation. In a specific embodiment, IL4 and/or IL10 are used to enhance the TR17-mediated proliferation of B cells.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

In yet another embodiment of the invention, the activity of TR17 polypeptide can be reduced using a "dominant negative." To this end, constructs which encode defective TR17 polypeptide, such as, for example, mutants lacking all or a portion of the TNF-conserved domain, can be used in gene therapy approaches to diminish the activity of TR17 on appropriate target cells. For example, nucleotide sequences that direct host cell expression of TR17 polypeptide in which all or a portion of the TNFR-conserved domain is altered or missing can be introduced into monocytic cells or other cells or tissues (either by in vivo or ex vivo gene therapy methods described herein or otherwise known in the art). Alternatively, targeted homologous recombination can be utilized to introduce such deletions or mutations into the subject's endogenous TR17 gene in monocytes. The engineered cells will express non-functional TR17 polypeptides (i.e., a receptor (e.g., multimer) that may be capable of binding, but which is incapable of inducing signal transduction).

Diagnostic Assays

The compounds of the present invention are useful for diagnosis or treatment of various immune system-related disorders in mammals, preferably humans. Such disorders include but are not limited to tumors (e.g., B cell and monocytic cell leukemias and lymphomas) and tumor metastasis, infections by bacteria, viruses and other parasites, immunodeficiencies, inflammatory diseases, lymphadenopathy, autoimmune diseases, and graft versus host disease.

TR17 is expressed in B cells and spleen. For a number of immune system-related disorders, substantially altered (increased or decreased) levels of TR17 gene expression can be detected in immune system tissue or other cells or bodily fluids (e.g., sera, plasma, urine, synovial fluid or spinal fluid) taken from an individual having such a disorder, relative to a "standard" TR17 gene expression level, that is, the TR17 expression level in immune system tissues or bodily fluids from an individual not having the immune system disorder. Thus, the invention provides a diagnostic method useful during diagnosis of an system disorder, which involves measuring the expression level of the gene encoding the TR17 polypeptide in immune system tissue or other cells or body fluid from an individual and comparing the measured gene expression level with a standard TR17 gene expression level, whereby an increase or decrease in the gene expression level(s) compared to the standard is indicative of an immune system disorder or normal activation, proliferation, differentiation, and/or death.

In particular, it is believed that certain tissues in mammals with cancer of cells or tissue of the immune system express significantly enhanced or reduced levels of normal or altered TR17 polypeptide and mRNA encoding the TR17 polypeptide when compared to a corresponding "standard" level. Further, it is believed that enhanced or depressed levels of the TR17 polypeptide can be detected in certain body fluids (e.g., sera, plasma, urine, and spinal fluid) or cells or tissue from mammals with such a cancer when compared to sera from mammals of the same species not having the cancer.

For example, as disclosed herein, TR17 are expressed in B cells. Accordingly, polynucleotides of the invention (e.g., polynucleotide sequences complementary to all or a portion of TR17 mRNA) and antibodies (and antibody fragments) directed against the polypeptides of the invention may be used to quantitate or qualitate concentrations of cells of B cell lineage (e.g., B cell leukemia cells) expressing TR17 on their cell surfaces. These antibodies additionally have diagnostic applications in detecting abnormalities in the level of TR17 gene expression, or abnormalities in the structure and/or temporal, tissue, cellular, or subcellular location of TR17. These diagnostic assays may be performed in vivo or in vitro, such as, for example, on blood samples, biopsy tissue or autopsy tissue.

Thus, the invention provides a diagnostic method useful during diagnosis of a immune system disorder, including cancers of this system, which involves measuring the expression level of the gene encoding the TR17 polypeptide in immune system tissue or other cells or body fluid from an individual and comparing the measured gene expression level with a standard TR17 gene expression level, whereby an increase or decrease in the gene expression level compared to the standard is indicative of an immune system disorder.

Where a diagnosis of a disorder in the immune system, including diagnosis of a tumor, has already been made according to conventional methods, the present invention is useful as a prognostic indicator, whereby patients exhibiting enhanced or depressed TR17 gene expression will experience a worse clinical outcome relative to patients expressing the gene at a level nearer the standard level.

By "assaying the expression level of the gene encoding the TR17 polypeptide" is intended qualitatively or quantitatively measuring or estimating the level of the TR17 polypeptide or the level of the mRNA encoding the TR17 polypeptide in a first biological sample either directly (e.g., by determining or estimating absolute protein level or mRNA level) or relatively (e.g., by comparing to the TR17 polypeptide level or mRNA level in a second biological sample). Preferably, the TR17 polypeptide level or mRNA level in the first biological sample is measured or estimated and compared to a standard TR17 polypeptide level or mRNA level, the standard being taken from a second biological sample obtained from an individual not having the disorder or being determined by averaging levels from a population of individuals not having a disorder of the immune system. As will be appreciated in the art, once a standard TR17 polypeptide level or mRNA level is known, it can be used repeatedly as a standard for comparison.

By "biological sample" is intended any biological sample obtained from an individual, cell line, tissue culture, or other source containing TR17 receptor protein (including portions thereof) or mRNA. As indicated, biological samples include body fluids (such as sera, plasma, urine, synovial fluid and spinal fluid) which contain free extracellular domains of the TR17 polypeptide, immune system tissue, and other tissue sources found to express complete or free extracellular domain of the TR17 receptor. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the TR17 polypeptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

The present invention also relates to diagnostic assays such as quantitative and diagnostic assays for detecting levels of TR17 receptor protein, or the soluble form thereof, in a biological sample (e.g., cells and tissues), including determination of normal and abnormal levels of polypeptides. Thus, for instance, a diagnostic assay in accordance with the invention for detecting over-expression of TR17, or soluble form thereof, compared to normal control tissue samples may be used to detect the presence of tumors, for example. Assay techniques that can be used to determine levels of a protein, such as a TR17 protein of the present invention, or a soluble form thereof, in a sample derived from a host are well-known to those of skill in the art. Such assay methods include radioimmunoassays, competitive-binding assays, Western Blot analysis and ELISA assays. Assaying TR17 protein levels in a biological sample can occur using any art-known method.

Assaying TR17 polypeptide levels in a biological sample can occur using antibody-based techniques. For example, TR17 polypeptide expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting TR17 polypeptide gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

The tissue or cell type to be analyzed will generally include those which are known, or suspected, to express the TR17 gene (such as, for example, cells of B cell lineage and the spleen) or cells or tissue which are known, or suspected, to express the TR17 ligand gene (such as, for example, cells of monocytic lineage). The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the TR17 gene or TR17 ligand gene.

For example, antibodies, or fragments of antibodies, such as those described herein, may be used to quantitatively or qualitatively detect the presence of TR17 gene products or conserved variants or peptide fragments thereof. This can be accomplished, for example, by immunofluorescence techniques employing a fluorescently labeled antibody coupled with light microscopic, flow cytometric, or fluorimetric detection.

The antibodies (or fragments thereof), TR17 polypeptides, and/or TR17 ligands (e.g., Neutrokine-alpha and/or APRIL) of the present invention may, additionally, be employed histologically, as in immunofluorescence, immunoelectron microscopy or non-immunological assays, for in situ detection of TR17 gene products or conserved variants or peptide fragments thereof, or for TR17 binding to TR17 ligand. In situ detection may be accomplished by removing a histological specimen from a patient, and applying thereto a labeled antibody or TR17 polypeptide of the present invention. The antibody (or fragment) or TR17 polypeptide is preferably applied by overlaying the labeled antibody (or fragment) onto a biological sample. Through the use of such a procedure, it is possible to determine not only the presence of the TR17 gene product, or conserved variants or peptide fragments, or TR17 polypeptide binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for TR17 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding TR17 gene products or conserved variants or peptide fragments thereof, and detecting the bound antibody by any of a number of techniques well-known in the art.

Immunoassays and non-immunoassays for TR17 ligand gene products or conserved variants or peptide fragments thereof will typically comprise incubating a sample, such as a biological fluid, a tissue extract, freshly harvested cells, or lysates of cells which have been incubated in cell culture, in the presence of a detectable or labeled TR17 polypeptide capable of identifying TR17 ligand gene products or conserved variants or peptide fragments thereof, and detecting the bound TR17 polypeptide by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-TR17 antibody or detectable TR17 polypeptide. The solid phase support may then be washed with the buffer a second time to remove unbound antibody or polypeptide. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-TR17 antibody or TR17 polypeptide may be determined according to well known methods. Those skilled in the art will be able to determine operative and optimal assay conditions for each determination by employing routine experimentation.

In addition to assaying TR17 polypeptide levels or polynucleotide levels in a biological sample obtained from an individual, TR17 polypeptide or polynucleotide can also be detected in vivo by imaging. For example, in one embodiment of the invention, TR17 polypeptide is used to image monocytic leukemias or lymphomas. In another embodiment, TR17 polynucleotides of the invention and/or anti-TR17 antibodies (e.g., polynucleotides complementary to all or a portion of TR17 mRNA) are used to image B cell leukemias or lymphomas.

Antibody labels or markers for in vivo imaging of TR17 polypeptide include those detectable by X-radiography, NMR, MRI, CAT-scans or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. Where in vivo imaging is used to detect enhanced levels of TR17 polypeptide for diagnosis in humans, it may be preferable to use human antibodies or "humanized" chimeric monoclonal antibodies. Such antibodies can be produced using techniques described herein or otherwise known in the art. For example methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Additionally, any TR17 polypeptide whose presence can be detected, can be administered. For example, TR17 polypeptides labeled with a radio-opaque or other appropriate compound can be administered and visualized in vivo, as discussed, above for labeled antibodies. Further such TR17 polypeptides can be utilized for in vitro diagnostic procedures.

A TR17 polypeptide-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TR17 protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

With respect to antibodies, one of the ways in which the anti-TR17 antibody can be detectably labeled is by linking the same to an enzyme and using the linked product in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller et al., *J. Clin. Pathol.* 31:507–520 (1978); Butler, J. E., *Meth. Enzymol.* 73:482–523 (1981); Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect TR17 through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by means including, but not limited to, a gamma counter, a scintillation counter, or autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, ophthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Antibodies

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes monoclonal, polyclonal, chimeric, humanized, and human monoclonal and human polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. *J. Immunol.* 147:60–69 (1991); U.S. Pat. Nos. 5,573,920, 4,474,893, 5,601,819, 4,714,681, 4,925,648; Kostelny, S. A. et al. *J. Immunol.* 148:1547–1553 (1992).

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not a limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art and taught in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties). Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. *J. Immunol. Methods* 182:41–50 (1995); Ames, R. S. et al. *J. Immunol. Methods* 184:177–186 (1995); Kettleborough, C. A. et al. *Eur. J. Immunol.* 24:952–958 (1994); Persic, L. et al. *Gene* 187:9–18 (1997); Burton, D. R. et al. *Advances in Immunology* 57:191–280 (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al. *BioTechniques* 12(6):864–869 (1992); and Sawai, H. et al. *AJRI* 34:26–34 (1995); and Better, M. et al. *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al. *Methods in Enzymology* 203:46–88 (1991); Shu, L. et al. *PNAS* 90:7995–7999 (1993); and Skerra, A. et al. *Science* 240:1038–1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, *Science* 229:1202 (1985); Oi et al., *BioTechniques* 4:214 (1986); Gillies, S. D. et al. *J. Immunol. Methods* 125:191–202 (1989); and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., *Molecular Immunology* 28(4/5):489–498 (1991); Studnicka G. M. et al. *Protein Engineering* 7(6):805–814 (1994); Roguska M. A. et al. *PNAS* 91:969–973 (1994)), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and International Patent application publication numbers WO 98/46645, WO 98/50433, WO 98/24893, WO 98/16654, WO 96/34096, WO 96/33735, and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. *Immunol. Lett.* 39:91–99 (1994); U.S. Pat. No. 5,474,981; Gillies, S. O. et al. *PNAS* 89:1428–1432 (1992); Fell, H. P. et al. *J. Immunol.* 146:2446–2452 (1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. *PNAS* 88:10535–10539 (1991); Zheng, X. X. et al. *J. Immunol.* 154:5590–5600 (1995); and Vil, H. et al. *PNAS* 89:11337–11341 (1992) (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. *Blood* 92(6):1981–1988 (1998); Chen, Z. et al. *Cancer Res.* 58(16):3668–3678 (1998); Harrop, J. A. et al. *J. Immunol.* 161(4):1786–1794 (1998); Zhu, Z. et al. *Cancer Res.* 58(15):3209–3214 (1998); Yoon, D. Y. et al. *J. Immunol.* 160(7):3170–3179 (1998); Prat, M. et al. *J. Cell. Sci.* 111(Pt2):237–247 (1998); Pitard, V. et al. *J. Immunol. Methods* 205(2):177–190 (1997); Liautard, J. et al. *Cytokinde* 9(4):233–241 (1997); Carlson, N. G. et al. *J. Biol. Chem.* 272(17):11295–11301 (1997); Taryman, R. E. et al. *Neuron* 14(4):755–762 (1995); Muller, Y. A. et al. *Structure* 6(9):1153–1167 (1998); Bartunek, P. et al. *Cytokine* 8(1):14–20 (1996) (said references incorporated by reference in their entireties).

For example, the present invention includes antibodies which disrupt the ability of the proteins of the invention to multimerize. In another example, the present invention includes antibodies which allow the proteins of the invention to multimerize, but disrupts the ability of the proteins of the invention to bind one or more TR17 ligand(s) (e.g., Neutrokine-alpha and/or APRIL). In yet another example, the present invention includes antibodies which allow the proteins of the invention to multimerize, and bind TR17 ligand(s), but blocks biological activity associated with the TR17/ligand complex.

As discussed above, antibodies to the TR17 proteins of the invention can, in turn, be utilized to generate anti-idiotype antibodies that "mimic" TR17 using techniques well known to those skilled in the art. (See, e.g., Greenspan & Bona, *FASEB J.* 7(5):437–444; (1989) and Nissinoff, *J. Immunol.* 147(8):2429–2438 (1991)). For example, antibodies which bind to TR17 and competitively inhibit TR17 multimerization and/or binding to ligand can be used to generate anti-idiotypes that "mimic" the TR17 mutimerization and/or binding domain and, as a consequence, bind to and neutralize TR17 and/or its ligands (e.g., Neutrokine-alpha and/or APRIL). Such neutralizing anti-idiotypes or Fab fragments of such anti-idiotypes can be used in therapeutic regimens to neutralize TR17 ligands (e.g., Neutrokine-alpha and/or APRIL). For example, such anti-idiotypic antibodies can be used to bind TR17, or to bind TR17 ligands, and thereby block TR17 mediated cell signalling.

Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (D. V. Goeddel et al., "Tumor Necrosis Factors: Gene Structure and Biological Activities," *Symp. Quant. Biol.* 51:597–609 (1986), Cold Spring Harbor; B. Beutler and A. Cerami, *Annu. Rev. Biochem.* 57:505–518 (1988); L. J. Old, *Sci. Am.* 258:59–75 (1988); W. Fiers, *FEBS Lett.* 285:199–224 (1991)). The TNF-family ligands induce such various cellular responses by binding to TNF-family receptors, including the TR17 of the present invention.

TR17 polynucleotides, polypeptides, agonists and/or antagonists (e.g., agonistic antibodies) of the invention may be administered to a patient (e.g., mammal, preferably human) afflicted with any disease or disorder mediated (directly or indirectly) by defective, or deficient levels of, TR17. Alternatively, a gene therapy approach may be applied to treat such diseases or disorders. In one embodiment of the invention, TR17 polynucleotide sequences are used to detect mutein TR17 genes, including defective genes. Mutein genes may be identified in in vitro diagnostic assays, and by comparison of the TR17 nucleotide sequence disclosed herein with that of a TR17 gene obtained from a patient suspected of harboring a defect in this gene. Defective genes may be replaced with normal TR17-encoding genes using techniques known to one skilled in the art.

In another embodiment, the TR17 polypeptides, polynucleotides, agonists and/or antagonists of the present invention are used as research tools for studying the phenotypic effects that result from inhibiting TR17/TR17 ligand interactions on various cell types. TR17 polypeptides and antagonists (e.g. monoclonal antibodies to TR17) also may be used in in vitro assays for detecting TR17, TR17 ligands, or the interactions thereof.

Cells or tissue which express the TR17 polypeptide and are believed to have a potent cellular response to TR17 ligands include B cells, spleen, brain, and testis. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated dysregulation of these physiological responses, such as, for example, diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes (J. C. Ameisen, *AIDS* 8:1197–1213 (1994); P. H. Krammer et al., *Curr. Opin. Immunol.* 6:279–289 (1994)).

Diseases associated with increased cell survival, or the inhibition of apoptosis, and that may be treated or prevented by the polynucleotides, polypeptides and/or agonists or antagonists of the invention include, but are not limited to, cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostrate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. In preferred embodiments, TR17 polynucleotides, polypeptides, and/or antagonists of the invention are used to inhibit growth, progression, and/or metasis of cancers, in particular those listed above, or in the paragraph that follows.

Additional diseases or conditions associated with increased cell survival and that may be treated or prevented by the polynucleotides, polypeptides and/or agonists or antagonists of the invention include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Thus, in preferred embodiments TR17 polynucleotides or polypeptides of the invention and agonists or antagonists thereof, are used to treat or prevent autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment TR17 polynucleotides or polypeptides of the invention and/or agonists or antagonists thereof, are used to activate, differentiate or proliferate cancerous cells or tissue (e.g., B cell lineage related cancers (e.g., CLL and MLL), lymphocytic leukemia, or lymphoma) and thereby render the cells more vulnerable to cancer therapy (e.g., chemotherapy or radiation therapy).

Diseases associated with increased apoptosis and that may be treated or prevented by the polynucleotides, polypeptides and/or agonists or antagonists of the invention include, but are not limited to, AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis); myelodysplastic syndromes (such as aplastic anemia), graft v. host disease, ischemic injury (such as that caused by myocardial infarction, stroke and reperfusion injury), liver injury (such as hepatitis related liver injury, ischemia/reperfusion injury, cholestosis (bile duct injury) and liver cancer); toxin-induced liver disease (such as that caused by alcohol), septic shock, cachexia and anorexia. In preferred embodiments, TR17 polynucleotides, polypeptides and/or agonists are used to treat the diseases and disorders listed above.

Many of the pathologies associated with HIV are mediated by apoptosis, including HIV-induced nephropathy and HIV encephalitis. Thus, in additional preferred embodiments, TR17 polynucleotides, polypeptides, and/or TR17 agonists (e.g., anti-TR17 antibodies) or antagonists of the invention are used to treat AIDS and pathologies associated with AIDS.

The state of immunodeficiency that defines AIDS is secondary to a decrease in the number and function of CD4$^+$ T-lymphocytes. Recent reports estimate the daily loss of CD4$^+$ T cells to be between $3.5 \times 10^7$ and $2 \times 10^9$ cells (Wei et al., *Nature* 373:117–122 (1995)). One cause of CD4$^+$ T cell depletion in the setting of HIV infection is believed to be HIV-induced apoptosis (see, for example, Meyaard et al., *Science* 257:217–219, 1992; Groux et al., *J. Exp. Med.*, 175:331, 1992; and Oyaizu et al., in *Cell Activation and Apoptosis in HIV Infection*, Andrieu and Lu, Eds., Plenum Press, New York, 1995, pp. 101–114). Indeed, HIV-induced apoptotic cell death has been demonstrated not only in vitro but also, more importantly, in infected individuals (J. C. Ameisen, *AIDS* 8:1197–1213 (1994); T. H. Finkel and N. K. Banda, *Curr. Opin. Immunol.* 6:605–615(1995); C. A. Muro-Cacho et al., *J. Immunol.* 154:5555–5566 (1995)). Furthermore, apoptosis and CD4$^+$ T-lymphocyte depletion is tightly correlated in different animal models of AIDS (T. Brunner et al., *Nature* 373:441–444 (1995); M. L. Gougeon et al., *AIDS Res. Hum. Retroviruses* 9:553–563 (1993)) and, apoptosis is not observed in those animal models in which viral replication does not result in AIDS. Id. Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (A. D. Badley et al., *J. Virol.* 70:199–206 (1996)). Further, the TNF-family ligand was detectable in uninfected macrophages and its expression was upregulated following HIV infection resulting in selective killing of uninfected CD4 T-lymphocytes. Id. Thus, by the invention, a method for treating HIV$^+$ individuals is provided which involves administering TR17 and/or TR17 agonists (e.g., anti-TR17 antibodies) or antagonists of the present invention to reduce selective killing of CD4$^+$ T-lymphocytes. Modes of administration and dosages are discussed in detail below.

Activated human T cells are induced to undergo programmed cell death (apoptosis) upon triggering through the CD3/T cell receptor complex, a process termed activated-induced cell death (AICD). AICD of CD4$^+$ T cells isolated from HIV-Infected asymptomatic individuals has been reported (Groux et al., supra). Thus, AICD may play a role in the depletion of CD4$^+$ T cells and the progression to AIDS in HIV-infected individuals. Thus, the present invention provides a method of inhibiting TNF ligand-mediated T cell death in HIV patients, comprising administering a TR17 polypeptide of the invention (preferably, a soluble TR17 polypeptide) to the patients. In one embodiment, the patient is asymptomatic when treatment with TR17 commences. If desired, prior to treatment, peripheral blood T cells may be extracted from an HIV patient, and tested for susceptibility to TNF ligand-mediated cell death by procedures known in the art. In one embodiment, a patient's blood or plasma is contacted with TR17 ex vivo. The TR17 may be bound to a suitable chromatography matrix by procedures known in the art. The patient's blood or plasma flows through a chromatography column containing TR17 bound to the matrix, before being returned to the patient. The immobilized TR17 binds TNF ligand, thus removing TNF ligand protein from the patient's blood.

In additional embodiments a TR17 polypeptide of the invention is administered in combination with other inhibitors of T cell apoptosis. For example, Fas-mediated apoptosis and TRAIL-mediated apoptosis have also has been implicated in loss of T cells in HIV individuals (See, e.g., Katsikis et al., *J. Exp. Med.* 181:2029–2036 (1995)). Thus, a patient susceptible to Fas ligand mediated and/or TRAIL mediated T cell death may be treated with an agent that blocks Fas-ligand/Fas receptor interactions and/or an agent that blocks TRAIL/TRAIL interactions.

Suitable agents for blocking binding of Fas-ligand to Fas that may be administered with the TR17 polynucleotides or polypeptides of the invention (including TR17 agonists (e.g., angonistic antibodies) and/or antagonists) include, but are not limited to, soluble Fas polypeptides; mulitmeric forms of soluble Fas polypeptides (e.g., dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Preferably, the antibodies employed according to this method are monoclonal antibodies. Examples of suitable agents for blocking Fas-ligand/Fas interactions, including blocking anti-Fas monoclonal antibodies, are described in International application publication number WO 95/10540, hereby incorporated by reference.

Suitable agents, which also block binding of TRAIL to a TRAIL receptor that may be administered with the polynucleotides and/or polypeptides of the present invention include, but are not limited to, soluble TRAIL receptor polypeptides (e.g., a soluble form of OPG, DR4 (International application publication number WO 98/32856); TR5 (International application publication number WO 98/30693); and DR5 (International application publication number WO 98/41629)); multimeric forms of soluble TRAIL receptor polypeptides; and TRAIL receptor antibodies that bind the TRAIL receptor without transducing the biological signal that results in apoptosis, anti-TRAIL antibodies that block binding of TRAIL to one or more TRAIL receptors, and muteins of TRAIL that bind TRAIL receptors but do not transduce the biological signal that results in apoptosis. Preferably, the antibodies employed according to this method are monoclonal antibodies.

TR17 polypeptides or polynucleotides encoding TR17 of the invention may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, Patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects, and conditions characterized by clotting of small blood vessels.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, thrombotic microangiopathies (e.g., thrombotic thrombocytopenic purpura (TTP) and hemolytic-uremic syndrome (HUS)), and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630–634 (1991); Folkman et al., *N. Engl. J Med.*, 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., *Science* 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases or disorders associated with neovascularization by administration of the TR17 polynucleotides and/or polypeptides of the invention (including TR17 agonists (e.g., agonistic antibodies) and/or antagonists). Malignant and metastatic conditions which can be treated with the polynucleotides and polypeptides of the invention include, but are not limited to those malignancies, solid tumors, and cancers described herein and otherwise known in the art (for a review of such disorders, see Fishman et al., Medicine, 2d Ed., J. B. Lippincott Co., Philadelphia (1985)).

Additionally, ocular disorders associated with neovascularization which can be treated with the TR17 polynucleotides and polypeptides of the present invention (including TR17 agonists and TR17 antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Additionally, disorders which can be treated with the TR17 polynucleotides and polypeptides of the present invention (including TR17 agonists and TR17 antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

The polynucleotides and/or polypeptides of the invention and/or agonists and/or antagonists thereof, can also be employed to inhibit the proliferation and differentiation of hematopoietic cells and therefore may be employed to protect bone marrow stem cells from chemotherapeutic agents during chemotherapy. This antiproliferative effect may allow administration of higher doses of chemotherapeutic agents and, therefore, more effective chemotherapeutic treatment.

The polynucleotides and/or polypeptides of the invention and/or agonists and/or antagonists thereof, may also be employed for the expansion of immature hematopoeitic progenitor cells, for example, granulocytes, macrophages or monocytes (e.g., C-kit+, Sca-1+), by temporarily preventing their differentiation. These bone marrow cells may be cultured in vitro. Thus, TR17 may be useful as a modulator of hematopoietic stem cells in vitro for the purpose of bone marrow transplantation and/or gene therapy. Since stem cells are rare and are most useful for introducing genes into for gene therapy, TR17 can be used to isolate enriched populations of stem cells. Stem cells can be enriched by culturing cells in the presence of cytotoxins, such as 5-Fu, which kills rapidly dividing cells, where as the stem cells will be protected by TR17. These stem cells can be returned to a bone marrow transplant patient or can then be used for transfection of the desired gene for gene therapy. In addition, TR17 can be injected into animals which results in the release of stem cells from the bone marrow of the animal into the peripheral blood. These stem cells can be isolated for the purpose of autologous bone marrow transplantation or manipulation for gene therapy. After the patient has finished chemotherapy or radiation treatment, the isolated stem cells can be returned to the patient.

In a specific embodiment, polynucleotides and/or polypeptides of the invention and/or angonists and/or antagonists thereof may be used to increase the concentration of blood cells in individuals in need of such increase (i.e., in hematopoietin therapy). Conditions that may be ameliorated by administering the compositions of the invention include, but are not limited to, neutropenia, anemia, and thrombocytopenia.

In a specific embodiment, the polynucleotides and/or polypeptides of the invention (and/or agonists or antagonists thereof) are used in erythropoietin therapy, which is directed toward supplementing the oxygen carrying capacity of blood. Polynucleotides and/or polypeptides of the invention (and/or agonists or antagonists thereof) may be used to treat or prevent diseases or conditions in patients generally requiring blood transfusions, such as, for example, trauma victims, surgical patients, dialysis patients, and patients with a variety of blood composition-affecting disorders, such as, for example, hemophilia, cystic fibrosis, pregnancy, menstrual disorders, early anemia of prematurity, spinal cord injury, aging, various neoplastic disease states, and the like. Examples of patient conditions that require supplementation of the oxygen carrying capacity of blood and which are within the scope of this invention, include, but are not limited to: treatment of blood disorders characterized by low or defective red blood cell production, anemia associated with chronic renal failure, stimulation of reticulocyte response, development of ferrokinetic effects (such as plasma iron turnover effects and marrow transit time effects), erythrocyte mass changes, stimulation of hemoglobin C synthesis, and increasing levels of hematocrit in vertebrates. The invention also provides for treatment to enhance the oxygen-carrying capacity of an individual, such as for example, an individual encountering hypoxic environmental conditions.

TR17 polynucleotides, polypeptides and/or agonists or antagonists may also be employed to regulate hematopoiesis, by regulating the activation and differentiation of various hematopoietic progenitor cells, for example, to release mature leukocytes from the bone marrow following chemotherapy, i.e., in stem cell mobilization. TR17 polynucleotides, polypeptides and/or agonists or antagonists may also be employed to treat sepsis.

TR17 polynucleotides, polypeptides and/or agonists or antagonists may also be employed to inhibit T-cell proliferation by the inhibition of IL-2 biosynthesis for the treatment of T-cell mediated auto-immune diseases and lymphocytic leukemias (including, for example, chronic lymphocytic leukemia (CLL)).

TR17 polynucleotides, polypeptides and/or agonists or antagonists may also be employed to stimulate wound healing, both via the recruitment of debris clearing and connective tissue promoting inflammatory cells. In this same manner, TR17 polynucleotides, polypeptides and/or agonists or antagonists may also be employed to treat other fibrotic disorders, including liver cirrhosis, osteoarthritis and pulmonary fibrosis.

TR17 polynucleotides, polypeptides and/or agonists or antagonists may also be employed to enhance host defenses against resistant chronic and acute infections, for example, myobacterial infections via the attraction and activation of microbicidal leukocytes.

TR17 polynucleotides, polypeptides and/or agonists or antagonists also increases the presence of eosinophils which have the distinctive function of killing the larvae of parasites that invade tissues, as in schistosomiasis, trichinosis and ascariasis.

TR17 polynucleotides or polypeptides, or agonists of TR17 (e.g., agonistic antibodies), can be used in the treatment of infectious agents. For example, by increasing the immune response, particularly increasing the proliferation and differentiation of B cells, infectious diseases may be treated. The immune response may be increased by either enhancing an existing immune response, or by initiating a new immune response. Alternatively, TR17 polynucleotides or polypeptides, or agonists or antagonists of TR17, may also directly inhibit the infectious agent, without necessarily eliciting an immune response.

Viruses are one example of an infectious agent that can cause disease or symptoms that can be treated by TR17 polynucleotides or polypeptides, or agonists or antagonists of TR17. Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. TR17 polynucleotides or polypeptides, or agonists or antagonists of TR17, can be used to treat or detect any of these symptoms or diseases. In specific embodiments, TR17 polynucleotides, polypeptides, or agonists are used to treat: meningitis, Dengue, EBV, and/or hepatitis (e.g., hepatitis B). In an additional specific embodiment TR17 polynucleotides, polypeptides, or agonists are used to treat patients nonresponsive to one or more other commercially available hepatitis vaccines. In a further specific embodiment, TR17 polynucleotides, polypeptides, or agonists are used to treat AIDS.

Similarly, bacterial or fungal agents that can cause disease or symptoms and that can be treated by TR17 polynucleotides or polypeptides, or agonists or antagonists of TR17, include, but not limited to, the following Gram-Negative and Gram-positive bacteria and bacterial families and fungi: Actinomycetales (e.g., *Corynebacterium, Mycobacterium, Norcardia*), *Cryptococcus neoformans,* Aspergillosis, Bacillaceae (e.g., Anthrax, *Clostridium*), Bacteroidaceae, Blastomycosis, *Bordetella, Borrelia* (e.g., *Borrelia burgdorferi*, Brucellosis, Candidiasis, *Campylobacter*, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi,* and *Salmonella paratyphi*), *Serratia, Yersinia*), *Erysipelothrix, Helicobacter*, Legionellosis, Leptospirosis, *Listeria, Mycoplasmatales, Mycobacterium leprae, Vibrio cholerae*, Neisseriaceae (e.g., *Acinetobacter*, Gonorrhea, Menigococcal), Meisseria meningitidis, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. TR17 polynucleotides or polypeptides, or agonists or antagonists of TR17, can be used to treat or detect any of these symptoms or diseases. In specific embodiments, TR17 polynucleotides, polypeptides, or agonists thereof are used to treat: tetanus, Diptheria, botulism, and/or meningitis type B.

Moreover, parasitic agents causing disease or symptoms that can be treated by TR17 polynucleotides or polypeptides, or agonists or antagonists of TR17, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and *Trichomonas* and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. TR17 polynucleotides or polypeptides, or agonists or antagonists of TR17, can be used to treat or detect any of these symptoms or diseases. In specific embodiments, TR17 polynucleotides, polypeptides, or agonists or antagonists thereof are used to treat malaria.

In another embodiment, the invention provides a method of delivering compositions containing the polypeptides of the invention (e.g., compositions containing TR17 polypeptides or anti-TR17 antibodies associated with heterologous polypeptides, heterologous nucleic acids, toxins, or prodrugs) to targeted cells, such as, for example, B cells expressing TR17, or monocytes expressing the cell surface bound form of a TNF ligand that binds TR17. TR17 polypeptides of the invention, TNF ligands that bind TR17, or anti-TR17 antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., TR17 polypeptides or anti-TR17 antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., TR17 polypeptides or anti-TR17 antibodies) in association with toxins or cytotoxic prodrugs.

In a specific embodiment, the invention provides a method for the specific destruction of cells of B cell lineage (e.g., B cell related leukemias or lymphomas) by administering anti-TR17 antibodies or TNF ligands that bind TR17, in association with toxins or cytotoxic prodrugs.

In another specific embodiment, the invention provides a method for the specific destruction of cells of monocytic lineage (e.g., monocytic leukemias or lymphomas) by administering TR17 polypeptides of the invention (e.g., soluble TR17 polypeptides) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

An additional condition, disease or symptom that can be treated by TR17 polynucleotides or polypeptides, or agonists or antagonist of TR17, is osteomyelitis.

Preferably, treatment using TR17 polynucleotides or polypeptides, or agonists (e.g., agonistic antibodies directed to TR17) or antagonists of TR17, could either be by administering an effective amount of TR17 polynucleotide or polypeptide to the patient, or by removing cells from the patient, supplying the cells with TR17 polynucleotide, and returning the engineered cells to the patient (ex vivo therapy). Moreover, as further discussed herein, the TR17 polypeptide or polynucleotide can be used as an adjuvant in a vaccine to raise an immune response against infectious disease.

Additional preferred embodiments of the invention include, but are not limited to, the use of TR17 polypeptides, TR17 polynucleotides, TR17 antibodies and functional agonists thereof, in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741.

A vaccine adjuvant that enhances immune responsiveness to specific antigen. In a specific embodiment, the vaccine adjuvant is a TR17 polypeptide described herein. In another specific embodiment, the vaccine adjuvant is a TR17 polynucleotide described herein (i.e., the TR17 polynucleotide is a genetic vaccine adjuvant). As discussed herein, TR17 polynucleotides may be administered using techniques known in the art, including but not limited to, liposomal delivery, recombinant vector delivery, injection of naked DNA, and gene gun delivery.

An adjuvant to enhance tumor-specific immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions of the invention are used as an adjuvant to enhance an immune response to the HIV gp120 antigen.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae,* Group B *streptococcus, Shigella* spp., Enterotoxigenic *Escherichia coli,* Enterohemorrhagic *E. coli, Borrelia burgdorferi,* and *Plasmodium* (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria).

As a stimulator of B cell responsiveness to pathogens.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among B cell immunodeficient individuals. B cell immunodeficiencies that may be ameliorated or treated by administering the TR17 polypeptides or polynucleotides of the invention, or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVI) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymophoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

In a specific embodiment, TR17 polypeptides or polynucleotides of the invention, or agonists thereof, is administered to treat or ameliorate selective IgA deficiency.

In another specific embodiment, TR17 polypeptides or polynucleotides of the invention, or agonists thereof, is administered to treat or ameliorate ataxia-telangiectasia.

In another specific embodiment, TR17 polypeptides or polynucleotides of the invention, or agonists thereof, is administered to treat or ameliorate common variable immunodeficiency.

In another specific embodiment, TR17 polypeptides or polynucleotides of the invention, or agonists thereof, is administered to treat or ameliorate X-linked agammaglobulinemia.

In another specific embodiment, TR17 polypeptides or polynucleotides of the invention, or agonists thereof, is administered to treat or ameliorate severe combined immunodeficiency (SCID).

In another specific embodiment, TR17 polypeptides or polynucleotides of the invention, or agonists thereof, is administered to treat or ameliorate Wiskott-Aldrich syndrome.

In another specific embodiment, TR17 polypeptides or polynucleotides of the invention, or agonists thereof, is administered to treat or ameliorate severe combined immunodeficiency (SCID).

In another specific embodiment, TR17 polypeptides or polynucleotides of the invention, or agonists thereof, is administered to treat or ameliorate X-linked Ig deficiency with hyper IgM.

As an agent to boost immunoresponsiveness among individuals having an acquired loss of B cell function. Conditions resulting in an acquired loss of B cell function that may be ameliorated or treated by administering the TR17 polypeptides or polynucleotides of the invention, or agonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the TR17 polypeptides or polynucleotides of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, and/or B-cells. In one embodiment, TR17 polypeptides (in soluble, membrane-bound or transmembrane forms) or polynucleotides enhance antigen presentation or antagonize antigen presentation in vitro or in vivo. Moreover, in related embodiments, said enhancement or antagonization of antigen presentation may be useful as an anti-tumor treatment or to modulate the immune system.

As a mediator of mucosal immune responses.

As an agent to direct an individuals immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a monocyte cell specific binding protein to which specific activators or inhibitors of cell growth may be attached. The result would be to focus the activity of such activators or inhibitors onto normal, diseased, or neoplastic B cell populations.

As a means of detecting B-lineage cells.

As a stimulator of B cell production in pathologies such as AIDS, chronic lymphocyte disorder and/or Common Variable Immunodificiency.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance TR17 mediated responses.

As a means of activating monocytes/macrophages to defend against parasitic diseases that effect monocytes such as Leshmania.

As pretreatment of bone marrow samples prior to transplant. Such treatment would increase B cell representation and thus accelerate recover.

As a means of regulating secreted cytokines that are elicited by TR17.

TR17 polypeptides or polynucleotides of the invention, or agonists may be used to modulate IgE concentrations in vitro or in vivo.

Additionally, TR17 polypeptides or polynucleotides of the invention, or agonists thereof, may be used to treat or prevent IgE-mediated allergic reactions. Such allergic reactions include, but are not limited to, asthma, rhinitis, and eczema.

All of the above described applications as they may apply to veterinary medicine.

Antagonists of TR17 include binding and/or inhibitory antibodies, antisense nucleic acids, ribozymes, soluble forms of TR17, or TNF-ligands that bind TR17. These would be expected to reverse many of the activities of the ligand described above as well as find clinical or practical application as:

A means of blocking various aspects of immune responses to foreign agents or self. Examples include autoimmune disorders such as lupus, and arthritis, as well as immunoresponsiveness to skin allergies, inflammation, bowel disease, injury and pathogens.

A therapy for preventing the B cell proliferation and Ig secretion associated with autoimmune diseases such as idiopathic thrombocytopenic purpura, systemic lupus erythramatosus and MS.

An inhibitor of graft versus host disease or transplant rejection.

A therapy for B cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

As a B cell specific binding protein to which specific activators or inhibitors of cell growth may be attached. The result would be to focus the activity of such activators or inhibitors onto normal, diseased, or neoplastic B cell populations.

As part of a B cell selection device the function of which is to isolate B cells from a heterogenous mixture of cell types. Anti-TR17 antibody or TNF ligands that bind TR17 could be coupled to a solid support to which B cells would then specifically bind. Unbound cells would be washed out and the bound cells subsequently eluted. This technique would allow purging of tumor cells from, for example, bone marrow or peripheral blood prior to transplant.

An immunosuppressive agent(s).

TR17 polypeptides or polynucleotides of the invention, or antagonists may be used to modulate IgE concentrations in vitro or in vivo.

In another embodiment, administration of TR17 polypeptides or polynucleotides of the invention, or antagonists thereof, may be used to treat or prevent IgE-mediated allergic reactions including, but not limited to, asthma, rhinitis, and eczema.

An inhibitor of signaling pathways involving ERK1, COX2 and Cyclin D2 which have been associated with TR17 induced B cell activation.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

The agonists and antagonists may be employed in a composition with a pharmaceutically acceptable carrier, e.g., as described above.

The antagonists may be employed for instance to inhibit TR17 the chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the TR17 polypeptides of the present invention. The antagonists may also be employed for treating atherosclerosis, by preventing monocyte infiltration in the artery wall. The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by TR17. The antagonists may also be employed to treat cases of bone marrow failure, for example, aplastic anemia and myelodysplastic syndrome. The antagonists may also be employed to treat asthma and allergy by preventing eosinophil accumulation in the lung. The antagonists may also be employed to treat subepithelial basement membrane fibrosis which is a prominent feature of the asthmatic lung. The antagonists may also be employed to treat lymphomas (e.g., one or more of the extensive, but not limiting, list of lymphomas provided herein).

Antibodies against TR17 may be employed to bind to and inhibit TR17 activity to treat ARDS, by preventing infiltration of neutrophils into the lung after injury. The antagonists and antagonists of the instant may be employed in a composition with a pharmaceutically acceptable carrier, e.g., as described hereinafter.

TR17 polynucleotides, polypeptides, and/or agonists and antagonists may be employed in a composition with a pharmaceutically acceptable carrier, e.g., as described hererin.

Polynucleotides and/or polypeptides of the invention and/or agonists and/or antagonists thereof are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.))), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, regulating hematopoiesis and wound healing (e.g., wounds, burns, and bone fractures).

Polynucleotides and/or polypeptides of the invention and/or agonists and/or antagonists thereof are also useful as an adjuvant to enhance immune responsiveness to specific antigen, anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

In one aspect, the present invention is directed to a method for enhancing TR17 mediated signaling by a TNF-family ligand, which involves administering to a cell which expresses the TR17 polypeptide an effective amount of TR17 ligand, analog or an agonist capable of increasing TR17 mediated signaling. Preferably, TR17 mediated signaling is increased to treat a disease wherein increased apoptosis, decreased cytokine and adhesion molecule expression, or decreased cell proliferation is exhibited. An agonist can include soluble forms of TR17 and monoclonal antibodies directed against the TR17 polypeptide.

In a further aspect, the present invention is directed to a method for inhibiting TR17 mediaated signaling induced by a TNF-family ligand, which involves administering to a cell which expresses the TR17 polypeptide an effective amount of an antagonist capable of decreasing TR17 mediated signaling. Preferably, TR17 mediated signaling is decreased to treat a disease wherein decreased apoptosis or NFkB expression, or increased cell proliferation, is exhibited. An antagonist can include soluble forms of TR17 and monoclonal antibodies directed against the TR17 polypeptide.

By "agonist" is intended naturally occurring and synthetic compounds capable of enhancing or potentiating TR17 mediated signaling. By "antagonist" is intended naturally occurring and synthetic compounds capable of inhibiting apoptosis. Whether any candidate "agonist" or "antagonist" of the present invention can enhance or inhibit TR17 mediated signaling can be determined using art-known TNF-family ligand/receptor cellular response assays, including those described in more detail below.

One such screening procedure involves the use of melanophores which are transfected to express the receptor of the present invention. Such a screening technique is described in PCT WO 92/01810. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation. For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into *Xenopus* oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique well known in the art involves expressing in cells a construct wherein the receptor is linked to a phospholipase C or D. Exemplary cells include endothelial cells, smooth muscle cells, embryonic kidney cells, etc. The screening may be accomplished as hereinabove described by detecting activation of the receptor or inhibition of activation of the receptor from the phospholipase signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonists and antagonists of the present invention are described in L. A. Tartaglia and D. V. Goeddel, *J. Biol. Chem.* 267:4304–4307(1992).

Thus, in a further aspect, a screening method is provided for determining whether a candidate agonist or antagonist is capable of enhancing or inhibiting a cellular response to a TNF-family ligand. The method involves contacting cells which express the TR17 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in B and/or T cell proliferation or tritiated thymidine labeling). By the invention, a cell expressing the TR17 polypeptide can be contacted with either an endogenous or exogenously administered TNF-family ligand.

Agonists according to the present invention include naturally occurring and synthetic compounds such as, for example, the CD40 ligand, neutral amino acids, zinc, estrogen, androgens, viral genes (such as Adenovirus ElB, Baculovirus p35 and IAP, Cowpox virus crmA, Epstein-Barr virus BHRF1, LMP-1, African swine fever virus LMW5-HL, and Herpesvirus yl 34.5), calpain inhibitors, cysteine protease inhibitors, and tumor promoters (such as PMA, Phenobarbital, and _-Hexachlorocyclohexane).

Antagonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457–1458 (1995)). Further preferred agonists include TR17 polypeptides of the invention, polyclonal and monoclonal antibodies raised against the TR17 polypeptide, or a fragment thereof. Such agonist antibodies raised against a TNF-family receptor are disclosed in L. A. Tartaglia et al., *Proc. Natl. Acad. Sci. USA* 88:9292–9296 (1991); and L. A. Tartaglia and D. V. Goeddel, *J. Biol. Chem.* 267:4304–4307 (1992). See, also, PCT Application WO 94/09137.

Other potential antagonists according to the invention include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression,* CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

In specific embodiments, antagonists according to the present invention are nucleic acids corresponding to the sequences contained in TR17 (FIG. 1; SEQ ID NO:1). In one embodiment, antisense sequence is generated internally by the organism, in another embodiment, the antisense sequence is separately administered (see, for example, Okano H. et al., *J. Neurochem.* 56:560 (1991), and Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, *Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

In one embodiment, the TR17 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TR17 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding TR17, or fragments thereof, can be by any promoter known in the art to act in vertebrate, preferably human cells. Such promoters can be inducible or constitutive. Such promoters include, but are not limited to, the SV40 early promoter region (Bernoist and Chambon, *Nature* 29:304–310 (1981), the promoter contained in the 3' long terminal repeat of Rous sarcoma virus (Yamamoto et al., *Cell* 22:787–797 (1980), the herpes thymidine promoter (Wagner et al., *Proc. Nat. Acad. Sci. U.S.A.* 78:1441–1445 (1981), the regulatory sequences of the metallothionein gene (Brinster, et al., *Nature* 296:39–42 (1982)), etc.

The antisense nucleic acids of the invention comprise a sequence complementary to at least a portion of an RNA transcript of a TR17 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TR17 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a TR17 RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333–335 (1994). Thus, oligonucleotides complementary to either the 5'- or 3'- non-translated, non-coding regions of the TR17 shown in FIG. 1 could be used in an antisense approach to inhibit translation of endogenous TR17 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. While antisense nucleotides complementary to the TR17 coding region sequence may be used, those complementary to the transcribed untranslated region are most preferred. Whether designed to hybridize to the 5'-, 3'- or coding region of TR17 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553–6556 (1989); Lemaitre et al., *Proc. Natl. Acad. Sci.* 84:648–652 (1987); PCT Publication No. WO88/09810) or the blood-brain barrier (see, e.g., PCT Publication No. WO89/10134), hybridization-triggered cleavage agents. (See, e.g., Krol et al., *BioTechniques* 6:958–976 (1988)) or intercalating agents. (See, e.g., Zon, *Pharm. Res.* 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625–6641 (1987)). The oligonucleotide is a 2'-0-methylribonucleotide (Inoue et al., *Nucl. Acids Res.* 15:6131–6148 (1987)), or a chimeric RNA-DNA analogue (Inoue et al., *FEBS Lett.* 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448–7451 (1988)), etc.

Potential antagonists according to the invention also include catalytic RNA, or a ribozyme (See, e.g., PCT International Publication WO 90/11364; Sarver et al, *Science* 247:1222–1225 (1990). While ribozymes that cleave mRNA at site specific recognition sequences can be used to destroy TR17 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of TR17 (FIG. 1 (SEQ ID NO:1)). Preferably, the ribozyme is engineered so that the cleavage recognition site is located near the 5' end of the TR17 mRNA; i.e., to increase efficiency and minimize the intracellular accumulation of non-functional mRNA transcripts.

As in the antisense approach, the ribozymes of the invention can be composed of modified oligonucleotides (e.g., for improved stability, targeting, etc.) and should be delivered to cells which express TR17 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TR17 messages and inhibit translation. Since ribozymes unlike antisense molecules, are catalytic, a lower intracellular concentration is required for efficiency.

Endogenous gene expression can also be reduced by inactivating or "knocking out" the TR17 gene and/or its promoter using targeted homologous recombination. (E.g., see Smithies et al., *Nature* 317:230–234 (1985); Thomas & Capecchi, *Cell* 51:503–512 (1987); Thompson et al., *Cell* 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

The techniques of gene-shuffling, motif-shuffling, exon-shuffling, and/or codon-shuffling (collectively referred to as "DNA shuffling") may be employed to modulate the activities of TR17 thereby effectively generating agonists and antagonists of TR17. See generally, International Publication No. WO 99/29902, U.S. Pat. Nos. 5,605,793, 5,811,238, 5,830,721, 5,834,252, and 5,837,458, and Patten et al., *Curr. Opinion Biotechnol.* 8:724–33 (1997); Harayama, *Trends Biotechnol.* 16(2):76–82 (1998); Hansson et al., *J. Mol. Biol.* 287:265–76 (1999); and Lorenzo and Blasco, *Biotechniques* 24(2):308–13 (1998) (each of these Patents and publications are hereby incorporated by reference). In one embodiment, alteration of TR17 polynucleotides and corresponding polypeptides may be achieved by DNA shuffling. DNA shuffling involves the assembly of two or more DNA segments into a desired TR17 molecule by homologous, or site-specific, recombination. In another embodiment, TR17 polynucleotides and corresponding polypeptides may be alterred by being subjected to random mutagenesis by error-prone PCR, random nucleotide insertion or other methods prior to recombination. In another embodiment, one or more components, motifs, sections, parts, domains, fragments, etc., of TR17 may be recombined with one or more components, motifs, sections, parts, domains, fragments, etc. of one or more heterologous molecules. In preferred embodiments, the heterologous molecules are include, but are not limited to, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (International Publication Number WO 97/33902; J. Exp. Med. 188(6):1185–1190 (1998)), endokine-alpha (International Publication No. WO 98/07880), neutrokine alpha (International Publication No.WO98/18921), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), 312C2 (International Publication No. WO 98/06842), and TR12, and soluble forms of BCMA (See e.g., Laabis et al., Nucleic acids research, 22(7) 1147–1154 (1994); Genbank Accession Number Z29574), CD154, CD70, and CD153. In further preferred embodiments, the heterologous molecules are any member of the TNF family.

In other embodiments, antagonists according to the present invention include soluble forms of TR17 (e.g., fragments of the TR17 shown in FIG. 1 (SEQ ID NO:2) that include one or more of the cysteine rich domains from the extracellular region of the full length receptor). Such soluble forms of the TR17, which may be naturally occurring or synthetic, antagonize TR17 mediated signaling by competing with the cell surface bound forms of the receptor for binding to TNF-family ligands. Antagonists of the present invention also include antibodies specific for TNF-family ligands and TR17-Fc fusion proteins.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (International Publication Number WO 97/33902; J. Exp. Med. 188(6):1185–1190 (1998)), endokine-alpha (International Publication No. WO 98/07880), Neutrokine alpha (International Publication No.WO98/18921), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), 312C2 (International Publication No. WO 98/06842), and TR12, and soluble forms CD154, CD70, and CD153. In specific embodiments, the TNF family ligand is Neutrokine-alpha, or fragments or variants thereof. In another specific embodiment, the TNF family ligand is APRIL, or fragments or variants thereof.

TNF-α has been shown to protect mice from infection with herpes simplex virus type 1 (HSV-1). Rossol-Voth et al., J. Gen. Virol. 72:143–147 (1991). The mechanism of the protective effect of TNF-α is unknown but appears to involve neither interferons nor NK cell killing. One member of the family has been shown to mediate HSV-1 entry into cells. Montgomery et al., Eur. Cytokine Newt. 7:159 (1996). Further, antibodies specific for the extracellular domain of this block HSV-1 entry into cells. Thus, TR17 antagonists of the present invention include both TR17 amino acid sequences and antibodies capable of preventing mediated viral entry into cells. Such sequences and antibodies can function by either competing with cell surface localized for binding to virus or by directly blocking binding of virus to cell surface receptors.

Antibodies according to the present invention may be prepared by any of a variety of methods using TR17 antigens (e.g., immunogens) of the present invention. As indicated, such TR17 antigens include the full length TR17 polypeptide (which may or may not include the leader sequence) and TR17 polypeptide fragments such as the extracellular domain, the cysteine rich domain, one or more of the TR17 cysteine-rich domains, the transmembrane domain, and the intracellular domain, or any combination thereof.

Polyclonal and monoclonal antibody agonists or antagonists according to the present invention can be raised according to the methods disclosed herein and and/or known in the art, such as, for example, those methods described in Tartaglia and Goeddel, J. Biol. Chem. 267(7):4304–4307(1992); Tartaglia et al., Cell 73:213–216 (1993), and PCT Application WO 94/09137 (the contents of each of these three publications are herein incorporated by reference in their entireties), and are preferably specific to TR17 polypeptides of the invention having the amino acid sequence of SEQ ID NO:2.

Antagonists according to the present invention include soluble forms of TR17, i.e., TR17 fragments that include one or more of the the cytsteine rich domains from the extracellular region of the full length receptor. Such soluble forms of the receptor, which may be naturally occurring or synthetic, antagonize TR17 mediated signaling by competing with the cell surface TR17 for binding to TNF-family ligands. Thus, soluble forms of the receptor that include tone or more of the cysteine-rich motifs of TR17 are novel cytokines capable of inhibiting TR17 mediated signaling induced by TNF-family ligands. These soluble forms are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (D. P. Hughes and I. N. Crispe, J. Exp. Med. 182:1395–1401 (1995)).

Proteins and other compounds which bind the TR17 domains are also candidate agonists and antagonists according to the present invention. Such binding compounds can be "captured" using the yeast two-hybrid system (Fields and Song, Nature 340:245–246 (1989)). A modified version of the yeast two-hybrid system has been described by Roger Brent and his colleagues (J. Gyuris, Cell 75:791–803 (1993); A. S. Zervos et al., Cell 72:223–232 (1993)). Preferably, the yeast two-hybrid system is used according to the present invention to capture compounds which bind to either one or more of th TR17 extracellular rich motifs or to the TR17 intracellular domain. Such compounds are good candidate agonists and antagonists of the present invention.

Modes of Administration

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients.

It will be understood that, when administered to a human patient, the total daily usage of the compounds and compositions of the present invention will be decided by the attending physician within the scope of sound medical judgment. The specific therapeutically effective dose level for any particular patient will depend upon factors well known in the medical arts.

As a general proposition, the total pharmaceutically effective amount of TR17 polypeptide administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TR17 polypeptide is typically administered at a dose rate of about 1 ug/kg/hour to about 50 ug/kg/hour, either by 1–4 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

Pharmaceutical compositions containing the TR17 polypeptide of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a nontoxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

In addition to soluble TR17 polypeptides, TR17 polypeptides containing the transmembrane region can also be used when appropriately solubilized by including detergents, such as CHAPS or NP-40, with buffer.

TR17 compositions of the invention are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988).

Sustained-release compositions also include liposomally entrapped compositions of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing TR17 polypeptide my be prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal TR17 polypeptide therapy.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990), which is hereby incorporated by reference in its entirety).

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are admninistered in combination with alum. In another specific embodiment, compositions of the invention are administered in combination with QS-21. Further adjuvants that may be administered with the compositions of the invention include, but are not limited to, Monophosphoryl lipid immunomodulator, AdjuVax 100a, QS-18, CRL1005, Aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual.

Administration "in combination" further includes the separate administration of one of the compounds or agents given first, followed by the second.

The compositions of the invention may be administered alone or in combination with other therapeutic agents. Therapeutic agents that may be administered in combination with the compositions of the invention, include but are not limited to, other members of the TNF family, chemotherapeutic agents, antibiotics, antivirals, steroidal and non-steroidal anti-inflammatories, conventional immunotherapeutic agents, cytokines, chemokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (International Publication Number WO 97/33902; *J. Exp. Med.* 188(6):1185–1190 (1998)), endokine-alpha (International Publication No. WO 98/07880), Neutrokine-alpha (Internatioanl Application Publication No. WO 98/18921), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), 312C2 (International Publication No. WO 98/06842), and TR12, and soluble forms of BCMA (See e.g., Laabis et al., Nucleic acids research, 22(7) 1147–1154 (1994); Genbank Accession Number Z29574), CD154, CD70, and CD153.

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

Additional NRTIs include LODENOSINE™ (F-ddA; an acid-stable adenosine NRTI; Triangle/Abbott; COVIRACIL™ (emtricitabine/FTC; structurally related to lamivudine (3TC) but with 3- to 10-fold greater activity in vitro; Triangle/Abbott); dOTC (BCH-10652, also structurally related to lamivudine but retains activity against a substantial proportion of lamivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/Abbott); D-D4FC (related to 3TC, with activity against AZT/3TC-resistant virus); GW420867X (Glaxo Wellcome); ZIAGEN™ (abacavir/159U89; Glaxo Wellcome Inc.); CS-87 (3'azido-2',3'-dideoxyuridine; WO 99/66936); and S-acyl-2-thioethyl (SATE)-bearing prodrug forms of β-L-FD4C and β-L-FddC (WO 98/17281).

Additional NNRTIs include COACTINON™ (Emivirine/MKC-442, potent NNRTI of the HEPT class; Triangle/Abbott); CAPRAVIRINE™ (AG-1549/S-1153, a next generation NNRTI with activity against viruses containing the K103N mutation; Agouron); PNU-142721 (has 20- to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW-420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; Abbott Laboratories); BMS-232632 (an azapeptide; Bristol-Myres Squibb); TIPRANAVIR™ (PNU-140690, a non-peptic dihydropyrone; Pharmacia & Upjohn); PD-178390 (a nonpeptidic dihydropyrone; Parke-Davis); BMS 232632 (an azapeptide; Bristol-Myers Squibb); L-756, 423 (an indinavir analog; Merck); DMP-450 (a cyclic urea compound; Avid & DuPont); AG-1776 (a peptidomimetic with in vitro activity against protease inhibitor-resistant viruses; Agouron); VX-175/GW-433908 (phosphate prodrug of amprenavir; Vertex & Glaxo Welcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643–678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX40-4C (a cationic peptide), T22 (an 18 amino acid peptide; Trimeris) and the T22 analogs T134 and T140; CCR5 antagonists such as RANTES (9–68), AOP-RANTES, NNY-RANTES, and TAK-779; and CCR5/

CXCR4 antagonists such as NSC 651016 (a distamycin analog). Also included are CCR2B, CCR3, and CCR6 antagonists. Chemokine recpetor agonists such as RANTES, SDF-1, MIP-1α, MIP-1β, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compunds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors sucha as VX-497 (Vertex); and myvopholic acids such as CellCept (mycophenolate mofetil; Roche).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1α, MIP-1β, SDF-1α, IL-2, PROLEUKIN™ (aldesleukin/L2-7001; Chiron), IL-4, IL-10, IL-12, and IL-13; interferons such as IFN-α2a; antagonists of TNFs, NFκB, GM-CSF, M-CSF, and IL-10; agents that modulate immune activation such as cyclosporin and prednisone; vaccines such as Remune™ (HIV Immunogen), APL 400-003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targetted to the ER to block surface expression of newly synthesized CCR5 (Yang et al., PNAS 94:11567–72 (1997); Chen et al., Nat. Med. 3:1110–16 (1997)); antibodies such as the anti-CXCR4 antibody 12G5, the anti-CCR5 antibodies 2D7, 5C7, PA8, PA9, PA10, PA11, PA12, and PA14, the anti-CD4 antibodies Q4120 and RPA-T4, the anti-CCR3 antibody 7B 1, the anti-gp120 antibodies 17b, 48d, 447-52D, 257-D, 268-D and 50.1, anti-Tat antibodies, anti-TNF-αantibodies, and monoclonal antibody 33A; aryl hydrocarbon (AH) receptor agonists and antagonists such as TCDD, 3,3',4,4',5-pentachlorobiphenyl, 3,3',4,4'-tetrachlorobiphenyl, and α-naphthoflavone (WO 98/30213); and antioxidants such as γ-L-glutamyl-L-cysteine ethyl ester (γ-GCE; WO 99/56764).

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIM™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMNE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, compositions of the invention are used in any combination with GANCICLOVIR™, FOSCARNET™, and/or CIDOFOVIR™ to prophylactically treat or prevent an opportunistic cytomegalovirus infection. In another specific embodiment, compositions of the invention are used in any combination with FLUCONAZOLE™, ITRACONAZOLE™, and/or KETOCONAZOLE™ to prophylactically treat or prevent an opportunistic fungal infection. In another specific embodiment, compositions of the invention are used in any combination with ACYCLOVIR™ and/or FAMCICOLVIR™ to prophylactically treat or prevent an opportunistic herpes simplex virus type I and/or type II infection. In another specific embodiment, compositions of the invention are used in any combination with PYRIMETHAMINE™ and/or LEUCOVORIN™ to prophylactically treat or prevent an opportunistic *Toxoplasma gondii* infection. In another specific embodiment, compositions of the invention are used in any combination with LEUCOVORIN™ and/or NEUPOGEN™ to prophylactically treat or prevent an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

Additional immunosuppressants preparations that may be administered with the compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituxmab and CHOP, or Rituxmab and any combination one or more of the components of CHOP.

In an additional embodiment, the compositions of the invention are administered in combination with cytokines. Cytokines that may be administered with the compositions of the invention include, but are not limited to, GM-CSF, G-CSF, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, anti-CD40L, IFN-gamma and TNF-alpha. In one embodiment, the compositions of the invention are administered in combination with one or more chemokines. In specific embodiments, the compositions of the invention are administered in combination with an $\alpha$(C×C) chemokine selected from the group consisting of gamma-interferon inducible protein-10 ($\gamma$IP-10), interleukin-8 (IL-8), platelet factor-4 (PF4), neutrophil activating protein (NAP-2), GRO-$\alpha$, GRO-$\beta$, GRO-$\gamma$, neutrophil-activating peptide (ENA-78), granulocyte chemoattractant protein-2 (GCP-2), and stromal cell-derived factor-1 (SDF-1, or pre-B cell stimulatory factor (PBSF)); and/or a $\beta$(CC) chemokine selected from the group consisting of: RANTES (regulated on activation, normal T expressed and secreted), macrophage inflammatory protein-i alpha (MIP-1$\alpha$), macrophage inflammatory protein-1 beta (MIP-1$\beta$), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1$\gamma$), macrophage inflammatory protein-3 alpha (MIP-3$\alpha$), macrophage inflammatory protein-3 beta (MIP-3$\beta$), macrophage inflammatory protein-4 (MIP-4/DC-CK-1/PARC), eotaxin, Exodus, and I-309; and/or the $\gamma$(C) chemokine, lymphotactin.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

The invention also encompasses combining the polynucleotides and/or polypeptides of the invention (and/or agonists or antagonists thereof) with other proposed or conventional hematopoietic therapies. Thus, for example, the polynucleotides and/or polypeptides of the invention (and/or agonists or antagonists thereof) can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations of the compositions of the invention with compounds generally used to treat aplastic anemia, such as, for example, methenolene, stanozolol, and nandrolone; to treat iron-deficiency anemia, such as, for example, iron preparations; to treat malignant anemia, such as, for example, vitamin $B_{12}$ and/or folic acid; and to treat hemolytic anemia, such as, for example, adrenocortical steroids, e.g., corticoids. See e.g., Resegotti et al., Panminerva Medica, 23:243–248 (1981); Kurtz, FEBS Letters, 14a:105–108 (1982); McGonigle et al., Kidney Int., 25:437–444 (1984); and Pavlovic-Kantera, Expt. Hematol., 8(supp. 8) 283–291 (1980), the contents of each of which are hereby incorporated by reference in their entireties.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins, See for e.g., Dunn, "Current Concepts in Erythropoiesis", John Wiley and Sons (Chichester, England, 1983); Kalmani, Kidney Int., 22:383–391 (1982); Shahidi, New Eng. J. Med., 289:72–80

(1973); Urabe et al., J. Exp. Med., 149:1314–1325 (1979); Billat et al., Expt. Hematol., 10:133–140 (1982); Naughton et al., Acta Haemat, 69:171–179 (1983); Cognote et al. in abstract 364, Proceedings 7th Intl. Cong. of Endocrinology (Quebec City, Quebec, Jul. 1–7, 1984); and Rothman et al., 1982, J. Surg. Oncol., 20:105–108 (1982). Methods for stimulating hematopoiesis comprise administering a hematopoietically effective amount (i.e., an amount which effects the formation of blood cells) of a pharmaceutical composition containing polynucleotides and/or poylpeptides of the invention (and/or agonists or antagonists thereof) to a patient. The polynucleotides and/or polypeptides of the invention and/or agonists or antagonists thereof is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin $B_{12}$, folic acid and/or adrenocortical steroids.

In additional prefered embodiments, the compositions of the invention are administered in combination with hematopoietic growth factors. Hematopoietic growth factors that may be administered with the compositions of the invention included, but are not limited to, LEUKINE™ (SARGRAMOSTIM™) and NEUPOGEN™ (FILGRASTIM™).

In additional embodiments, the compositions of the invention are administered in combination with other therapeutic or prophylactic regimens, such as, for example, radiation therapy.

Chromosome Assays

The nucleic acid molecules of the present invention are also valuable for chromosome identification.

In certain preferred embodiments in this regard, the cDNA herein disclosed is used to clone genomic DNA of a TR17 receptor gene. This can be accomplished using a variety of well known techniques and libraries, which generally are available commercially. The genomic DNA is then used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with cDNA as short as 50 or 60 bp. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man,* available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLE 1

Protein Fusions of TR17

TR17 polypeptides of the invention are optionally fused to other proteins. These fusion proteins can be used for a variety of applications. For example, fusion of TR17 polypeptides to His-tag, HA-tag, protein A, IgG domains, and maltose binding protein facilitates purification. (See EP A 394,827; Traunecker, et al., *Nature* 331:84–86 (1988)). Similarly, fusion to IgG-1, IgG-3, and albumin increases the halflife time in vivo. Nuclear localization signals fused to TR17 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described below (SEQ ID NO:XX). These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3' BamHI site should be destroyed. Next, the vector containing the human Fc portion is re-restricted with BamHI, linearizing the vector, and TR17 polynucleotide is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

GGGATCCGGAGCCCAAATCTTCTGACAAAACTCACACATGCCCACCGTGCCCAGCACCTGAAT    (SEQ ID NO:XX)

TCGAGGGTGCACCGTCAGTCTTCCTCTTCCCCCCAAAACCCAAGGACACCCTCATGATCTCCCG

-continued

```
GACTCCTGAGGTCACATGCGTGGTGGTGGACGTAAGCCACGAAGACCCTGAGGTCAAGTTCAA

CTGGTACGTGGACGGCGTGGAGGTGCATAATGCCAAGACAAAGCCGCGGGAGGAGCAGTACA

ACAGCACGTACCGTGTGGTCAGCGTCCTCACCGTCCTGCACCAGGACTGGCTGAATGGCAAGG

AGTACAAGTGCAAGGTCTCCAACAAAGCCCTCCCAACCCCCATCGAGAAAACCATCTCCAAAG

CCAAAGGGCAGCCCCGAGAACCACAGGTGTACACCCTGCCCCCATCCCGGGATGAGCTGACCA

AGAACCAGGTCAGCCTGACCTGCCTGGTCAAAGGCTTCTATCCAAGCGACATCGCCGTGGAGT

GGGAGAGCAATGGGCAGCCGGAGAACAACTACAAGACCACGCCTCCCGTGCTGGACTCCGAC

GGCTCCTTCTTCCTCTACAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCTGT

CTCCGGGTAAATGAGTGCGACGGCCGCGACTCTAGAGGAT
```

EXAMPLE 2
Production of an anti-TR17 Antibody
a) Hybridoma Technology

The antibodies of the present invention can be prepared by a variety of methods. (See, Current Protocols, Chapter 2.) As one example of such methods, cells expressing TR17 polypeptides are administered to an animal to induce the production of sera containing polyclonal antibodies. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

In a preferred method, a preparation of TR17 polypeptides is prepared and purified to render it substantially free of natural contaminants. Such a preparation is then introduced into an animal in order to produce polyclonal antisera of greater specific activity.

Monoclonal antibodies specific for TR17 polypeptides of the present invention are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with TR17 polypeptides of the present invention or, more preferably, with a soluble form of TR17.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding a TR17 polypeptide of the present invention.

Alternatively, additional antibodies capable of binding to a TR17 polypeptide of the present invention can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the TR17-specific antibody can be blocked by a TR17 polypeptide of the present invention. Such antibodies comprise anti-idiotypic antibodies to the TR17-specific antibody and are used to immunize an animal to induce formation of further TR17-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of Antibody Fragments Directed Against Polypeptides of the Present Invention from a Library of scFvs.

Naturally occuring V-genes isolated from human PBLs are constructed into a large library of antibody fragments which contain reactivities against polypeptides of the present invention to which the donor may or may not have been exposed (see e.g., U.S. Pat. No. 5,885,793 incorporated herein in its entirety by reference).

Rescue of the Library

A library of scFvs is constructed from the RNA of human PBLs as described in WO92/01047. To rescue phage displaying antibody fragments, approximately $10^9$ E. coli harbouring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, 2×10⁸ TU of Δ gene 3 helper phage (M13 Δ gene III, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 ug/ml ampicillin and 50 ug/ml kanamycin and grown overnight. Phage are prepared as described in WO92/01047.

M13 Δ gene III is prepared as follows: M13 Δ gene III helper phage does not encode gene III protein, hence the phage(mid) displaying antibody fragments have a greater avidity of binding to antigen. Infectious M13 Δ gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the Library

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 ug/ml ampicillin. The resulting bacterial library is then rescued with Δ gene III helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

EXAMPLE 3

Method of Determining Alterations in the TR17 Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60–120 seconds at 52–58° C.; and 60–120 seconds at 70° C., using buffer solutions described in Sidransky, D., et al., *Science* 252:706 (1991).

PCR products are then sequenced using primers labeled at their 5' end with T4 polynucleotide kinase, employing SequiTherm Polymerase. (Epicentre Technologies). The intron-exon borders of selected exons of TR17 are also determined and genomic PCR products analyzed to confirm the results. PCR products harboring suspected mutations in TR17 is then cloned and sequenced to validate the results of the direct sequencing.

PCR products of TR17 are cloned into T-tailed vectors as described in Holton, T. A. and Graham, M. W., *Nucleic Acids Research*, 19:1156 (1991) and sequenced with T7 polymerase (United States Biochemical). Affected individuals are identified by mutations in TR17 not present in unaffected individuals.

Genomic rearrangements are also observed as a method of determining alterations in the TR17 gene. Genomic clones isolated using techniques known in the art are nick-translated with digoxigenindeoxy-uridine 5'-triphosphate (Boehringer Manheim), and FISH performed as described in Johnson, Cg. et al., *Methods Cell Biol.* 35:73–99 (1991). Hybridization with the labeled probe is carried out using a vast excess of human cot-1 DNA for specific hybridization to the TR17 genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., *Genet. Anal. Tech. Appl.*, 8:75 (1991).) Image collection, analysis and chromosomal fractional length measurements are performed using the ISee Graphical Program System. (Inovision Corporation, Durham, N.C.) Chromosome alterations of the genomic region of TR17 (hybridized by the probe) are identified as insertions, deletions, and translocations. These TR17 alterations are used as a diagnostic marker for an associated disease.

EXAMPLE 4

Method of Detecting Abnormal Levels of TR17 in a Biological Sample

TR17 polypeptides can be detected in a biological sample, and if an increased or decreased level of TR17 is detected, this polypeptide is a marker for a particular phenotype. Methods of detection are numerous, and thus, it is understood that one skilled in the art can modify the following assay to fit their particular needs.

For example, antibody-sandwich ELISAs are used to detect TR17 in a sample, preferably a biological sample. Wells of a microtiter plate are coated with specific antibodies to TR17, at a final concentration of 0.2 to 10 ug/ml. The antibodies are either monoclonal or polyclonal and are produced using technique known in the art. The wells are blocked so that non-specific binding of TR17 to the well is reduced.

The coated wells are then incubated for >2 hours at RT with a sample containing TR17. Preferably, serial dilutions of the sample should be used to validate results. The plates are then washed three times with deionized or distilled water to remove unbounded TR17.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

75 ul of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is prepared using the experimental results from serial dilutions of a control sample with the sample concentration plotted on the X-axis (log scale) and fluorescence or absorbance on the Y-axis (linear scale). The TR17 polypeptide concentration in a sample is then interpolated using the standard curve based on the measured flourescence of that sample.

EXAMPLE 5
Method of Treating Decreased Levels of TR17

The present invention relates to a method for treating an individual in need of a decreased level of TR17 biological activity in the body comprising, administering to such an individual a composition comprising a therapeutically effective amount of TR17 antagonist. Preferred antagonists for use in the present invention are TR17-specific antibodies.

Moreover, it will be appreciated that conditions caused by a decrease in the standard or normal expression level of TR17 in an individual can be treated by administering TR17, preferably in a soluble and/or secreted form. Thus, the invention also provides a method of treatment of an individual in need of an increased level of TR17 polypeptide comprising administering to such an individual a pharmaceutical composition comprising an amount of TR17 to increase the biological activity level of TR17 in such an individual.

For example, a patient with decreased levels of TR17 polypeptide receives a daily dose 0.1–100 ug/kg of the polypeptide for six consecutive days. Preferably, the polypeptide is in a soluble and/or secreted form.

EXAMPLE 6
Method of Treating Increased Levels of TR17

The present invention also relates to a method for treating an individual in need of an increased level of TR17 biological activity in the body comprising administering to such an individual a composition comprising a therapeutically effective amount of TR17 or an agonist thereof.

Antisense technology is used to inhibit production of TR17. This technology is one example of a method of decreasing levels of TR17 polypeptide, preferably a soluble and/or secreted form, due to a variety of etiologies, such as cancer.

For example, a patient diagnosed with abnormally increased levels of TR17 is administered intravenously antisense polynucleotides at 0.5, 1.0, 1.5, 2.0 and 3.0 mg/kg day for 21 days. This treatment is repeated after a 7-day rest period if the is determined to be well tolerated.

EXAMPLE 7
Method of Treatment Using Gene Therapy—Ex Vivo

One method of gene therapy transplants fibroblasts, which are capable of expressing soluble and/or mature TR17 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA*, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding TR17 can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanamycin for the purpose of confirming that the vector contains properly inserted TR17.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the TR17 gene is then added to the media and the packaging cells transduced with the vector. The packaging cells now produce infectious viral particles containing the TR17 gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether TR17 protein is produced.

The engineered fibroblasts are then transplanted onto the host, either alone or after having been grown to confluence on cytodex 3 microcarrier beads.

EXAMPLE 8
Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) TR17 sequences into an animal to increase or decrease the expression of the TR17 polypeptide. The TR17 polynucleotide may be operatively linked to a promoter or any other genetic elements necessary for the expression of the TR17 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al., *Cardiovasc. Res.* 35:470–479 (1997); Chao J. et al., *Pharmacol. Res.* 35:517–522 (1997); Wolff J. A. *Neuromuscul. Disord.* 7:314–318 (1997); Schwartz B. et al., *Gene Ther.* 3:405–411 (1996); Tsurumi Y. et al., *Circulation* 94:3281–3290 (1996) (incorporated herein by reference).

The TR17 polynucleotide constructs may be delivered by any method that delivers injectable materials to the cells of an animal, such as, injection into the interstitial space of tissues (heart, muscle, skin, lung, liver, intestine and the like). The TR17 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the TR17 polynucleotides may also be delivered in liposome formulations (such as those taught in Felgner P. L., et al. Ann. NY Acad. Sci. 772:126–139 (1995), and Abdallah B., et al. Biol. Cell 85(1):1–7 (1995)) which can be prepared by methods well known to those skilled in the art.

The TR17 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The TR17 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked TR17 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked TR17 polynucleotide constructs can be delivered to arteries during angioplasty by the catheter used in the procedure.

The dose response effects of injected TR17 polynucleotide in muscle in vivo is determined as follows. Suitable TR17 template DNA for production of mRNA coding for TR17 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The TR17 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for TR17 protein expression. A time course for TR17 protein expression may be done in a similar fashion except that quadriceps from different mice are harvested at different times. Persistence of TR17 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using TR17 naked DNA.

EXAMPLE 9

Gene Therapy Using Endogenous TR17 Gene

Another method of gene therapy according to the present invention involves operably associating the endogenous TR17 sequence with a promoter via homologous recombination as described, for example, in U.S. Pat. No. 5,641,670, issued Jun. 24, 1997; International Publication Number WO 96/2941 1; International Publication Number WO 94/12650; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous TR17, flanking the promoter. The targeting sequence will be sufficiently near the 5' end of TR17 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous TR17 sequence. This results in the expression of TR17 in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the TR17 locus, plasmid pUC18 (MBI Fermentas, Amherst, N.Y.) is digested with HindIII. The CMV promoter is amplified by PCR with an XbaI site on the 5' end and a BamHI site on the 3'end. Two TR17 non-coding sequences are amplified via PCR: one TR17 non-coding sequence (TR17 fragment 1) is amplified with a HindIII site at the 5' end and an Xba site at the 3'end; the other TR17 non-coding sequence (TR17 fragment 2) is amplified with a BamHI site at the 5'end and a HindIII site at the 3'end. The CMV promoter and TR17 fragments are digested with the appropriate enzymes (CMV promoter—XbaI and BamHI; TR17 fragment 1—XbaI; TR17 fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 $\mu$g/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 $\mu$F and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

EXAMPLE 10

Bioassay for the Effect of TR17Polypeptides, Agonists, or Antagonists on Hematopoietic Progenitor Cells and/or Differentiation.

Mouse bone marrow cells are used as target cells to examine the effect of TR17 polypeptides of the invention on hematopoietic progenitor cells and/or differentiation. Briefly, unfractionated bone marrow cells are first washed 2× with a serum-free IMDM that is supplemented with 10% (V/V) BIT (Bovine serum albumin, Insulin and Transferrin supplement from Stem Cell Technologies, Vancouver, Canada). The washed cells are then resuspended in the same growth medium and plated in the 96-well tissue culture plate ($5 \times 10^4$ cells/well) in 0.2 ml of the above medium in the presence or absence of cytokines and TR17. Stem cell factor (SCF) and IL-3 are included as positive mediators of cell proliferation. Cells are allowed to grow in a low oxygen environment (5% $CO_2$, 7% $O^2$, and 88% $N_2$) tissue culture incubator for 6 days. On the sixth day, 0.5 $\mu$Ci of Tritiated thymidine is added to each well and incubation is continued for an additional 16–18 hours, at which point the cells are harvested. The level of radioactivity incorporated into cellular DNA is determined by scintillation spectrometry and reflects the amount of cell proliferation.

The studies described in this example test the activity of TR17 polypeptides of the invention. However, one skilled in the art could easily modify the exemplified studies to test the activity of TR17 polynucleotides (e.g., gene therapy), agonists, and/or antagonists of TR17. Potential agonists would be expected to inhibit hematopoietic cell proliferation in the presence of SCF and/or IL3 and/or to increase the inhibition of cell proliferation in the presence of cytokines and TR17 in this assay. Potential antagonists would be expected to reduce the inhibition of cell proliferation in the presence of cytokines and TR17 in this assay.

EXAMPLE 11

Bioassay for the Effect of TR17Polypeptides, Agonists or Antagonists on IL-3 and SCF Stimulated Proliferation and Differentiation of Hematopoietic Progenitor Cells.

To determine if TR17 polypeptides of the invention inhibit specific hematopoietic lineages, mouse bone marrow cells are first washed 2× with a serum-free IMDM that is supplemented with 10% (V/V) BIT (Bovine serum albumin, Insulin and Transferrin supplement from Stem Cell Technologies, Vancouver, Canada). The washed cells are then resuspended in the same growth medium and plated in the 96-well tissue culture plate ($5 \times 10^4$ cells/well) in 0.2 ml of the above medium in the presence of IL-3 (1 ng/ml) plus SCF (5 ng/ml) with or without TR17. Cells are allowed to grow in a low oxygen environment (5% $CO_2$, 7% $O^2$, and 88% $N_2$) tissue culture incubator, and after 7 days, analyzed for expression of differentiation antigens by staining with various monoclonal antibodies and FACScan.

The studies described in this example test the activity of TR17 polypeptides of the invention. However, one skilled in the art could easily modify the exemplified studies to test the activity of TR17 polynucleotides (e.g., gene therapy), agonists, and/or antagonists of TR17. Potential agonists tested in this assay would be expected to inhibit cell proliferation in the presence of cytokines and/or to increase the inhibition of cell proliferation in the presence of cytokines and TR17. Potential antagonists tested in this assay would be expected to reduce the inhibition of cell proliferation in the presence of cytokines and TR17.

EXAMPLE 12

Effect of TR17 on IL-3 and SCF Stimulated Proliferation and Differentiation of Lin-population of Bone Marrow Cells A population of mouse bone marrow cells enriched in primitive hematopoietic progenitors can be obtained using a negative selection procedure, where the committed cells of most of the lineages are removed using a panel of monoclonal antibodies (anti cd11b, CD4, CD8, CD45R and Gr-1 antigens) and magnetic beads. The resulting population of cells (lineage depleted cells) are plated ($5\times10^4$ cells/ml) in the presence or absence of TR17 polypeptide of the invention (in a range of concentrations) in a growth medium supplemented with IL-3 (5 ng/ml) plus SCF (100 ng/ml). After seven days of incubation at 37° C. in a humidified incubator (5% $CO_2$, 7% $O_2$, and 88% $N_2$ environment), cells are harvested and assayed for the HPP-CFC, and immature progenitors. In addition, cells are analyzed for the expression of certain differentiation antigens by FACScan. Colony data is expressed as mean number of colonies +/−SD) and are obtained from assays performed in six dishes for each population of cells.

EXAMPLE 13

Assays to Detect Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL5, IL6, IL-7, IL10, IL-13, IL14 and IL15. Interestingly, these signals are by themselves weak effectors but can, in combination with various co-stimulatory proteins, induce activation, proliferation, differentiation, homing, tolerance and death among B cell populations. One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

a. In Vitro Assay—Purified TR17 polylpeptides of the invention (e.g., soluble TR17) or agonists or antagonists thereof, is assessed for its ability to induce activation, proliferation, differentiation or inhibition and/or death in B-cell populations and their precursors. The activity of TR17 polypeptides, or agonists or antagonists thereof on purified human tonsillar B cells, measured qualitatively over the dose range from 0.1 to 10,000 ng/ml, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220). Various dilutions of each sample are placed into individual wells of a 96-well plate to which are added $10^5$ B-cells suspended in culture medium (RPMI 1640 containing 10% FBS, $5\times10^{-5}$M βME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with ³H-thymidine (6.7 Ci/mM) beginning 72 h post factor addition. The positive and negative controls are IL2 and medium respectively.

b. In Vivo Assay—BALB/c mice are injected (i.p.) twice per day with buffer only, or 2 mg/Kg of TR17 polypeptide (e.g., soluble TR17) or agonists or antagonists thereof. Mice receive this treatment for 4 consecutive days, at which time they are sacrificed and various tissues and serum collected for analyses. Comparison of H&E sections from normal and TR17 polypeptide-treated spleens identify the results of the activity of TR17 polypeptide on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R (B220), are used to determine whether any physiological changes to splenic cells, such as splenic disorganization, are due to increased B-cell representation within loosely defined B-cell zones that infiltrate established T-cell regions.

Flow cytometric analyses of the spleens from TR17 polypeptide-treated mice is used to indicate whether TR17 polypeptide specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and TR17 polypeptide-treated mice.

The studies described in this example test the activity in TR17 polypeptide. However, one skilled in the art could easily modify the exemplified studies to test the activity of TR17 polynucleotides (e.g., gene therapy), and agonists, and/or antagonists of TR17.

EXAMPLE 14

Assaay for TR17 Inhibition of B Cell Proliferation in an in vitro Co-stimulatory Assay This example provides a co-stimulatory assay using *Staphylococcus aureus* Cowan 1 (SAC) as priming agent and Neutrokine-alpha (Internatioanl Application Publication No. WO 98/18921) or IL-2 as a second signal to assay for TR17 polypeptide antagonists of Neutrokine-alpha (or IL-2) mediated B cell proliferation.

A soluble TR17 polypeptide is prepared (e.g., a soluble form of TR17 corresponding to a portion of the TR17 extracellular domain linked to the Fc portion of a human IgG1 immunogloulin molecule). The ability of this protein to alter the proliferative response of human B cells is assessed in a standard co-stimulatory assay. Briefly, human tonsillar B cells are purified by magnetic bead (MACS) depletion of CD3-positive cells. The resulting cell population is routinely greater than 95% B cells as assessed by expression of CD19 and CD20 staining. Various dilutions of rHuNeutrokine-alpha (International Application Publication No. WO 98/18921) or rHuIL2 are placed into individual wells of a 96-well plate to which is added $10^5$ B cells suspended in culture medium (RPMI 1640 containing 10% FBS, $5\times10^{-5}$M 2ME, 100 U/ml penicillin, 10 ug/ml streptomycin, and $10^{-5}$ dilution of formalin-fixed *Staphylococcus aureus* Cowan I (SAC) also known as Pansorbin (Pan)) in a total volume of 150 ul. The TR17 polypeptide is then added at various concentrations and the plates are placed in the incubator (37° C. 5% $CO_2$, 95% humidity) for three days. Proliferation is quantitated by a 20 h pulse (1 μ Ci/well) of ³H-thymidine (6.7 Ci/mM) beginning 72 h post factor addition. The positive and negative controls are SAC exposed B cells with rHuNeutrokine-alpha (or rHuIL2) and medium (in the absence of the TR17 polypeptide), respectively.

Antagonists of rHuNeutrokine-alpha (or rHuIL2) mediated B cell proliferation demonstrate a reduced level of B cell proliferation in the samples containing the TR17 polypeptides when compared to the positive control.

EXAMPLE 15

T Cell Proliferation Assay

A CD3-induced proliferation assay is performed on PBMCs and is measured by the uptake of $^3$H-thymidine. The assay is performed as follows. Ninety-six well plates are coated with 100 µl/well of mAb to CD3 (HIT3a, Pharmingen) or isotype-matched control mAb (B33.1) overnight at 4° C. (1 µg/ml in 0.05M bicarbonate buffer, pH 9.5), then washed three times with PBS. PBMC are isolated by F/H gradient centrifugation from human peripheral blood and added to quadruplicate wells ($5 \times 10^4$/well) of mAb coated plates in RPMI containing 10% FCS and P/S in the presence of varying concentrations of TR17 protein (total volume 200 µl). Relevant protein buffer and medium alone are controls. After 48 hr. culture at 37° C., plates are spun for 2 min. at 1000 rpm and 100 µl of supernatant is removed and stored –20° C. for measurement of IL-2 (or other cytokines) if effect on proliferation is observed. Wells are supplemented with 100 µl of medium containing 0.5 µCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of TR17 proteins.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 16

Effect of TR17 on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of TR17 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of TR17 for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of TR17 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. TR17, agonists, or antagonists of TR17 can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

1. Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2 \times 10^6$/ml in PBS containing PI at a final concentration of 5 µg/ml, and then incubated at room temperature for 5 minutes before FAC Scan analysis. PI uptake has been demonstrated to correlate with DNA fragmentation in this experimental paradigm.

2. Effect on Cytokine Release. An important function of monocytes/macrophages is their regulatory activity on other cellular populations of the immune system through the release of cytokines after stimulation. An ELISA to measure cytokine release is performed as follows. Human monocytes are incubated at a density of $5 \times 10^5$ cells/ml with increasing concentrations of TR17 and under the same conditions, but in the absence of TR17. For IL-12 production, the cells are primed overnight with IFN-γ (100 U/ml) in presence of TR17. LPS (10 ng/ml) is then added. Conditioned media are collected after 24 h and kept frozen until use. Measurement of TNF-α, IL-10, MCP-1 and IL-8 is then performed using a commercially available ELISA kit (e.g., R & D Systems (Minneapolis, Minn.)) applying the standard protocols provided with the kit.

3. Oxidative Burst. Purified monocytes are plated in 96-well plate at $2-1 \times 10^5$ cell/well. Increasing concentrations of TR17 are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 μM PMA). The plates are incubated at 37° C. for 2 hours and the reaction is stopped by adding 20 μl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 17
The Effect of TR17 on the Growth of Vascular Endothelial Cells

On day 1, human umbilical vein endothelial cells (HUVEC) are seeded at $2-5 \times 10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. TR17 protein of SEQ ID NO. 2, and positive controls, such as VEGF and basic FGF (bFGF) are added, at varying concentrations. On days 4 and 6, the medium is replaced. On day 8, cell number is determined with a Coulter Counter. An increase in the number of HUVEC cells indicates that TR17 may proliferate vascular endothelial cells.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 18
Stimulatory Effect of TR17 on the Proliferation of Vascular Endothelial Cells For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 ml serum-supplemented medium and are allowed to attach overnight. After serum-starvation for 12 hours in 0.5% FBS, conditions (bFGF, $VEGF_{165}$ or TR17 in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512–518 (1994).

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 19
Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4° C. for 2 h after exposing to denaturing solution and then with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., *J. Biol. Chem.* 6;271(36):21985–21992 (1996).

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 20
Stimulation of Endothelial Migration

This example will be used to explore the possibility that TR17 may stimulate lymphatic endothelial cell migration.

Endothelial cell migration assays are performed using a 48 well microchemotaxis chamber (Neuroprobe Inc., Cabin John, MD; Falk, W., Goodwin, R. H. J., and Leonard, E. J. "A 48 well micro chemotaxis assembly for rapid and accurate measurement of leukocyte migration." *J. Immunological Methods* 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, $2.5 \times 10^5$ cells suspended in 50 ul M199 containing 1% FBS are seeded in the upper compartment. The apparatus is then incubated for 5 hours at 37° C. in a humidified chamber with 5% $CO_2$ to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 21
Stimulation of Nitric Oxide Production by Endothelial Cells

Nitric oxide released by the vascular endothelium is believed to be a mediator of vascular endothelium relaxation. Thus, TR17 activity can be assayed by determining nitric oxide production by endothelial cells in response to TR17.

Nitric oxide is measured in 96-well plates of confluent microvascular endothelial cells after 24 hours starvation and a subsequent 4 hr exposure to various levels of a positive control (such as VEGF-1) and TR17. Nitric oxide in the medium is determined by use of the Griess reagent to measure total nitrite after reduction of nitric oxide-derived nitrate by nitrate reductase. The effect of TR17 on nitric oxide release is examined on HUVEC.

Briefly, NO release from cultured HUVEC monolayer is measured with a NO-specific polarographic electrode connected to a NO meter (Iso-NO, World Precision Instruments Inc.). Calibration of the NO element is performed according to the following equation: 2KNO2+2KI+2 H2SO4 6 2 NO+I2+2 H2O+2 K2SO4

The standard calibration curve is obtained by adding graded concentrations of KNO2 (0, 5, 10, 25, 50, 100, 250, and 500 nmol/L) into the calibration solution containing KI and H2SO4. The specificity of the Iso-NO electrode to NO is previously determined by measurement of NO from authentic NO gas. The culture medium is removed and HJUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) to maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1\times10^6$ endothelial cells. All values reported are means of four to six measurements in each group (number of cell culture wells). See, Leak et al. *Biochem. and Biophys. Res. Comm.* 217:96–105 (1995).

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 22
Effect of TR17 on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 μl/well) for 30 min. at 37° C. CADMEC are seeded onto the coated wells at 7,500 cells/well and cultured overnight in Growth Medium. The Growth Medium is then replaced with 300 μg Cell Applications° Chord Formation Medium containing control buffer or TR17 (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 23
Angiogenic Effect on Chick Chorioallantoic Membrane

Chick chorioallantoic membrane (CAM) is a well-established system to examine angiogenesis. Blood vessel formation on CAM is easily visible and quantifiable. The ability of TR17 to stimulate angiogenesis in CAM can be examined.

Fertilized eggs of the White Leghorn chick (*Gallus gallus*) and the Japanese quail (*Coturnix coturnix*) are incubated at 37.8° C. and 80% humidity. Differentiated CAM of 16-day-old chick and 13-day-old quail embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors, and the protein to be tested, are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 24
Angiogenesis Assay Using a Matrigel Implant in Mouse

In order to establish an in vivo model for angiogenesis to test TR17 protein activities, mice and rats are implanted subcutaneously with methylcellulose disks containing either 20 mg of BSA (negative control), 1 mg of TR17, or 0.5 mg of VEGF-1 (positive control). The negative control disks should contain little vascularization, while the positive control disks should show signs of vessel formation.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 25
Rescue of Ischemia in Rabbit Lower Limb Model

To study the in vivo effects of TR17 on ischemia, a rabbit hindlimb ischemia model is created by surgical removal of one femoral arteries as described previously (Takeshita, S. et al., *Am J. Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al., *Am J. Pathol* 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked TR17 expression plasmid by arterial gene transfer technology using a hydrogel-coated balloon catheter as described (Riessen, R. et al., *Hum Gene Ther.* 4:749–758 (1993); Leclerc, G. et al., *J. Clin. Invest.* 90: 936–944 (1992)). When TR17 is used in the treatment, a single bolus of 500 mg TR17 protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 26

Rat Ischemic Skin Flap Model

The evaluation parameters include skin blood flow, skin temperature, and factor VIII immunohistochemistry or endothelial alkaline phosphatase reaction. TR17 expression, during the skin ischemia, is studied using in situ hybridization.

The study in this model is divided into three parts as follows:
 a) Ischemic skin
 b) Ischemic skin wounds
 c) Normal wounds The experimental protocol includes:
 a) Raising a 3×4 cm, single pedicle full-thickness random skin flap (myocutaneous flap over the lower back of the animal).
 b) An excisional wounding (4–6 mm in diameter) in the ischemic skin skin-flap).
 c) Topical treatment with TR17 of the excisional wounds (day 0, 1, 2, 3, 4 post-wounding) at the following various dosage ranges: 1 mg to 100 mg.
 d) Harvesting the wound tissues at day 3, 5, 7, 10, 14 and 21 post-wounding for histological, immunohistochemical, and in situ studies.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 27

Peripheral Arterial Disease Model

Angiogenic therapy using TR17 is a novel therapeutic strategy to obtain restoration of blood flow around the ischemia in case of peripheral arterial diseases. The experimental protocol includes:
 a) One side of the femoral artery is ligated to create ischemic muscle of the hindlimb, the other side of hindlimb serves as a control.
 b) TR17 protein, in a dosage range of 20 mg –500 mg, is delivered intravenously and/or intramuscularly 3 times (perhaps more) per week for 2–3 weeks.
 c) The ischemic muscle tissue is collected after ligation of the femoral artery at 1, 2, and 3 weeks for the analysis of TR17 expression and histology. Biopsy is also performed on the other side of normal muscle of the contralateral hindlimb.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 28

Ischemic Myocardial Disease Model

TR17 is evaluated as a potent mitogen capable of stimulating the development of collateral vessels, and restructuring new vessels after coronary artery occlusion. Alteration of TR17 expression is investigated in situ. The experimental protocol includes:
 a) The heart is exposed through a left-side thoracotomy in the rat. Immediately, the left coronary artery is occluded with a thin suture (6-0) and the thorax is closed.
 b) TR17 protein, in a dosage range of 20 mg –500 mg, is delivered intravenously and/or intramuscularly 3 times (perhaps more) per week for 2–4 weeks.
 c) Thirty days after the surgery, the heart is removed and cross-sectioned for morphometric and in situ analyzes.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 29

Rat Corneal Wound Healing Model

This animal model shows the effect of TR17 on neovascularization. The experimental protocol includes:
 a) Making a 1–1.5 mm long incision from the center of cornea into the stromal layer.
 b) Inserting a spatula below the lip of the incision facing the outer corner of the eye.
 c) Making a pocket (its base is 1–1.5 mm form the edge of the eye).
 d) Positioning a pellet, containing 50 ng-5 ug of TR17, within the pocket.
 e) TR17 treatment can also be applied topically to the corneal wounds in a dosage range of 20mg –500mg (daily treatment for five days).

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 30
Diabetic Mouse and Glucocorticoid-Impaired Wound Healing Models

A. Diabetic db+/db+Mouse Model.

To demonstrate that TR17 accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et al., *Lab Invest.* 40(4):460–473 (1979); Coleman, D. L., *Diabetes* 31 (Suppl): 1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and were 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

TR17 is administered using at a range different doses of TR17, from 4mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) TR17.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 was 64 mm$^2$, the corresponding size of the dermal punch. Calculations were made using the following formula:

$$[\text{Open area on day 8}] - [\text{Open area on day 1}]/[\text{Open area on day 1}]$$

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with TR17. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer served as a positive tissue control and human brain tissue is used as a negative tissue control. Each specimen included a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, S. M. Glucocorticoids and Wound healing. In: Anti- Inflammatory Steroid Action: Basic and Clinical Aspects. 280–302 (1989); Wahl, S. M. et al., *J. Immunol.* 115: 476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991); Haynes, B. F. et al., *J. Clin. Invest.* 61: 703–797 (1978)) and producing a transient reduction of circulating monocytes (Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck, L. S. et al., *Growth Factors.* 5: 295–304 (1991); Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989); Pierce, G. F. et al., *Proc. Natl. Acad. Sci. USA* 86: 2229–2233 (1989)).

To demonstrate that TR17 can accelerate the healing process, the effects of multiple topical applications of TR17 on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and were 9 weeks old at the beginning of the study. The healing response of rats is impaired by the systemic administration of methylprednisolone (1 7mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue was no longer visible and the wound is covered by a continuous epithelium.

TR17 is administered using at a range different doses of TR17, from 4mg to 500mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) were evaluated: 1) Untreated group 2) Vehicle placebo control 3) TR17 treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 was 64 $mm^2$, the corresponding size of the dermal punch. Calculations were made using the following formula:

[Open area on day 8]–[Open area on day 1]/[Open area on day 1]

Specimens are fixed in 10% buffered formalin and paraffin embedded blocks are sectioned perpendicular to the wound surface (5mm) and cut using an Olympus microtome. Routine hematoxylin-eosin (H&E) staining was performed on cross-sections of bisected wounds. Histologic examination of the wounds allows assessment of whether the healing process and the morphologic appearance of the repaired skin was improved by treatment with TR17. A calibrated lens micrometer is used by a blinded observer to determine the distance of the wound gap.

Experimental data are analyzed using an unpaired t test. A p value of <0.05 is considered significant.

The studies described in this example test the activity in TR17 protein. However, one skilled in the art could easily modify the exemplified studies to test the activity of TR17 polynucleotides (e.g., gene therapy), agonists, and/or antagonists of TR17.

EXAMPLE 31

Lymphadema Animal Model

The purpose of this experimental approach is to create an appropriate and consistent lymphedema model for testing the therapeutic effects of TR17 in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located.

The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (A J Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs were amputated using a quillitine, then both experimental and control legs were cut at the ligature and weighed. A second weighing is done as the tibiocacaneal joint was disarticulated and the foot was weighed.

Histological Preparations: The transverse muscle located behind the knee (popliteal) area is dissected and arranged in a metal mold, filled with freezeGel, dipped into cold methylbutane, placed into labeled sample bags at −80 EC until sectioning. Upon sectioning, the muscle was observed under fluorescent microscopy for lymphatics. Other immuno/histological methods are currently being evaluated.

The studies described in this example test the activity in TR17 protein. However, one skilled in the art could easily modify the exemplified studies to test the activity of TR17 polynucleotides (e.g., gene therapy), agonists, and/or antagonists of TR17.

The results of this experiment confirmed that TR17-Fc inhibited B cell proliferation in the co-stimulatory assay using *Staphylococcus Aureus* Cowan 1 (SAC) as priming agent and Neutrokine-alpha as a second signal (data not shown). It is important to note that other Tumor Necrosis Factor Receptors (TNFR) fusion proteins (e.g., DR4-Fc (Internatioanl Application Publication No. WO 98/32856), TR6-Fc (Internatioanl Application Publication No. WO 98/31799), and TR9-Fc (Internatioanl Application Publication No. WO 98/56892)) did not inhibit proliferation.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference.

Further, the Sequence Listing submitted herewith, in both computer and paper forms, is hereby incorporated by reference in its entirety.

The entire disclosure (including the specification, sequence listing, and drawings) of each of the following U.S. applications are herein incorporated by reference in their entirety: Application No. 60/254,874 filed on Dec. 13, 2000; Application No. 60/235,991 filed on Sep. 26, 2000; application Ser. No. 09/533,822 filed on Mar. 24, 2000; and Application No. 60/188, 208 filed on Mar. 10, 2000.

What is claimed is:

1. A method of inhibiting B cell proliferation, comprising contacting a B cell with an effective amount of an agonistic anti-TR17 antibody or fragment thereof, wherein said anti-TR17 antibody or fragment thereof specifically binds a TR17 protein expressed on the surface of a cell wherein said TR17 protein is encoded by a polynucleotide that encodes amino acids 1 to 293 of SEQ ID NO:2 and wherein said anti-TR17 antibody inhibits B cell proliferation.

2. The method of claim 1 wherein said antibody or fragment thereof is a inonoclonal antibody.

3. The method of claim 1 wherein said antibody or fragment thereof is a polyclonal antibody.

4. The method of claim 1 wherein said antibody or fragment thereof is selected from the group consisting of:
   (a) a chimeric antibody;
   (b) a humanized antibody;
   (c) a human antibody;
   (d) a single chain antibody; and
   (e) a Fab fragment.

5. The method of claim wherein said antibody or fragment thereof is conjugated to a cytotoxin.

6. The method of claim 1 which is in vitro.

7. A method of inhibiting immunoglobulin production, comprising contacting a B cell with an effective amount of an agonistic anti-TR17 antibody or fragment thereof, wherein said anti-TR17 antibody or fragment thereof specifically binds a TR17 protein expressed on the surface of a cell wherein said TR17 protein is encoded by a polynucleotide that encodes amino acids 1 to 293 of SEQ ID NO:2 and wherein said anti-TR17 antibody inhibits immunoglobulin production.

8. The method of claim 7 wherein said antibody or fragment thereof is a monoclonal antibody.

9. The method of claim 7 wherein said antibody or fragment thereof is a polyclonal antibody.

10. The method of claim 7 wherein said antibody or fragment thereof is selected from the group consisting of:
    (a) a chimeric antibody;
    (b) a humanized antibody;
    (c) a human antibody;
    (d) a single chain antibody; and
    (e) a Fab fragment.

11. The method of claim 7 wherein said antibody or fragment thereof is conjugated to a cytotoxin.

12. The method of claim 7 which is in vitro.

* * * * *

UNITED STATES PATENT AND TRADEMARK OFFICE
CERTIFICATE OF CORRECTION

PATENT NO. : 6,969,519 B2  Page 1 of 1
APPLICATION NO. : 09/961376
DATED : November 29, 2005
INVENTOR(S) : Ruben et al.

It is certified that error appears in the above-identified patent and that said Letters Patent is hereby corrected as shown below:

<u>In the Title:</u>   On Title page, Item (54) col. 1

Delete "Methods of Using an Agonistic Antibody Human Tumor Necrosis Factor Receptor (TR17)" and replace with --Methods of Using An Agonistic Human Tumor Necrosis Factor Receptor (TR17) Antibody--.

<u>Title Page:</u>   On Title Page, Item (56) col. 2

Under "Other Publications," INID (56), at the Marriette et al. reference, delete "$_z$TNF4" and insert therefor --zTNF4--.

Claim 2, at column 229, delete "inonoclonal" and insert therefor --monoclonal--.

Claim 5, at column 229, delete "claim wherein" and insert therefor --claim 1 wherein--.

Signed and Sealed this

Fifteenth Day of August, 2006

JON W. DUDAS
*Director of the United States Patent and Trademark Office*